(12) United States Patent
Pouzet et al.

(10) Patent No.: US 8,822,474 B2
(45) Date of Patent: *Sep. 2, 2014

(54) 6,7-DIHYDROTHIENO[3,2-D]PYRIMIDINE FOR THE TREATMENT OF INFLAMMATORY DISEASES

(71) Applicants: Pascale Pouzet, Biberach (DE); Christoph Hoenke, Ingelheim (DE); Rolf Goeggel, Biberach (DE); Birgit Jung, Laupheim (DE); Peter Nickolaus, Warthausen (DE); Dennis Fiegen, Biberach (DE); Thomas Fox, Biberach (DE)

(72) Inventors: Pascale Pouzet, Biberach (DE); Christoph Hoenke, Ingelheim (DE); Rolf Goeggel, Biberach (DE); Birgit Jung, Laupheim (DE); Peter Nickolaus, Warthausen (DE); Dennis Fiegen, Biberach (DE); Thomas Fox, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/019,019

(22) Filed: Sep. 5, 2013

(65) Prior Publication Data

US 2014/0005154 A1     Jan. 2, 2014

Related U.S. Application Data

(62) Division of application No. 13/343,391, filed on Jan. 4, 2012, now Pat. No. 8,604,039, which is a division of application No. 11/736,703, filed on Apr. 18, 2007, now Pat. No. 8,114,878.

(30) Foreign Application Priority Data

Apr. 19, 2006   (EP) .................................... 06112779

(51) Int. Cl.
| A61K 31/5377 | (2006.01) |
| A61K 31/519 | (2006.01) |
| C07D 519/00 | (2006.01) |
| A61K 45/06 | (2006.01) |
| C07D 495/04 | (2006.01) |
| A61P 29/00 | (2006.01) |
| A61P 25/28 | (2006.01) |
| A61P 25/18 | (2006.01) |
| A61P 25/24 | (2006.01) |
| A61P 25/22 | (2006.01) |

(52) U.S. Cl.
CPC .......... *A61K 31/5377* (2013.01); *C07D 519/00* (2013.01); *C07D 495/04* (2013.01); *A61K 31/519* (2013.01); *A61K 45/06* (2013.01)
USPC . 514/252.16; 544/278; 514/171; 514/210.18; 514/234.2; 514/252.11

(58) Field of Classification Search
CPC .............................. C07D 495/04; A61K 31/519
USPC .......................... 544/278; 514/260.1, 252.16
See application file for complete search history.

(56) References Cited

U.S. PATENT DOCUMENTS

| 3,272,811 | A | 9/1966 | Ohnacker |
| 3,318,881 | A | 5/1967 | Ohnacker |
| 3,318,883 | A | 5/1967 | Ohnacker |
| 7,511,045 | B2 | 3/2009 | Hoenke |
| 8,486,948 | B2 | 7/2013 | Pouzet |
| 2007/0259846 | A1 | 11/2007 | Hoenke |
| 2010/0222585 | A1 | 9/2010 | Frutos |
| 2010/0305102 | A1 | 12/2010 | Pouzet |
| 2011/0021501 | A1 | 1/2011 | Pouzet |
| 2011/0028441 | A1 | 2/2011 | Pouzet |

FOREIGN PATENT DOCUMENTS

| AR | 53235 | 4/2007 |
| AU | 2006237354 | 10/2006 |
| CA | 2605161 | 10/2006 |
| DE | 102005019201 | 11/2006 |
| WO | WO 2005035775 | 4/2005 |
| WO | WO 2006111549 | 10/2006 |
| WO | WO 2009050236 | 4/2009 |

(Continued)

OTHER PUBLICATIONS

Chakraborti, et al: "3D-QSAR studies on thieno[3,2-d]pyrimidines as phosphodiesterase IV inhibitors", 13(8):1403-1408, Bioorganic and Medicinal Chemistry Letters, Department of Medicinal chemistry, National Institute of Pharmaceutical Education and Research, Punjab, India. (2003).

(Continued)

*Primary Examiner* — Susanna Moore
(74) *Attorney, Agent, or Firm* — Michael P. Morris; Timothy X. Witkowski

(57) ABSTRACT

The invention relates to new dihydrothienopyrimidine of formula 1, as well as pharmacologically acceptable salts, diastereomers, enantiomers, racemates, hydrates or solvates thereof,

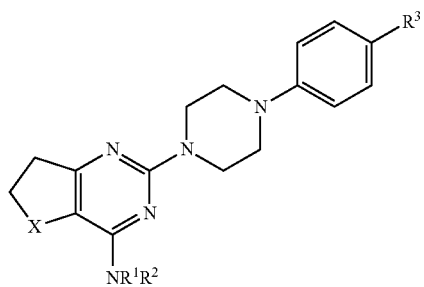

wherein X is SO or $SO_2$, but preferably SO, and wherein $R^1$, $R^2$ and $R^3$ have the meanings given in the description, and which are suitable for the treatment of respiratory or gastrointestinal complaints or diseases, inflammatory diseases of the joints, skin or eyes, diseases of the peripheral or central nervous system or cancers, as well as pharmaceutical compositions which contain these compounds.

36 Claims, No Drawings

(56) References Cited

FOREIGN PATENT DOCUMENTS

| WO | WO 2009050242 | 4/2009 |
|----|---------------|--------|
| WO | WO 2009050248 | 4/2009 |
| WO | WO 2009052138 | 4/2009 |
| WO | WO 2009053268 | 4/2009 |

OTHER PUBLICATIONS

Gavezzotti, "Are Crystal Structures Predictable?" Acc. Chem. Res. 27:309-314 (1994).

PCT International Search report of International Publication in WO 2007/118793. Completed on Jun. 29, 2007. International Application No. PCT/EP2007/053255, International Filing Date: Apr. 3, 2007. Applicant: Boehringer Ingelheim Pharma GmbH & Co. KG.

Vippagunta et al. "Crystalline Solids" Advanced Drug Delivery Reviews, 48:3-26 (2001).

Brown, W.M., (Int. J. Chron. Obstruct. Pulmon. Dis., 2007, 2(4), pp. 517-533).

Kolosionek, E. et al (Molecular Biology of the Cell, 2009, 20 pp. 4751-4765).

Kumar, N. et al. (BMC Medicine, 2013, 11:96, pp. 1-8).

Salari-Sharif, P. et al. (Current Pharmaceutical Design, 2010, 16, pp. 3661-3667).

6,7-DIHYDROTHIENO[3,2-D]PYRIMIDINE FOR THE TREATMENT OF INFLAMMATORY DISEASES

STATEMENT OF RELATED CASES

This application is a divisional application of U.S. patent application Ser. No. 13/343,391, filed Jan. 4, 2012, now U.S. Pat. No. 8,604,039, which is a divisional application of U.S. patent application Ser. No. 11/736,703, filed Apr. 18, 2007, now U.S. Pat. No. 8,114,878, which are incorporated herein by reference in their entirety for all purposes.

The invention relates to new dihydrothienopyrimidines of formula 1, as well as pharmacologically acceptable salts, diastereomers, enantiomers, racemates, hydrates or solvates thereof,

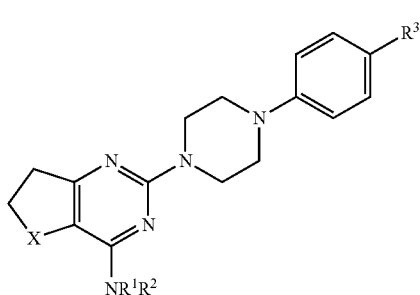

wherein X denotes SO or $SO_2$, but is preferably SO, which are suitable for the treatment of respiratory or gastrointestinal complaints or diseases, inflammatory diseases of the joints, skin or eyes, diseases of the peripheral or central nervous system or cancers, as well as pharmaceutical compositions which contain these compounds.

DESCRIPTION OF RELATED ART

U.S. Pat. No. 3,318,881 and BE 663693 disclose the preparation of dihydrothieno[3.2-d]pyrimidines which have cardiovascular and sedative properties.

DESCRIPTION OF THE INVENTION

Surprisingly it has now been found that dihydrothienopyrimidines of formula 1, particularly those wherein X denotes SO, are suitable for the treatment of inflammatory diseases.

The present invention therefore relates to compounds of formula 1

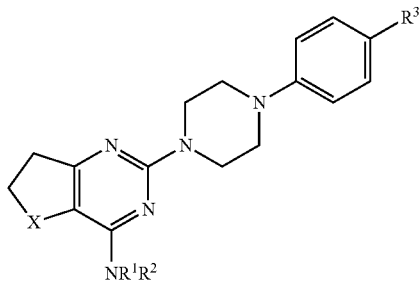

wherein
X denotes SO or $SO_2$; preferably SO,
$R^1$ denotes H, $C_{1-6}$-alkyl, $C_{2-6}$-alkenyl, $C_{2-6}$-alkynyl, $C_{6-10}$-aryl, $C_{6-10}$-aryl-$C_{1-6}$-alkylene or $C_{5-10}$-heteroaryl-$C_{1-6}$-alkylene $R^2$ is H or a group selected from among $C_{1-10}$-alkyl, $C_{2-6}$-alkenyl and $C_{2-6}$-alkynyl, which may optionally be substituted by halogen and which may optionally be substituted by one or more groups selected from among $OR^{2.1}$, $COOR^{2.1}$, $CONR^{2.2}R^{2.3}$, $SR^{2.1}$, $C_{6-10}$-aryl, a mono- or bicyclic $C_{3-10}$ heterocycle, a mono- or bicyclic $C_{5-10}$-heteroaryl, a mono- or bicyclic $C_{3-10}$-cycloalkyl, $CH_2$—$NR^{2.2}R^{2.3}$ and $NR^{2.2}R^{2.3}$, which may in turn optionally be substituted by one or more groups selected from among OH, halogen, $OR^{2.1}$, oxo, $C_{1-6}$-alkyl, $C_{1-6}$-aryl, $COOR^{2.1}$, $CH_2$—$NR^{2.2}R^{2.3}$ and $NR^{2.2}R^{2.3}$,
while $R^{2.1}$ is H or a group selected from among $C_{1-6}$-alkyl, $C_{1-6}$-alkanol, $C_{1-3}$-haloalkyl, mono- or bicyclic $C_{3-10}$ cycloalkyl, $C_{6-10}$-aryl-$C_{1-6}$-alkylene, mono- or bicyclic $C_{5-10}$-heteroaryl-$C_{1-6}$-alkylene, $C_{3-10}$-heterocycle-$C_{1-6}$-alkylene, $C_{3-10}$-cycloalkyl-$C_{1-6}$-alkylene, a mono- or bicyclic $C_{6-10}$-aryl, a mono- or bicyclic $C_{5-10}$-heteroaryl and a mono- or bicyclic, saturated or unsaturated heterocycle, which may optionally be substituted by one or more groups selected from among OH, halogen, $C_{1-6}$-alkyl and $C_{6-10}$-aryl,
while $R^{2.2}$ and $R^{2.3}$ independently of one another are H or a group selected from among halogen, $C_{1-6}$-alkyl, mono- or bicyclic $C_{3-10}$ cycloalkyl, $C_{6-10}$-aryl-$C_{1-6}$-alkylene, $C_{5-10}$-heteroaryl-$C_{1-6}$-alkylene, mono- or bicyclic $C_{6-10}$-aryl, mono- or bicyclic $C_{3-10}$ heterocycle, mono- or bicyclic $C_{5-10}$-heteroaryl, CO—$NH_2$, CO—$NHCH_3$, CO—$N(CH_3)_2$, $SO_2(C_1-C_2$-alkyl), CO—$R^{2.1}$ and $COOR^{2.1}$, which may optionally be substituted by one or more groups selected from among OH, halogen, $C_{1-6}$-alkyl, $C_{6-10}$-aryl and $COOR^{2.1}$, or $R^2$ denotes a mono- or polycyclic $C_{3-10}$ cycloalkyl, which may optionally be bridged by one or more $C_{1-3}$-alkyl groups and which may optionally be substituted by a group selected from among branched or unbranched $C_{1-6}$-alkanol, $OR^{2.1}$, $COOR^{2.1}$, $SO_2NR^{2.2}R^{2.3}$, $C_{3-10}$ heterocycle, $C_{6-10}$-aryl, $C_{1-6}$-alkyl, $C_{6-10}$-aryl-$C_{1-6}$-alkylene, $C_{5-10}$-heteroaryl-$C_{1-6}$-alkylene, mono- or bicyclic $C_{3-10}$ cycloalkyl and $NR^{2.2}R^{2.3}$, which may optionally be substituted by one or more groups selected from among OH, $OR^{2.1}$, oxo, halogen, $C_{1-6}$-alkyl, $C_{6-10}$-aryl and $NR^{2.2}R^{2.3}$, or $R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{3-10}$-cycloalkyl, $C_{3-10}$ heterocycle, $C_{1-6}$-alkyl, $C_{6-10}$-aryl-$C_{1-6}$-alkylene, $C_{3-10}$-heterocycle-$C_{1-6}$-alkylene, $C_{5-10}$-heteroaryl-$C_{1-6}$-alkylene, $C_{6-10}$-aryl, $SO_2$—$CH_3$, $SO_2$—$CH_2CH_3$ and $SO_2$—$NR^{2.2}R^{2.3}$, which may in turn optionally be substituted by one or more groups selected from among OH, $OR^{2.1}$, oxo, halogen, $C_{1-6}$-alkyl, $C_{6-10}$-aryl and $NR^{2.2}R^{2.3}$, or $R^2$ denotes a group selected from among mono- or bicyclic, saturated or unsaturated $C_{3-10}$ heterocycle and a mono- or bicyclic $C_{5-10}$-heteroaryl, which includes 1 to 4 heteroatoms selected from among S, O and N and optionally by one or more groups selected from among halogen, OH, oxo and SH or by one or more groups selected from among $OR^{2.1}$, $SR^{2.1}$, $COOR^{2.1}$, $COR^{2.1}$, $C_{1-6}$-alkanol, $C_{3-10}$-cycloalkyl, $C_{6-10}$-aryl, $C_{1-6}$-alkyl, $C_{6-10}$-aryl-$C_{1-6}$-alkylene, $C_{5-10}$-heteroaryl-$C_{1-6}$-alkylene, $C_{5-10}$ heterocycle, $C_{5-10}$-heteroaryl, $C_{1-6}$-alkanol and $NR^{2.2}R^{2.3}$, which may in turn optionally be substituted by one or more groups selected from among OH, $OR^{2.1}$, oxo, halogen, $C_{1-6}$-alkyl, $C_{6-10}$-aryl, $CH_2$—$NR^{2.2}R^{2.3}$ and $NR^{2.2}R^{2.3}$, or wherein $NR^1R^2$ together denote a heterocyclic $C_{4-7}$ ring, which may optionally be bridged, which contains 1, 2 or 3 heteroatoms selected from among N, O and S and which may optionally be substituted by one or more groups selected from among OH, OR$^{2.1}$, C$_{1-6}$-alkanol, oxo, halogen, C$_{1-6}$-alkyl, C$_{6-10}$-aryl, COOR$^{2.1}$, CH$_2$—NR$^{2,2}$-COO—R$^{2.1}$, CH$_2$NR$^{2,2}$—CO—R$^{2.1}$, CH$_2$—NR$^{2,2}$-CO—CH$_2$—NR$^{2.2}$R$^{2.3}$, CH$_2$—NR$^{2,2}$-SO$_2$—C$_{1-3}$-alkyl, CH$_2$—NR$^{2,2}$-SO$_2$—NR$^{2.2}$R$^{2.3}$, CH$_2$—NR$^{2,2}$-CO—NR$^{2.2}$R$^{2.3}$, CO—NR$^{2.2}$R$^{2.3}$ and NR$^{2.2}$R$^{2.3}$, and wherein R$^3$ is selected from among fluorine, chlorine, bromine, iodine, hydroxy, SO$_2$—CH$_3$, COOR$^{2.1}$, nitrile group and C$_{3-10}$ heterocycle-C$_{1-6}$-alkylene, wherein the C$_{3-10}$ heterocycle may be mono- or bicyclic and may optionally be substituted by a group selected from among OH, halogen, oxo, C$_{1-6}$-alkyl and C$_{6-10}$-aryl, or is a group selected from among C$_{1-6}$-alkyl, C$_{2-6}$-alkenyl, C$_{2-6}$-alkynyl, C$_{6-10}$-aryl; C$_{6-10}$-aryl-C$_{1-6}$-alkylene, C$_{5-10}$-heteroaryl-C$_{1-6}$-alkylene, C$_{3-10}$ heterocycle and C$_{3-10}$-cycloalkyl, which may optionally be substituted by a group selected from among OH, halogen, oxo, C$_{1-6}$-alkyl and C$_{6-10}$-aryl, or R$^3$ denotes the group —CO—NR$^{3.1}$R$^{3.2}$, wherein R$^{3.1}$ and R$^{3.2}$ independently of one another are H or groups selected from among C$_{1-6}$-alkyl, C$_{2-6}$-alkenyl, C$_{2-6}$-alkynyl, C$_{6-10}$-aryl; C$_{6-10}$-aryl-C$_{1-6}$-alkylene, C$_{5-10}$-heteroaryl-C$_{1-6}$-alkylene, C$_{5-10}$-heteroaryl-C$_{1-6}$-alkynylene, C$_{5-10}$-heteroaryl-C$_{1-6}$-alkenylene, mono- or bicyclic, C$_{3-10}$ heterocycle, C$_{3-10}$-heterocycle-C$_{1-6}$-alkylene and mono- or bicyclic C$_{5-10}$-heteroaryl, wherein the group in each case may optionally be substituted by one or more groups selected from among OH, oxo, halogen, C$_{1-6}$-alkyl and O—C$_{1-6}$-alkyl, or wherein R$^3$ denotes the group —NR$^{3.3}$—CO—R$^{3.4}$, wherein R$^{3.3}$ is H or a group selected from among C$_{1-6}$-alkyl, C$_{2-6}$-alkenyl, C$_{2-6}$-alkynyl, C$_{6-10}$-aryl; C$_{6-10}$-aryl-C$_{1-6}$-alkylene, C$_{5-10}$-heteroaryl-C$_{1-6}$-alkylene, C$_{3-10}$ heterocycle and a C$_{5-10}$-heteroaryl, which may optionally be substituted by one or more groups selected from among OH, OR$^{2.1}$, oxo, NH$_2$, NR$^{2.2}$R$^{2.3}$, halogen, C$_{1-6}$-alkyl and C$_{6-10}$-aryl, and wherein R$^{3.4}$ is H or a group selected from among C$_{1-6}$-alkyl, C$_{2-6}$-alkenyl, C$_{2-6}$-alkynyl, C$_{1-6}$-alkanol, OR$^{2.1}$, CH$_2$—O—CO—C$_{1-6}$-alkyl, CH$_2$—NR$^{2.2}$R$^{2.3}$, NR$^{2.2}$R$^{2.3}$, C$_{6-10}$-aryl; C$_{6-10}$-aryl-C$_{1-6}$-alkylene, C$_{5-10}$-heteroaryl-C$_{1-6}$-alkylene, mono- or bicyclic, saturated, partially saturated or unsaturated C$_{3-10}$ heterocycle with 1, 2 or 3 heteroatoms selected from among S, O and N and a mono- or bicyclic C$_{5-10}$-heteroaryl with 1, 2 or 3 heteroatoms selected from among S, O and N, which may optionally be substituted by one or more groups selected from among OH, OR$^{2.1}$, oxo, NH$_2$, NR$^{2.1}$R$^{2.3}$, halogen, C$_{1-6}$-alkyl and C$_{6-10}$-aryl, or wherein R$^3$ denotes an optionally mono- or di-N-substituted sulphonamide group SO$_2$—NR$^{3.5}$R$^{3.6}$, wherein R$^{3.5}$ and R$^{3.6}$ may each independently of one another be C$_{1-6}$-alkyl or C$_{6-10}$-aryl, as well as pharmacologically acceptable salts, diastereomers, enantiomers, racemates, hydrates or solvates thereof.

The invention preferably relates to the above compounds of formula 1, wherein

X denotes SO

R$^1$ denotes H, C$_{1-6}$-alkyl, C$_{6-10}$-aryl, C$_{6-10}$-aryl-C$_{1-6}$-alkylene or C$_{5-10}$-heteroaryl-C$_{1-6}$-alkylene R$^2$ is H or C$_{1-6}$-alkyl, which may optionally be substituted by halogen and which may be substituted by one or more groups selected from among OR$^{2.1}$, COOR$^{2.1}$, CONR$^{2.2}$R$^{2.3}$, SR$^{2.1}$, C$_{6-10}$-aryl, a mono- or bicyclic C$_{3-10}$ heterocycle, a mono- or bicyclic C$_{5-10}$-heteroaryl, a mono- or bicyclic C$_{3-10}$-cycloalkyl, CH$_2$—NR$^{2.2}$R$^{2.3}$ and NR$^{2.2}$R$^{2.3}$, which may in turn optionally be substituted by one or more groups selected from among OH, halogen, OR$^{2.1}$, oxo, C$_{1-6}$-alkyl, C$_{6-10}$-aryl, COOR$^{2.1}$, CH$_2$—NR$^{2.2}$R$^{2.3}$ and NR$^{2.2}$R$^{2.3}$, wherein R$^{2.1}$ is H or a group selected from among C$_{1-6}$-alkyl, C$_{1-6}$-alkanol, C$_{1-3}$-haloalkyl, a mono- or bicyclic C$_{3-10}$ cycloalkyl, a C$_{6-10}$-aryl-C$_{1-6}$-alkylene or C$_{5-10}$-heteroaryl-C$_{1-6}$-alkylene, C$_{3-10}$ heterocycle-C$_{1-6}$-alkylene, C$_{3-10}$-cycloalkyl-C$_{1-6}$-alkylene, a mono- or bicyclic C$_{6-10}$-aryl, a mono- or bicyclic C$_{5-10}$-heteroaryl and a mono- or bicyclic, saturated or unsaturated C$_{3-10}$ heterocycle, which may optionally be substituted by one or more groups selected from among OH, halogen, C$_{1-6}$-alkyl, C$_{6-10}$-aryl, wherein R$^{2.2}$ and R$^{2.3}$ independently of one another are H or are selected from among halogen, C$_{1-6}$-alkyl, mono- or bicyclic C$_{3-10}$ cycloalkyl, C$_{6-10}$-aryl-C$_{1-6}$-alkylene, C$_{5-10}$-heteroaryl-C$_{1-6}$-alkylene, mono- or bicyclic C$_{6-10}$-aryl, mono- or bicyclic, saturated or unsaturated C$_{3-10}$ heterocycle, mono- or bicyclic C$_{5-10}$-heteroaryl, CO—NH$_2$, CO—NHCH$_3$, CO—N(CH$_3$)$_2$, SO$_2$(C$_1$-C$_2$-alkyl), CO—R$^{2.1}$ and COOR$^{2.1}$, which may optionally be substituted by one or more groups selected from among OH, halogen, C$_{1-6}$-alkyl, C$_{6-10}$-aryl and COOR$^{2.1}$, or R$^2$ denotes a mono- or polycyclic C$_{3-10}$-cycloalkyl, which may optionally be bridged by one or more C$_{1-3}$-alkyl groups and which may optionally be mono- or polysubstituted by OH or halogen or by one or more groups selected from among branched or unbranched C$_{1-6}$-alkanol, OR$^{2.1}$, COOR$^{2.1}$, SO$_2$NR$^{2.2}$R$^{2.3}$, C$_{3-10}$ heterocycle, C$_{6-10}$-aryl, C$_{1-6}$-alkyl, C$_{6-10}$-aryl-C$_{1-6}$-alkylene, C$_{5-10}$-heteroaryl-C$_{1-6}$-alkylene, mono- or bicyclic C$_{3-10}$-cycloalkyl and NR$^{2.2}$R$^{2.3}$, which may optionally be substituted by one or more groups selected from among OH, OR$^{2.1}$, oxo, halogen, C$_{1-6}$-alkyl, C$_{6-10}$-aryl and NR$^{2.2}$R$^{2.3}$, or R$^2$ denotes a mono- or polycyclic C$_{6-10}$-aryl, which may optionally be substituted by OH, SH or halogen or by one or more groups selected from among OR$^{2.1}$, COOR$^{2.1}$, NR$^{2.2}$R$^{2.3}$, CH$_2$—NR$^{2.2}$R$^{2.3}$, C$_{3-10}$-cycloalkyl, C$_{3-10}$ heterocycle, C$_{1-6}$-alkyl, C$_{6-10}$-aryl-C$_{1-6}$-alkylene, C$_{3-10}$ heterocycle-C$_{1-6}$-alkylene, C$_{5-10}$-heteroaryl-C$_{1-6}$-alkylene, C$_{6-10}$-aryl, SO$_2$—CH$_3$, SO$_2$—CH$_2$CH$_3$ and SO$_2$—NR$^{2.2}$R$^{2.3}$, which may in turn optionally be substituted by one or more groups selected from among OH, OR$^{2.1}$, oxo, halogen, C$_{1-6}$-alkyl, C$_{1-10}$-aryl and NR$^{2.2}$R$^{2.3}$, or R$^2$ denotes a group selected from among mono or bicyclic, saturated or unsaturated C$_{3-10}$ heterocycle and a mono- or bicyclic C$_{5-10}$-heteroaryl, which includes 1 to 4 heteroatoms selected from among S, O and N and may optionally be substituted by one or more groups selected from among halogen, OH, oxo and SH or by one or more groups selected from among OR$^{2.1}$, SR$^{2.1}$, COOR$^{2.1}$, COR$^{2.1}$, C$_{1-6}$-alkanol, C$_{3-10}$-cycloalkyl, C$_{6-10}$-aryl, C$_{1-6}$-alkyl, C$_{6-10}$-aryl-C$_{1-6}$-alkylene, C$_{5-10}$-heteroaryl-C$_{1-6}$-alkylene, C$_{5-10}$ heterocycle, C$_{5-10}$-heteroaryl, C$_{1-6}$-alkanol and NR$^{2.2}$R$^{2.3}$, which may in turn optionally be substituted by one or more groups selected from among OH, OR$^{2.1}$, oxo, halogen, C$_{1-6}$-alkyl, C$_{6-10}$-aryl and NR$^{2.1}$R$^{2.3}$, or NR$^1$R$^2$ together denotes a heterocyclic C$_{4-7}$ ring, which may optionally be bridged, which contains 1, 2 or 3 heteroatoms selected from among N, O and S and which may optionally be substituted by one or more groups selected from among OH, OR$^{2.1}$, C$_{1-6}$-alkanol, oxo, halogen, C$_{1-6}$-alkyl, C$_{6-10}$-aryl, COOR$^{2.1}$, CH$_2$—NR$^{2,2}$-COO—R$^{2.1}$, CH$_2$—NR$^{2,2}$-CO—R$^{2.1}$, CH$_2$—NR$^{2,2}$-CO—CH$_2$—NR$^{2.2}$R$^{2.3}$, CH$_2$—NR$^{2,2}$-SO$_2$—C$_{1-3}$-alkyl, CH$_2$—NR$^{2,2}$-SO$_2$—NR$^{2.2}$R$^{2.3}$, CH$_2$—NR$^{2,2}$-CO—NR$^{2.2}$R$^{2.3}$, CO—NR$^{2.2}$R$^{2.3}$, CH$_2$—NR$^{2.2}$R$^{2.3}$ and NR$^{2.2}$R$^{2.3}$, as well as pharmacologically acceptable salts, diastereomers, enantiomers, racemates, hydrates or solvates thereof.

Also preferred are the above-mentioned compounds of formula 1, wherein
X denotes SO,
and
R$^1$ denotes H, C$_{1-6}$-alkyl, C$_{6-10}$-aryl, C$_{6-10}$-aryl-C$_{1-6}$-alkylene or C$_{5-10}$-heteroaryl-C$_{1-6}$-alkylene,
and
R$^2$ is H or C$_{1-6}$-alkyl, which may optionally be substituted by halogen and which may optionally be substituted by one or more groups selected from among OR$^{2.1}$, COOR$^{2.1}$, CONR$^{2.2}$R$^{2.3}$, SR$^{2.1}$, phenyl, a mono- or bicyclic C$_{5-10}$ heterocycle, C$_{5-6}$-heteroaryl, a mono- or bicyclic C$_{5-10}$-cycloalkyl, CH$_2$—NR$^{2.2}$R$^{2.3}$ and NR$^{2.2}$R$^{2.3}$, which may in turn optionally be substituted by one or more groups selected from among OH, halogen, OR$^{2.1}$, oxo, C$_{1-6}$-alkyl, phenyl, COOR$^{2.1}$, CH$_2$—NR$^{2.2}$R$^{2.3}$ and NR$^{2.2}$R$^{2.3}$,
wherein R$^{2.1}$ is H or a group selected from among C$_{1-6}$-alkyl, C$_{1-6}$-alkanol, C$_{1-3}$-haloalkyl, a mono- or bicyclic C$_{5-10}$ cycloalkyl, a phenyl-C$_{1-6}$-alkylene, a C$_{5-6}$-heteroaryl-C$_{1-6}$-alkylene, C$_{5-10}$-heterocycle-C$_{1-6}$-alkylene, C$_{5-10}$-cycloalkyl-C$_{1-6}$-alkylene, phenyl, a mono- or bicyclic C$_{5-10}$-heteroaryl and a mono- or bicyclic, saturated or unsaturated C$_{5-10}$ heterocycle, which may optionally be substituted by one or more groups selected from among OH, halogen, C$_{1-6}$-alkyl and phenyl,
wherein R$^{2.2}$ and R$^{2.3}$ independently of one another are H or a group selected from among halogen, C$_{1-6}$-alkyl, mono- or bicyclic C$_{5-10}$ cycloalkyl, phenyl-C$_{1-6}$-alkylene, C$_{5-6}$-heteroaryl-C$_{1-6}$-alkylene, phenyl, mono or bicyclic C$_{5-10}$ heterocycle, mono- or bicyclic C$_{5-6}$-heteroaryl, CO—NH$_2$, CO—NHCH$_3$, CO—N(CH$_3$)$_2$, SO$_2$ (C$_1$-C$_2$-alkyl), CO—R$^{2.1}$ and COOR$^{2.1}$, which may optionally be substituted by one or more groups selected from among OH, halogen, C$_{1-6}$-alkyl, phenyl and COOR$^{2.1}$, or
R$^2$ denotes a mono- or polycyclic C$_{5-10}$-cycloalkyl, which may optionally be bridged by one or more C$_{1-3}$-alkyl groups and which may optionally be mono- or polysubstituted by OH or halogen or by one or more groups selected from among branched or unbranched C$_{1-3}$-alkanol, OR$^{2.1}$, COOR$^{2.1}$, SO$_2$NR$^{2.2}$R$^{2.3}$, C$_{5-10}$ heterocycle, phenyl, C$_{1-6}$-alkyl, phenyl-C$_{1-6}$-alkylene, C$_{5-6}$-heteroaryl-C$_{1-6}$-alkylene, mono- or bicyclic C$_{5-10}$-cycloalkyl and NR$^{2.2}$R$^{2.3}$, which may optionally be substituted by one or more groups selected from among OH, OR$^{2.1}$, oxo, halogen, C$_{1-6}$-alkyl, phenyl and NR$^{2.2}$R$^{2.3}$,
R$^2$ or phenyl, which may optionally be substituted by OH, SH or halogen or by one or more groups selected from among OR$^{2.1}$, COOR$^{2.1}$, NR$^{2.2}$R$^{2.3}$, CH$_2$—NR$^{2.2}$R$^{2.3}$, C$_{5-10}$-cycloalkyl, C$_{5-10}$ heterocycle, C$_{1-6}$-alkyl, phenyl-C$_{1-6}$-alkylene, C$_{5-10}$ heterocycle-C$_{1-6}$-alkylene, C$_{5-6}$-heteroaryl-C$_{1-6}$-alkylene, phenyl, SO$_2$—CH$_3$, SO$_2$—CH$_2$CH$_3$ and SO$_2$—NR$^{2.2}$R$^{2.3}$, which may in turn optionally be substituted by one or more groups selected from among OH, OR$^{2.1}$, oxo, halogen, C$_{1-6}$-alkyl, C$_{6-10}$-aryl and NR$^{2.2}$R$^{2.3}$,
R$^2$ or a group selected from among mono or bicyclic, saturated or unsaturated C$_{5-10}$ heterocycle and mono- or bicyclic C$_{5-6}$-heteroaryl, which contains 1 to 4 heteroatoms selected from among S, O and N and may optionally be substituted by one or more groups selected from among halogen, OH, oxo and SH or by one or more groups selected from among OR$^{2.1}$, SR$^{2.1}$, COOR$^{2.1}$, COR$^{2.1}$, C$_{1-6}$-alkanol, C$_{3-10}$-cycloalkyl, phenyl, C$_{1-6}$-alkyl, phenyl-C$_{1-6}$-alkylene, C$_{5-6}$-heteroaryl-C$_{1-6}$ alkylene, C$_{5-10}$ heterocycle, C$_{5-6}$-heteroaryl, C$_{1-6}$-alkanol and NR$^{2.2}$R$^{2.3}$, which may in turn optionally be substituted by one or more groups selected from among OH, OR$^{2.1}$, oxo, halogen, C$_{1-6}$-alkyl, phenyl and NR$^{2.2}$R$^{2.3}$, as well as pharmacologically acceptable salts, diastereomers, enantiomers, racemates, hydrates or solvates thereof Also particularly preferred are the above compounds of formula 1, wherein
NR$^1$R$^2$ together denotes a heterocyclic C$_{4-7}$ ring, which may optionally be bridged, which contains 1, 2 or 3 heteroatoms selected from among N, O and S and which may optionally be substituted by one or more groups selected from among OH, OR$^{2.1}$, C$_{1-6}$-alkanol, oxo, halogen, C$_{1-6}$-alkyl, C$_{6-10}$-aryl, COOR$^{2.1}$, CH$_2$—NR$^{2,2}$-COO—R$^{2.1}$, CH$_2$—NR$^{2,2}$-CO—R$^{2.1}$, CH$_2$—NR$^{2,2}$-CO—CH$_2$—NR$^{2.2}$R$^{2.3}$, CH$_2$—NR$^{2,2}$-SO$_2$—C$_{1-3}$-alkyl, CH$_2$—NR$^{2,2}$-SO$_2$—NR$^{2.2}$R$^{2.3}$, CH$_2$—NR$^{2,2}$-CO—NR$^{2.2}$R$^{2.3}$, CO—NR$^{2.2}$R$^{2.3}$, CH$_2$—NR$^{2.2}$R$^{2.3}$ and NR$^{2.2}$R$^{2.3}$, as well as pharmacologically acceptable salts, diastereomers, enantiomers, racemates, hydrates or solvates thereof.

The invention preferably also relates to the above compounds according to formula 1, wherein
R$^1$ is H or methyl,
as well as pharmacologically acceptable salts, diastereomers, enantiomers, racemates, hydrates or solvates thereof.

The invention preferably also relates to the above compounds according to formula 1, wherein
NR$^1$R$^2$ together form a pyrrolidine ring, which may optionally be substituted by one or more groups selected from among OH, OR$^{2.1}$, CH$_2$—OH, CH$_2$—CH$_2$—OH, oxo, Cl, F, Br, methyl, ethyl, propyl, phenyl, COOR$^{2.1}$, CH$_2$—NR$^{2,2}$-COO—R$^{2.1}$, CH$_2$—NR$^{2,2}$-CO—R$^{2.1}$, CH$_2$—NR$^{2,2}$-CO—CH$_2$—NR$^{2.2}$R$^{2.3}$, CH$_2$—NR$^{2,2}$-SO$_2$—C$_{1-3}$-alkyl, CH$_2$—NR$^{2,2}$-SO$_2$—NR$^{2.2}$R$^{2.3}$, CH$_2$—NR$^{2,2}$-CO—NR$^{2.2}$R$^{2.3}$, CO—NR$^{2.2}$R$^{2.3}$, CH$_2$—NR$^{2.2}$R$^{2.3}$ and NR$^{2.2}$R$^{2.3}$, as well as pharmacologically acceptable salts, diastereomers, enantiomers, racemates, hydrates or solvates thereof.

The invention preferably also relates to the above compounds according to formula 1, wherein
R$^2$ denotes phenyl, which is mono- or polysubstituted by OH, SH or halogen and/or by one or more groups selected from among OR$^{2.1}$, COOR$^{2.1}$, NR$^{2.2}$R$^{2.3}$, CH$_2$—NR$^{2.2}$R$^{2.3}$, C$_{5-10}$-cycloalkyl, C$_{5-10}$ heterocycle, C$_{1-6}$-alkyl, phenyl-C$_{1-6}$-alkylene, C$_{5-10}$ heterocycle-C$_{1-6}$-alkylene, C$_{5-6}$-heteroaryl-C$_{1-6}$-alkylene, phenyl, SO$_2$—CH$_3$, SO$_2$—CH$_2$CH$_3$ and SO$_2$—NR$^{2.2}$R$^{2.3}$ at any position, which may in turn optionally be substituted by one or more groups selected from among OH, OR$^{2.1}$, oxo, halogen, C$_{1-6}$-alkyl, phenyl and NR$^{2.2}$R$^{2.3}$, as well as pharmacologically acceptable salts, diastereomers, enantiomers, racemates, hydrates or solvates thereof.

The invention preferably also relates to the above compounds according to formula 1, wherein
R$^2$ is phenyl, which may be substituted in at least one of the two meta positions by OH, SH or halogen or by one or more groups selected from among OR$^{2.1}$, COOR$^{2.1}$, NR$^{2.2}$R$^{2.3}$, CH$_2$—NR$^{2.2}$R$^{2.3}$, C$_{5-10}$-cycloalkyl, C$_{5-10}$ heterocycle, C$_{1-6}$-alkyl, phenyl-C$_{1-6}$-alkylene, C$_{5-10}$ heterocycle-C$_{1-6}$-alkylene, C$_{5-6}$-heteroaryl-C$_{1-6}$-alkylene, phenyl SO$_2$—

CH$_3$, SO$_2$—CH$_2$CH$_3$ and SO$_2$—NR$^{2.2}$R$^{2.3}$, which may in turn optionally be substituted by one or more groups selected from among OH, OR$^{2.1}$, oxo, halogen, C$_{1-6}$-alkyl, phenyl and NR$^{2.2}$R$^{2.3}$,
as well as pharmacologically acceptable salts, diastereomers, enantiomers, racemates, hydrates or solvates thereof.

The invention preferably also relates to the above compounds according to formula 1, wherein
R$^2$ is phenyl, which is substituted in at least one of the two meta positions by one or more groups selected from among methyl, F, Cl, OH, OR$^{2.1}$, COOR$^{2.1}$, NH$_2$ and N(CH$_3$)$_2$,
as well as pharmacologically acceptable salts, diastereomers, enantiomers, racemates, hydrates or solvates thereof.

The invention preferably also relates to the above compounds according to formula 1, wherein
R$^2$ is C$_{1-6}$-alkyl, which may optionally be substituted by halogen and which may optionally be substituted by one or more groups selected from among OR$^{2.1}$, COOR$^{2.1}$, CONR$^{2.2}$R$^{2.3}$, SR$^{2.1}$, phenyl, a mono- or bicyclic C$_{5-10}$ heterocycle, C$_{5-6}$-heteroaryl, a mono- or bicyclic C$_{5-10}$-cycloalkyl, CH$_2$—NR$^{2.2}$R$^{2.3}$ and NR$^{2.2}$R$^{2.3}$, which in turn may be substituted by one or more groups selected from among OH, halogen, OR$^{2.1}$, oxo, C$_{1-6}$-alkyl, phenyl, COOR$^{2.1}$, CH$_2$—NR$^{2.2}$R$^{2.3}$ and NR$^{2.2}$R$^{2.3}$,
as well as pharmacologically acceptable salts, diastereomers, enantiomers, racemates, hydrates or solvates thereof.

The invention preferably also relates to the above compounds according to formula 1, wherein
R$^2$ is methyl, ethyl or propyl,
as well as pharmacologically acceptable salts, diastereomers, enantiomers, racemates, hydrates or solvates thereof.

The invention preferably also relates to the above compounds according to formula 1, wherein
R$^2$ is C$_{1-6}$-alkyl, which is optionally substituted by one or more groups selected from among OH, COOR$^{2.1}$, CON(CH$_3$)$_2$, C$_{1-6}$-alkyl, phenyl, cyclopropyl and NR$^{2.2}$R$^{2.3}$, which may in turn optionally be substituted by one or more groups selected from among OH, fluorine, chlorine, bromine, iodine, OR$^{2.1}$, oxo, C$_{1-6}$-alkyl, phenyl, C$_{1-3}$-alkanol, CH$_2$—NR$^{2.2}$R$^{2.3}$ and NR$^{2.2}$R$^{2.3}$,
as well as pharmacologically acceptable salts, diastereomers, enantiomers, racemates, hydrates or solvates thereof.

The invention preferably also relates to the above compounds according to formula 1, wherein
R$^2$ is C$_{1-6}$-alkyl, which is substituted by one or more groups selected from among OH, phenyl, COOR$^{2.1}$, NH$_2$, while the phenyl may in turn optionally be substituted by one or more groups selected from among OH, fluorine, chlorine, bromine, iodine, OR$^{2.1}$, C$_{1-6}$-alkyl, CH$_2$—NH$_2$, CH$_2$(CH$_3$)$_2$, NH$_2$ and N(CH$_3$)$_2$.
as well as pharmacologically acceptable salts, diastereomers, enantiomers, racemates, hydrates or solvates thereof.

The invention preferably also relates to the above compounds according to formula 1, wherein
R$^2$ is a group according to formula 2

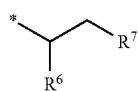

wherein R$^7$ is OH or NH$_2$ and
wherein R$^6$ is a group selected from among C$_{1-6}$-alkyl, C$_{5-10}$-heteroaryl and C$_{6-10}$-aryl, preferably phenyl, which may optionally be substituted by one or more groups selected from among halogen, OH, COOR$^{2.1}$, OR$^{2.1}$, NH$_2$, C$_{1-6}$-alkyl, C$_{1-6}$-haloalkyl and C$_{1-6}$-alkanol,
as well as pharmacologically acceptable salts, diastereomers, enantiomers, racemates, hydrates or solvates thereof.

The invention preferably also relates to the above compounds of formula 1, wherein
R$^2$ is a group according to formula 2

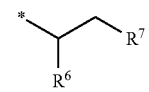

wherein R$^7$ is OH or NH$_2$ is and
R$^6$ is methyl, ethyl, propyl, isopropyl.

The invention preferably also relates to the above compounds of formula 1, wherein
R$^2$ is a monocyclic C$_{3-7}$-cycloalkyl ring which may be substituted in the spiro position by a group selected from among —OH, —CH$_2$OH, —CH$_2$—CH$_2$—OH, branched or unbranched C$_{3-6}$-alkanol, —OR$^{2.1}$, methyl, ethyl, propyl, isopropyl, butyl, isobutyl and halogen, wherein R$^{2.1}$ may be selected from among methyl, ethyl, propyl, isopropyl, butyl, isobutyl.

The invention preferably also relates to the above compounds of formula 1, wherein
R$^2$ denotes a group selected from among monocyclic, saturated three-, four-, five-, six- or seven-membered heterocycle with 1, 2 or 3 heteroatoms in each case selected from among N, O and S, which may optionally be substituted by one or more groups selected from among fluorine, chlorine, bromine, OH, oxo and SH or by one or more groups selected from among OR$^{2.1}$, SR$^{2.1}$, COOR$^{2.1}$, COR$^{2.1}$, C$_{1-6}$-alkanol, C$_{3-10}$-cycloalkyl, phenyl, C$_{1-6}$-alkyl, phenyl-C$_{1-6}$-alkylene, C$_{5-10}$-heteroaryl-C$_{1-6}$-alkylene, C$_{5-10}$ heterocycle, C$_{5-10}$-heteroaryl and NR$^{2.2}$R$^{2.3}$, which may in turn optionally be substituted by one or more groups selected from among OH, OR$^{2.1}$, oxo, halogen, C$_{1-6}$-alkyl, phenyl and NR$^{2.1}$R$^{2.3}$, wherein
R$^{2.1}$ denotes H or a group selected from among C$_{1-6}$-alkyl, Cl$_{1-6}$-alkanol, C$_{1-3}$-haloalkyl, mono- or bicyclic C$_{3-10}$ cycloalkyl, phenyl-C$_{1-6}$-alkylene, mono- or bicyclic C$_{5-10}$-heteroaryl-C$_{1-6}$-alkylene, C$_{3-10}$ heterocycle-C$_{1-6}$-alkylene, C$_{3-7}$-cycloalkyl-C$_{1-6}$-alkylene, phenyl, a mono- or bicyclic C$_{5-10}$-heteroaryl and a monocyclic, saturated or unsaturated, five, six or seven-membered heterocycle with 1, 2 or 3 heteroatoms selected from among N, O and S, which may optionally be substituted by one or more groups selected from among OH, halogen, C$_{1-6}$-alkyl and phenyl,
wherein R$^{2.2}$ and R$^{2.3}$ independently of one another are H or a group selected from among halogen, C$_{1-6}$-alkyl, mono- or bicyclic C$_{3-10}$ cycloalkyl, phenyl-C$_{1-6}$-alkylene, C$_{5-10}$-heteroaryl-C$_{1-6}$-alkylene, phenyl, mono or bicyclic C$_{3-10}$ heterocycle, mono- or bicyclic C$_{5-10}$-heteroaryl, CO—NH$_2$, CO—NHCH$_3$, CO—N(CH$_3$)$_2$, SO$_2$(C$_1$-C$_2$-alkyl), CO—R$^{2.1}$ and COOR$^{2.1}$, which may optionally be substituted by one or more groups selected from among OH, halogen, C$_{1-6}$-alkyl, phenyl and COOR$^{2.1}$.

The invention preferably also relates to the above compounds according to formula 1, wherein
R$^3$ denotes fluorine, chlorine, bromine, iodine or CN,
as well as pharmacologically acceptable salts, diastereomers, enantiomers, racemates, hydrates or solvates thereof.

The invention preferably also relates to the above compounds according to formula 1, wherein
$R^3$ denotes the group —CO—NR$^{3.1}$R$^{3.2}$,
wherein R$^{3.1}$ and R$^{3.2}$ independently of one another are H or groups selected from among C$_{1-6}$-alkyl, C$_{2-6}$-alkenyl, C$_{2-6}$-alkynyl, C$_{6-10}$-aryl; C$_{6-10}$-aryl-C$_{1-6}$-alkylene, C$_{5-10}$-heteroaryl-C$_{1-6}$-alkylene, C$_{5-10}$-heteroaryl-C$_{1-6}$-alkynylene, C$_{5-10}$-heteroaryl-C$_{1-6}$-alkenylene, mono- or bicyclic, C$_{5-10}$ heterocycle, C$_{5-10}$ heterocycle-C$_{1-6}$-alkylene and mono- or bicyclic C$_{5-10}$-heteroaryl, while the group in each case may optionally be substituted by one or more groups selected from among OH, oxo, halogen, C$_{1-6}$-alkyl and O—C$_{1-6}$-alkyl,
as well as pharmacologically acceptable salts, diastereomers, enantiomers, racemates, hydrates or solvates thereof.

The invention preferably also relates to the above compounds according to formula 1, wherein
$R^3$ denotes the group —CO—NR$^{3.1}$R$^{3.2}$,
wherein
R$^{3.1}$ is hydrogen or methyl
and
R$^{3.2}$ denotes a group selected from among C$_{1-6}$-alkyl, C$_{2-6}$-alkenyl C$_{2-6}$-alkynyl, C$_{6-10}$-aryl; C$_{6-10}$-aryl-C$_{1-6}$-alkylene, C$_{5-10}$-heteroaryl-C$_{1-6}$-alkylene, C$_{5-10}$-heteroaryl-C$_{1-6}$-alkynylene, C$_{5-10}$-heteroaryl-C$_{1-6}$-alkenylene, mono- or bicyclic, C$_{5-10}$ heterocycle, C$_{5-10}$ heterocycle-C$_{1-6}$-alkylene and mono- or bicyclic C$_{5-10}$-heteroaryl, while the group in each case may optionally be substituted by one or more groups selected from among OH, oxo, halogen, C$_{1-6}$-alkyl and O—C$_{1-6}$-alkyl,
as well as pharmacologically acceptable salts, diastereomers, enantiomers, racemates, hydrates or solvates thereof.

The invention preferably also relates to the above compounds according to formula 1, wherein
$R^3$ denotes the group —CO—NR$^{3.1}$R$^{3.2}$,
wherein R$^{3.1}$ and R$^{3.2}$ independently of one another are H or groups selected from among C$_{1-6}$-alkyl, phenyl; phenyl-C$_{1-6}$-alkylene, C$_{5-6}$-heteroaryl-C$_{1-6}$-alkylene, C$_{5-6}$-heteroaryl-C$_{1-6}$-alkynylene, C$_{5-6}$-heteroaryl-C$_{1-6}$-alkenylene, mono- or bicyclic, C$_{5-10}$ heterocycle, C$_{5-10}$ heterocycle-C$_{1-6}$-alkylene and mono- or bicyclic C$_{5-10}$-heteroaryl, while the group may in each case optionally be substituted by one or more groups selected from among OH, oxo, halogen, C$_{1-6}$-alkyl and O—C$_{1-6}$-alkyl
as well as pharmacologically acceptable salts, diastereomers, enantiomers, racemates, hydrates or solvates thereof.

The invention preferably also relates to the above compounds according to formula 1, wherein
$R^3$ denotes the group —NR$^{3.3}$—CO—R$^{3.4}$,
wherein R$^{3.3}$ is H or a group selected from among C$_{1-6}$-alkyl, C$_{2-6}$-alkenyl, C$_{2-6}$-alkynyl, C$_{6-10}$-aryl; C$_{6-10}$-aryl-C$_{1-6}$-alkylene, C$_{5-10}$-heteroaryl-C$_{1-6}$-alkylene, C$_{3-10}$ heterocycle and einem C$_{5-10}$-heteroaryl is, which may optionally be substituted by one or more groups ausgewählt aus der group bestchend aus OH, OR$^{2.1}$, oxo, NH$_2$, NR$^{2.2}$R$^{2.3}$, halogen, C$_{1-6}$-alkyl and C$_{6-10}$-aryl may be substituted, and
wherein R$^{3.4}$ is H or a group selected from among C$_{1-6}$-alkyl, C$_{2-6}$-alkenyl, C$_{2-6}$-alkynyl, C$_{1-6}$-alkanol, OR$^{2.1}$, CH$_2$—O—CO—C$_{1-6}$-alkyl, CH$_2$NR$^{2.2}$R$^{2.3}$, NR$^{2.2}$R$^{2.3}$, C$_{6-10}$-aryl; C$_{6-10}$-aryl-C$_{1-6}$-alkylene, C$_{5-10}$-heteroaryl-C$_{1-6}$-alkylene, mono- or bicyclic, saturated or unsaturated C$_{3-10}$-heterocycle with 1, 2 or 3 heteroatoms selected from among O, S and N and a mono- or bicyclic C$_{5-10}$-heteroaryl with 1, 2 or 3 heteroatoms selected from among O, S and N, which may optionally be substituted by one or more groups selected from among OH, OR$^{2.1}$, oxo, NH$_2$, NR$^{2.2}$R$^{2.3}$, halogen, C$_{1-6}$-alkyl and C$_{6-10}$-aryl,
as well as pharmacologically acceptable salts, diastereomers, enantiomers, racemates, hydrates or solvates thereof.

The invention preferably also relates to the above compounds according to formula 1, wherein
$R^3$ denotes the group —NR$^{3.3}$—CO—R$^{3.4}$,
wherein R$^{3.3}$ is hydrogen or methyl
and
wherein R$^{3.4}$ denotes a group selected from among C$_{1-6}$-alkyl, C$_{2-6}$-alkenyl, C$_{2-6}$-alkynyl, C$_{1-6}$-alkanol, OR$^{2.1}$, CH$_2$—O—CO—C$_{1-6}$-alkyl, CH$_2$NR$^{2.2}$R$^{2.3}$, NR$^{2.2}$R$^{2.3}$, C$_{1-10}$-aryl; C$_{6-10}$-aryl-C$_{1-6}$-alkylene, C$_{5-10}$-heteroaryl-C$_{1-6}$-alkylene, mono- or bicyclic, saturated or unsaturated C$_{3-10}$-heterocycle with 1, 2 or 3 heteroatoms selected from among N; S and O and a mono- or bicyclic C$_{5-10}$-heteroaryl with 1, 2 or 3 heteroatoms selected from among N; S and O, which may optionally be substituted by one or more groups selected from among OH, OR$^{2.1}$, oxo, NH$_2$, NR$^{2.2}$R$^{2.3}$, halogen, C$_{1-6}$-alkyl and C$_{6-10}$-aryl,
as well as pharmacologically acceptable salts, diastereomers, enantiomers, racemates, hydrates or solvates thereof.

The invention preferably also relates to the above compounds according to formula 1, wherein
$R^3$ denotes the group —NR$^{3.3}$—CO—R$^{3.4}$,
wherein R$^{3.3}$ is H or a group selected from among C$_{1-6}$-allyl, phenyl; phenyl-C$_{1-6}$-alkylene, C$_{5-10}$-heteroaryl-C$_{1-6}$-alkylene, C$_{5-10}$-heterocycle and a C$_{5-10}$-heteroaryl, which may optionally be substituted by one or more groups selected from among OH, OR$^{2.1}$, oxo, NH$_2$, N(CH$_3$)$_2$, halogen, C$_{1-6}$-alkyl and phenyl, and
wherein R$^{3.4}$ is H or a group selected from among C$_{1-6}$-alkyl, C$_{1-6}$-alkanol, OR$^{2.1}$, CH$_2$—O—CO—C$_{1-6}$-alkyl, CH$_2$—NH$_2$, CH$_2$—N(CH$_3$)$_2$, NH$_2$, N(CH$_3$)$_2$, phenyl; phenyl-C$_{1-6}$-alkylene, C$_{5-10}$-heteroaryl-C$_{1-6}$-alkylene, mono- or bicyclic, saturated or unsaturated C$_{5-10}$ heterocycle with 1, 2 or 3 heteroatoms selected from among N; S and O and a mono- or bicyclic C$_{5-10}$-heteroaryl with 1, 2 or 3 heteroatoms selected from among N; S and O, which may optionally be substituted by one or more groups selected from among OH, OR$^{2.1}$, oxo, NH$_2$, N(CH$_3$)$_2$, halogen, C$_{1-6}$-alkyl and phenyl,
as well as pharmacologically acceptable salts, diastereomers, enantiomers, racemates, hydrates or solvates thereof.

The invention preferably also relates to the above compounds according to formula 1, wherein
$R^1$ is H
and
$R^2$ is selected from among H, methyl, ethyl, propyl,

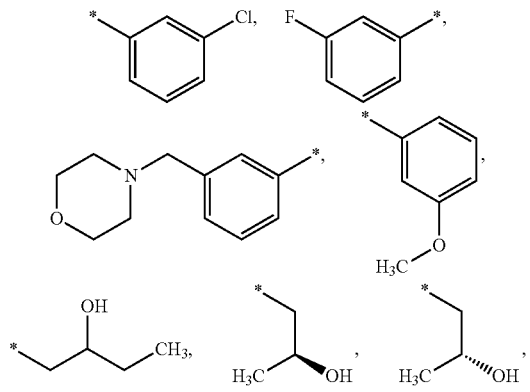

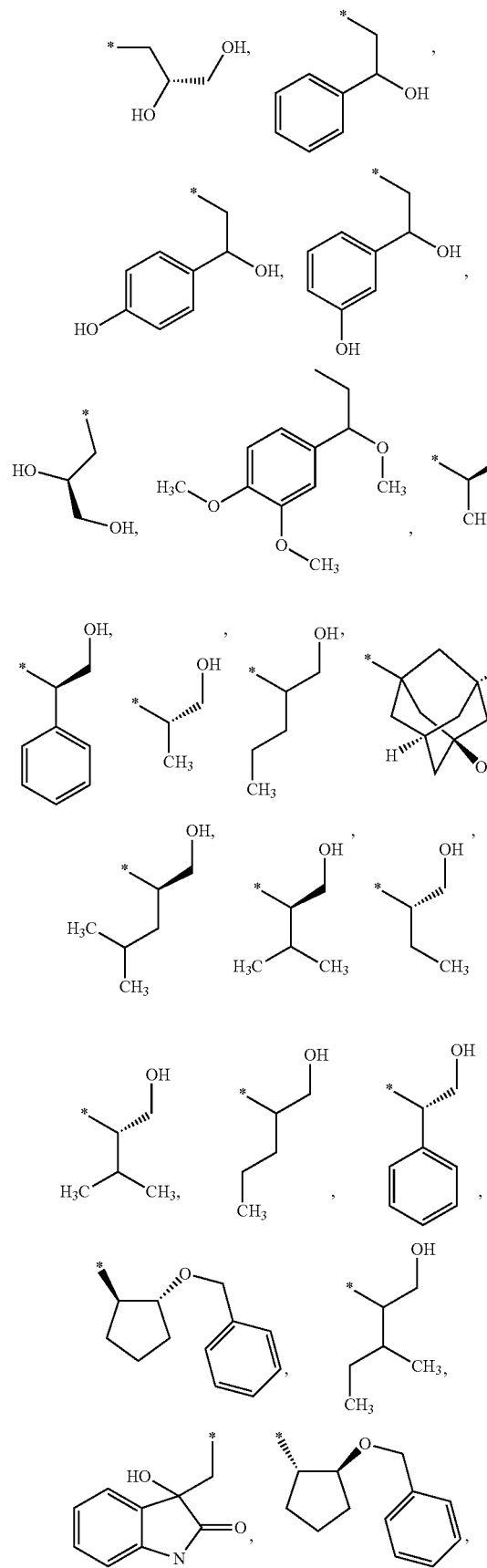
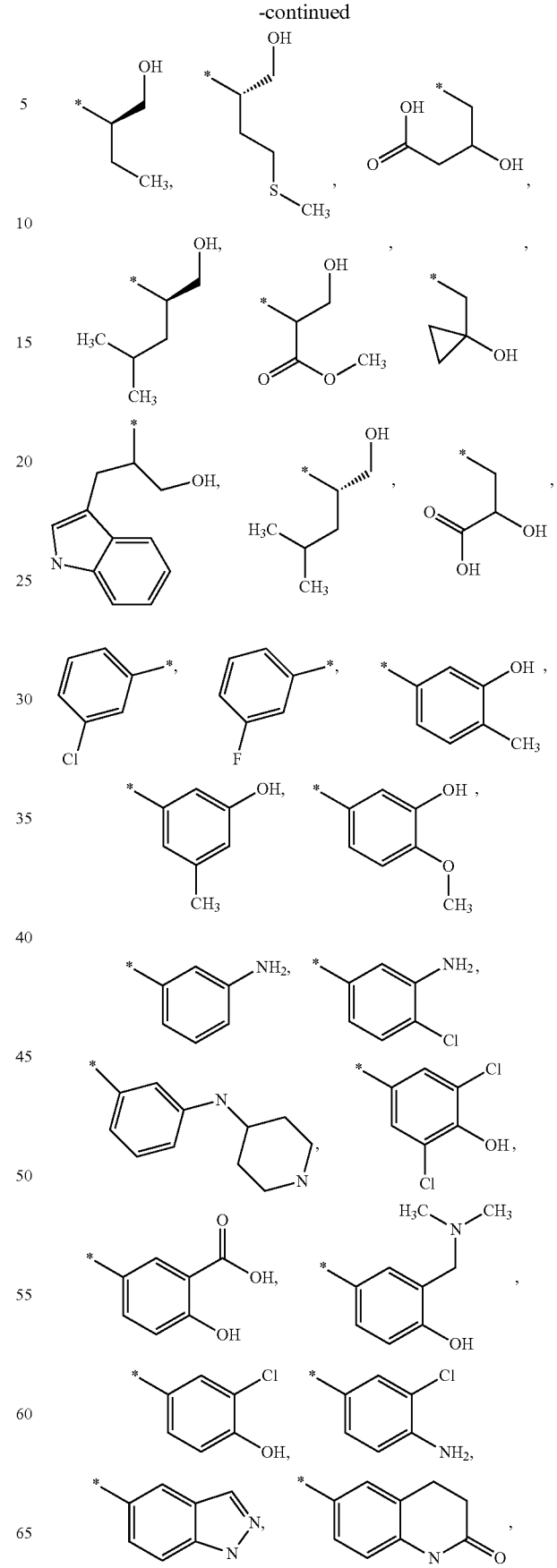

-continued
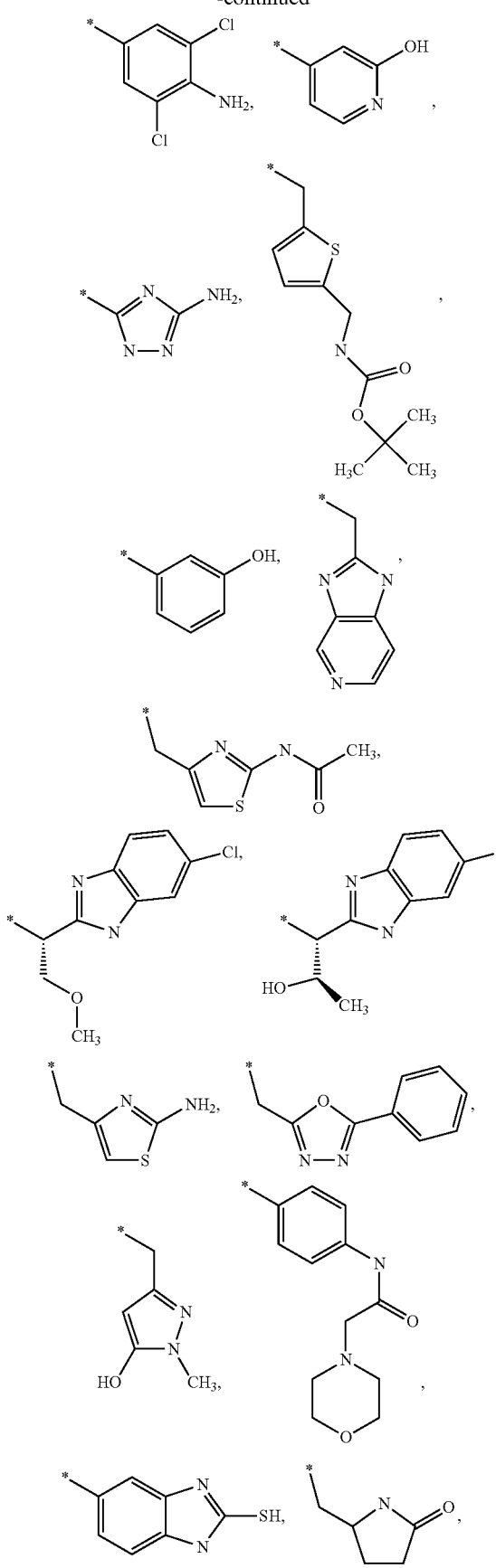
-continued
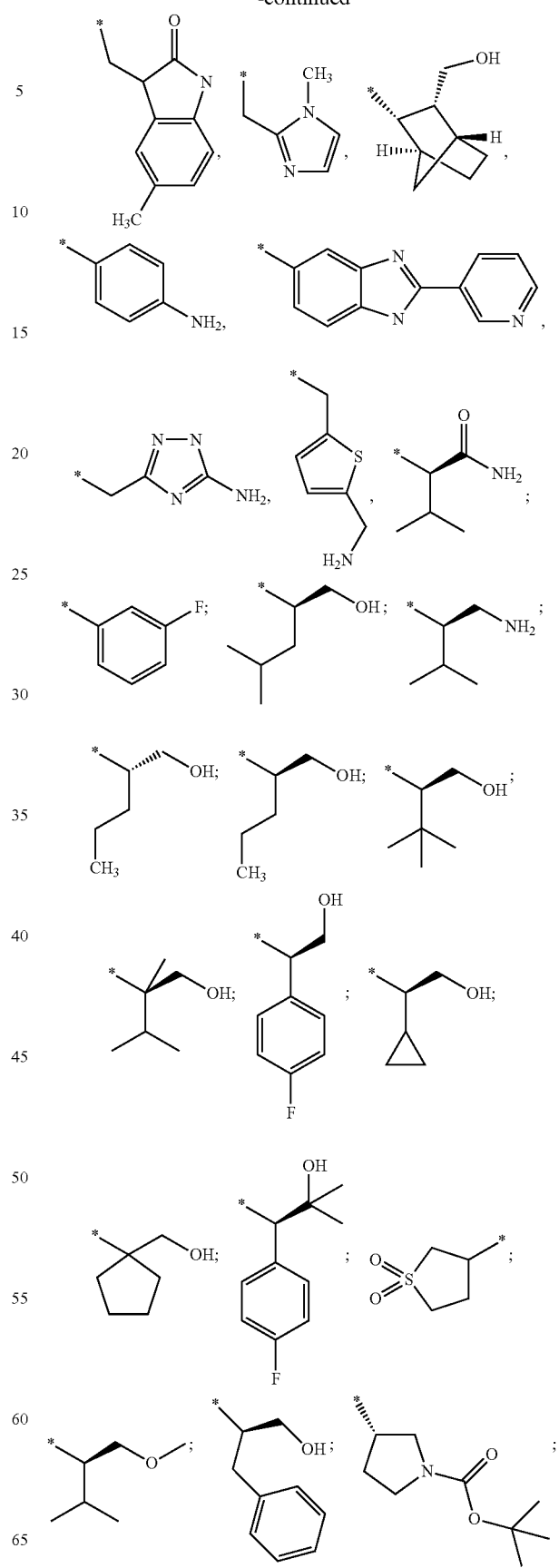

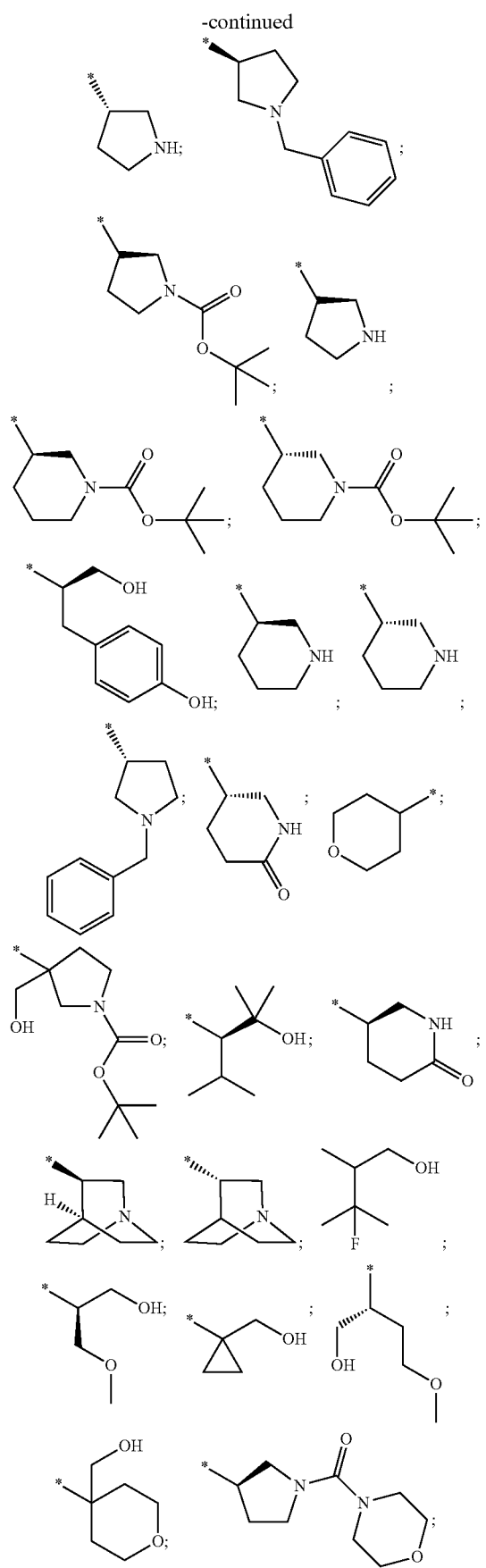
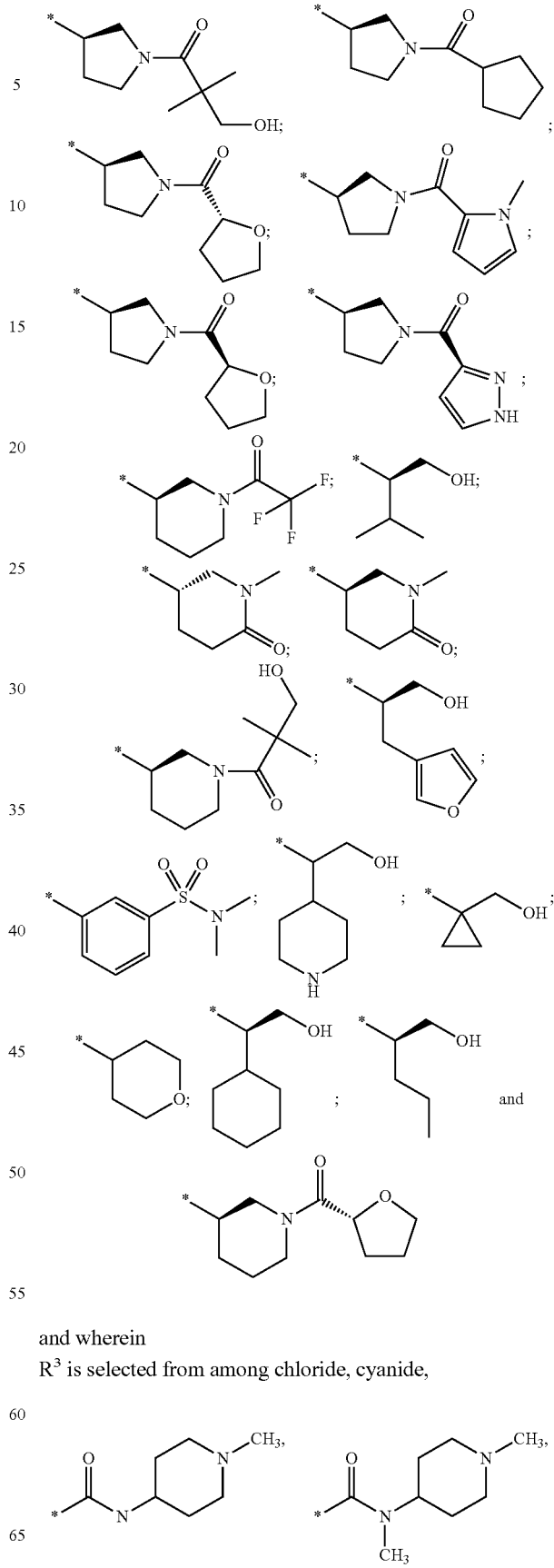
and wherein
R[3] is selected from among chloride, cyanide, -continued
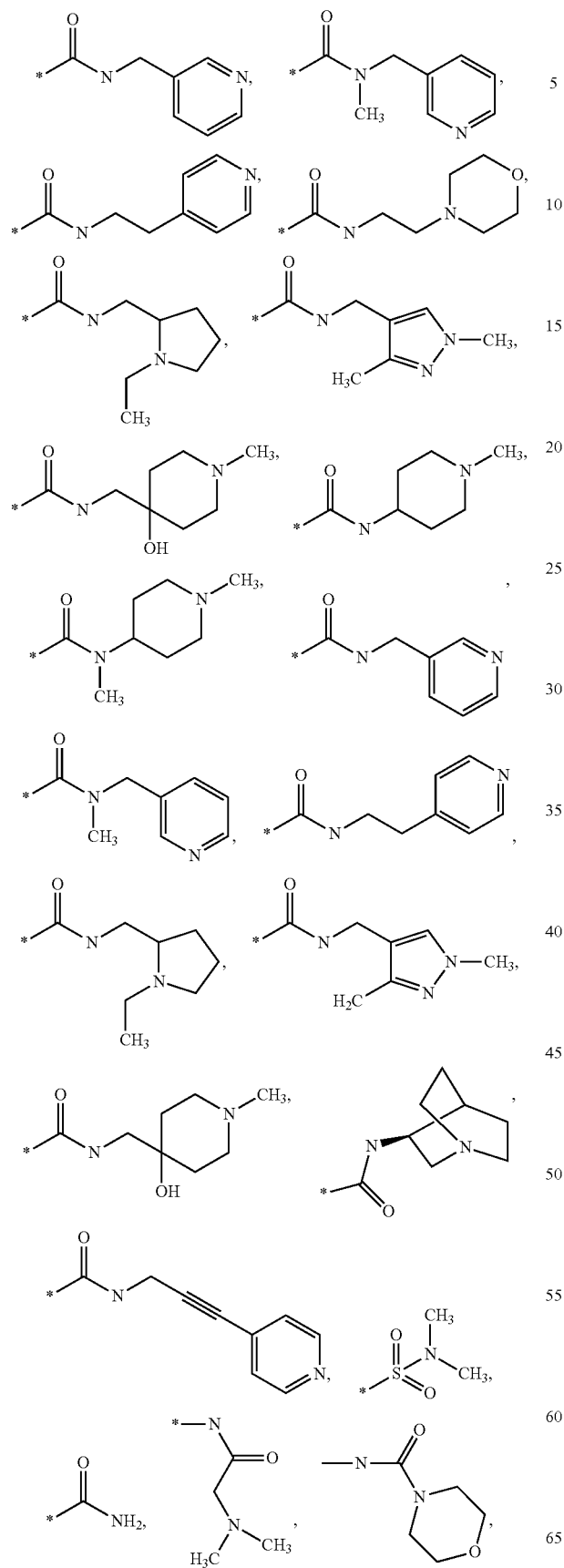
-continued
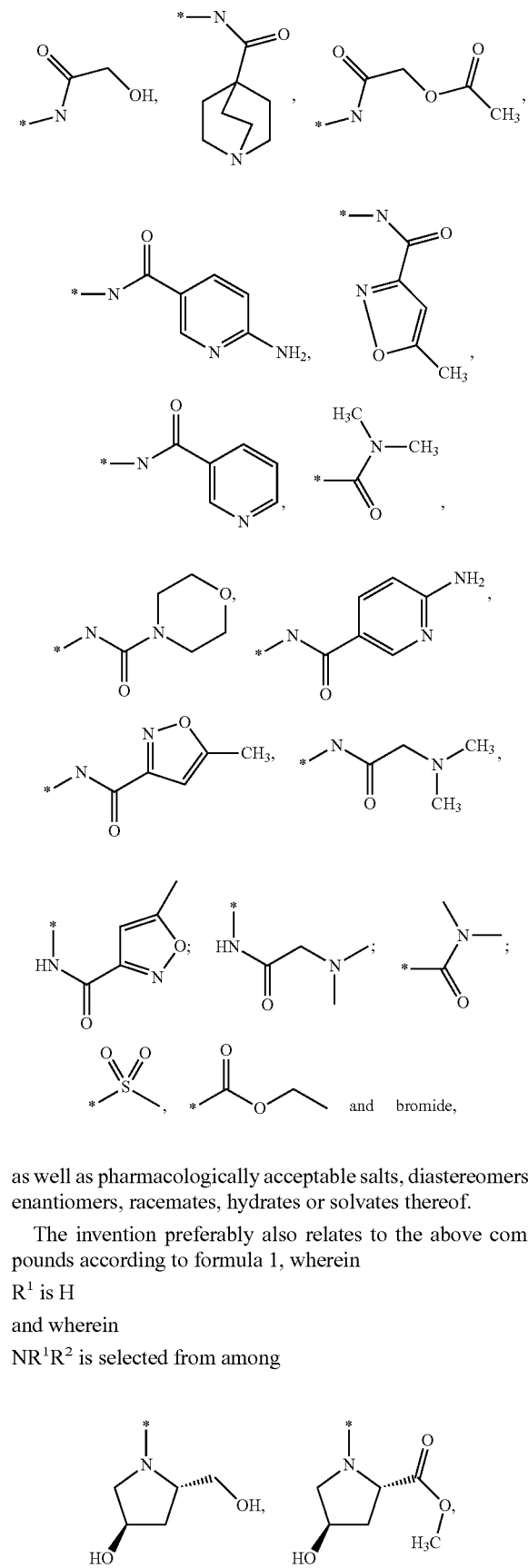
as well as pharmacologically acceptable salts, diastereomers, enantiomers, racemates, hydrates or solvates thereof.
The invention preferably also relates to the above compounds according to formula 1, wherein
$R^1$ is H
and wherein
$NR^1R^2$ is selected from among
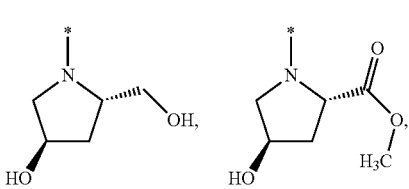

-continued
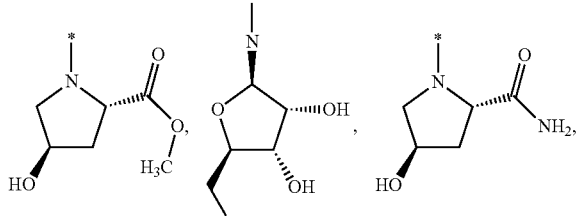
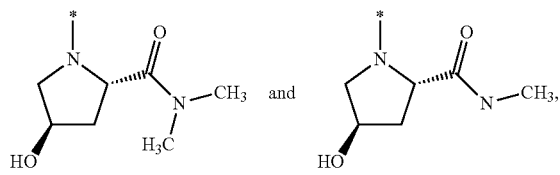
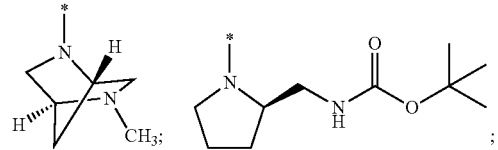
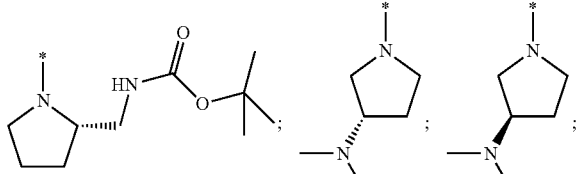
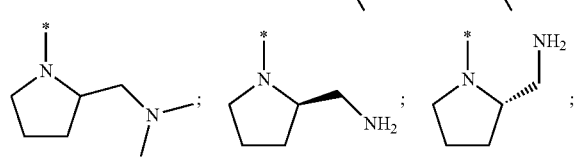
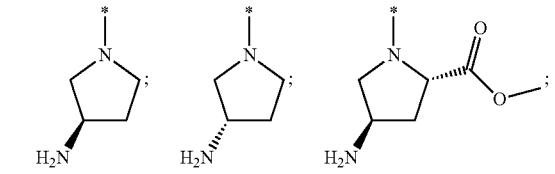
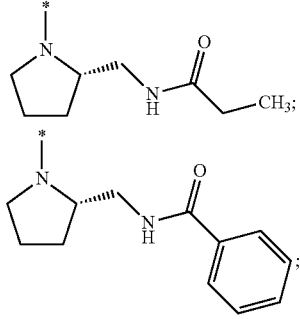
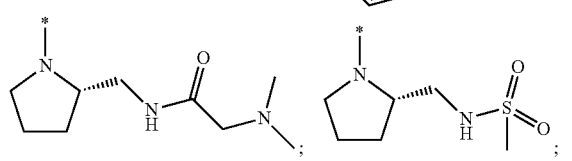
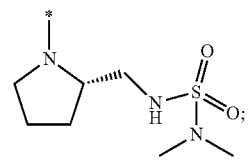
-continued
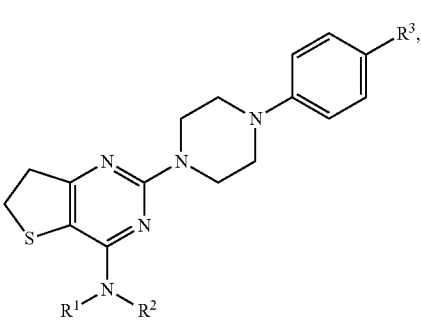
and wherein
$R^3$ is fluoride, chloride, bromide, nitrile or hydroxy,
as well as pharmacologically acceptable salts, diastereomers, enantiomers, racemates, hydrates or solvates thereof.
The invention further relates to intermediate products of synthesis scheme 1 of formula
3 wherein $R^1$, $R^2$ and $R^3$ are defined as hereinbefore described,
as well as pharmacologically acceptable salts, diastereomers, enantiomers, racemates, hydrates or solvates thereof.

The invention further relates to intermediate products of synthesis scheme 2 of formula 4

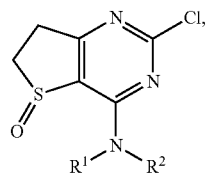

wherein $R^1$ and $R^2$ are as hereinbefore defined,
as well as pharmacologically acceptable salts, diastereomers, enantiomers, racemates, hydrates or solvates thereof.

The invention further relates to intermediate products of synthesis scheme 3 of formula 5

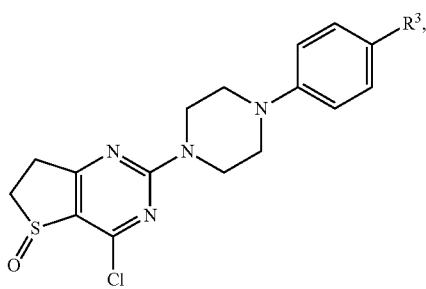

wherein $R^3$ is as hereinbefore defined,
as well as pharmacologically acceptable salts, diastereomers, enantiomers, racemates, hydrates or solvates thereof.

The invention further relates to intermediate products of synthesis scheme 4 of formula 6

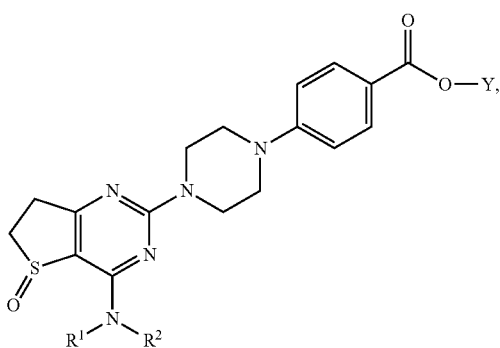

wherein $R^1$ and $R^2$ are as hereinbefore defined and wherein Y denotes H, methyl or ethyl,
as well as pharmacologically acceptable salts, diastereomers, enantiomers, racemates, hydrates or solvates thereof.

The invention further relates to intermediate products of synthesis scheme 5 of formula

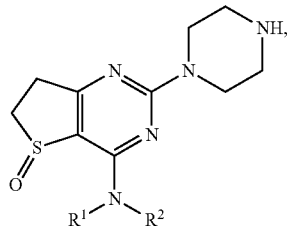

wherein $R^1$ and $R^2$ are as hereinbefore defined,
as well as pharmacologically acceptable salts, diastereomers, enantiomers, racemates, hydrates or solvates thereof.

The invention further relates to intermediate products of synthesis scheme 6 of formula

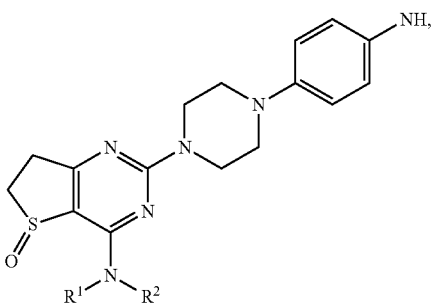

wherein $R^1$ and $R^2$ are as hereinbefore defined,
as well as pharmacologically acceptable salts, diastereomers, enantiomers, racemates, hydrates or solvates thereof.

The invention further relates to the above compounds of formula 1 as pharmaceutical compositions.

The invention further relates to the use of the above compounds according to formula 1 for preparing a medicament for the treatment of diseases that can be treated by inhibiting the PDE4 enzyme.

The invention further relates to the use of the above compounds according to formula 1 for preparing a medicament for the treatment of respiratory or gastrointestinal complaints or diseases, as well as inflammatory diseases of the joints, skin or eyes, cancers, and diseases of the peripheral or central nervous system.

The invention further relates to the use of the above compounds according to formula 1 for preparing a medicament for the prevention and treatment of respiratory or pulmonary diseases which are accompanied by increased mucus production, inflammations and/or obstructive diseases of the respiratory tract.

The invention further relates to the use of the above compounds according to formula 1 for preparing a medicament for the treatment of inflammatory and obstructive diseases such as COPD, chronic sinusitis, asthma, Crohn's disease, ulcerative colitis.

The invention further relates to the use of the above compounds according to formula 1 for preparing a medicament for the treatment of inflammatory diseases of the gastrointestinal tract.

The invention further relates to the use of the above compounds according to formula 1 for preparing a medicament for the prevention and treatment of diseases of the peripheral or central nervous system such as depression, bipolar or manic depression, acute and chronic anxiety states, schizophrenia, Alzheimer's disease, Parkinson's disease, acute and chronic multiple sclerosis or acute and chronic pain as well as brain injury caused by stroke, hypoxia or cerebro-cranial trauma.

The invention further relates to pharmaceutical formulations which contain one or more of the above compounds according to formula 1.

TERMS AND DEFINITIONS USED

Unless otherwise stated, all the substituents are independent of one another. If for example there might be a plurality of $C_{1-6}$alkyl groups as substituents in one group, in the case of three substituents $C_{1-6}$-alkyl, one may represent methyl, one n-propyl and one tert-butyl.

Within the scope of this application, in the definition of possible substituents, these may also be represented in the form of a structural formula. An asterisk (*) in the structural formula of the substituent is to be understood as being the linking point to the rest of the molecule. Moreover, the atom of the substituent which follows the linking point is referred to as the atom in position number 1. Thus for example the groups N-piperidinyl (I), 4-piperidinyl (II), 2-tolyl (III), 3-tolyl (IV) and 4-tolyl (V) are shown as follows:

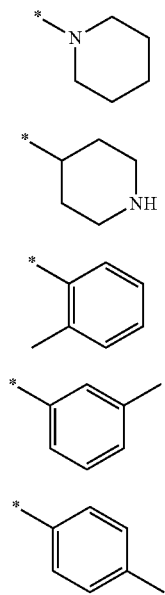

If there is no asterisk (*) in the structural formula of the substituent, each hydrogen atom may be removed at the substituent of each hydrogen atom and the valency thus freed may serve as a binding site to the rest of a molecule. Thus, for example, VI may represent 2-tolyl, 3-tolyl, 4-tolyl and benzyl.

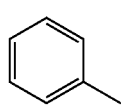

By the term "$C_{1-10}$-alkyl" (including those which are part of other groups) are meant branched and unbranched alkyl groups with 1 to 10 carbon atoms, by the term "$C_{1-6}$-alkyl" are meant accordingly branched and unbranched alkyl groups with 1 to 6 carbon atoms. "$C_{1-4}$-alkyl" accordingly denotes branched and unbranched alkyl groups with 1 to 4 carbon atoms. Alkyl groups with 1 to 4 carbon atoms are preferred. Examples include: methyl, ethyl, n-propyl, iso-propyl, n-butyl, iso-butyl, sec-butyl, tert-butyl, n-pentyl, iso-pentyl, neopentyl or hexyl. Optionally the abbreviations Me, Et, n-Pr, i-Pr, n-Bu, i-Bu, t-Bu, etc. may also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant a branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

If the carbon chain is to be substituted by a group which together with one or two carbon atoms of the alkylene chain forms a carbocyclic ring with 3, 5 or 6 carbon atoms, this includes, inter alia, the following examples of the rings:

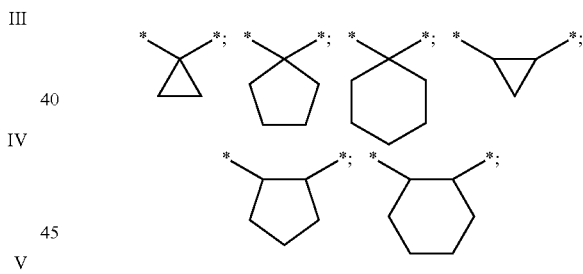

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1,2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Alkynylene groups with 2 to 4 carbon atoms are preferred. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

By the term "aryl" (including those which are part of other groups) are meant aromatic ring systems with 6 to 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms which are substituted by an aromatic ring system with 6 or 10 carbon atoms. Examples include: benzyl, 1- or 2-phenylethyl or 1- or 2-naphthylethyl. Unless otherwise stated, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—although already included under "aryl-$C_{1-6}$-alkylene"—branched and unbranched alkylene groups with 1 to 6 carbon atoms, which are substituted by a heteroaryl.

A heteroaryl of this kind includes five or six-membered heterocyclic aromatic groups or 5-10 membered, bicyclic heteroaryl rings which may contain one, two or three heteroatoms, selected from among oxygen, sulphur and nitrogen and sufficient conjugated double bonds to form an aromatic system. The following are examples of five- or six-membered heterocyclic aromatic groups:

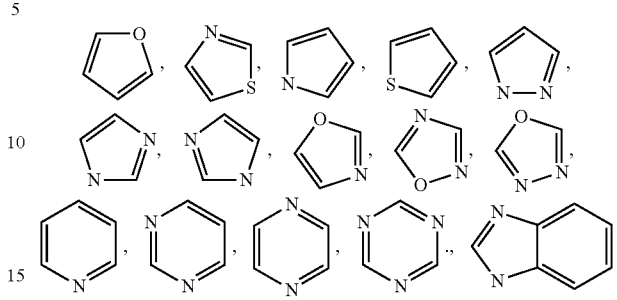

Unless stated otherwise, these heteroaryls may be substituted by one or more groups selected from among methyl, ethyl, iso-propyl, tert-butyl, hydroxy, fluorine, chlorine, bromine and iodine.

The following are examples of the heteroaryl-$C_{1-6}$-alkylenes:

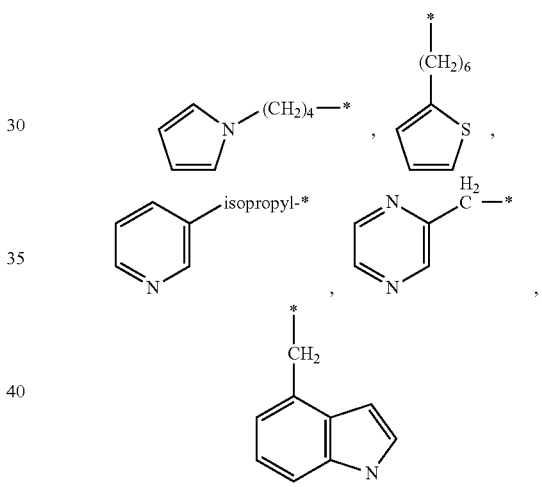

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "$C_{3-7}$-cycloalkyl" (including those which are part of other groups) are meant cyclic alkyl groups with 3 to 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{3-10}$-cycloalkyl" are meant, in addition, monocyclic alkyl groups with 3 to 7 carbon atoms and also bicyclic alkyl groups with 7 to 10 carbon atoms or also monocyclic alkyl groups which are bridged by at least one $C_{1-3}$-carbon bridge.

By the term "heterocyclic rings" or also "heterocycles" are meant five-, six- or seven-membered, saturated or unsaturated heterocyclic rings which may contain one, two or three heteroatoms, selected from among oxygen, sulphur and nitrogen, while at the same time the ring may be linked to the molecule through a carbon atom or, if available, through a nitrogen atom. Although included under the term "heterocyclic rings" or "heterocycle", the term "heterocyclic non-aromatic rings" defines five-, six- or seven-membered unsaturated rings. Examples include:

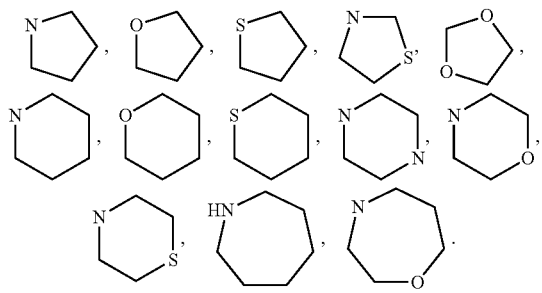

Although included within the term "heterocyclic rings" or "heterocycle", the term "heterocyclic, aromatic rings" or "heteroaryl" defines five- or six-membered heterocyclic aromatic groups or 5-10 membered, bicyclic heteroaryl rings which may contain one, two, three or four heteroatoms, selected from among oxygen, sulphur and nitrogen, and sufficient conjugated double bonds to form an aromatic system. The following are examples of five- or six-membered heterocyclic aromatic groups:

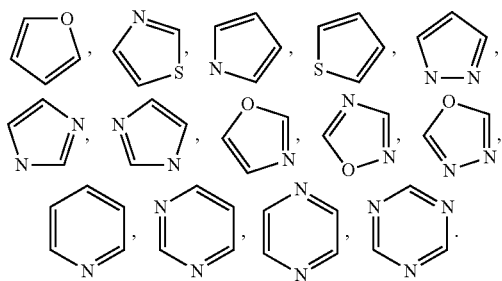

Unless otherwise mentioned, a heterocyclic ring (or "heterocycle") may be provided with a keto group. The following are examples of this.

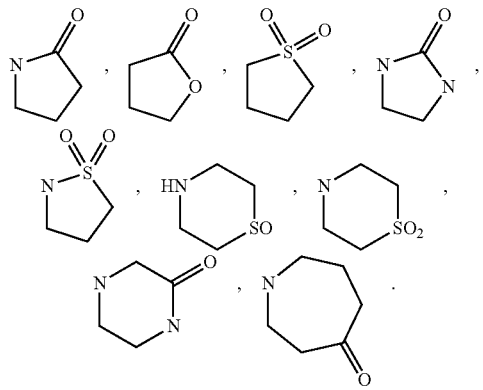

Although already included under "cycloalkyl", the term "bicyclic cycloalkyls" generally denotes eight-, nine- or ten-membered bicyclic carbon rings. The following are mentioned by way of example:

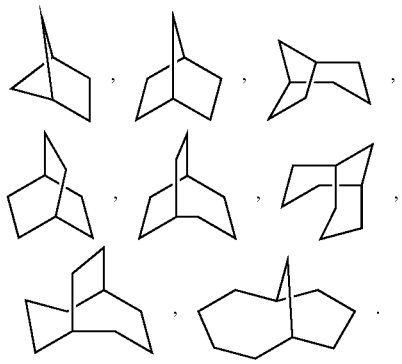

Although already included under "heterocycle", the term "bicyclic heterocycles" generally denotes eight-, nine- or ten-membered bicyclic rings which may contain one or more heteroatoms, preferably 1-4, more preferably 1-3, still more preferably 1-2, particularly one heteroatom, selected from among oxygen, sulphur and nitrogen. At the same time the ring may be linked to the molecule through a carbon atom of the ring or, if available, through a nitrogen atom of the ring. The following are mentioned by way of example:

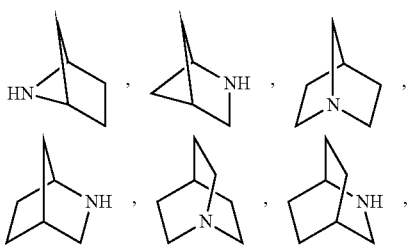

Although already included under "aryl", by a "bicyclic aryl" is meant a 5-10 membered, bicyclic aryl ring which contains sufficient conjugated double bonds to form an aromatic system. One example of a bicyclic aryl is naphthyl.

Although already included under "heteroaryl", by a "bicyclic heteroaryl" is meant a 5-10 membered, bicyclic heteroaryl ring which may contain one, two, three or four heteroatoms, selected from among oxygen, sulphur and nitrogen, and contains sufficient conjugated double bonds to form an aromatic system.

Although included by the term "bicyclic cycloalkyls" or "bicyclic aryl", the term "condensed cycloalkyl" or "condensed aryl" defines bicyclic rings, wherein the bridge separating the rings denotes a direct single bond. The following are mentioned as examples of a condensed bicyclic cycloalkyl:

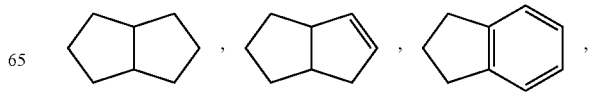

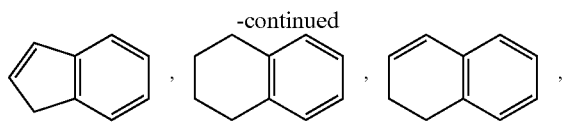

Although included by the term "bicyclic heterocycles" or "bicyclic heteroaryls", the term "condensed, bicyclic heterocycles" or "condensed, bicyclic heteroaryls" defines bicyclic 5-10 membered heterorings which contain one, two or three heteroatoms, selected from among oxygen, sulphur and nitrogen and wherein the bridge separating the rings denotes a direct single bond. The "condensed bicyclic heteroaryls" also contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

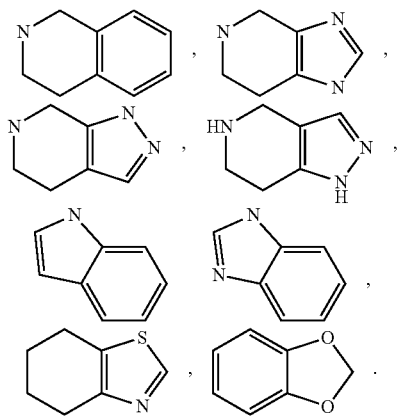

By the term "heterocyclic spiro rings" (spiro) are meant 5-10 membered, spirocyclic rings so which may optionally contain one, two or three heteroatoms, selected from among oxygen, sulphur and nitrogen, while at the same time the ring may be linked to the molecule through a carbon atom or if available through a nitrogen atom. Unless otherwise mentioned, a spirocyclic ring may be provided with an oxo, methyl or ethyl group. Examples of this include:

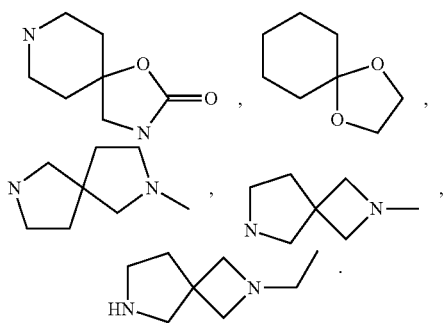

"Halogen" within the scope of the present invention denotes fluorine, chlorine, bromine or iodine. Unless stated to the contrary, fluorine, chlorine and bromine are regarded as preferred halogens.

Compounds of general formula 1 may have acid groups, chiefly carboxyl groups, and/or basic groups such as e.g. amino functions. Compounds of general formula 1 may therefore occur as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali or alkaline earth metal hydroxides or carbonates, zinc or ammonium hydroxides or organic amines such as e.g. diethylamine, triethylamine, triethanolamine inter alia.

As mentioned hereinbefore, the compounds of formula 1 may be converted into the salts thereof, particularly for pharmaceutical use, into the physiologically and pharmacologically acceptable salts thereof. These salts may on the one hand be in the form of the physiologically and pharmacologically acceptable acid addition salts of the compounds of formula 1 with inorganic or organic acids. On the other hand, if R is hydrogen, the compound of formula 1 may also be converted by reaction with inorganic bases into physiologically and pharmacologically acceptable salts with alkali or alkaline earth metal cations as counter ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. The alkali and alkaline earth metal salts of the compound of formula 1 are preferably prepared using the alkali and alkaline earth metal hydroxides and hydrides thereof, of which the hydroxides and hydrides of the alkaline earth metals, particularly of sodium and potassium, are preferred and sodium and potassium hydroxide are particularly preferred.

If desired, the compounds of general formula (1) may be converted into the salts thereof, particularly, for pharmaceutical use, into the pharmacologically acceptable acid addition salts with an inorganic or organic acid. Suitable acids include for example succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds in question, optionally in the form of the individual optical isomers, mixtures of the individual enantiomers or racemates, in the form of the tautomers as well as in the form of the free bases or the corresponding acid addition salts is with pharmacologically acceptable acids—such as for example acid addition salts with hydrohalic acids—for example hydrochloric or hydrobromic acid or organic acids—such as for example oxalic, fumaric, diglycolic or methanesulphonic acid.

The compounds according to the invention may optionally occur as racemates, but they may also be obtained as pure enantiomers, i.e. in the (R) or (S) form. Preferred compounds are those which occur as racemates or as the (S) form.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

Methods of Synthesis

Synthesis schemes 1, 2, 3, 4, 5 and 6 for preparing the Examples listed in Table I are explained hereinafter.

SCHEME 1

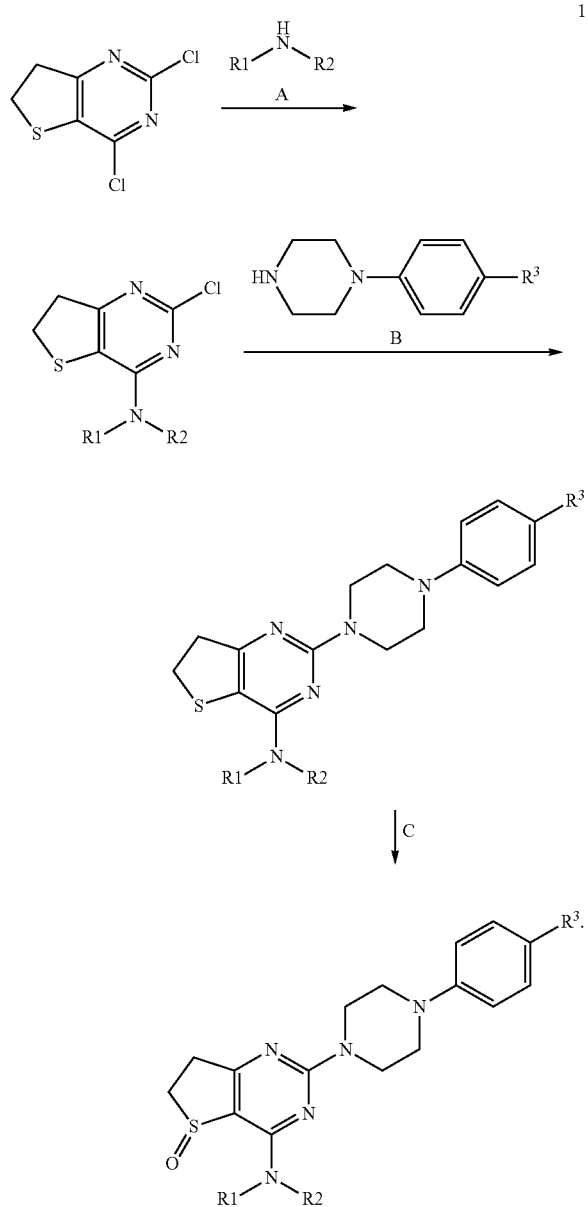

1.1 Synthesis of {2-[4-(4-chloro-phenyl)-piperazin-1-yl]-5-oxo-6,7-dihydro-5H-5λ⁴-thieno[3,2-d]pyrimidin-4-yl}-(3-morpholin-4-ylmethyl-phenyl)-amine, Example 21 (See Scheme 1)

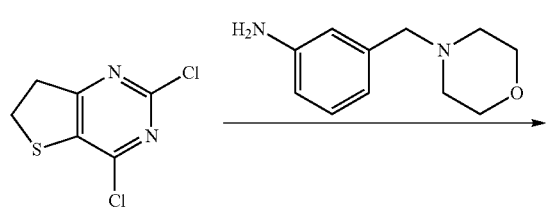

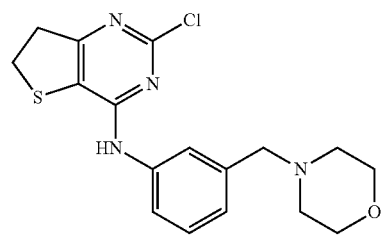

1.1.1 (2-chloro-6,7-dihydro-thieno[3,2-d]pyrimidin-4-yl)-(3-morpholin-4-ylmethyl-phenyl)-amine (Scheme 1, Step A)

1.25 g 2,4-dichloro-6,7-dihydro-thieno[3,2-d]pyrimidine are placed in 5 ml dimethylformamide, first 1.05 ml diisopropylethylamine, then 0.960 g 3-morpholin-4-ylmethyl-phenylamine (*J. Med. Chem.* 1990, 33, 327) are added. The reaction mixture is sf 20 hours at 60° C., then after cooling evaporated down. The residue is extracted with dichloromethane and water, the organic phase is dried and evaporated to dryness. The residue is crystallised with petroleum ether/ethyl acetate. 1.28 g of the product are obtained as a powder.

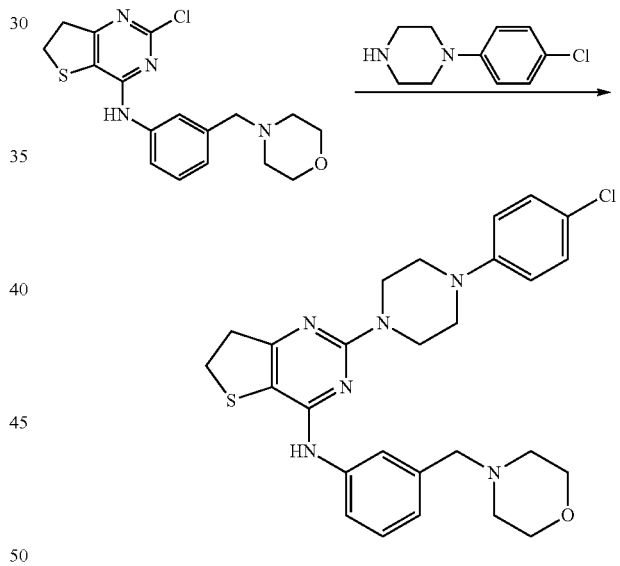

1.1.2 {2-[4-(4-chloro-phenyl)-piperazin-1-yl]-6,7-dihydro-thieno[3,2-d]pyrimidin-4-yl}-(3-morpholin-4-ylmethyl-phenyl)-amine (Scheme 1, Step B)

1.09 g (2-chloro-6,7-dihydro-thieno[3,2-d]pyrimidin-4-yl)-(3-morpholin-4-ylmethyl-phenyl)-amine, 1.77 g 1-(4-chloro-phenyl)-piperazine and 1.03 ml diisopropylethylamine are placed in 12 ml dioxane, then heated in the microwave for 1 hour at 160° C. Then water is added and the mixture is extracted with dichloromethane. The organic phase is separated off using a phase transfer cartridge and evaporated to dryness. The residue is crystallised with methanol. 1.17 g of the product are obtained as a powder (m.p 177°-178° C.).

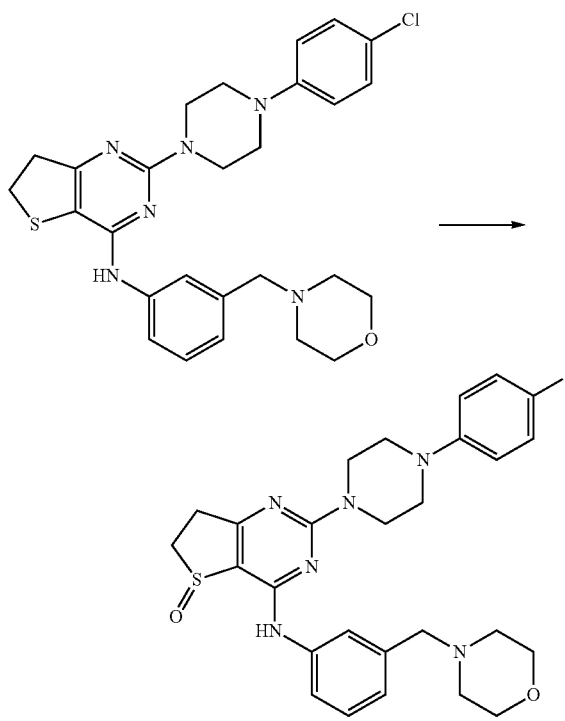

1.1.3 {2-[4-(4-chloro-phenyl)-piperazin-1-yl]-5-oxo-6,7-dihydro-5H-5λ⁴-thieno[3,2-d]pyrimidin-4-yl}-(3-morpholin-ylmethyl-phenyl)-amine (Scheme 1, Step C)

313.80 mg {2-[4-(4-chloro-phenyl)-piperazin-1-yl]-6,7-dihydro-thieno[3,2-d]pyrimidin-4-yl}-(3-morpholin-4-ylmethyl-phenyl)-amine are placed in 2.70 ml glacial acetic acid and cooled to 10° C. 57 µl hydrogen peroxide (35%) are added dropwise, then the mixture is stirred for 0.25 hours. Then the reaction mixture is stirred in 30 ml ice water and made basic with cold ammonia solution. The precipitate formed is suction filtered, washed with water and dried. The crude product is extracted with petroleum ether and diethyl ether, suction filtered and dried. The product is purified by chromatography (10 g Chromabond SiOH-cartridge). 140.0 mg of the product are obtained as a powder (m.p 244°-248° C.).

1.2 Synthesis of (R)—N²-{2-[4-(4-chloro-phenyl)-piperazin-1-yl]-5-oxo-6,7-dihydro-5H-5λ⁴-thieno[3,2-d]pyrimidin-4-yl}-3-methyl-butan-1,2-diamine trifluoroacetate, Example 141 (see Scheme 1)

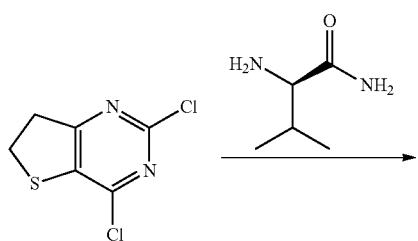

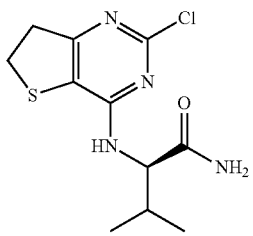

1.2.1 (R)-2-(2-chloro-6,7-dihydro-thieno[3,2-d]pyrimidin-4-ylamino)-3-methyl-butyramide (Scheme 1, Step A)

800 mg 2,4-dichloro-6,7-dihydro-thieno[3,2-d]pyrimidine and 800 mg D-valinamide hydrochloride are placed in 8 ml dioxane, then 2.7 ml diisopropylethylamine are added. The reaction mixture is heated to 120° C. in the microwave for 2 hours. The residue is mixed with water. The precipitate formed is suction filtered and dried. 820 mg of the product are obtained as a powder Analytical HPLC (method R): RT=2.64 min.

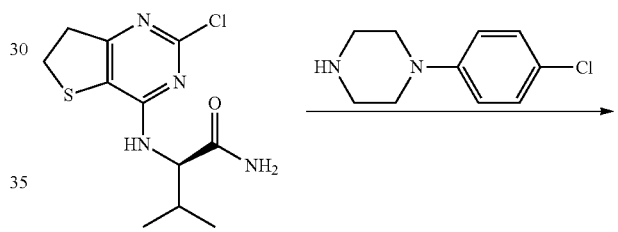

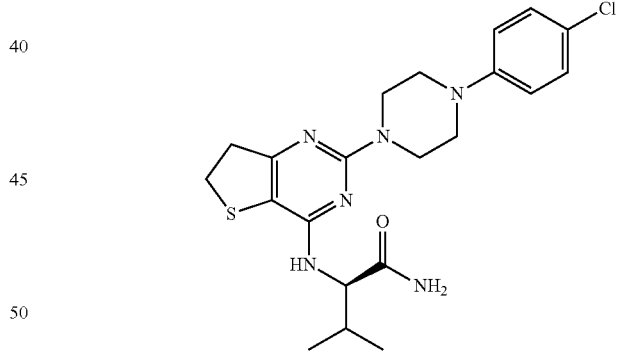

1.2.2 (R)-2-{2-[4-(4-chloro-phenyl)-piperazin-1-yl]-6,7-dihydro-thieno[3,2-d]pyrimidin-4-ylamino}-3-methyl-butyramide (Scheme 1, Step B)

400 mg (R)-2-(2-chloro-6,7-dihydro-thieno[3,2-d]pyrimidin-4-ylamino)-3-methyl-butyramide, 750 mg 1-(4-chlorophenyl)-piperazine and 1.2 ml diisopropylethylamine are placed in 9 ml dioxane, then heated in the microwave for 1 hour and 45 minutes at 160° C. Then water is added. The precipitate formed is suction filtered and dried. 550 mg of the product are obtained as a powder. Analytical HPLC (method B): RT=3.03 min.

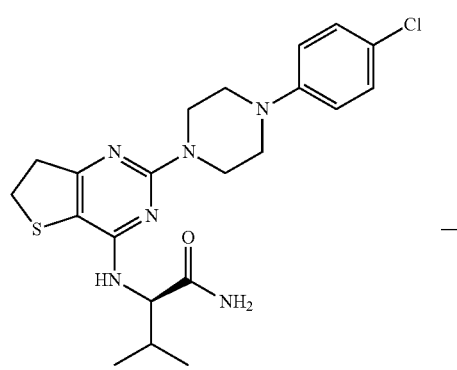

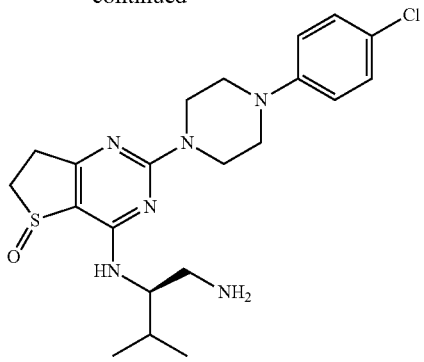

1.2.4 (R)—N-{2-[4-(4-chloro-phenyl)-piperazin-1-yl]-5-oxo-6,7-dihydro-5H-5λ⁴-thieno[3,2-d]pyrimidin-4-yl}-3-methyl-butan-1,2-diamine trifluoroacetate (Scheme 1, step C)

86 mg (R)—N²-{2-[4-(4-chloro-phenyl)-piperazin-1-yl]-6,7-dihydro-thieno[3,2-d]pyrimidin-4-yl}-3-methyl-butan-1,2-diamine trifluoroacetate are placed in 1.2 ml glacial acetic acid and cooled to 10° C. 18 µl hydrogen peroxide (35%) are added dropwise, then the mixture is stirred for 2.5 hours at ambient temperature. Then the reaction mixture is stirred into 30 ml of ice water and made basic with cold ammonia solution. The crude product is extracted with dichloromethane. The diastereomers are separated by semipreparative HPLC (method A). 20 mg Diastereomer 1 (Example 141) and 52 mg Diastereomer 2 are obtained as the trifluoroacetate. Analytical HPLC (method B): Diastereomer 1: RT=2.75 min; Diastereomer 2: RT: 2.87 min.

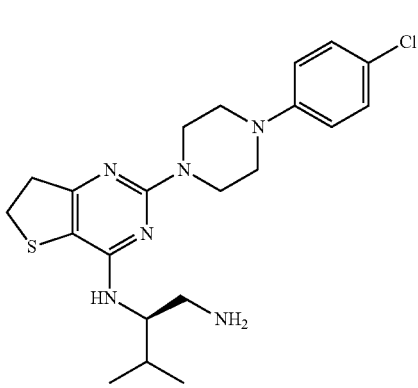

1.2.3 (R)—N²-{2-[4-(4-chloro-phenyl)-piperazin-1-yl]-6,7-dihydro-thieno[3,2-d]pyrimidin-4-yl}-3-methyl-butan-1,2-diamine trifluoroacetate 400 mg (R)-2-{2-[4-(4-chloro-phenyl)-piperazin-1-yl]-6,7-dihydro-thieno[3,2-d]pyrimidin-4-ylamino}-3-methyl-butyramide are placed in 15 ml abs. tetrahydrofuran and while cooling with an ice bath 3.5 ml of a solution of lithium aluminium hydride in tetrahydrofuran (1 M) is added. The reaction mixture is refluxed for 4 hours with stirring. A few drops of 1N NaOH are added to the residue, it is dried and filtered through Celite. The organic phase is evaporated to dryness. The product is purified by preparative HPLC (method A). 90 mg of the product are obtained as the trifluoroacetate. Analytical HPLC (method B): RT=2.90 min.

1.3 Synthesis of (1-{2-[4-(4-chloro-phenyl)-piperazin-1-yl]-5-oxo-6,7-dihydro-5H-5λ⁴-thieno[3,2-d]pyrimidin-4-ylamino}-cyclopentyl)-methanol, Examples 158 and 159 (See Scheme 1)

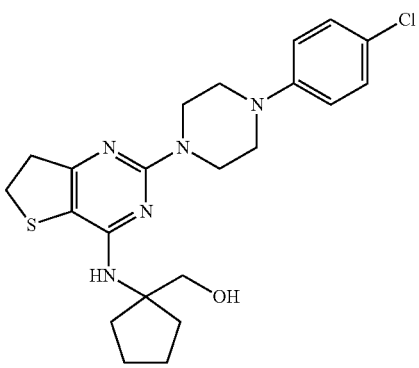 [SMILES: OCC1(Nc2nc(N3CCN(c4ccc(Cl)cc4)CC3)nc3c2SCC3)CCCC1]

Starting from 2,4-dichloro-6,7-dihydro-thieno[3,2-d]pyrimidine and cycloleucinol, (1-{2-[4-(4-chloro-phenyl)-piperazin-1-yl]-5-oxo-6,7-dihydro-5H-5λ⁴-thieno[3,2-d]pyrimidin-4-ylamino}-cyclopentyl)-methanol may be prepared as described in Example 21 (see scheme 1). Analytical HPLC-MS (method D): RT=1.29 min.

The two enantiomers may be separated by chiral HPLC (column: Diacel AS-H, 250×4.6 mm, 5 µm, eluant: (hexane+cyclohexylamine (0.2%))/ethanol (70/30), flow rate: 1

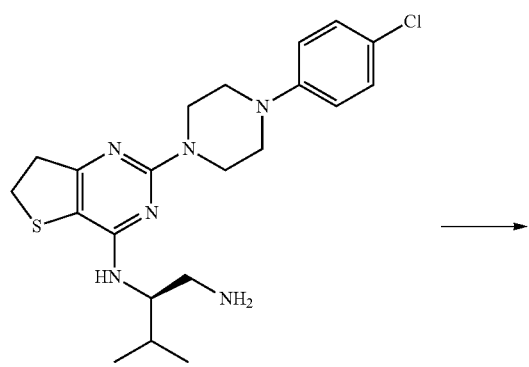

ml/min): enantiomer 1: RT=4.00 min (Example 159); enantiomer 2: RT=5.35 min (Example 158).

SCHEME 2

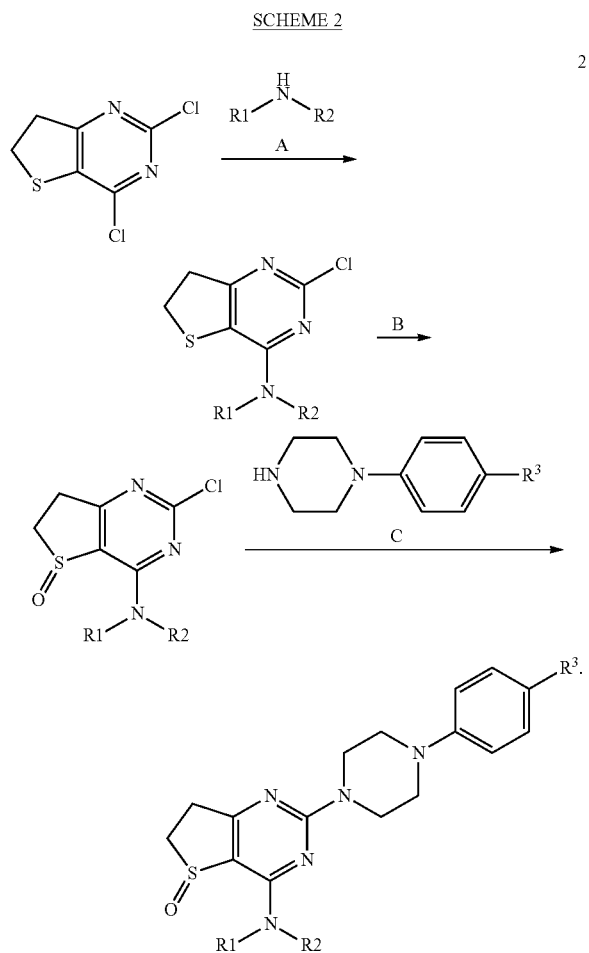

2.1 synthesis of 4-{4-[4-(3-fluoro-phenylamino)-5-oxo-6,7-dihydro-5H-5λ⁴-thieno[3,2-d]pyrimidin-2-yl]-piperazin-1-yl}-N,N-dimethylbenzolsulphonamide, Example 28 (See Scheme 2)

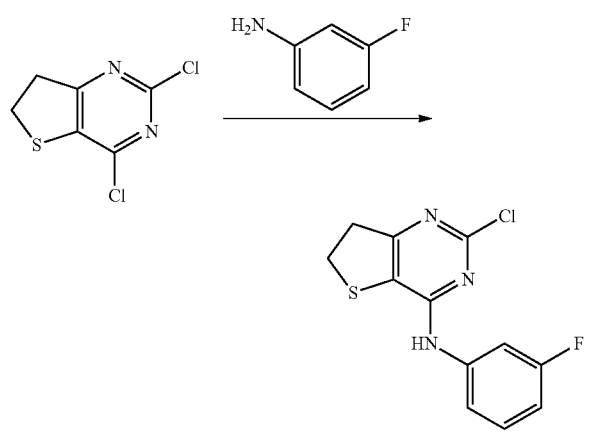

2.1.1 (2-chloro-6,7-dihydro-thieno[3,2-d]pyrimidin-4-yl)-(3-fluoro-phenyl)-amine (Scheme 2, Step A)

4.00 g 2,4-dichloro-6,7-dihydro-thieno[3,2-d]pyrimidine are placed in 15 ml dimethylformamide, then first 4.50 ml diisopropylethylamine, then 2.50 ml 3-fluoro-aniline are added. The reaction mixture is stirred for 7 hours at 120° C., and after cooling evaporated down. The residue is extracted with dichloromethane and water, the organic phase is washed with saturated sodium chloride solution, dried and evaporated to dryness. The residue is purified by chromatography (NP_MPLC, Biotage cartridge (4*15 cm)). 2.60 g of the product are obtained as a powder.

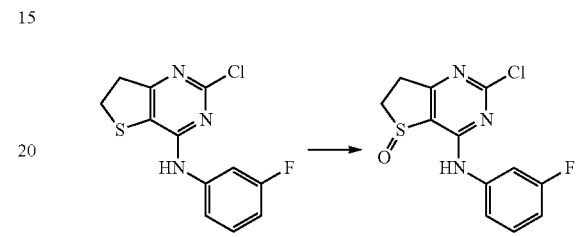

2.1.2 2-chloro-5-oxo-6,7-dihydro-5H-5λ⁴-thieno[3,2-d]pyrimidin-4-yl)-(3-fluoro-phenyl)-amine (Scheme 2, Step B)

2.60 g (2-chloro-6,7-dihydro-thieno[3,2-d]pyrimidin-4-yl)-(3-fluoro-phenyl)-amine are placed in 40 ml glacial acetic acid, 1.80 ml hydrogen peroxide (35%) are added dropwise, then the mixture is stirred for 2 hours. Then the reaction mixture is stirred into ice water, made basic with ammonia solution. The precipitate formed is suction filtered, washed with water and dried. 2.40 g of the product are obtained as a powder.

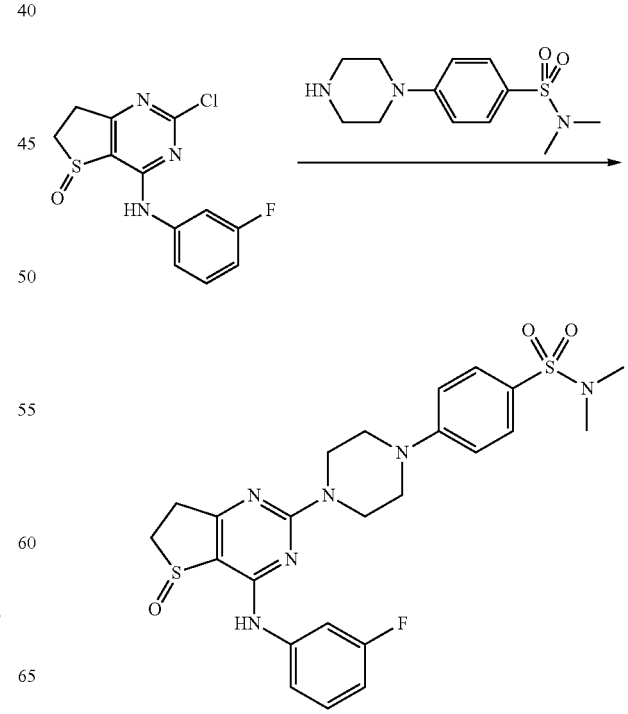

2.1.3 4-{4-[4-(3-fluoro-phenylamino)-5-oxo-6,7-dihydro-5H-5λ⁴-thieno[3,2-d]pyrimidin-2-yl]-piperazin-1-yl}-N,N-dimethylbenzenesulphonamide (Scheme 2, Step C)

180 mg 2-chloro-5-oxo-6,7-dihydro-5H-5λ⁴-thieno[3,2-d]pyrimidin-4-yl)-(3-fluoro-phenyl)-amine, 360 mg N,N-dimethyl-4-piperazin-1-yl-benzenesulphonamide (WO 03/105853) and 230 μl diisopropylethylamine are placed in 2 ml dioxane, then heated in the microwave for 0.75 hours at 160° C. Then water is added, the precipitate formed is suction filtered, washed and dried. The crude product is purified by preparative HPLC (method A). 109 mg of the product are obtained as a powder. Analytical HPLC (method A): RT=3.73 min.

2.2 Synthesis of (R)-1-{2-[4-(4-chloro-phenyl)-piperazin-1-yl]-5-oxo-6,7-dihydro-5H-5λ⁴-thieno[3,2-d]pyrimidin-4-ylamino}-1-(4-fluoro-phenyl)-2-methyl-propan-2-ol, Examples 160 and 161 (See Scheme 2)

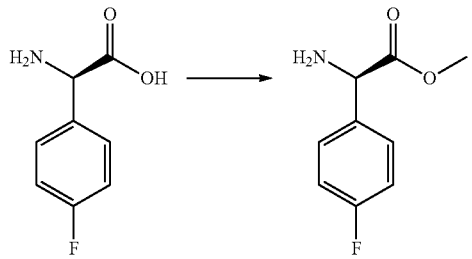

2,2,1 Methyl (R)-amino(4-fluoro(4-fluoro-phenyl)-acetate 4 g (R)-4-fluorophenylglycine are suspended in 80 ml of methanol. While cooling with the ice bath 3.28 ml of thionylcloride are slowly added dropwise, so that the temperature is maintained between 15° C. and 20° C. The reaction mixture is stirred for 12 hours at ambient temperature and then evaporated to dryness. 5.1 g of the product are obtained as the hydrochloride.

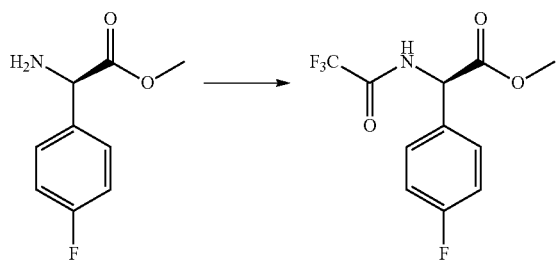 [SMILES: COC(=O)[C@H](N)c1ccc(F)cc1 ; COC(=O)[C@H](NC(=O)C(F)(F)F)c1ccc(F)cc1]

2,2,2 methyl (R)-(4-fluoro-phenyl)-(2,2,2-trifluoro-acetylamino)-acetate 5.1 g methyl (R)-amino-(4-fluoro-phenyl)-acetate are placed in 36.5 abs. tetrahydrofuran, then 3.9 ml triethylamine are added. The reaction mixture is cooled to −70° C. 3.9 ml trifluoroacetic anhydride are then slowly added dropwise, so that the temperature does not exceed −60° C. The reaction mixture is stirred for 12 hours at ambient temperature and then mixed with water. Potassium hydrogen carbonate is then added until no more foaming can be seen. The product is extracted with ethyl acetate and then the organic phase is dried and evaporated to dryness. 6.2 g of the product are obtained as an oil.

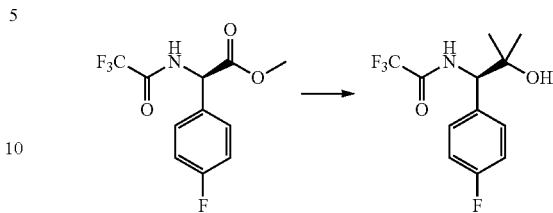

2.2.3 2,2,2-trifluoro-N—[(R)-1-(4-fluoro-phenyl)-2-hydroxy-2-methyl-propyl]-acetamide 6.2 g methyl (R)-(4-fluoro-phenyl)-(2,2,2-trifluoro-acetylamino)-acetate are placed in 195.1 ml abs. tetrahydrofuran and the reaction mixture is cooled to +3° C. 37.2 ml of a methylmagnesiumiodide solution (3 M) are slowly added dropwise, so that the temperature does not rise above +10° C. The reaction mixture is stirred for 12 hours at ambient temperature and then stirred into ice water. Ammonium chloride is added, so that the precipitate dissolves. The product is extracted with ethyl acetate and then the organic phase is dried and evaporated to dryness. 5.6 g of the product are obtained as an oil.

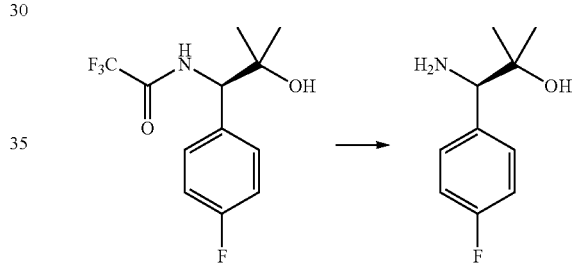

2.2.4 (R)-1-amino-1-(4-fluoro-phenyl)-2-methyl-propan-2-ol 5.6 g of 2,2,2-trifluoro-N—[(R)-1-(4-fluoro-phenyl)-2-hydroxy-2-methyl-propyl]-acetamide and 2.27 g KOH are suspended in 61.1 ml of methanol. The reaction mixture is stirred for 20 hours at 60° C. and then combined with water and dichloromethane, the organic phase is dried and evaporated to dryness. 3.2 g of the product are obtained as an oil.

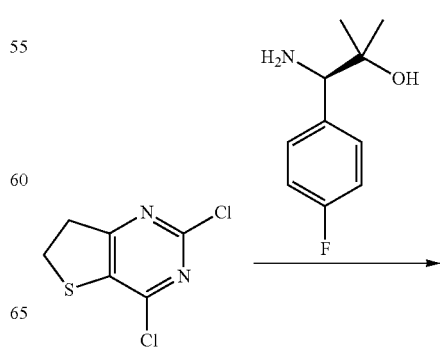

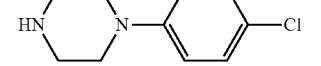

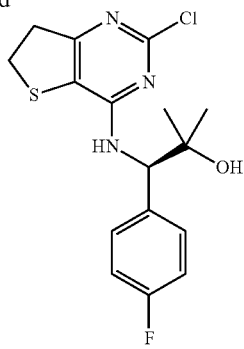 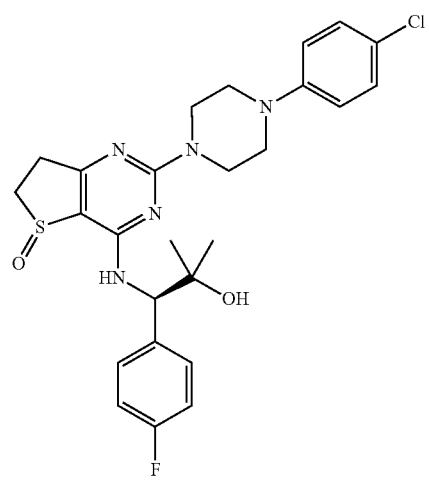

2.2.5 (R)-1-(2-chloro-6,7-dihydro-thieno[3,2-d]pyrimidin-4-ylamino)-1-(4-fluoro-phenyl)-2-methyl-propan-2-ol (Scheme 2, Step A)

533 mg 2,4-dichloro-6,7-dihydro-thieno[3,2-d]pyrimidine, 850 mg (R)-1-amino-1-(4-fluoro-phenyl)-2-methyl-propan-2-ol and 1.3 ml diisopropylethylamine are suspended in 9.8 ml dioxane. The reaction mixture is stirred for 2 hours in the microwave at 80° C. and then evaporated to dryness. The residue is mixed with water. The precipitate formed is suction filtered and purified by chromatography (silica gel, petroleum ether/ethyl acetate 100/0 to 60/40). 260 mg of the product are obtained as a solid.

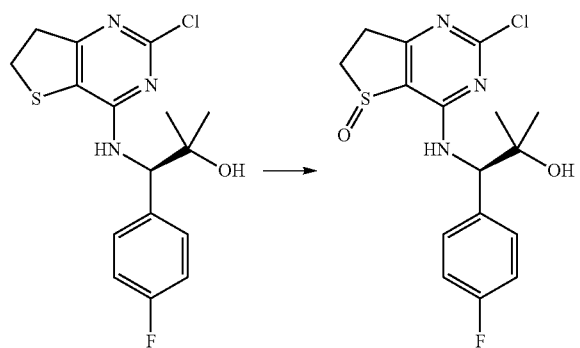 [SMILES: CC(C)(O)[C@H](Nc1nc(Cl)nc2c1SCC2)c1ccc(F)cc1 ; CC(C)(O)[C@H](Nc1nc(Cl)nc2c1S(=O)CC2)c1ccc(F)cc1]

2.2.6 (R)-1-(2-chloro-5-oxo-6,7-dihydro-5H-5$\lambda^4$-thieno[3,2-d]pyrimidin-4-ylamino)-1-(4-fluoro-phenyl)-2-methyl-propan-2-ol (Scheme 2, Step B)

300 mg (R)-1-(2-chloro-6,7-dihydro-thieno[3,2-d]pyrimidin-4-ylamino)-1-(4-fluoro-phenyl)-2-methyl-propan-2-ol are placed in 2.0 ml acetic acid. The reaction mixture is cooled to +10° C. 127 μl hydrogen peroxide (35%) are added dropwise. The reaction mixture is stirred for 1 hour at +10° C. and then stirred into ice water. It is then made basic with an ammonia solution. The precipitate formed is suction filtered and purified by chromatography (silica gel, petroleum ether/ethyl acetate 50/50 to 0/100 then ethyl acetate/methanol 50/50). 70 mg of the product are obtained as an oil. Analytical HPLC-MS (method D): RT=1.17 min.

2.2.7 (R)-1-{2-[4-(4-chloro-phenyl)-piperazin-1-yl]-5-oxo-6,7-dihydro-5H-5$\lambda^4$-thieno[3,2-d]pyrimidin-4-ylamino}-1-(4-fluoro-phenyl)-2-methyl-propan-2-ol (Scheme 2, step C)

50.0 mg (R)-1-(2-chloro-5-oxo-6,7-dihydro-5H-5$\lambda^4$-thieno[3,2-d]pyrimidin-4-ylamino)-1-(4-fluoro-phenyl)-2-methyl-propan-2-ol, 76.4 mg 1-(4-chlorophenylpiperazin) and 99 μl diisopropylethylamine are placed in 850 μl dioxane, then heated in the microwave for 0.3 hours at 120° C. Then the reaction mixture is evaporated to dryness. The diastereomers are separated by semipreparative HPLC (method B). 10.5 mg of Diastereomer 1 (Example 160) and 13.3 mg of Diastereomer 2 (Example 161) are obtained as a solid. Analytical HPLC-MS (method D): Diastereomer 1: RT=1.31 min; Diastereomer 2: RT=1.40 min.

2.3 Synthesis of {2-[4-(4-chloro-phenyl)-piperazin-1-yl]-5-oxo-6,7-dihydro-5H-5$\lambda^4$-thieno[3,2-d]pyrimidin-4-yl}-(tetrahydro-pyran-4-yl)-amine, Example 181 (See Scheme 2)

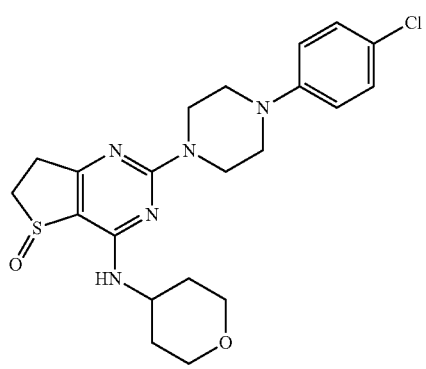 [SMILES: O=S1CCc2nc(N3CCN(c4ccc(Cl)cc4)CC3)nc(NC3CCOCC3)c21]

Starting from 2,4-dichloro-6,7-dihydro-thieno[3,2-d]pyrimidine and 4-aminotetrahydropyran, {2-[4-(4-chloro-phenyl)-piperazin-1-yl]-5-oxo-6,7-dihydro-5H-5λ⁴-thieno[3,2-d]pyrimidin-4-yl}-(tetrahydro-pyran-4-yl)-amine may be prepared as described in Example 28 (see scheme 2). Analytical HPLC-MS (method D): RT=1.23 min. The two enantiomers may be separated by chiral HPLC (column: Diacel AS-H, 250×4.6 mm, 5 μm, eluant: (hexane+cyclohexylamine (0.2%))/ethanol (80/20), flow rate: 1 ml/min): enantiomer 1: RT=9.54 min; enantiomer 2: RT=11.81 min (Example 181).

2.4 Synthesis of (1-(2-[4-(4-chloro-phenyl)-piperazin-1-yl]-5-oxo-6,7-dihydro-5H-5λ⁴-thieno[3,2-d]pyrimidin-4-ylamino)-cyclopropyl)-methanol, Example 189 (See Scheme 2)

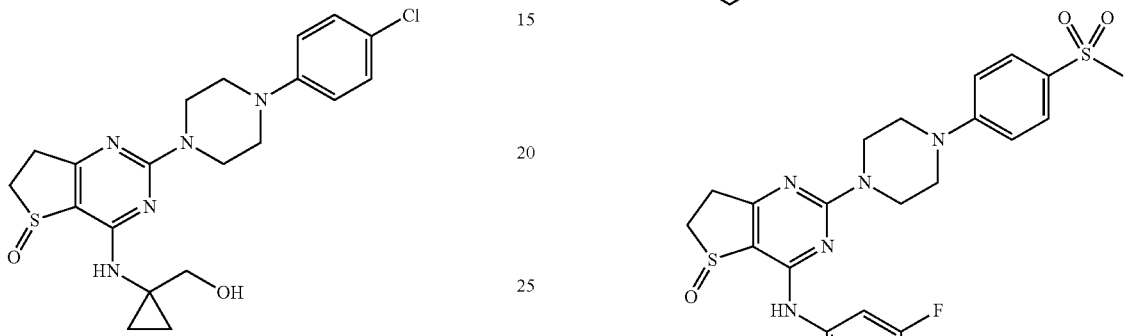

Starting from 2,4-dichloro-6,7-dihydro-thieno[3,2-d]pyrimidine and 1-amino-cyclopropanemethanol, (1-{2-[4-(4-chloro-phenyl)-piperazin-1-yl]-5-oxo-6,7-dihydro-5H-5λ⁴-thieno[3,2-d]pyrimidin-4-ylamino}-cyclopropyl)-methanol may be prepared as described in Example 28 (see scheme 2). Analytical HPLC-MS (method D): RT=1.20 min.

The two enantiomers may be separated by chiral HPLC (column: Diacel IA, 250×4.6 mm, 5 μm, eluant: (hexane+cyclohexylamine (0.2%))/ethanol (80/20), flow rate: 1 ml/min): enantiomer 1: RT=17.8 min; enantiomer 2: RT=21.9 min (Example 189).

2.5 Synthesis of (3-fluoro-phenyl)-{2-[4-(4-methanesulphonyl-phenyl)-piperazin-1-yl]-5-oxo-6,7-dihydro-5H-5λ⁴-thieno[3,2-d]pyrimidin-4-yl}-amine Example 202 (See Scheme 2)

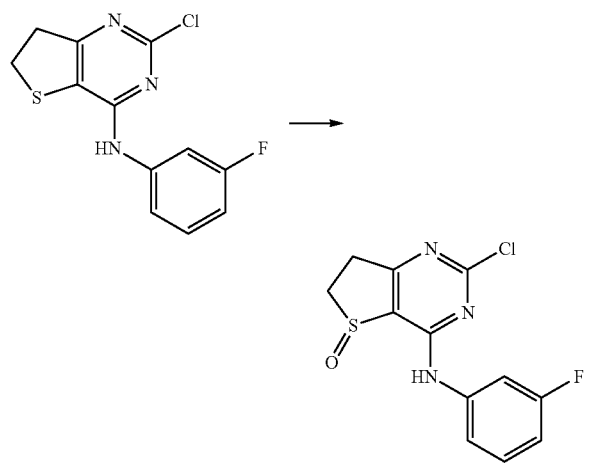

2.5.1 2-chloro-5-oxo-6,7-dihydro-5H-5λ⁴-thieno[3,2-d]pyrimidin-4-yl)-(3-fluoro-phenyl)-amine (cf 2.1.2)

2-chloro-5-oxo-6,7-dihydro-5H-5λ⁴-thieno[3,2-d]pyrimidin-4-yl)-(3-fluoro-phenyl)-amine is prepared as described in Example 28 (see scheme 2, 2.1.2).

The two enantiomers may be separated by chiral HPLC (column: Diacel AS-H, 250×4.6 mm, 5 μm, eluant: (hexane+cyclohexylamine (0.2%))/(ethanol+methanol (1/1)) (80/20), flow rate: 1 ml/min): enantiomer 1: RT=5.9 min; enantiomer 2: RT=7.4 min.

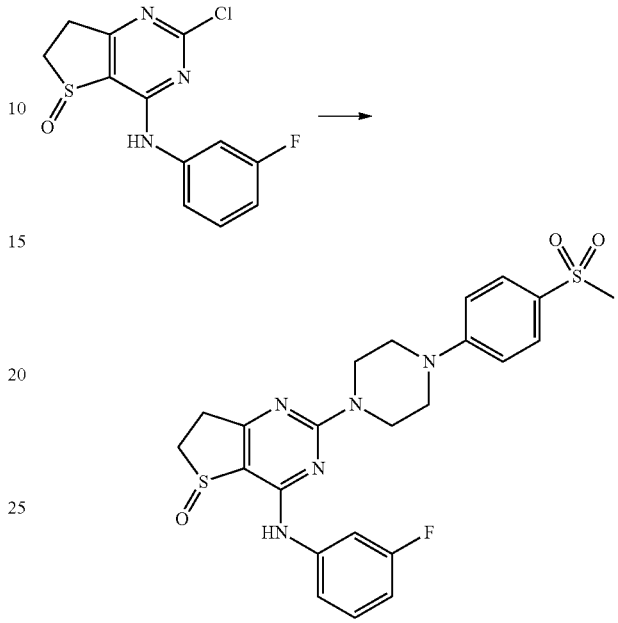

2.5.2 (3-fluoro-phenyl)-{2-[4-(4-methanesulphonyl-phenyl)-piperazin-1-yl]-5-oxo-6,7-dihydro-5H-5λ⁴-thieno[3,2-d]pyrimidin-4-yl}-amine Starting from 2-chloro-5-oxo-6,7-dihydro-5H-5λ⁴-thieno[3,2-d]pyrimidin-4-yl)-(3-fluoro-phenyl)-amine enantiomer 1 and 1-(4-(methyl-sulphonyl)phenyl)piperazine, Example 202 may be prepared as described in Example 28 (see scheme 2, step C, 2.1.3). Analytical HPLC-MS (method D): RT=1.24 min.

2.6 Synthesis of (S)-5-{2-[4-(4-chloro-phenyl)-piperazin-1-yl]-5-oxo-6,7-dihydro-5H-5λ⁴-thieno[3,2-d]pyrimidin-4-ylamino}-1-methyl-piperidin-2-one, Example 203 (See Scheme 2)

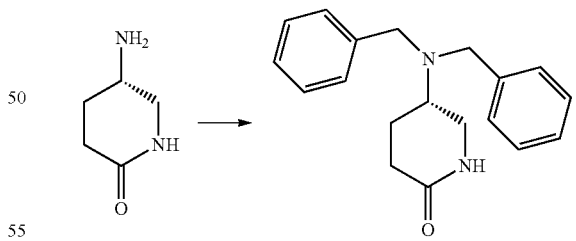

2.6.1 (S)-5-dibenzylamino-piperidin-2-one 600 mg 4-(S)-amino-delta-valerolactam hydrochloride, 970 μl benzylbromide and 1.5 g sodium hydrogen carbonate are suspended in 30 ml of ethanol. The reaction mixture is then stirred for 8 hours at 80° C. and then evaporated to dryness. The residue is suspended in water and the product is extracted with dichloromethane. The product is then purified by chromatography (silica gel, dichloromethane/methanol 100/0 to 95/5). 500 mg of the product are obtained as an oil. Analytical HPLC-MS (method D): RT=1.01 min.

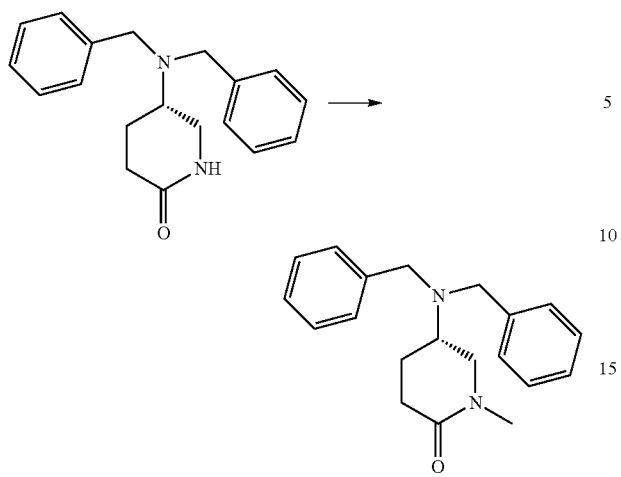

2.6.2 (S)-5-dibenzylamino-1-methyl-piperidin-2-one 500 mg (S)-5-dibenzylamino-piperidin-2-one are suspended in 15 ml of tetrahydrofuran. While cooling with the ice bath 175 mg potassium-tert-butoxide are added. The reaction mixture is then stirred for 30 minutes at ambient temperature. While cooling with the ice bath 95 µl methyliodide are added. The reaction mixture is then stirred for 48 hours at ambient temperature and then combined with a saturated NaCl solution and ethyl acetate. The organic phase is dried and evaporated to dryness. 450 mg of the product are obtained as an oil. Analytical HPLC-MS (method D): RT=−1.07 min.

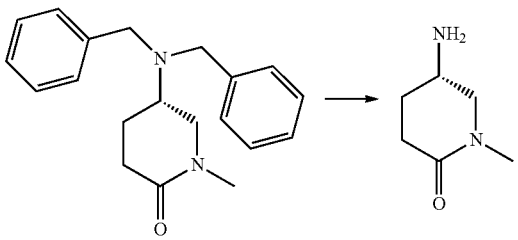

2.6.3 (S)-5-amino-1-methyl-piperidin-2-one 450 mg (S)-5-dibenzylamino-1-methyl-piperidin-2-one are suspended in 25 ml of methanol and hydrogenated with 150 mg Pd/C 10% under a pressure of 3 bar and at a temperature of 60° C. After 16 hours the catalyst is removed by suction filtering and the filtrate is evaporated to dryness. 190 mg of the product are obtained as an oil.

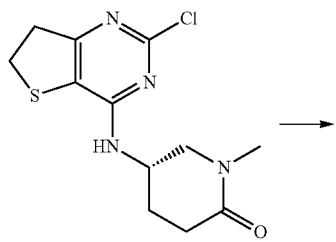

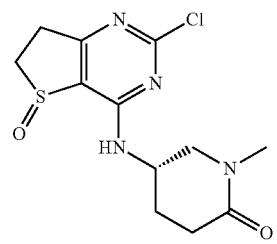

2.6.4 (S)-5-(2-chloro-5-oxo-6,7-dihydro-5H-5λ$^4$-thieno[3,2-d]pyrimidin-4-ylamino)-1-methyl-piperidin-2-one Starting from 2,4-dichloro-6,7-dihydro-thieno[3,2-d]pyrimidine and (S)-5-amino-1-methyl-piperidin-2-one, (S)-5-(2-chloro-5-oxo-6,7-dihydro-5H-5λ$^4$-thieno[3,2-d]pyrimidin-4-ylamino)-1-methyl-piperidin-2-one may be prepared as described in Example 28 (see scheme 2, 2.1.2).

The two diasteromers may be separated by chiral HPLC (column: Diacel AS-H, 250×4.6 mm, 5 µm, eluant: (hexane+cyclohexylamine (0.2%))/ethanol (70/30), flow rate: 1 ml/min): Diastereomer 1: RT=8.84 min; Diastereomer 2: RT=15.7 min.

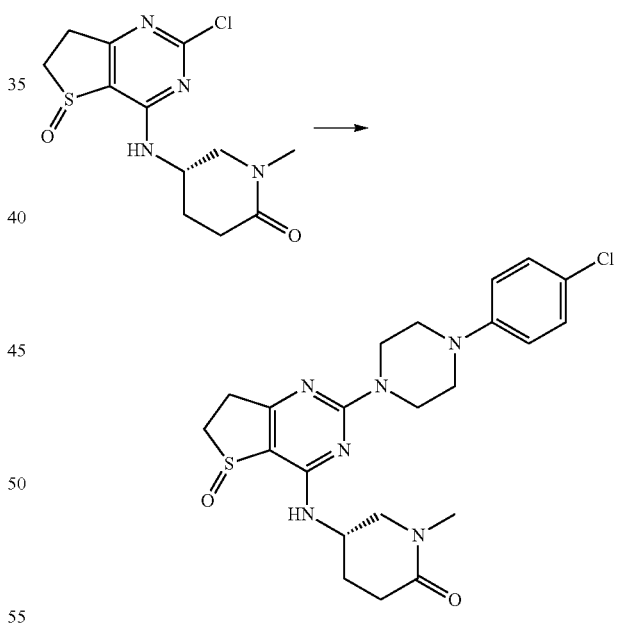

2.6.5 (S)-5-{2-[4-(4-chloro-phenyl)-piperazin-1-yl]-5-oxo-6,7-dihydro-5H-5λ$^4$-thieno[3,2-d]pyrimidin-4-ylamino}-1-methyl-piperidin-2-one Starting from (S)-5-(2-chloro-5-oxo-6,7-dihydro-5H-5λ$^4$-thieno[3,2-d]pyrimidin-4-ylamino)-1-methyl-piperidin-2-one Diastereomer I (cf 2.6.4), Example 203 may be prepared as described in Example 28 (see scheme 2, step C, 2.1.3). Analytical HPLC-MS (method D): RT=1.18 min.

2.7 Synthesis of (R)-5-{2-[4-(4-chloro-phenyl)-piperazin-1-yl]-5-oxo-6,7-dihydro-5H-5λ⁴-thieno[3,2-d]pyrimidin-4-ylamino}-1-methyl-piperidin-2-one, Example 204 (See Scheme 2)

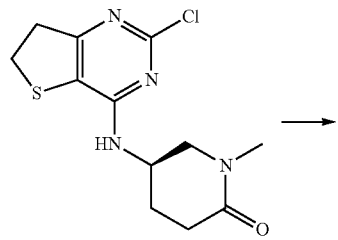

2.7.1 (R)-5-(2-chloro-5-oxo-6,7-dihydro-5H-5λ⁴-thieno[3,2-d]pyrimidin-4-ylamino)-1-methyl-piperidin-2-one Starting from 2,4-dichloro-6,7-dihydro-thieno[3,2-d]pyrimidine and (R)-5-amino-1-methyl-piperidin-2-one (prepared from the 4-(R)-amino-delta-valerolactam hydrochloride, as described in Example 203 (cf 2.6)) (R)-5-(2-chloro-5-oxo-6,7-dihydro-5H-5λ⁴-thieno[3,2-d]pyrimidin-4-ylamino)-1-methyl-piperidin-2-one may be prepared as described in Example 28 (see scheme 2, 2.1.2).

The two diastereomers may be separated by chiral HPLC (column: Diacel AS-H, 250×4.6 mm, 5 μm, eluant: (hexane+cyclohexylamine (0.2%))/ethanol (70/30), flow rate: 1 ml/min): Diastereomer 1: RT=9.4 min; Diastereomer 2: RT=21.8 min.

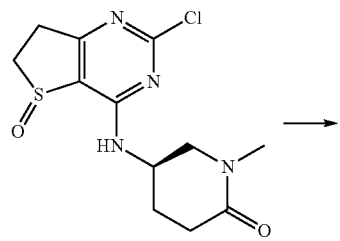

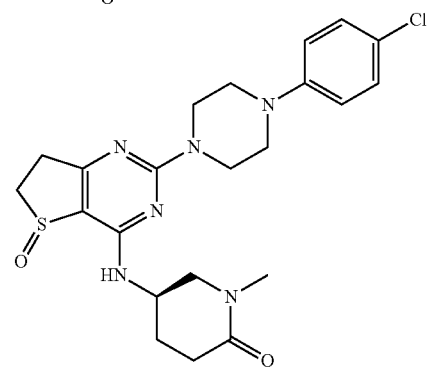

2.7.2 (R)-5-{2-[4-(4-chloro-phenyl)-piperazin-1-yl]-5-oxo-6,7-dihydro-5H-5λ⁴-thieno[3,2-d]pyrimidin-4-ylamino}-1-methyl-piperidin-2-one Starting from (R)-5-(2-chloro-5-oxo-6,7-dihydro-5H-5λ⁴-thieno[3,2-d]pyrimidin-4-ylamino)-1-methyl-piperidin-2-one Diastereomer I Example 204 may be prepared as described in Example 28 (see scheme 2, step C, 2.1.3). Analytical HPLC-MS (method D): RT=1.19 min.

2.8 Synthesis of (R)-2-{2-[4-(4-bromo-phenyl)-piperazin-1-yl]-5-oxo-6,7-dihydro-5H-5λ⁴-thieno[3,2-d]pyrimidin-4-ylamino}-3-methyl-butan-1-ol, Example 208 (See Scheme 2)

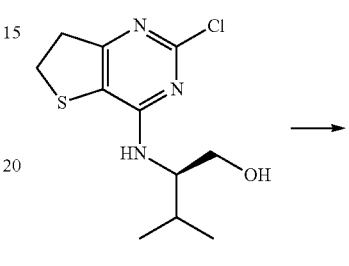

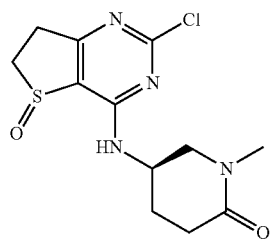

2.8.1 (R)-2-(2-chloro-5-oxo-6,7-dihydro-5H-5λ⁴-thieno[3,2-d]pyrimidin-4-ylamino)-3-methyl-butan-1-ol (Scheme 2, Step B)

Starting from 2,4-dichloro-6,7-dihydro-thieno[3,2-d]pyrimidine and D-Valinol the two diastereomers of (R)-2-(2-chloro-5-oxo-6,7-dihydro-5H-5λ⁴-thieno[3,2-d]pyrimidin-4-ylamino)-3-methyl-butan-1-ol may be prepared as described in Example 28 (cf 2.1.2). The diastereomers may be separated by preparative HPLC (method A). Analytical HPLC-MS (method A): Diastereomer 1: RT=2.13 min; Diastereomer 2: RT=2.25 min.

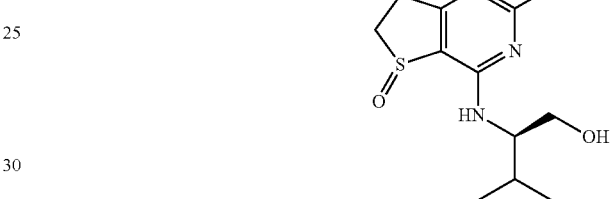

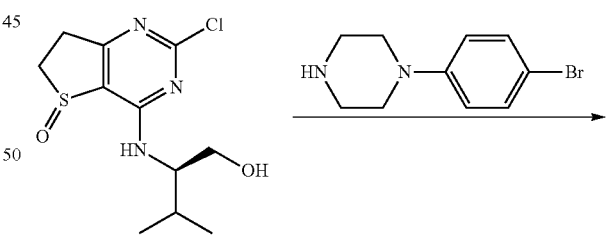

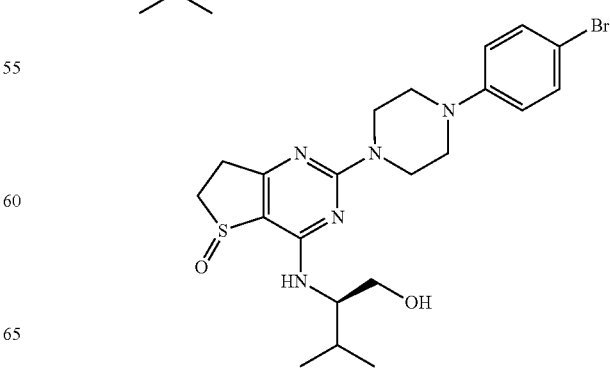

2.8.2 (R)-2-{2-[4-(4-bromo-phenyl)-piperazin-1-yl]-5-oxo-6,7-dihydro-5H-5λ⁴-thieno[3,2-d]pyrimidin-1-ylamino}-3-methyl-butan-1-ol (Scheme 2, Step C)

Starting from (R)-2-(2-chloro-5-oxo-6,7-dihydro-5H-5λ⁴-thieno[3,2-d]pyrimidin-4-ylamino)-3-methyl-butan-1-ol Diastereomer 1 (cf 2.8.1), Example 208 may be prepared as described in Example 28 (cf 2.1.3). Analytical HPLC-MS (method D): RT=1.21 min.

2.9 Synthesis of (1-{2-[4-(4-bromo-phenyl)-piperazin-1-yl]-5-oxo-6,7-dihydro-5H-5λ⁴-thieno[3,2-d]pyrimidin-4-ylamino}-cyclopropyl)-methanol, Example 211 (See Scheme 2)

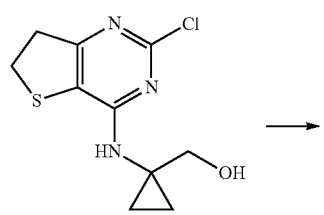

2.9.1 [1-(2-chloro-5-oxo-6,7-dihydro-5H-5λ⁴-thieno[3,2-d]pyrimidin-1-ylamino)-cyclopropyl]-methanol (Scheme 2, Step B)

Starting from 2,4-dichloro-6,7-dihydro-thieno[3,2-d]pyrimidine and 1-amino-cyclopropanmethanol the two enantiomers of [1-(2-chloro-5-oxo-6,7-dihydro-5H-5λ⁴-thieno[3,2-d]pyrimidin-4-ylamino)-cyclopropyl]-methanol may be prepared as described in Example 28 (cf 2.1.2). The enantiomers may be separated by chiral HPLC (column Diacel IA, 250×4.6 mm, 5 m, eluant: (hexane+cyclohexylamine (0.2%))/ethanol (80/20), flow rate: 1 ml/min): enantiomer 1: RT=11.1 min; enantiomer 2: RT=16.5 min.

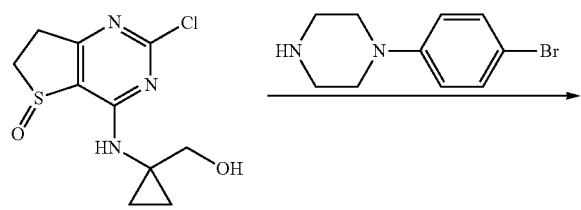

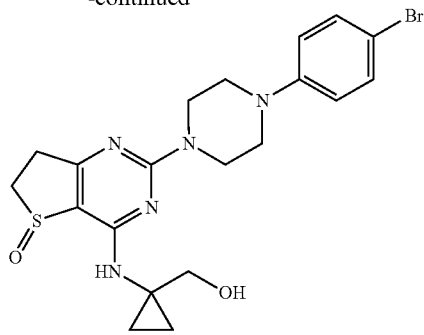

2.9.2 (L-{2-[4-(4-bromo-phenyl)-piperazin-1-yl]-5-oxo-6,7-dihydro-5H-5λ⁴-thieno[3,2-d]pyrimidin-4-ylamino}-cyclopropyl)-methanol (Scheme 2, Step C)

Starting from [1-(2-chloro-5-oxo-6,7-dihydro-5H-5λ⁴-thieno[3,2-d]pyrimidin-4-ylamino)-cyclopropyl]-methanol enantiomer 1 (cf 2.9.1), Example 211 may be prepared as described in Example 28 (cf 2.1.3). Analytical HPLC-MS (method D): RT=1.18 min.

2.10 Synthesis of ethyl 4-{4-[4-((R)-1-hydroxymethyl-2-methyl-propylamino)-5-oxo-6,7-dihydro-5H-5λ⁴-thieno[3,2-d]pyrimidin-2-yl]-piperazin-1-yl}-benzoate, Example 212 (See Scheme 2)

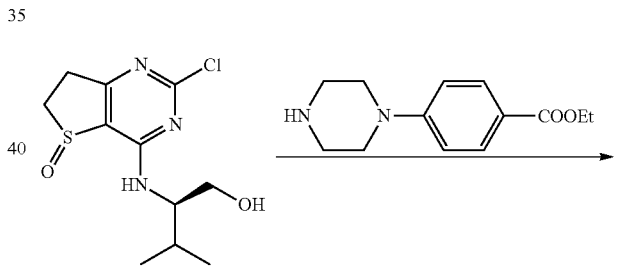

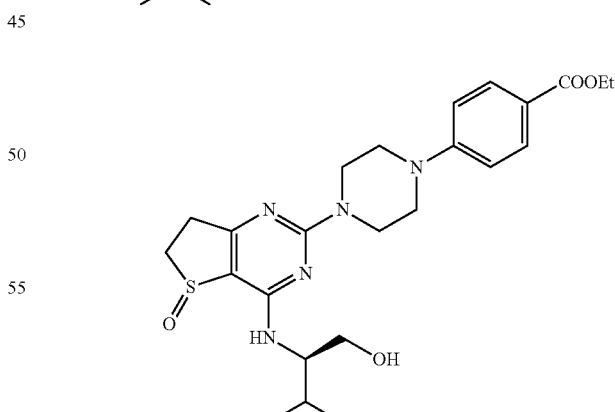

Starting from (R)-2-(2-chloro-5-oxo-6,7-dihydro-5H-5λ⁴-thieno[3,2-d]pyrimidin-4-ylamino)-3-methyl-butan-1-ol Diastereomer 1 (cf Example 208, 2.8.1), Example 212 may be prepared as described in Example 28 (cf 2.1.3). Analytical HPLC-MS (method D): RT=1.2 min.

2.11 synthesis of ethyl 4-{4-[5-oxo-4-(tetrahydro-pyran-4-ylamino)-6,7-dihydro-5H-5λ⁴-thieno[3,2-d]pyrimidin-2-yl]-piperazin-1-yl}-benzoate, Example 214 (See Scheme 2)

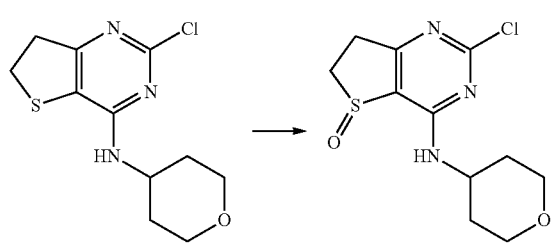 [SMILES: Clc1nc2c(c(NC3CCOCC3)n1)SCC2 ; O=S1CCc2nc(Cl)nc(NC3CCOCC3)c21]

2.11.1 (2-chloro-5-oxo-6,7-dihydro-5H-5λ⁴-thieno[3,2-d]pyrimidin-4-yl)-(tetrahydro-pyran-4-yl)-amine (Scheme 2, Step B)

Starting from 2,4-dichloro-6,7-dihydro-thieno[3,2-d]pyrimidine and 4-aminotetrahydropyran the two enantiomers of (2-chloro-5-oxo-6,7-dihydro-5H-5λ⁴-thieno[3,2-d]pyrimidin-4-yl)-(tetrahydro-pyran-4-yl)-amine may be prepared as described in Example 28 (cf 2.1.2). The enantiomers may be separated by chiral HPLC (column: Diacel AS-H, 250×4.6 mm, 5 μm, eluant: (hexane+cyclohexylamine (0.2%))/ethanol (80/20), flow rate: 1 ml/min): enantiomer 1: RT=7.51 min; enantiomer 2: RT=12.3 min.

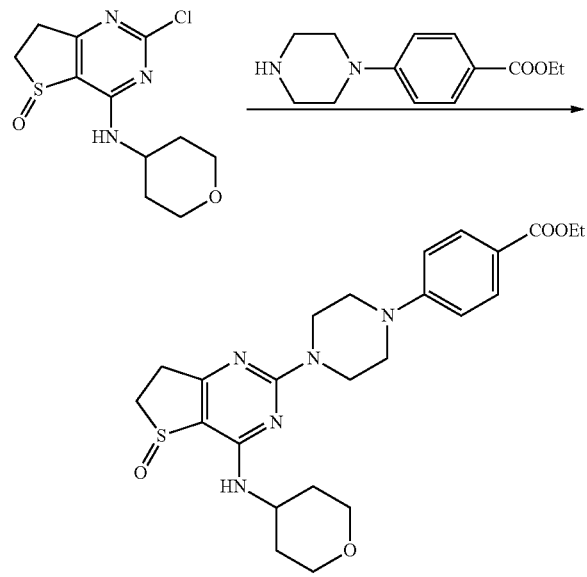

2.11.2 ethyl 4-(4-[5-oxo-4-(tetrahydro-pyran-4-ylamino)-6,7-dihydro-5H-5λ⁴-thieno[3,2-d]pyrimidin-2-yl]-piperazin-1-yl)-benzoate (Scheme 2, Step C)

Starting from (2-chloro-5-oxo-6,7-dihydro-5H-5λ⁴-thieno[3,2-d]pyrimidin-4-yl)-(tetrahydro-pyran-4-yl)-amine enantiomer 1 (cf 2.11.1), Example 214 may be prepared as described in Example 28 (cf 2.1.3). Analytical HPLC-MS (method D): RT=1.2 min.

2.12 Synthesis of (R)-2-{2-[4-(4-bromo-phenyl)-piperazin-1-yl]-5-oxo-6,7-dihydro-5H-5λ⁴-thieno[3,2-d]pyrimidin-4-ylamino}-pentan-1-ol, Example 216 (See Scheme 2)

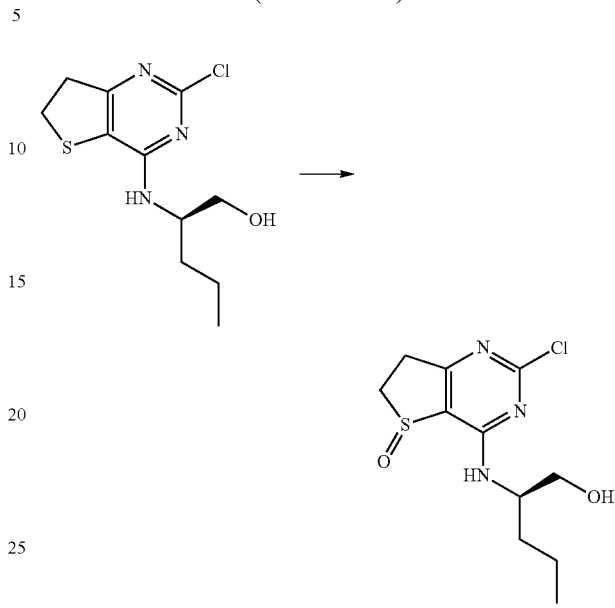

2.12.1 (R)-2-(2-chloro-5-oxo-6,7-dihydro-5H-5λ⁴-thieno[3,2-d]pyrimidin-4-ylamino)-pentan-1-ol (Scheme 2, Step B)

Starting from 2,4-dichloro-6,7-dihydro-thieno[3,2-d]pyrimidine and D-norvalinol the two diastereomers of (R)-2-(2-chloro-5-oxo-6,7-dihydro-5H-5λ⁴-thieno[3,2-d]pyrimidin-4-ylamino)-pentan-1-ol are prepared as described in Example 28 (cf 2.1.2). The diastereomers are separated by preparative HPLC (method B). Analytical HPLC (method B): Diastereomer 1: RT=2.43 min; Diastereomer 2: RT=2.56 min.

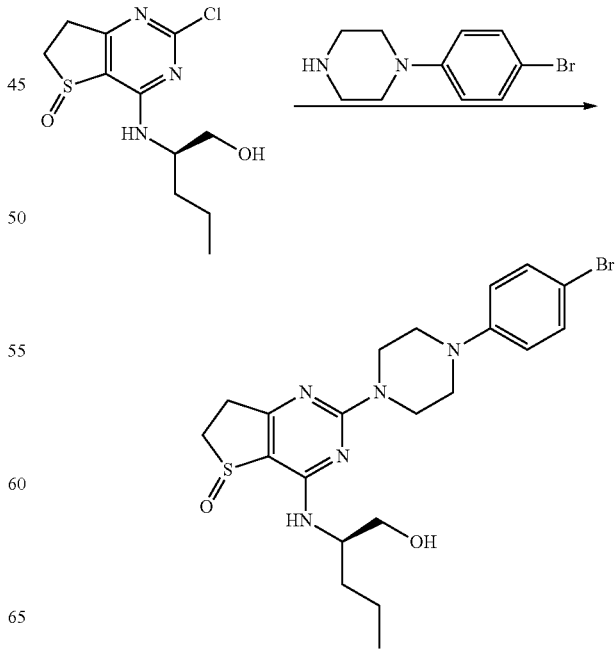

2.12.2 (R)-2-(2-[4-(4-bromo-phenyl)-piperazin-1-yl]-5-oxo-6,7-dihydro-5H-5λ⁴-thieno[3,2-d]pyrimidin-4-ylamino)-pentan-1-ol (Scheme 2, Step C)

Starting from (R)-2-(2-chloro-5-oxo-6,7-dihydro-5H-5λ⁴-thieno[3,2-d]pyrimidin-4-ylamino)-pentan-1-ol Diastereomer 1 (cf 2.12.1), Example 216 may be prepared as described in Example 28 (cf 2.1.3). Analytical HPLC-MS (method D): RT=1.23 min.

2.13 Synthesis of 2-{2-[4-(4-chloro-phenyl)-piperazin-1-yl]-5-oxo-6,7-dihydro-5H-5λ⁴-thieno[3,2-d]pyrimidin-4-ylamino}-3-fluoro-3-methyl-butan-1-ol, Example 187 (See Scheme 2)

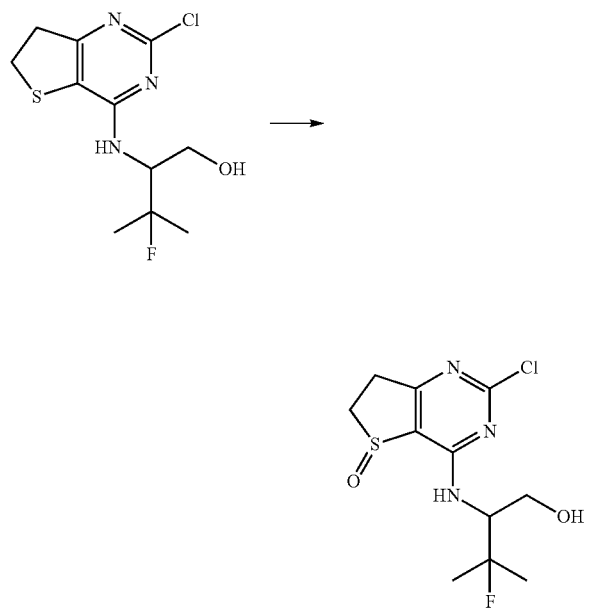 [SMILES: CC(C)(F)C(CO)Nc1nc(Cl)nc2c1SCC2 ; CC(C)(F)C(CO)Nc1nc(Cl)nc2c1S(=O)CC2]

2.13.1 2-(2-chloro-5-oxo-6,7-dihydro-5H-5λ⁴-thieno[3,2-d]pyrimidin-4-ylamino)-3-fluoro-3-methyl-butan-1-ol (Scheme 2, Step B)

Starting from 2,4-dichloro-6,7-dihydro-thieno[3,2-d]pyrimidine and 3-fluoro-DL-valinol (*J. Org. Chem.* 2000, 5037) a mixture of stereoisomers of 2-(2-chloro-5-oxo-6,7-dihydro-5H-5λ⁴-thieno[3,2-d]pyrimidin-4-ylamino)-3-fluoro-3-methyl-butan-1-ol is prepared as described in Example 28 (cf 2.1.2). The diastereomers are separated by semipreparative HPLC (method A). Analytical HPLC-MS (method D): Diastereomer 1: RT=0.92 min; Diastereomer 2: RT=0.99 min. The two diastereomers are obtained as racemates.

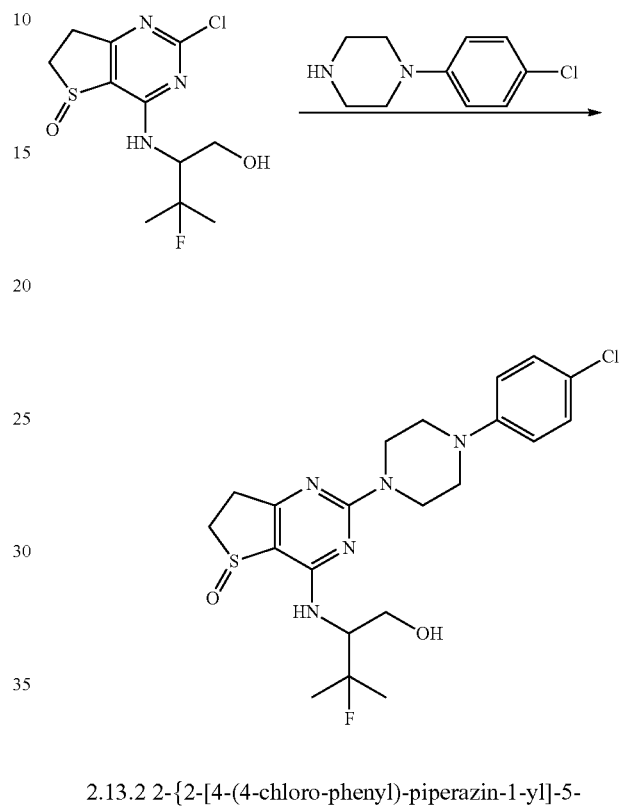

2.13.2 2-{2-[4-(4-chloro-phenyl)-piperazin-1-yl]-5-oxo-6,7-dihydro-5H-5λ⁴-thieno[3,2-d]pyrimidin-4-ylamino}-3-fluoro-3-methyl-butan-1-ol (Scheme 2, Step C)

Starting from 2-(2-chloro-5-oxo-6,7-dihydro-5H-5λ⁴-thieno[3,2-d]pyrimidin-4-ylamino)-3-fluoro-3-methyl-butan-1-ol Diastereomer 2 (cf 2.13.1), Example 187 is prepared as described in Example 28 (cf 2.1.3). The product is obtained as a racemate. Analytical HPLC-MS (method D): RT=1.26 min.

SCHEME 3

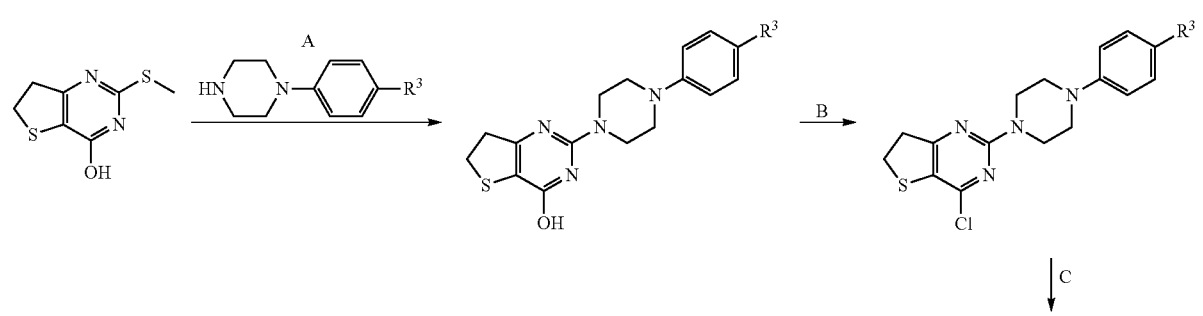

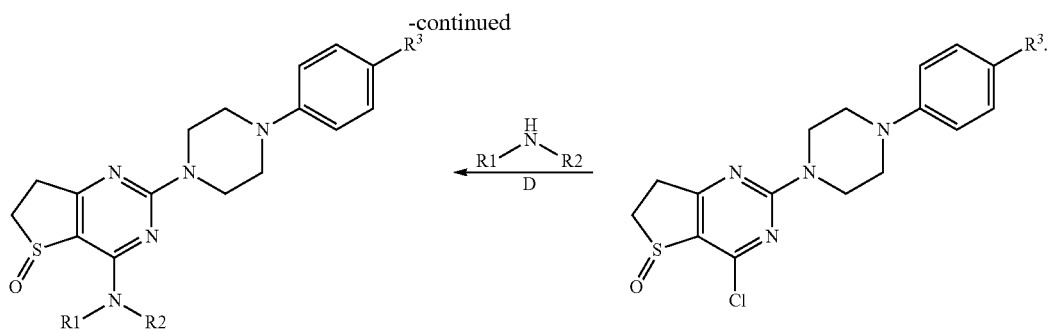

3.1 Synthesis of (3R,5S)-1-{2-[4-(4-chloro-phenyl)-piperazin-1-yl]-5-oxo-6,7-dihydro-5H-5λ⁴-thieno[3,2-d]pyrimidin-4-yl}-5-hydroxymethyl-pyrrolidin-3-ol, Example 124 (See Scheme 3)

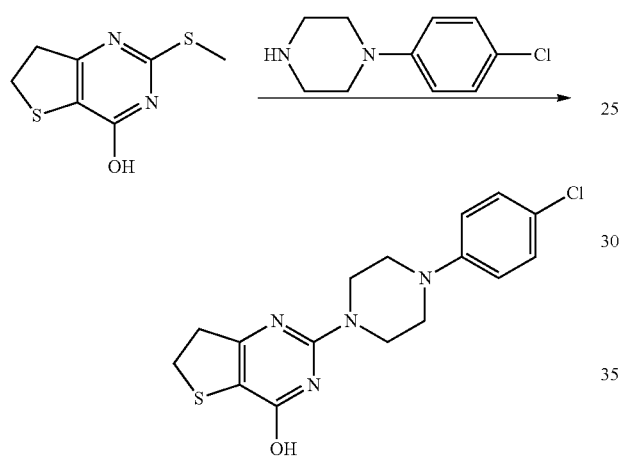

3.1.1 2-[4-(4-chloro-phenyl)-piperazin-1-yl]-6,7-dihydro-thieno[3,2-d]pyrimidin-4-ol (Scheme 3, Step A)

20.45 g 1-(4-chloro-phenyl)-piperazine are placed in 5.95 ml (104 mmol) glacial acetic acid and heated to 180° C. 8.01 g 2-methylsulphanyl-6,7-dihydro-thieno[3,2-d]pyrimidin-4-ol are added, the non-stirrable reaction mixture is heated for 2.5 hours to 180° C. After cooling, water is added, the precipitate is suction filtered and dried in the air. The substance is treated with ethanol under ultrasound, suction filtered and dried. 12.95 g of the product are obtained as a powder.

3.1.2 4-chloro-2-[4-(4-chloro-phenyl)-piperazin-1-yl]-6,7-dihydro-thieno[3,2-d]pyrimidine (Scheme 3, Step B)

12.95 g 2-[4-(4-chloro-phenyl)-piperazin-1-yl]-6,7-dihydro-thieno[3,2-d]pyrimidin-4-ol and 50.89 ml (546 mmol) phosphorus oxychloride are heated for 4 hours to 120° C. Then the reaction mixture is evaporated down, the residue is mixed with water. The precipitate formed is suction filtered, washed with water and dried. The crude product is stirred with methanol and suction filtered. 11.78 g of the product are obtained as a powder.

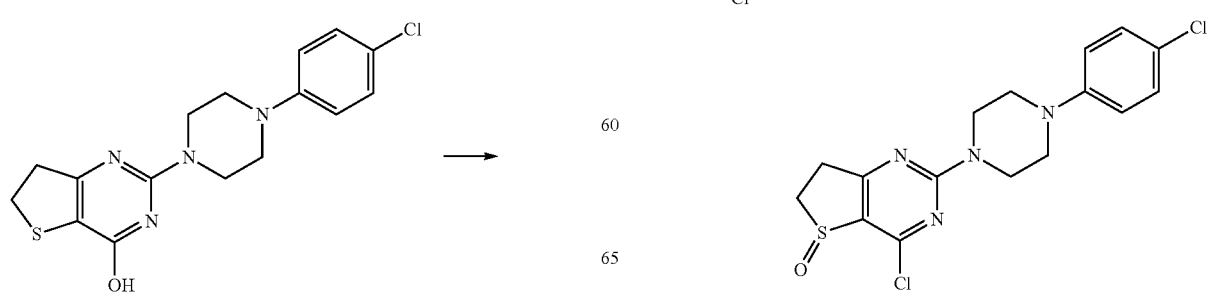

3.1.3 4-chloro-2-[4-(4-chloro-phenyl)-piperazin-1-yl]-6,7-dihydro-thieno[3,2-d]pyrimidine 5-oxide (Scheme 3, Step C)

14.69 g 4-chloro-2-[4-(4-chloro-phenyl)-piperazin-1-yl]-6,7-dihydro-thieno[3,2-d]pyrimidine are placed in 140 ml glacial acetic acid and cooled to 10° C. cooled. 3.79 ml hydrogen peroxide (35%) are added dropwise, then the mixture is stirred for 2 hours. A further 1 eq hydrogen peroxide is added, the mixture is stirred for 8 hours at ambient temperature. Then the reaction mixture is stirred into ice water, made basic with ammonia solution. The precipitate formed is suction filtered, washed with water and dried. 11.90 g of the product are obtained as a powder.

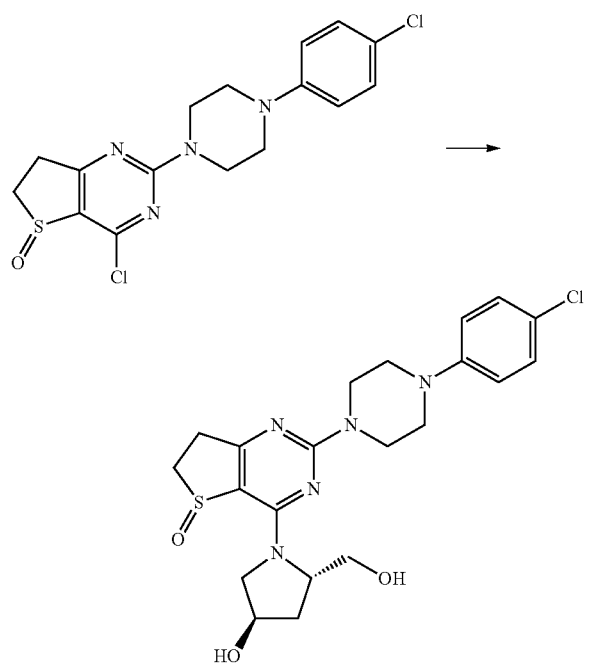

3.1.4 (3R,5S)-1-{2-[4-(4-chloro-phenyl)-piperazin-1-yl]-5-oxo-6,7-dihydro-5H-5$\lambda^4$-thieno[3,2-d]pyrimidin-4-yl}-5-hydroxymethyl-pyrrolidin-3-ol (Scheme 3, Step D)

220 mg (0.57 mmol) 4-chloro-2-[4-(4-chloro-phenyl)-piperazin-1-yl]-6,7-dihydro-thieno[3,2-d]pyrimidine 5-oxide, 159.23 mg (0.69 mmol) (3R,5S)-5-hydroxymethyl-pyrrolidin-3-ol trifluoroacetate (prepared from commercial Boc-trans-4-hydroxy-L-prolinol) and 197.52 µl (1.15 mmol) diisopropylethylamine are placed in 4 ml dioxane, and heated to 120° C. in the microwave for 0.3 hours. Then the reaction mixture is combined with water and dichloromethane and extracted. The organic phase is separated off using a phase separation cartridge and evaporated to dryness. 200.3 mg of the product (75%) are obtained as a racemic mixture. Analytical HPLC-MS (method A): RT=2.26 min.

3.2. Synthesis of methyl(2S,4R)-{2-[4-(4-chloro-phenyl)-piperazin-1-yl]-5-oxo-6,7-dihydro-5H-5$\lambda^4$-thieno[3,2-d]pyrimidin-4-yl}-4-hydroxy-pyrrolidine-2-carboxylate, Examples 125 and 126 (See Scheme 3, Step D)

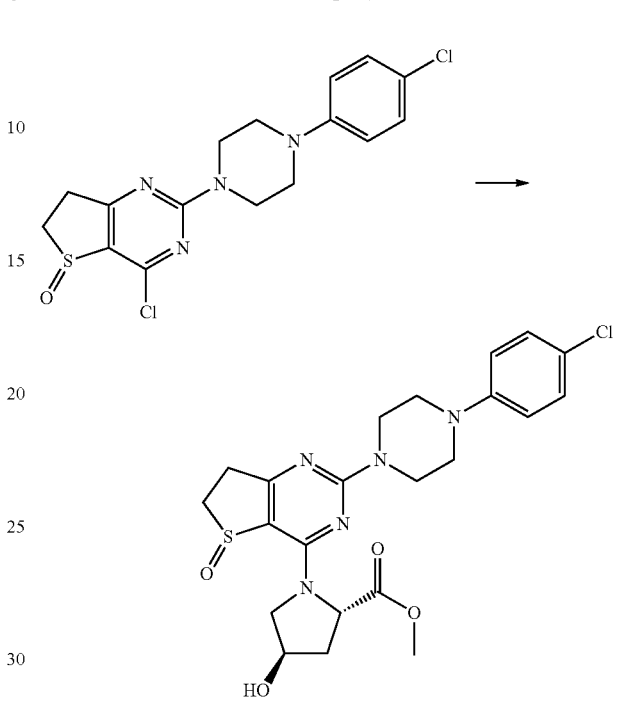

500 mg 4-chloro-2-[4-(4-chloro-phenyl)-piperazin-1-yl]-6,7-dihydro-thieno[3,2-d]pyrimidine 5-oxide (cf Example 124), 284.19 mg methyl (2S,4R)-4-hydroxy-pyrrolidine-2-carboxylate and 691.65 µl diisopropylethylamine are placed in 8 ml dioxane, heated to 120° C. in the microwave for 0.3 hours. Then the reaction mixture is combined with water and dichloromethane and extracted. The organic phase is separated off using a phase separation cartridge and evaporated to dryness. The diastereomers are separated by preparative HPLC (method B). 200 mg of Diastereomer I (Example 125) and 160 mg of a Diastereomer 2 (Example 126) are obtained as powders. Analytical HPLC-MS (method A): Diastereomer 1, RT=2.51 min, Diastereomer 2, RT=2.57 min.

3.3 Synthesis of (2S,4R)-1-{2-[4-(4-chloro-phenyl)-piperazin-1-yl]-5-oxo-6,7-dihydro-5H-5$\lambda^4$-thieno[3,2-d]pyrimidin-4-yl}-4-hydroxy-pyrrolidine-2-carboxylic acid amide, Example 128 (See Scheme 3)

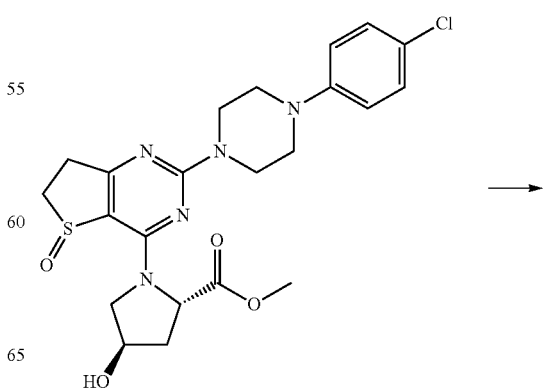

-continued

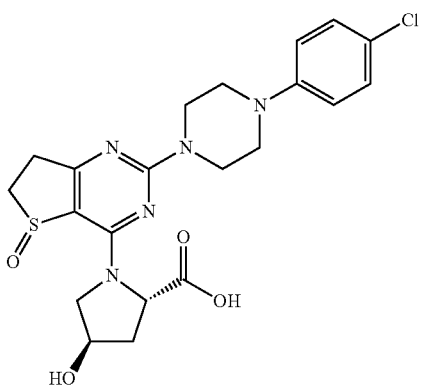

3.3.1 (2S,4R)-1-{2-[4-(4-chloro-phenyl)-piperazin-1-yl]-5-oxo-6,7-dihydro-5H-5λ⁴-thieno[3,2-d]pyrimidin-4-yl}-4-hydroxy-pyrrolidine-2-carboxylic acid 1.12 g methyl (2S,4R)-1-{2-[4-(4-chloro-phenyl)-piperazin-1-yl]-5-oxo-6,7-dihydro-5H-5λ⁴-thieno[3,2-d]pyrimidin-4-yl}-4-hydroxy-pyrrolidine-2-carboxylate as a mixture of diastereomers (cf Example 125) and 11.38 ml of 1 molar sodium hydroxide solution are placed in 10 ml of methanol, then refluxed for 4 hours with stirring. The resulting suspension is evaporated down, the residue is cooled and acidified with 2 molar hydrochloric acid and the suspension is evaporated down again. The product is purified by preparative HPLC (method A). 1.12 g of the product are obtained as a powder.

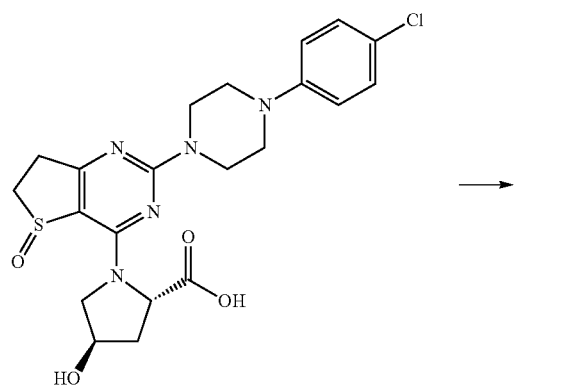

3.3.2 (2S,4R)-1-{2-[4-(4-chloro-phenyl)-piperazin-1-yl]-5-oxo-6,7-dihydro-5H-5λ⁴-thieno[3,2-d]pyrimidin-4-yl}-4-hydroxy-pyrrolidine-2-carboxylic acid amide 80 mg (2S,4R)-1-{2-[4-(4-chloro-phenyl)-piperazin-1-yl]-5-oxo-6,7-dihydro-5H-5λ⁴-thieno[3,2-d]pyrimidin-4-yl}-4-hydroxy-pyrrolidine-2-carboxylic acid are placed in 2.00 ml N,N-dimethylformamide and combined with 86.77 mg diisopropylethylamine and 76.20 mg O-(7-azabenzotriazol-1-yl-)-N,N,N',N'-tetramethyluronium-hexafluorophosphate (HATU). The mixture is stirred for 0.25 hours at ambient temperature, then 334 μl ammonia solution (0.5 M in dioxane) are added. The reaction mixture is stirred for 3 hours at ambient temperature, then acidified and water is added. The diastereomers are separated by preparative HPLC (method B). 11.7 mg of Diastereomer 1 and 15.3 mg of Diastereomer 2 (Example 128) are obtained as powders. Analytical HPLC-MS (method A): Diastereomer 1, RT=1.49 min, Diastereomer 2. RT=1.49 min.

3.4 Synthesis of (2S,4R)-1-{2-[4-(4-chloro-phenyl)-piperazin-1-yl]-5-oxo-6,7-dihydro-5H-5λ⁴-thieno[3,2-d]pyrimidin-4-yl}-4-hydroxy-pyrrolidine-2-carboxylic acid dimethylamide, Example 129 (See Scheme 3)

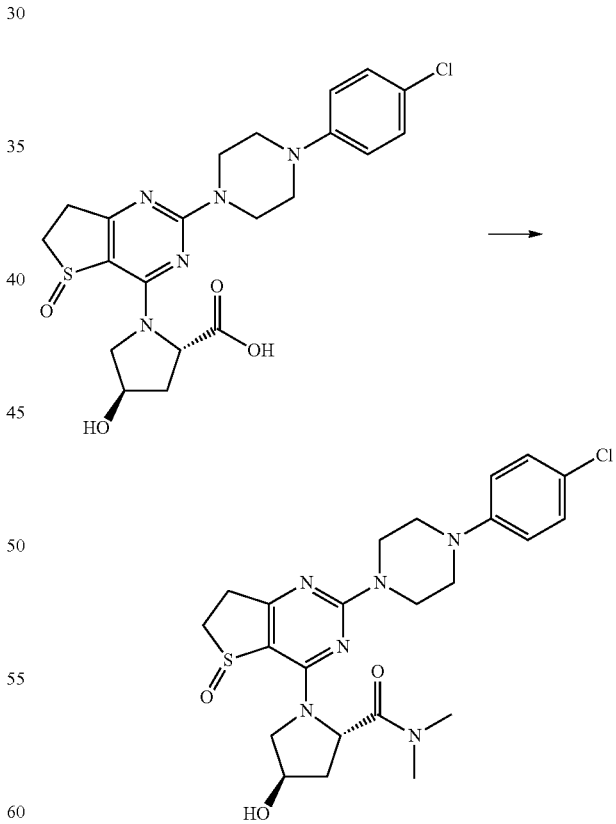

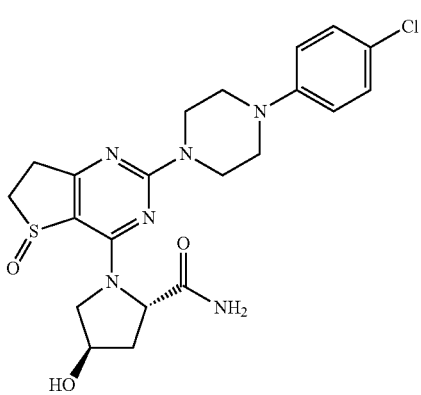

13.9 mg of Diastereomer 1 and 23.9 mg of Diastereomer 2 (Example 129) are obtained as powders from 80 mg (2S,4R)-1-{2-[4-(4-chloro-phenyl)-piperazin-1-yl]-5-oxo-6,7-dihydro-5H-5λ⁴-thieno[3,2-d]pyrimidin-4-yl}-4-hydroxy-pyrrolidine-2-carboxylic acid and 83.7 μl dimethylamine, as described in Example 128. Analytical HPLC-MS (method A): Diastereomer 1, RT=4.61 min, Diastereomer 2, RT=4.61 min.

3.5 Synthesis of (2S,4R)-1-{2-[4-(4-chloro-phenyl)-piperazin-1-yl]-5-oxo-6,7-dihydro-5H-5λ$^4$-thieno[3,2-d]pyrimidin-4-yl}-4-hydroxy-pyrrolidine-2-carboxylic acid methylamide, Example 130 (See Scheme 3)

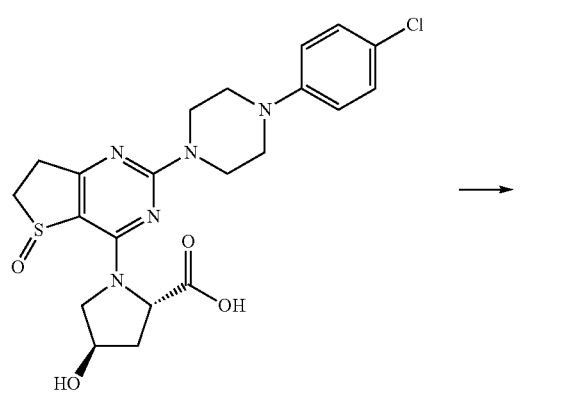

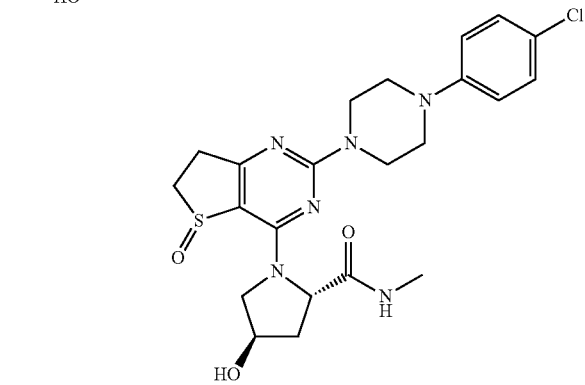

is 19.8 mg of the product is obtained as a powder from 70 mg (2S,4R)-1-{2-[4-(4-chloro-phenyl)-piperazin-1-yl]-5-oxo-6,7-dihydro-5H-5λ$^4$-thieno[3,2-d]pyrimidin-4-yl}-4-hydroxy-pyrrolidin-2- and 73.0 µl methylamine solution (2.0 M in THF) as described in Example 128. Analytical HPLC-MS, (method A): RT=1.57 min.

3.6 Synthesis of (R)-2-{2-[4-(4-chloro-phenyl)-piperazin-1-yl]-5-oxo-6,7-dihydro-5H-5λ$^4$-thieno[3,2-d]pyrimidin-4-ylamino}-3-methyl-butan-1-ol, Examples 54 and 57 (See Scheme 3, Step D)

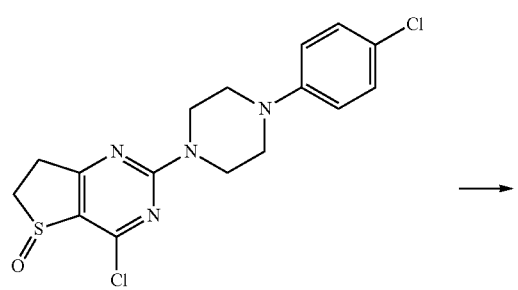

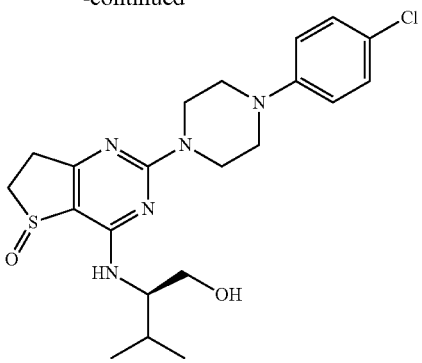

220 mg 4-chloro-2-[4-(4-chloro-phenyl)-piperazin-1-yl]-6,7-dihydro-thieno[3,2-d]pyrimidine 5-oxide (cf Example 124), 118.43 mg (R)-(−)-2-amino-3-methyl-butan-1-ol and 197.52 µl diisopropylethylamine are placed in 4 ml dioxane, and the mixture is heated to 120° C. in the microwave for 0.3 hours. Then the reaction mixture is mixed with water, the precipitate formed is suction filtered, washed and dried. The diastereomers are separated by preparative HPLC (method B). 25.5 mg of Diastereomer 1 (Example 54) and 40.5 mg of Diastereomer 2 (Example 57) are obtained as a powder. Analytical HPLC (method A): Diastereomer I: RT=3.61 min; Diastereomer 2, RT=3.71 min.

3.7 Synthesis of (R)-2-{2-[4-(4-chloro-phenyl)-piperazin-1-yl]-5-oxo-6,7-dihydro-5H-5λ$^4$-thieno[3,2-d]pyrimidin-4-ylamino}-2-phenyl-ethanol Examples 49 and 56 (See Scheme 3, Step D)

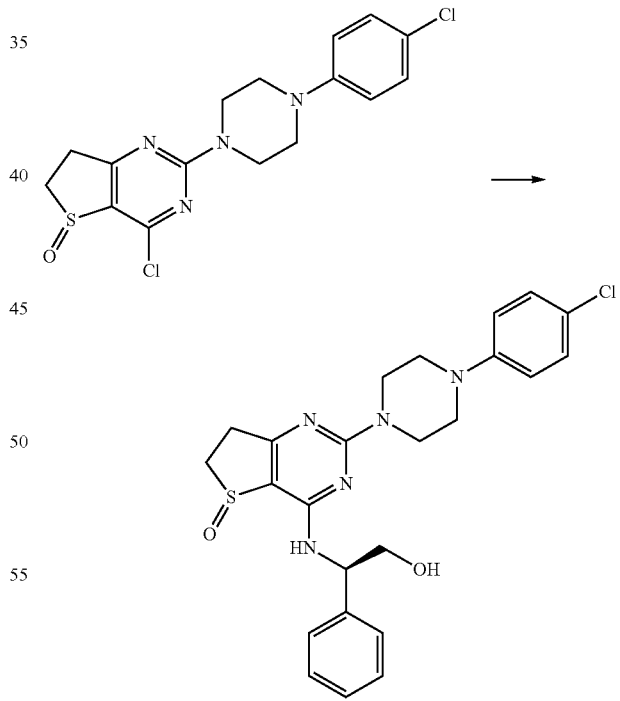

220 mg 4-chloro-2-[4-(4-chloro-phenyl)-piperazin-1-yl]-6,7-dihydro-thieno[3,2-d]pyrimidine 5-oxide (cf Example 124), 157.48 mg (R)-(−)-2-phenylglycinol and 197.52 µl diisopropylethylamine are placed in 4 ml dioxane, heated to 120° C. in the microwave for 0.3 hours. Then the reaction mixture is mixed with water, the precipitate formed is suction filtered, washed and dried. The diastereomers are separated by preparative HPLC (method B). 52.8 mg of Diastereomer 1 (Example 49) and 42.0 mg of Diastereomer 2 (Example 56) are obtained as a powder. ¹H NMR (400 MHz, DMSO): Diastereomer 1: 7.41-7.35 (m, 2H), 7.35-7.28 (m, 2H), 7.28-7.19 (m, 3H), 6.99-6.92 (m, 2H); Diastereomer 2: 7.42-7.35 (m, 2H), 7.33-7.15 (m, 5H), 6.99-6.92 (m, 2H).

3.8 Synthesis of (R)-2-{2-[4-(4-chloro-phenyl)-piperazin-1-yl]-5-oxo-6,7-dihydro-5H-5λ⁴-thieno[3,2-d]pyrimidin-4-ylamino}-4-methyl-pentan-1-ol Examples 53 and 69 (See Scheme 3, Step D)

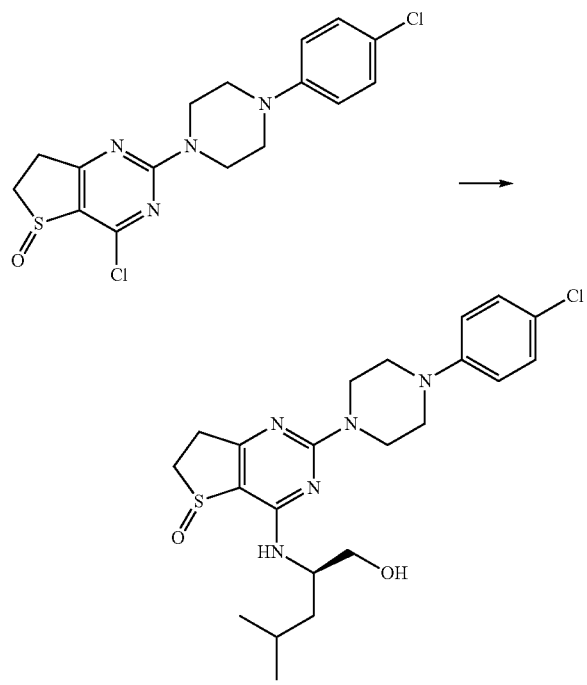

220 mg 4-chloro-2-[4-(4-chloro-phenyl)-piperazin-1-yl]-6,7-dihydro-thieno[3,2-d]pyrimidine 5-oxide (cf Example 124), 134.53 mg D-leucinol and 197.52 µl diisopropylethylamine are placed in 4 ml dioxane, heated to 120° C. in the microwave for 0.3 hours. Then the reaction mixture is mixed with water, the precipitate formed is suction filtered, washed and dried. The diastereomers are separated by preparative HPLC (method B). 43.9 mg of Diastereomer 1 (Example 53) and 46.9 mg of Diastereomer 2 (Example 69) are obtained as an oil. Analytical HPLC-MS (method B): Diastereomer 1, RT=1.86 min, Diastereomer 2, RT=1.90 min.

3.9 Synthesis of (2R,3R,4S,5R)-2-{2-[4-(4-chloro-phenyl)-piperazin-1-yl]-5-oxo-6,7-dihydro-5H-5λ⁴-thieno[3,2-d]pyrimidin-4-ylamino}-5-hydroxymethyl-tetrahydro-furan-3,4-diol, Example 127 (See Scheme 3, Step D)

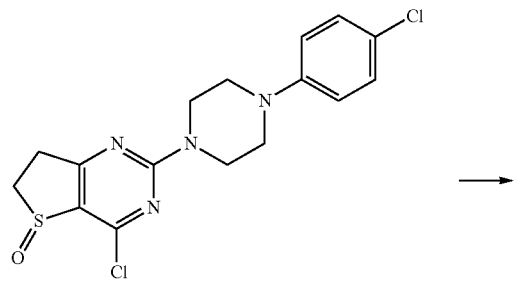

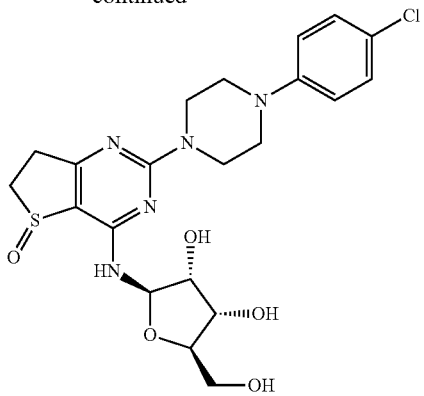

200 mg 4-chloro-2-[4-(4-chloro-phenyl)-piperazin-1-yl]-6,7-dihydro-thieno[3,2-d]pyrimidine 5-oxide (cf Example 124), 414.9 mg 2,3-O-isopropylidene-beta-D-ribofuranosylamine p-toluenesulphonate and 395.0 µl diisopropylethylamine are placed in 4 ml dioxane, heated to 120° C. in the microwave for 0.3 hours and for a further 0.6 hours to 130° C. Then the reaction mixture is combined with water and ethyl acetate and extracted. The organic phase is dried and evaporated to dryness. The product is purified by preparative HPLC (method B). 7 mg of the product are obtained as an oil. HPLC-MS (method A): RT=2.26 min.

3.10 Synthesis of tert-butyl[5-({2-[4-(4-chloro-phenyl)-piperazin-1-yl]-5-oxo-6,7-dihydro-5H-5λ⁴-thieno[3,2-d]pyrimidin-4-ylamino}-methyl)-thiophen-2-ylmethyl]-carbamidate, Example 101 (See Scheme 3)

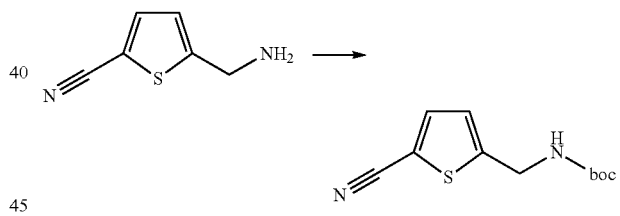

3.10.1 5-N-Boc-aminomethyl-2-cyanothiophene hydrochloride 17.5 g 5-aminomethyl-2-cyanothiophene hydrochloride (*Bioorg. Med. Chem. Lett.* 2002, 743) and 21.8 g Boc-anhydride are added batchwise to 250 ml chloroform. 50 ml cold water are slowly poured into the suspension. 8 g NaOH (50%) and 25 ml of water are slowly added dropwise at ambient temperature. The suspension is then stirred overnight. Then the reaction mixture is extracted with chloroform. 42.10 g of the product are obtained as an oil.

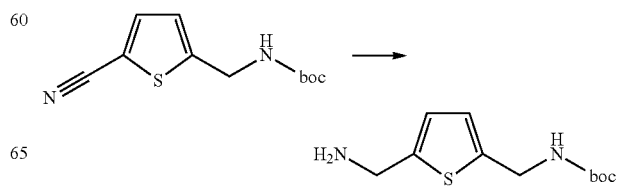

3.10.2
5-N-Boc-aminomethyl-2-aminomethylthiophene hydrochloride 23.8 g 5-N-Boc-aminomethyl-2-cyanothiophene are placed in 1 l ethanol and 50 ml of methanolic ammonia and hydrogenated with 40 g Raney nickel under a pressure of 40 bar. The catalyst is suction filtered, the filtrate evaporated down. The residue is taken up in tert-butylmethylether and while cooling with ice carefully precipitated as the hydrochloride with isopropanol/HCl. 32.8 g of the product are obtained as a powder.

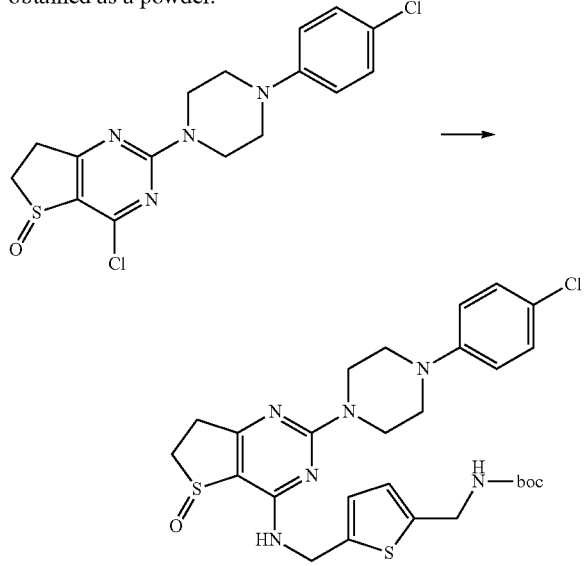

3.103 tert-butyl[5-({2-[4-(4-chloro-phenyl)-piperazin-1-yl]-5-oxo-6,7-dihydro-5H-5$\lambda^4$-thieno[3,2-d]pyrimidin-4-ylamino}-methyl)-thiophen-2-ylmethyl]-carbamidate (Scheme 3, Step D)

200 mg 4-chloro-2-[4-(4-chloro-phenyl)-piperazin-1-yl]-6,7-dihydro-thieno[3,2-d]pyrimidine 5-oxide (cf Example 124), 436.6 mg 5-N-Boc-aminomethyl-2-aminomethylthiophene hydrochloride and 269.4 µl diisopropylethylamine are placed in 4 ml dioxane, heated to 120° C. in the microwave for 0.3 hours. Then the reaction mixture is mixed with water. The precipitated substance is suction filtered and washed with water. The product is purified by semipreparative HPLC (method A). 130 mg of the product are obtained as a powder. Analytical HPLC-MS, (method B): RT=2.06 min.

3.11 Synthesis of (5-aminomethyl-thiophen-2-ylmethyl)-{2-[4-(4-chloro-phenyl)-piperazin-1-yl]-5-oxo-6,7-dihydro-5H-5$\lambda^4$-thieno[3,2-d]pyrimidin-4-yl}-amine, Examples 122 (See Scheme 3)

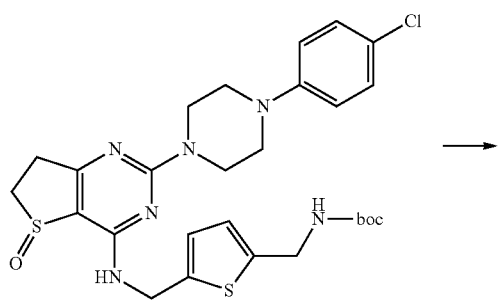

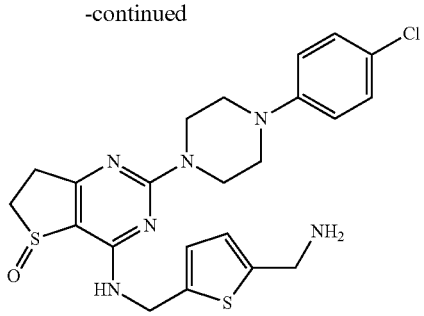

100 mg tert-butyl[5-({2-[4-(4-chloro-phenyl)-piperazin-1-yl]-5-oxo-6,7-dihydro-5H-5$\lambda^4$-thieno[3,2-d]pyrimidin-4-ylamino}-methyl)-thiophen-2-ylmethyl]-carbamidate (cf a Example 101) are suspended in 1 ml dichloromethane, 315 µl trifluoroacetic acid are added and the mixture is stirred for 2 days at ambient temperature. Then the reaction mixture is evaporated to dryness. 134 mg of the product are obtained as an oil. Analytical HPLC-MS (method A): RT=2.34 min.

3.12 Synthesis of 5-({2-[4-(4-chloro-phenyl)-piperazin-1-yl]-5-oxo-6,7-dihydro-5H-5$\square^4$-thieno[3,2-d]pyrimidin-4-ylamino}-methyl)-2-methyl-2H-pyrazol-3-ol, Example 110 (See Scheme 3)

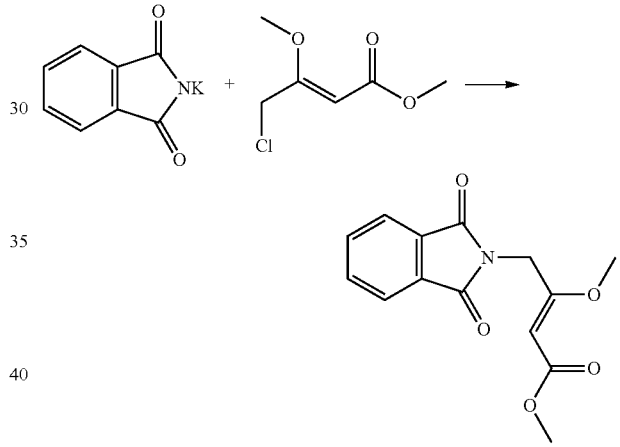

3.12.1 methyl (Z)-4-(1,3-dioxo-1,3-dihydro-isoindol-2-yl)-3-methoxy-but-2-enoate 18.5 potassium phthalimide are suspended in 50 ml DMF, the mixture is heated to 60° C. and 16.5 g methyl 4-chloro-3-methoxy-but-2-enoate in 50 ml DMF are added. After 2 days the reaction mixture is poured into 500 ml of water. The precipitate formed is suction filtered and washed with water. The residue is dissolved in ethyl acetate, dried and the solution is evaporated to dryness. The residue is triturated with ether. 21.77 g of the product are obtained as a powder.

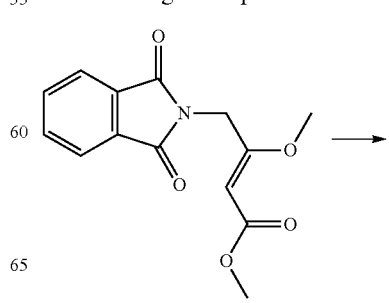

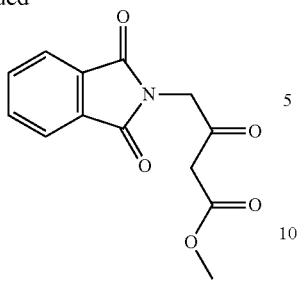

3.12.2 methyl 4-(1,3-dioxo-1,3-dihydro-isoindol-2-yl)-3-oxo-butyrate 7.4 g conc. sulphuric acid are suspended in 100 ml methylene chloride and 21.0 g methyl (Z)-4-(1,3-dioxo-1,3-dihydro-isoindol-2-yl)-3-methoxy-2-ene-butyrate are added. The suspension is stirred at ambient temperature. After 12 hours the reaction mixture is added to 1 l ether and stirred for 30 min. The precipitate formed is filtered and washed with ether. 16.69 g of the product are obtained as a powder.

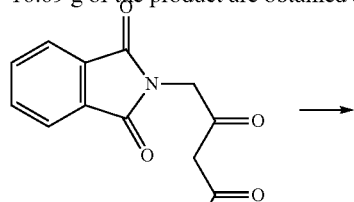

3.12.3 2-(5-hydroxy-1-methyl-1H-pyrazol-3-ylmethyl)-isoindol-1,3-dione 10.0 g methyl 4-(1,3-dioxo-1,3-dihydro-isoindol-2-yl)-3-oxo-butyrate are dissolved at 60° C. in 200 ml of ethanol and 1.94 g methylhydrazine are added. The reaction mixture is cooled and stirred further at ambient temperature. After 5 hours the precipitated substance is suction filtered and washed with ethanol. 7.91 g of the product are obtained as a powder.

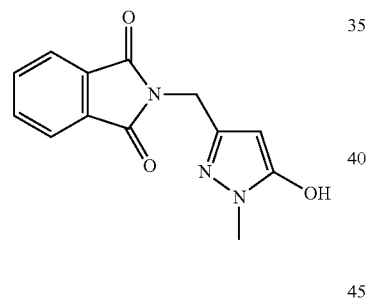

3.12.4 5-aminomethyl-2-methyl-2H-pyrazol-3-ole 1 is 7.88 g 2-(5-hydroxy-1-methyl-1H-pyrazol-3-ylmethyl)-isoindol-1,3-dione are suspended in 150 ml hydrochloric acid (6 M) and stirred at reflux temperature. After 4 hours the reaction mixture is cooled and left to stand overnight at 0° C. The precipitated substance is filtered. The filtrate is evaporated down and crystallised in ether/methanol. 4.9 g of the product are obtained as a powder.

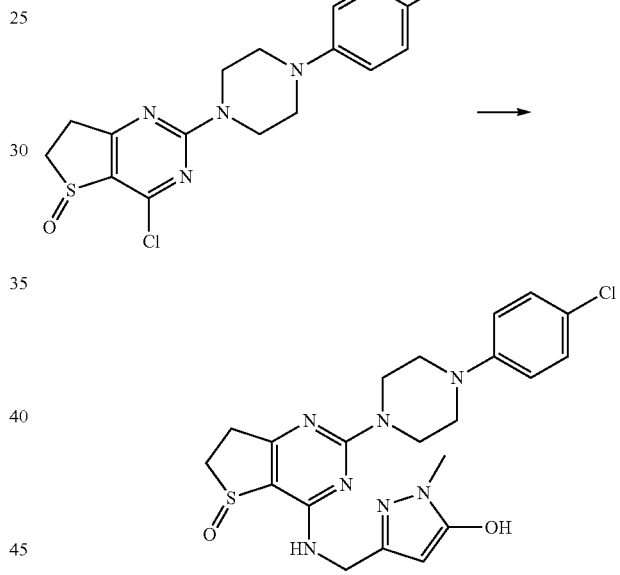

3.12.5 5-({2-[4-(4-chloro-phenyl)-piperazin-1-yl]-5-oxo-6,7-dihydro-5H-5λ⁴-thieno[3,2-d]pyrimidin-4-ylamino}-methyl)-2-methyl-2H-pyrazol-3-ol
(Scheme 3, step D)

200 mg 4-chloro-2-[4-(4-chloro-phenyl)-piperazin-1-yl]-6,7-dihydro-thieno[3,2-s d]pyrimidine 5-oxide (cf Example 124), 313.3 mg 5-aminomethyl-2-methyl-2H-pyrazol-3-ol and 359.25 µl diisopropylethylamine are placed in 4 ml dioxane, heated to 130° C. in the microwave for 0.3 hours and for a further 0.3 hours to 130° C. Then the reaction mixture is mixed with water. The precipitated substance is suction filtered and washed with water. The product is purified by semipreparative HPLC (method A). 130 mg of the product are obtained as a powder. Analytical HPLC-MS (method B): RT=1.61 min.

3.13 Synthesis of {2-[4-(4-chloro-phenyl)-piperazin-1-yl]-5-oxo-6,7-dihydro-5H-5λ⁴-thieno[3,2-d]pyrimidin-4-yl}-(3H-imidazo[4,5-C]pyridin-2-ylmethyl)-amine, Example 104 (See Scheme 3)

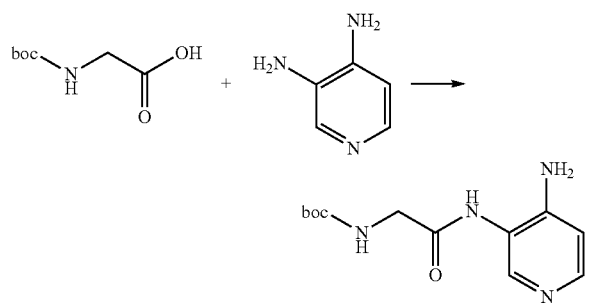

3.13.1 tert.butyl[(4-amino-pyridin-3-ylcarbamoyl)-methyl]-carbamidate 16.05 g N-Boc-glycine and 16.34 g carbonyldiimidazole are dissolved in 100 ml DMF under nitrogen and the mixture is stirred for 15 minutes at ambient temperature. 10.0 g of 3,4-diaminopyridine and 22.16 ml N-methylmorpholine are added. After 2 days the reaction mixture is evaporated down and the residue is combined with water and dichloromethane and extracted. The water phase is evaporated down. The crude product is purified by chromatography (silica gel, $CH_2Cl_2$/EtOH 95/5 to 60/40). 23.46 g of the product (70%) are obtained as an oil.

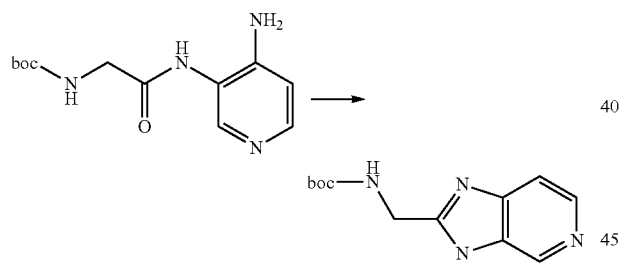

3.13.2 tert.butyl(3H-imidazo[4,5-c]pyridin-2-ylmethyl)-carbamidate 23.0 g tert.butyl[(4-amino-pyridin-3-ylcarbamoyl)-methyl]-carbamidate are suspended in 80 ml DMF and 3.45 ml glacial acetic acid are added. Under argon the reaction mixture is refluxed with stirring. After 4 hours the suspension is cooled slightly and 3 ml acetic acid are added. The reaction mixture is refluxed with stirring. After 12 hours the reaction mixture is evaporated down. The crude product is purified by chromatography (silica gel, $CH_2Cl_2$/EtOH 100/0 to 70/30). 14.15 g of the product are obtained.

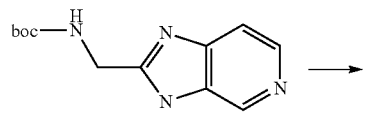

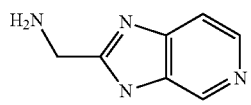

3.13.3 C-(3H-imidazo[4,5-c]pyridin-2-yl)-methylamine 14.15 g tert.butyl(3H-imidazo[4,5-c]pyridin-2-ylmethyl)-carbamidate are suspended in 100 ml of ethanolic HCl and stirred at ambient temperature. The reaction mixture is evaporated down. 12.8 g of the product are obtained. TLC (silica gel, $CH_2Cl_2$/EtOH 80/20, Rf=0.07).

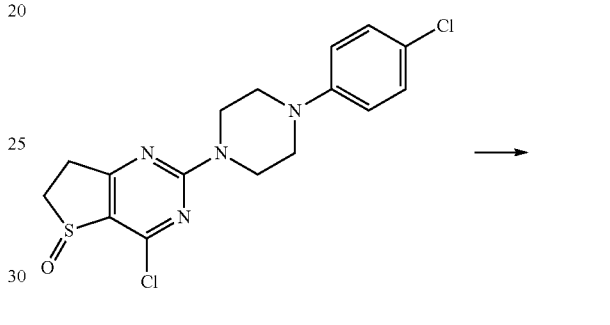

3.13.4 {2-[4-(4-(4-chloro-phenyl)-piperazin-1-yl]-5-exo-6,7-dihydro-5H-5λ⁴-thieno[3,2-d]pyrimidin-4-yl}-(3H-imidazo[4,5-c]pyridin-2-ylmethyl)-amine (Scheme 3, step D)

200 mg 4-chloro-2-[4-(4-chloro-phenyl)-piperazin-1-yl]-6,7-dihydro-thieno[3,2-d]pyrimidine 5-oxide (cf Example 124), 346.22 mg C-(3H-imidazo[4,5-c]pyridin-2-yl)-methylamine and 359.24 µl diisopropylethylamine are placed in 4 ml dioxane, heated to 120° C. in the microwave for 0.3 hours and heated for another 0.3 hours at 120° C. Then the reaction mixture is mixed with water. The precipitated substance is suction filtered and washed with water. The product is purified by semipreparative HPLC (method A). 50 mg of the product are obtained as a powder. Analytical HPLC-MS (method B): RT=1.55 min.

3.14 Synthesis of [(R)-1-(6-chloro-1H-benzimidazol-2-yl)-2-methoxy-ethyl]-{2-[4-(4-chloro-phenyl)-piperazin-1-yl]-5-oxo-6,7-dihydro-5H-5λ⁴-thieno[3,2-d]pyrimidin-4-yl}-amine, Example 106 (See Scheme 3)

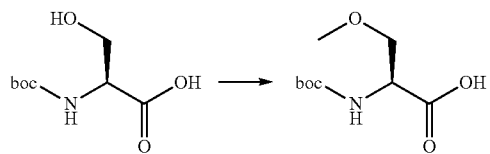

3.14.1 (S)-2-tert-butoxycarbonylamino-3-methoxy-propionic acid

Under nitrogen a mixture of 74 ml abs. THF and 6 ml abs. methanol is cooled to −70° C. and 2 g sodium hydride (55-65% dispersion) are added. The suspension is stirred for 0.4 hour at ambient temperature. Under nitrogen, 2.05 g N-Boc-L-serine are suspended in 100 ml abs. THF and 40 ml of the prepared sodium ethoxide solution are added. The suspension is stirred for 1 hour at ambient temperature and 1 ml methyliodide are added. After 1 hour the remainder of the sodium ethoxide solution and another 2 ml of methyliodide are added. After 18 hours the reaction mixture is evaporated to dryness. The residue is washed with water and ether and extracted. The water phase is acidified and extracted with ethyl acetate and dichloromethane. 0.52 g of the product are obtained.

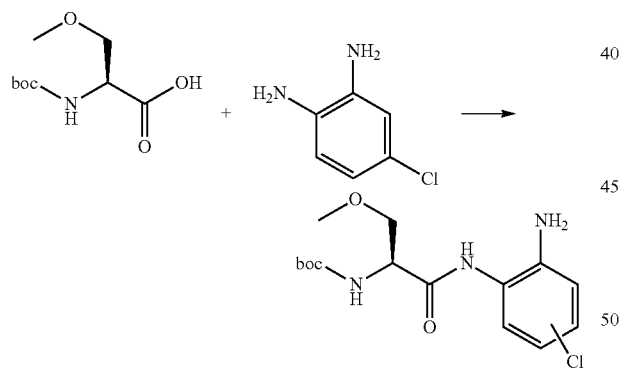

3.14.2 tert.butyl[(S)-1-(2-amino-4/5-chloro-phenyl-carbamoyl)-2-methoxy-ethyl]-carbamidate Under nitrogen 6.65 g (S)-2-tert-butoxycarbonylamino-3-methoxy-propionic acid and 4.33 g 4-chloro-1,2-phenylendiamine are suspended in 100 ml abs. THF and cooled to 5° C. 6.26 g dicyclohexylcarbodiimide in 50 ml abs. THF are slowly added dropwise. The reaction mixture is stirred for 0.5 hour at 5° C. and then at ambient temperature. After 18 hours the precipitated dicyclohexylurea is filtered off and the filtrate is evaporated to dryness. The crude product is purified by chromatography (silica gel, petroleum ether then petroleum ether/ethyl acetate (90/10), (80/20), (50/50) and (30/70)). 1.85 g of the product are obtained as a mixture of isomers.

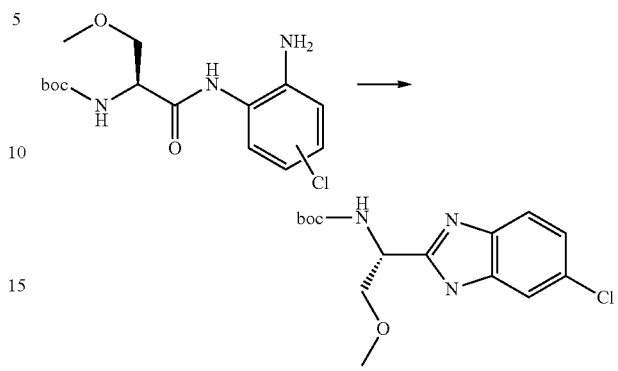

3.14.2 tert.butyl[(R)-1-(6-chloro-1H-benzimidazol-2-yl)-2-methoxy-ethyl]-carbamidate 5.0 g tert.butyl[(S)-1-(2-amino-4/5-chloro-phenylcarbamoyl)-2-methoxy-ethyl]-carbamidate as a mixture of isomers are suspended in 60 ml glacial acetic acid and stirred at 55° C. After 4 hours the glacial acetic acid is distilled off to leave of the volume. The suspension is cooled and made basic (pH 8) with ammonia (2N). The precipitated product is filtered off, washed with water and stirred with 40 ml of ethanol/ethyl acetate/ether/petroleum ether (1/1/1/1). 3.95 g of the product are obtained as a powder.

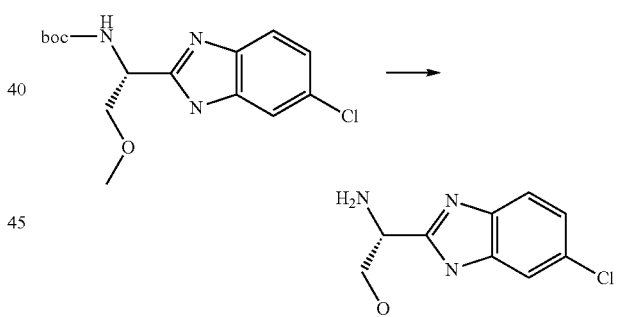

3.14.3 (R)-1-(6-chloro-1H-benzimidazol-2-yl)-2-methoxy-ethylamine 1.4 g tert.butyl[(R)-1-(6-chloro-1H-benzimidazol-2-yl)-2-methoxy-ethyl]-carbamidate are suspended in 10 ml dichloromethane and while cooling with an ice bath combined with 3.5 ml trifluoroacetic acid. The reaction mixture is stirred at ambient temperature and after 2 hours it is combined with 50 ml dichloromethane and 200 ml of water and extracted. The water phase is extracted with 50 ml ether, made basic (pH 9.5) with ammonia (conc.) and extracted with 150 ml of ethyl acetate. The residue is triturated in ether. 450 mg of the product are obtained as a powder.

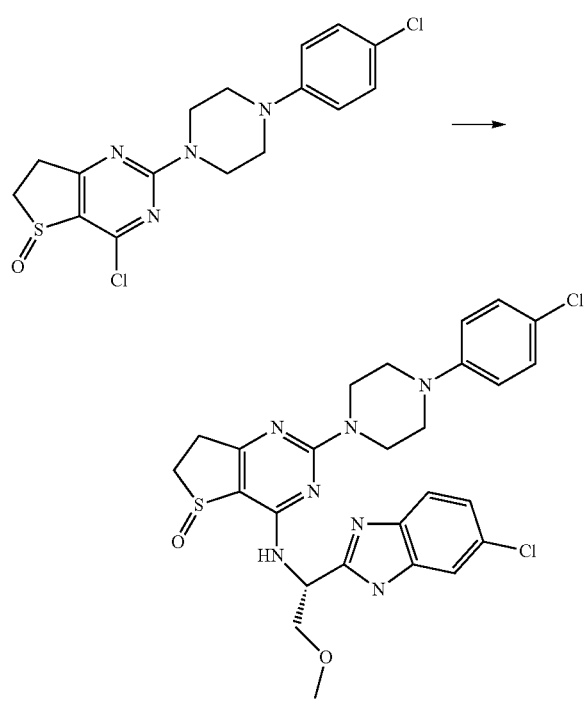

3.14.4 [(R)-1-(6-chloro-1H-benzimidazol-2-yl)-2-methoxy-ethyl]-{2-[4-(4-chloro-phenyl)-piperazin-1-yl]-5-oxo-6,7-dihydro-5H-5λ⁴-thieno[3,2-d]pyrimidin-4-yl}-amine (Scheme 3, Step D)

200 mg 4-chloro-2-[4-(4-chloro-phenyl)-piperazin-1-yl]-6,7-dihydro-thieno[3,2-d]pyrimidine 5-oxide (cf Example 124), 235 mg (R)-1-(6-chloro-1H-benzimidazol-2-yl)-2-methoxy-ethylamine and 179.62 µl diisopropylethylamine are placed in 4 ml dioxane, and the mixture is heated to 120° C. in the microwave for 0.3 hours. Then the reaction mixture is combined with water and dichloromethane and extracted. The product is purified by semipreparative HPLC (method A). 113 mg of the product are obtained as a powder. Analytical HPLC-MS, (method B): RT=1.88 min.

3.15 Synthesis (1R,2R)-1-(6-chloro-1H-benzimidazol-2-yl)-1-{2-[4-(4-chloro-phenyl)-piperazin-1-yl]-5-oxo-6,7-dihydro-5H-5λ⁴-thieno[3,2-]pyrimidin-4-ylamino}-propan-2-ol, Example 107 (See Scheme 3)

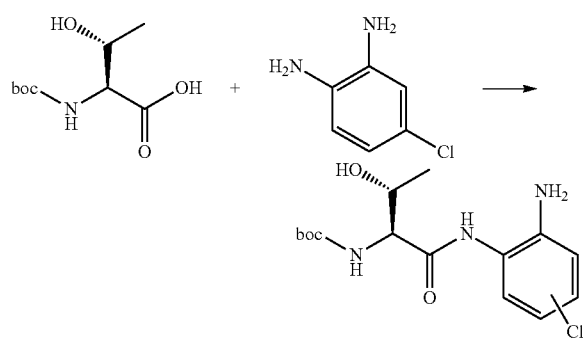

3.15.1 tert.butyl[(1S,2R)-1-(2-amino-4/5-chloro-phenylcarbamoyl)-2-hydroxy-propyl]-carbamidate 3.48 g (L)-threonine and 2.15 g 4-chloro-1,2-phenylenediamine are suspended in 50 ml THF, 6.27 ml triethylamine and 5.14 g O-(benzotriazol-1-yl-)-N,N,N',N'-tetramethyluronium tetrafluoroborate (TBTU) are added. The reaction mixture is stirred overnight at ambient temperature and evaporated to dryness. The residue is dissolved in 150 ml ethyl acetate and washed with 2×50 ml citric acid (5%) and 2×50 ml NaOH (2M). The crude product is recrystallised from tert-butylmethylether/petroleum ether. 1.93 g of the product are obtained as a mixture of isomers.

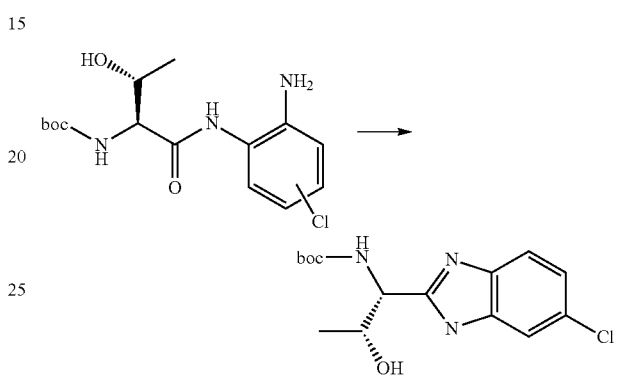

3.15.2 tert.butyl[(1R,2R)-1-(6-chloro-1H-benzimidazol-2-yl)-2-hydroxy-propyl]-carbamidate 1.80 g tertbutyl[(1S,2R)-1-(2-amino-4/5-chloro-phenylcarbamoyl)-2-hydroxy-propyl]-carbamidate as a mixture of isomers are suspended in 15 ml glacial acetic acid and stirred at 60° C. After 1 hour the reaction mixture is added to an NaOH solution (10 g NaOH in 100 ml of water). The crude product is extracted with ethyl acetate and purified by chromatography (silica gel, ethyl acetate/petroleum ether (50/50)). 1.7 g of the product are obtained as a foam.

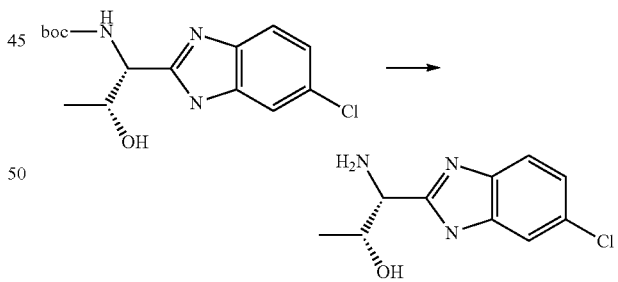

3.15.3 (1R,2R)-1-amino-1-(6-chloro-1H-benzimidazol-2-yl)-propan-2-ol 1.65 g tert.butyl[(1R,2R)-1-(6-chloro-1H-benzimidazol-2-yl)-2-hydroxy-propyl]-s carbamidate are suspended in 5 ml dichloromethane and combined with 5.0 ml trifluoroacetic acid. The reaction mixture is stirred at ambient temperature and after 3 hours mixed with water. The aqueous phase is made basic with NaOH and the product is extracted with tert-butylmethylether. 1.04 g of the product are obtained as a powder.

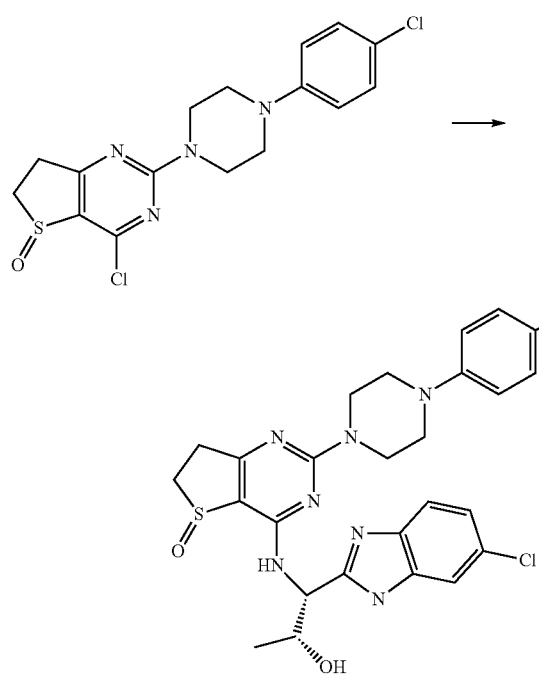

3.15.4 (1R,2R)-1-(6-chloro-1H-benzimidazol-2-yl)-1-{2-[4-(4-chloro-phenyl)-piperazin-1-yl]-5-oxo-6,7-dihydro-5H-5λ⁴-thieno[3,2-d]pyrimidin-4-ylamino}-propan-2-ol (Scheme 3, Step D)

200 mg 4-chloro-2-[4-(4-chloro-phenyl)-piperazin-1-yl]-6,7-dihydro-thieno[3,2-d]pyrimidine 5-oxide (cf Example 124), 353.41 mg (R)-1-(6-chloro-1H-benzimidazol-2-yl)-2-methoxy-ethylamine and 179.62 µl diisopropylethylamine are placed in 4 ml dioxane, heated to 120° C. in the microwave for 2×0.3 hours. Then the reaction mixture is combined with water and dichloromethane and extracted. The product is purified by semipreparative HPLC (method A). 150 mg of the product are obtained as a powder. Analytical HPLC-MS (method B): RT=1.90 min.

3.16 Synthesis of C—((R)-1-{(2-[4-(4-chloro-phenyl)-piperazin-1-yl]-5-oxo-6,7-dihydro-5H-5λ⁴-thieno[3,2-d]pyrimidin-4-yl}-pyrrolidin-2-yl)-methylamine trifluoroacetate, Example 224 (See Scheme 3, Step D)

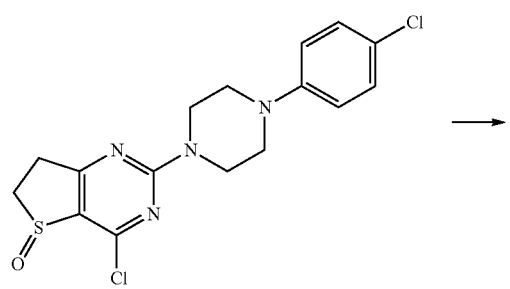

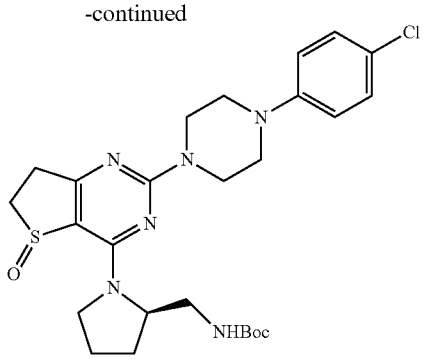

3.16.1 tert.Butyl((R)-1-{2-[4-(4-chloro-phenyl)-piperazin-1-yl]-5-oxo-6,7-dihydro-5H-5λ⁴-thieno[3,2-d]pyrimidin-4-yl}-pyrrolidin-2-ylmethyl)-carbamidate, Example 219 (Scheme 3, Step D)

200 mg of 4-chloro-2-[4-(4-chloro-phenyl)-piperazin-1-yl]-6,7-dihydro-thieno[3,2-d]pyrimidine 5-oxide (cf Example 124), 314 mg (R)-2-N-BOC-aminomethylpyrrolidine and 179.6 µl diisopropylethylamine are placed in 4 ml DMF and heated to 120° C. in the microwave for 0.3 hours. Then the reaction mixture is acidified with trifluoroacetic acid and mixed with water. The product is separated by semipreparative HPLC (method A). 68 mg product (Example 219) are obtained as a powder. Analytical HPLC-MS (method B): RT=2.0 min.

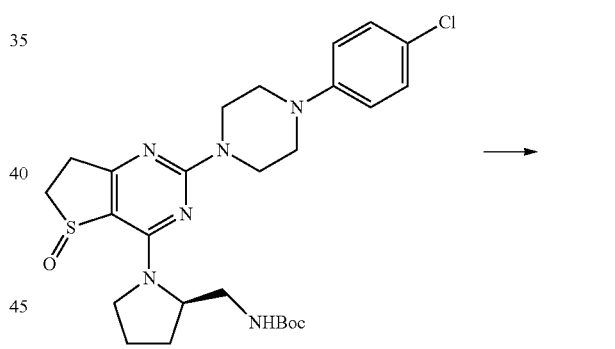

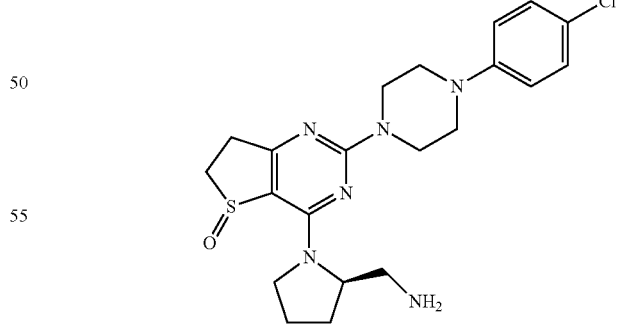

3.16.2 C—((R)-1-{2-[4-(4-chloro-phenyl)-piperazin-1-yl]-5-oxo-6,7-dihydro-5H-5λ⁴-thieno[3,2-d]pyrimidin-4-yl}-pyrrolidin-2-yl)-methylamine trifluoroacetate 38 mg tert.butyl ((R)-1-{2-[4-(4-chloro-phenyl)-piperazin-1-yl]-5-oxo-6,7-dihydro-5H-5λ⁴-thieno[3,2-d]pyrimidin-4-yl}-pyrrolidin-2-ylmethyl)-carbamidate are suspended in 1 ml dichloromethane and 86 µl trifluoroacetic acid are added. The reaction mixture is stirred at ambient temperature and after 12 hours evaporated to dryness. The diastereomers are separated by semipreparative HPLC (method A). 7.6 mg of Diastereomer 1 (Example 224) and 8.3 mg of Diastereomer 2 are obtained as the trifluoroacetate. Analytical HPLC-MS (method B): Diastereomer 1: RT=1.56 min; Diastereomer 2: RT=1.61 min.

3.17 Synthesis of C—((S)-1-{2-[4-(4-chloro-phenyl)-piperazin-1-yl]-5-oxo-6,7-dihydro-5H-5λ4-thieno[3,2-d]pyrimidin-4-yl}-pyrrolidin-2-yl)-methylamine, Examples 225 and 226 (See Scheme 3, Step D)

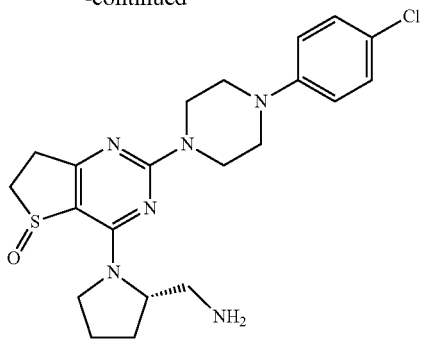

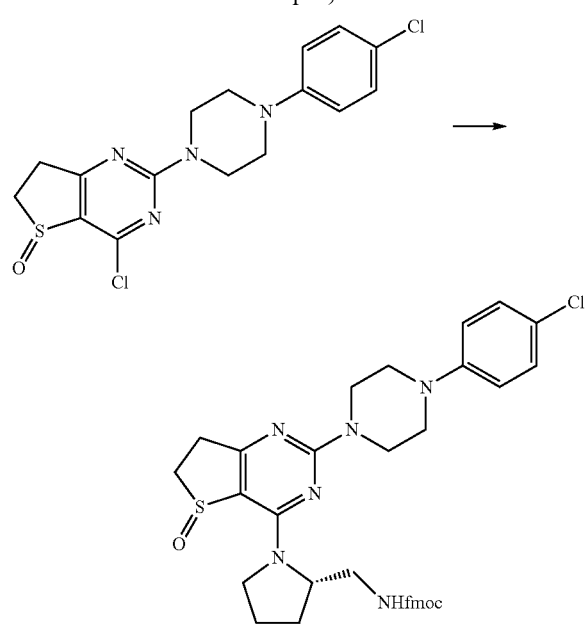

3.17.1 9H-fluoren-9-ylmethyl((S)-1-{2-[4-(4-chloro-phenyl)-piperazin-1-yl]-5-oxo-6,7-dihydro-5H-5λ4-thieno[3,2-d]pyrimidin-4-yl}-pyrrolidin-2-ylmethyl)-carboxylate (Scheme 3, Step D)

3.0 g 4-chloro-2-[4-(4-chloro-phenyl)-piperazin-1-yl]-6,7-dihydro-thieno[3,2-d]pyrimidine 5-oxide (cf Example 124), 2.8 g (S)-2-N-FMOC-aminomethylpyrrolidine and 2.7 ml diisopropylethylamine placed in 24 ml DMF. The reaction mixture is divided into 3 and heated to 120° C. in the microwave for 0.3 hours. Then the reaction mixture is diluted with dichloromethane and filtered. The filtrate is evaporated to dryness. 6.6 g product are obtained as an oil.

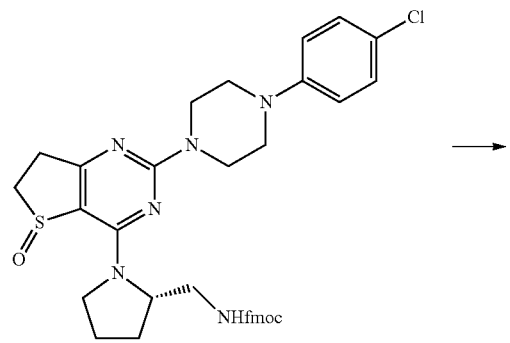

3.17.2 C—((S)-1-{2-[4-(4-chloro-phenyl)-piperazin-1-yl]-5-oxo-6,7-dihydro-5H-5λ$^4$-thieno[3,2-d]pyrimidin-4-yl}-pyrrolidin-2-yl)methylamine trifluoroacetate (see scheme 3)

6.6 g 9H-fluoren-9-ylmethyl((S)-1-{2-[4-(4-chloro-phenyl)-piperazin-1-yl]-5-oxo-6,7-dihydro-5H-5λ$^4$-thieno[3,2-d]pyrimidin-4-yl}-pyrrolidin-2-ylmethyl)-carboxylate are suspended in 80 ml dichloromethane and 5.5 ml piperidine are added. The reaction mixture is stirred for 5 hours at ambient temperature and then combined with water and a saturated NaCl solution. The organic phase is dried and evaporated to dryness. The diastereomers are separated by semipreparative HPLC (method B). 880 mg of Diastereomer 1 (Example 225) and 880 mg of Diastereomer 2 (Example 226) are obtained as the trifluoroacetate. Analytical HPLC-MS (method D): Diastereomer 1: RT=1.07 min; Diastereomer 2: RT=1.12 min.

3.18 Synthesis of Methyl(2S,4R)-4-amino-1-{2-[4-(4-chloro-phenyl)-piperazin-1-yl]-5-oxo-6,7-dihydro-5H-5λ$^4$-thieno[3,2-d]pyrimidin-4-yl}-pyrrolidine-2-carboxylate trifluoroacetate, Examples 229 and 230 (See Scheme 3, Step D)

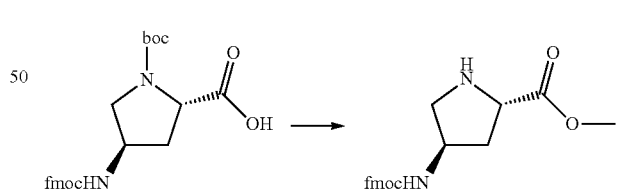

3.18.1 methyl (2S,4R)-4-(9H-fluoren-9-ylmethoxycarbonylamino)-pyrrolidine-2-carboxylate sulphate 850 mg 1-tert.butyl (2S,4R)-4-(9H-fluoren-9-ylmethoxycarbonylamino)-pyrrolidine-1,2-dicarboxylate and 60 µl sulphuric acid are placed in 12 ml abs. methanol. The reaction mixture is then refluxed for 48 hours with stirring and then evaporated to dryness. 1.0 g product is obtained as a foam. Analytical HPLC-MS (method B): RT=1.80 min.

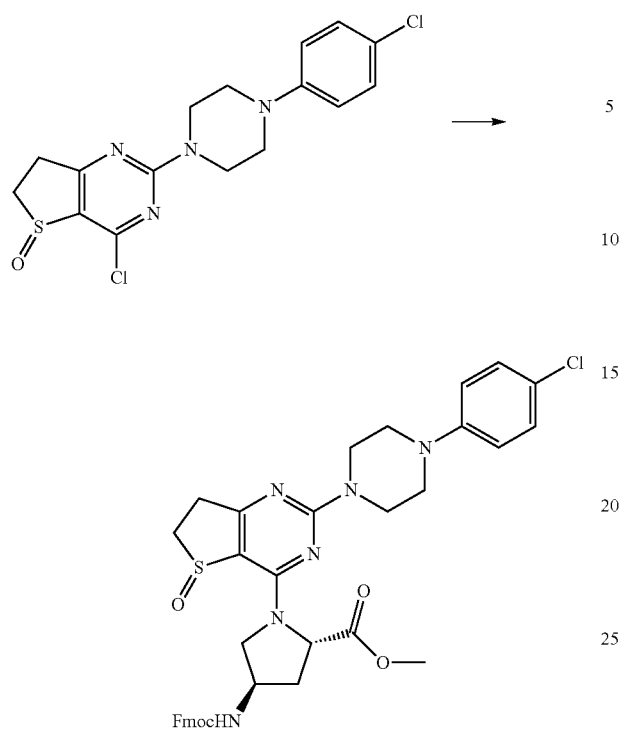

3.18.2 methyl (2S,4R)-1-{2-[4-(4-chloro-phenyl)-piperazin-1-yl]-5-oxo-6,7-dihydro-5H-5λ⁴-thieno[3,2-d]pyrimidin-4-yl}-4-(9H-fluoren-9-ylmethoxycarbonylamino)-pyrrolidine-2-carboxylate trifluoroacetate (Scheme 3, Step D)

280 mg 4-chloro-2-[4-(4-chloro-phenyl)-piperazin-1-yl]-6,7-dihydro-thieno[3,2-d]pyrimidine 5-oxide (cf Example 124), 600 mg methyl (2S,4R)-4-(9H-fluoren-9-ylmethoxycarbonylamino)-pyrrolidine-2-carboxylate and 450 µl diisopropylethylamine are placed in 3 ml dioxane and heated to 120° C. in the microwave for 0.3 hours. Then the reaction mixture is mixed with water. The precipitate formed is suction filtered and purified by preparative HPLC (method B). 200 mg product are obtained as the trifluoroacetate. Analytical HPLC (method B): RT=3.6 min.

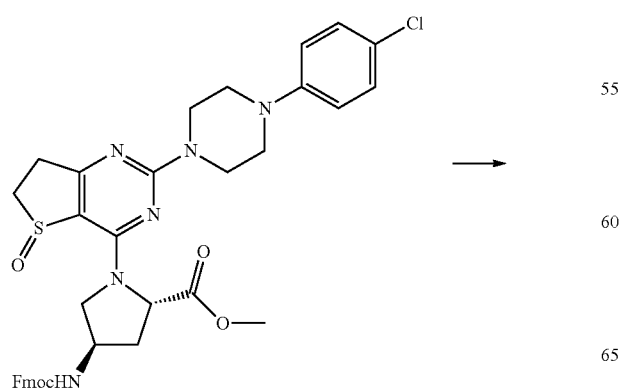

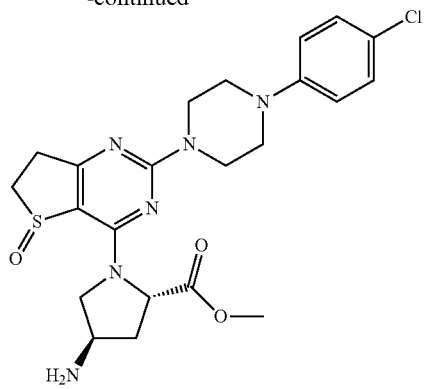

3.18.3 Synthesis of methyl (2S,4R)-4-amino-1-{2-[4-(4-chloro-phenyl)-piperazin-1-yl]-5-oxo-6,7-dihydro-5H-5λ⁴-thieno[3,2-d]pyrimidin-4-yl}-pyrrolidine-2-carboxylate trifluoroacetate 200 mg methyl (2S,4R)-1-{2-[4-(4-chloro-phenyl)-piperazin-1-yl]-5-oxo-6,7-dihydro-5H-5λ⁴-thieno[3,2-d]pyrimidin-4-yl}-4-(9H-fluoren-9-ylmethoxycarbonylamino)-pyrrolidine-2-carboxylate are suspended in 5 ml dichloromethane and combined with 300 µl piperidine. The reaction mixture is stirred at ambient temperature and after 4 hours evaporated to dryness. The diastereomers are separated by preparative HPLC (method B). 52.8 mg of Diastereomer 1 (Example 229) and 49.5 mg of Diastereomer 2 (Example 230) are obtained as the trifluoroacetate. Analytical HPLC (method B): Diastereomer 1: RT=2.79 min; Diastereomer 2: RT=2.83 min.

3.19 Synthesis of (R)-2-{2-[4-(4-chloro-phenyl)-piperazin-1-yl]-5-oxo-6,7-dihydro-5H-5λ⁴-thieno[3,2-d]pyrimidin-4-ylamino}-pentan-1-ol trifluoroacetate, Examples 143 and 144 (See Scheme 3, Step D)

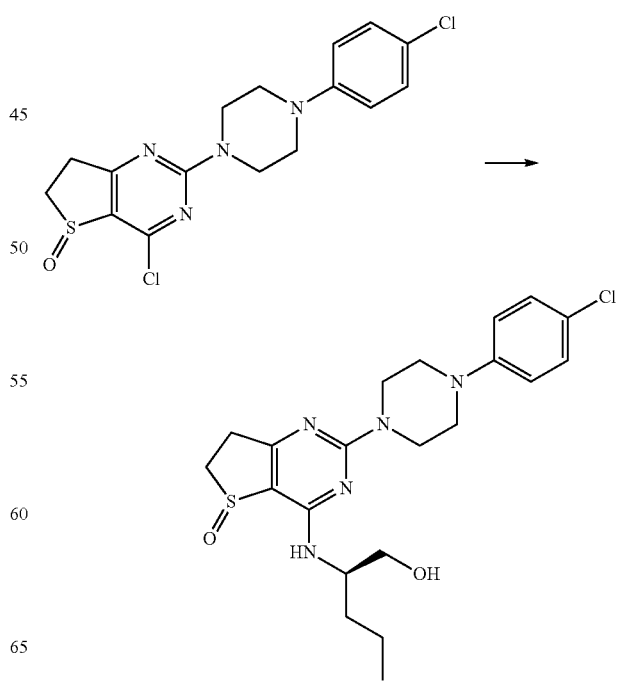

400 mg 4-chloro-2-[4-(4-chloro-phenyl)-piperazin-1-yl]-6,7-dihydro-thieno[3,2-d]pyrimidine 5-oxide (cf Example 124), 321.9 mg (R)-(−)-2-amino-1-pentanol and 362.3 μl diisopropylethylamine are placed in 10 ml dioxane, heated to 120° C. for 0.3 hours in the microwave. Then the reaction mixture is mixed with water, the precipitate formed is suction filtered, washed and dried. The diastereomers are separated by semipreparative HPLC (method B). 180 mg of Diastereomer 1 (Example 143) and 110 mg of Diastereomer 2 (Example 144) are obtained as the trifluoroacetate. Analytical HPLC-MS (method D): Diastereomer 1: RT=1.21 min; Diastereomer 2: RT=1.22 min.

3.20 Synthesis of ((1R,2R)-2-benzyloxy-cyclopentyl)-{2-[4-(4-chloro-phenyl)-piperazin-1-yl]-5-oxo-6,7-dihydro-5H-5λ⁴-thieno[3,2-d]pyrimidin-4-yl}-amine, Examples 61 (Mixture of Diastereomers), 151 (Diastereomer 1) and 152 (Diastereomer 2) (See Scheme 3, Step D)

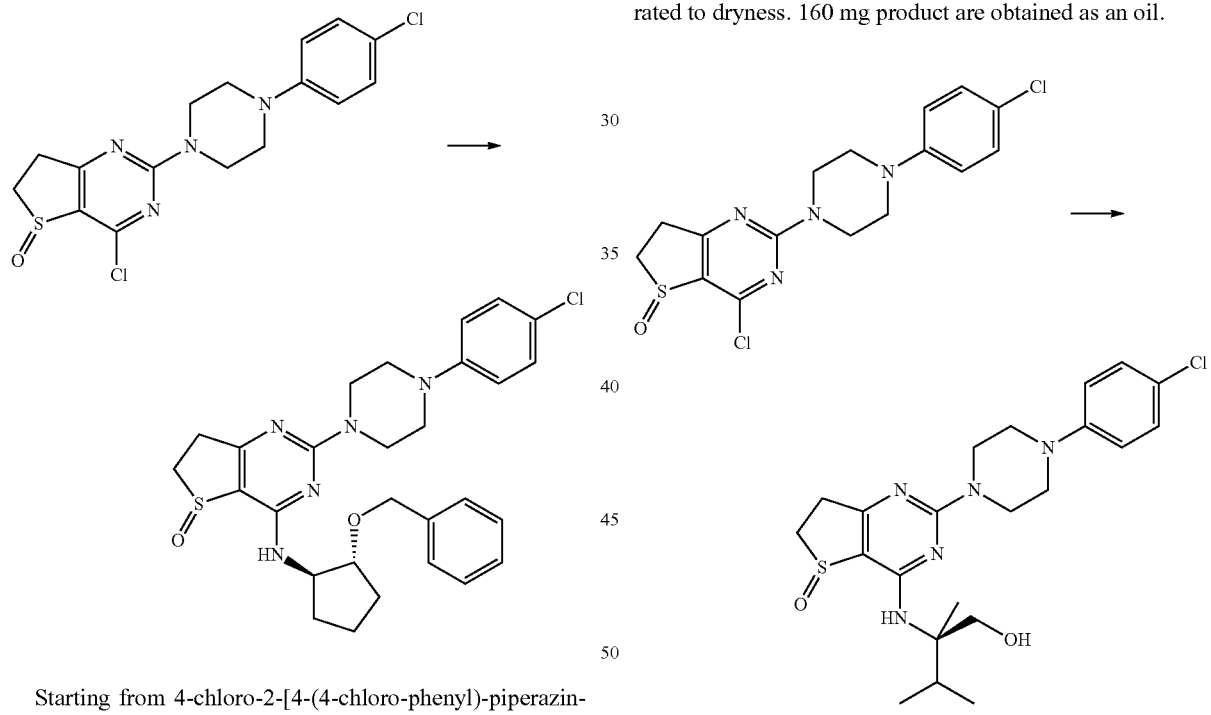

Starting from 4-chloro-2-[4-(4-chloro-phenyl)-piperazin-1-yl]-6,7-dihydro-thieno[3,2-d]pyrimidine 5-oxide (cf Example 124) and (1R,2R)-2-benzyloxycyclopentylamine, ((1R,2R)-2-benzyloxy-cyclopentyl)-{2-[4-(4-chloro-phenyl)-piperazin-1-yl]-5-oxo-6,7-dihydro-5H-5λ⁴-thieno[3,2-d]pyrimidin-4-yl}-amine is prepared as described in Example 124. The product is purified by preparative HPLC (method A). Analytical HPLC-MS (method A): RT=3.09 min.

The two diastereomers may be separated by chiral HPLC (column: Diacel IB, 250×4.6 mm, 5 μm, eluant: (hexane+cyclohexylamine (0.2%))/EtOH (60/40), flow rate: 1 ml/min): Diastereomer 1: RT=5.97 min (Example 151); Diastereomer 2: RT=7.92 min (Example 152).

3.21 Synthesis of (R)-2-{2-[4-(4-chloro-phenyl)-piperazin-1-yl]-5-oxo-6,7-dihydro-5H-5λ⁴-thieno[3,2-d]pyrimidin-4-ylamino}-2,3-dimethyl-butan-1-ol, Example 153 (See Scheme 3)

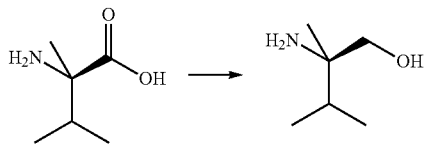

3.21.1 (R)-2-amino-2,3-dimethyl-butan-1-ol

Under argon 140 mg sodium borohydride are placed in 4 ml of tetrahydrofuran, then 200 mg H-α-methyl-D-valinol are added. While cooling with the ice bath 390 mg of iodine in 2 ml THF are slowly added dropwise. The reaction mixture is refluxed with stirring, after 12 hours methanol is added and the mixture is then evaporated to dryness. The residue is suspended in an aqueous KOH solution (20%) and stirred for 2 hours at ambient temperature. The product is then extracted with dichloromethane. The organic phase is dried and evaporated to dryness. 160 mg product are obtained as an oil.

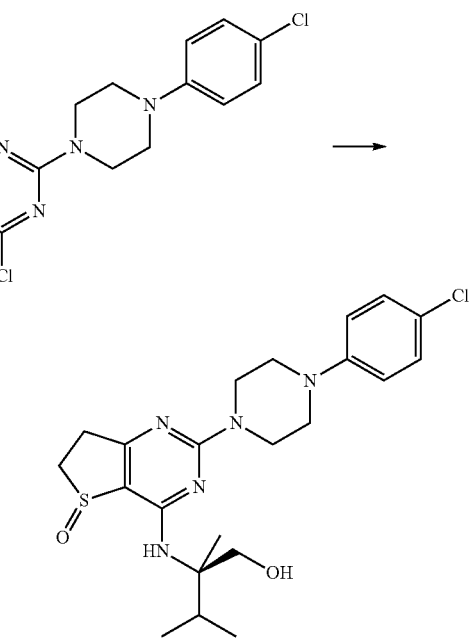

3.21.2 (R)-2-{2-[4-(4-chloro-phenyl)-piperazin-1-yl]-5-oxo-6,7-dihydro-5H-5λ⁴-thieno[3,2-d]pyrimidin-4-ylamino}-2,3-dimethyl-butan-1-ol (Scheme 3, Step D)

Starting from 4-chloro-2-[4-(4-chloro-phenyl)-piperazin-1-yl]-6,7-dihydro-thieno[3,2-d]pyrimidine 5-oxide (cf Example 124) and (R)-2-amino-2,3-dimethyl-butan-1-ol, (R)-2-{2-[4-(4-chloro-phenyl)-piperazin-1-yl]-5-oxo-6,7-dihydro-5H-5λ⁴-thieno[3,2-d]pyrimidin-4-ylamino}-2,3-dimethyl-butan-1-ol is prepared as a mixture of diastereomers. Analytical HPLC-MS (method D): RT=1.27 min (Example 153).

3.22 Synthesis of tert.butyl (R)-3-{2-[4-(4-chloro-phenyl)-piperazin-1-yl]-5-oxo-6,7-dihydro-5H-5λ⁴-thieno[3,2-d]pyrimidin-4-ylamino}-pyrrolidin-1-carboxylate, Example 170 and {2-[4-(4-chloro-phenyl)-piperazin-1-yl]-5-oxo-6,7-dihydro-5H-5λ⁴-thieno[3,2-d]pyrimidin-4-yl}-(R)-pyrrolidin-3-yl-amine, Examples 171 and 172 (See Scheme 3, Step D)

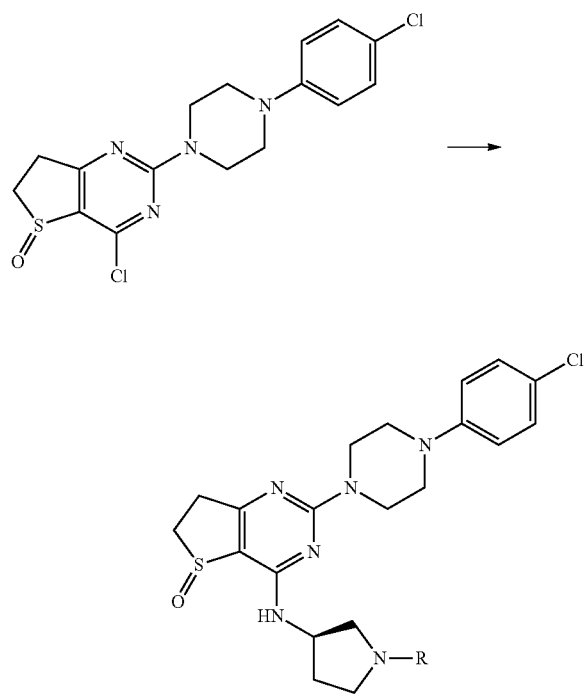

R = Boc (product 1, example 170) R = H (product 2, example 171 and product 3, example 172)

400 mg 4-chloro-2-[4-(4-chloro-phenyl)-piperazin-1-yl]-6,7-dihydro-thieno[3,2-d]pyrimidine 5-oxide (cf Example 124), 320 mg (R)-(+)-1-BOC-3-aminopyrrolidine and 370 µl diisopropylethylamine are placed in 4 ml dioxane, heated to 120° C. in the microwave for 0.3 hours. Then the reaction mixture is mixed with water. The precipitate formed is suction filtered, washed and dried. 80 mg of the product 1 (Example 170) are obtained as a mixture of diastereomers. Analytical HPLC-MS (method D): RT=1.39 min. Product 1 is suspended in 2 ml dichloromethane, then 1.5 ml trifluoroacetic acid is added. The reaction mixture is stirred for 2 hours at ambient temperature and then evaporated to dryness. The diastereomers are separated by preparative HPLC (method B). 96 mg of Diastereomer 1 (Example 171) and 85 mg of Diastereomer 2 (Example 172) are obtained as the trifluoroacetate. Analytical HPLC (method B): Diastereomer 1: RT=2.62 min; Diastereomer 2: RT=2.66 min.

3.23 Synthesis of 4-((R)-2-{2-[4-(4-chloro-phenyl)-piperazin-1-yl]-5-oxo-6,7-dihydro-5H-5λ⁴-thieno[3,2-d]pyrimidin-4-ylamino}-3-hydroxy-propyl)-phenol, Example 175 (See Scheme 3)

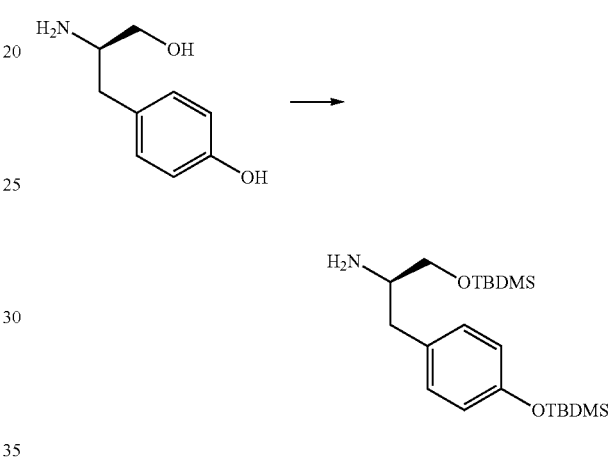

3.23.1 (R)-1-(tert-butyl-dimethyl-silanyloxymethyl)-2-[4-(tert-butyl-dimethyl-silanyloxy)-phenyl]-ethylamine 100 mg D-Tyrosinol hydrochloride are placed in 2 ml dimethylformamide, then 135 mg imidazole are added. The reaction mixture is stirred for 30 minutes at ambient temperature. While cooling with the ice bath 187 mg tert-butyldimethylchlorosilane are then added. The reaction mixture is stirred for 4 hours at ambient temperature and then combined with water and diethyl ether. The organic phase is washed with a saturated NaCl solution, dried and evaporated to dryness. 208 mg of the product are obtained as an oil. Analytical HPLC-MS (method D): RT=1.76 min.

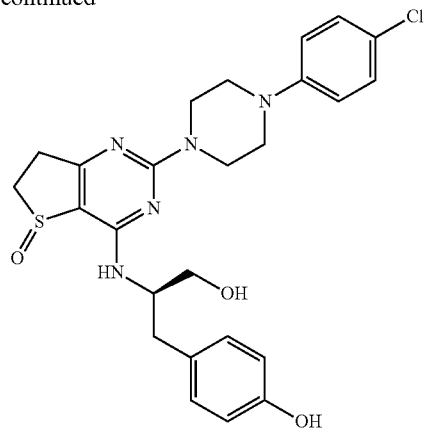

3.23.2 4-((R)-2-{2-[4-(4-chloro-phenyl)-piperazin-1-yl]-5-oxo-6,7-dihydro-5H-5λ⁴-thieno[3,2-d]pyrimidin-4-ylamino}-3-hydroxy-propyl)-phenol (Scheme 3, Step D)

350 mg 4-chloro-2-[4-(4-chloro-phenyl)-piperazin-1-yl]-6,7-dihydro-thieno[3,2-d]pyrimidine 5-oxide (cf Example 124), 600 mg (R)-1-(tert-butyl-dimethyl-silanyloxymethyl)-2-[4-tert-butyl-dimethyl-silanyloxy)-phenyl]-ethylamine and 350 µl diisopropylethylamine are placed in 4 ml dioxane, heated to 120° C. in the microwave for 0.2 hours. Then the reaction mixture is evaporated to dryness. The residue is suspended in water/acetonitrile/trifluoroacetic acid and stirred for 3 hours at ambient temperature. The reaction mixture is evaporated to dryness and the diastereomers are separated by preparative HPLC (method D). Analytical HPLC-MS (method E): Diastereomer 1: RT=1.20 min; Diastereomer 2: RT=1.25 min.

The Diastereomer I chromatographic fractions are combined, the acetonitrile is evaporated down and 600 µl trifluoroacetic acid are added. The reaction mixture is stirred for 3 hours at ambient temperature, made basic with ammonia and combined with dichloromethane. The organic phase is dried and evaporated to dryness. 145 mg of the product (Example 175) are obtained as a solid. Analytical HPLC-MS (method E): RT=0.60 min

3.24 Synthesis of (R)-2-{2-[4-(4-chloro-phenyl)-piperazin-1-yl]-5-oxo-6,7-dihydro-5H-5λ⁴-thieno[3,2-d]pyrimidin-4-ylamino}-3-furan-3-yl-propan-1-ol, Examples 206 and 207 (See Scheme 3)

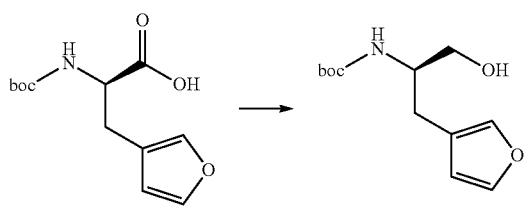

3.24.1 tert-butyl ((R)-1-furan-3-ylmethyl-2-hydroxy-ethyl)-carboxylate

Starting from (R)-2-amino-3-furan-3-yl-propionic acid (DE3829451), (R)-2-tert-butoxycarbonylamino-3-furan-3-yl-propionic acid is prepared. Under argon 420 mg (R)-2-tert-butoxycarbonylamino-3-furan-3-yl-propionic acid are suspended in 2.5 ml dimethoxyethane suspended. The reaction mixture is cooled to −30° C. 220 µl N-methylmorpholine are added and then 240 µl isobutylchloroformate in 1.5 ml dimethoxyethane is added dropwise. The reaction mixture is allowed to come up to −5° C. and the precipitate is quickly filtered. The filtrate is cooled to −15° C. 100 mg sodium borohydride and a few drops of water are added. The reaction mixture is stirred for 1 hour at ambient temperature and evaporated to dryness. The residue is suspended in ethyl acetate. The reaction mixture is dried and evaporated to dryness. 370 mg of the product are obtained as a solid. Analytical HPLC-MS (method D): RT=1.21 min.

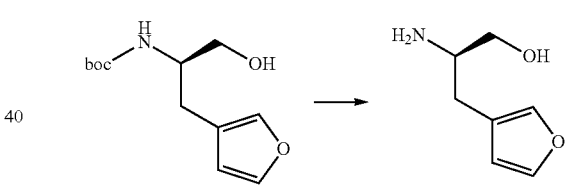

3.24.2 (R)-2-amino-3-furan-3-yl-propan-1-ol trifluoroacetate 970 mg tert.butyl ((R)-1-furan-3-ylmethyl-2-hydroxy-ethyl)-carboxylate are placed in 3 ml dichloromethane and 3 ml trifluoroacetic acid are added. The reaction mixture is stirred for 5 hours at ambient temperature and then evaporated to dryness. 830 mg of the product are obtained as an oil. Analytical HPLC-MS (method D): RT=0.28 min.

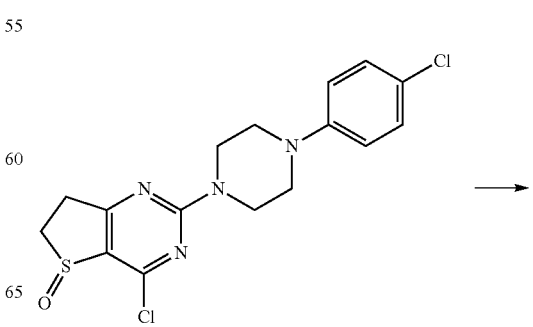

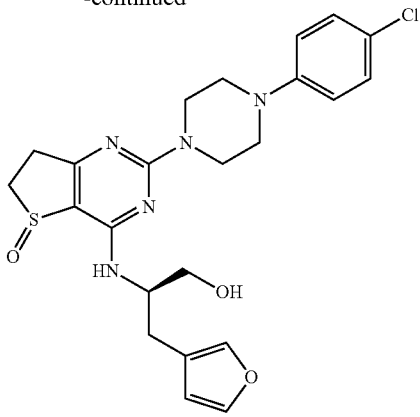

3.24.3 (R)-2-{2-[4-(4-chloro-phenyl)-piperazin-1-yl]-5-oxo-6,7-dihydro-5H-5λ⁴-thieno[3,2-d]pyrimidin-4-ylamino}-3-furan-3-yl-propan-1-ol (Scheme 3, Step D)

Starting from 4-chloro-2-[4-(4-chloro-phenyl)-piperazin-1-yl]-6,7-dihydro-thieno[3,2-d]pyrimidine 5-oxide (cf Example 124, 3.1.3) and (R)-2-amino-3-furan-3-yl-propan-1-ol trifluoroacetate, the two diastereomers of (R)-2-{2-[4-(4-chloro-phenyl)-piperazin-1-yl]-5-oxo-6,7-dihydro-5H-5λ⁴-thieno[3,2-d]pyrimidin-4-ylamino}-3-furan-3-yl-propan-1-ol are prepared as described in Example 124 (cf 3.1.4). The diastereomers are separated by preparative HPLC (method B). Analytical HPLC-MS (method D): Diastereomer 1: RT=1.23 min (Example 206); Diastereomer 2: RT=1.24 min (Example 207).

3.25 Synthesis of (1-{2-[4-(4-chloro-phenyl)-piperazin-1-yl]-5-oxo-6,7-dihydro-5H-5'-thieno[3,2-d]pyrimidin-4-yl}-pyrrolidin-2-ylmethyl)-dimethyl-amine, Example 223 (See Scheme 3, Step D)

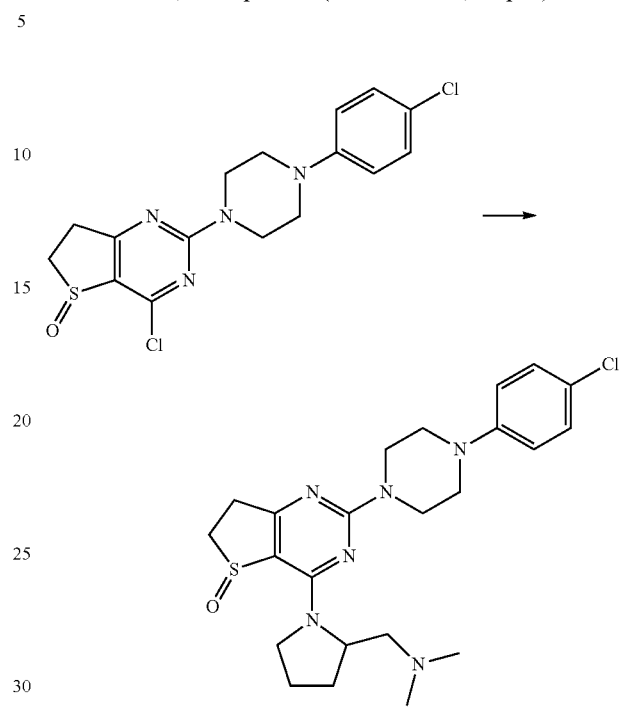

Starting from 4-chloro-2-[4-(4-chloro-phenyl)-piperazin-1-yl]-6,7-dihydro-thieno[3,2-d]pyrimidine 5-oxide (cf Example 124, 3.1.3) and dimethyl-pyrrolidin-2-ylmethyl-amine (*Chem. Pharm. Bull.* 1970, 1731) a mixture of stereoisomers of (1-{2-[4-(4-chloro-phenyl)-piperazin-1-yl]-5-oxo-6,7-dihydro-5H-5λ⁴-thieno[3,2-d]pyrimidin-4-yl}-pyrrolidin-2-ylmethyl)-dimethyl-amine is prepared as described in Example 124 (cf 3.1.4). The diastereomers are separated by semipreparative HPLC (method A). Analytical HPLC-MS (method A): Diastereomer 1: RT=2.29 min; Diastereomer 2: RT=2.38 min (Example 223). Example 223 is obtained as a racemate.

SCHEME 4

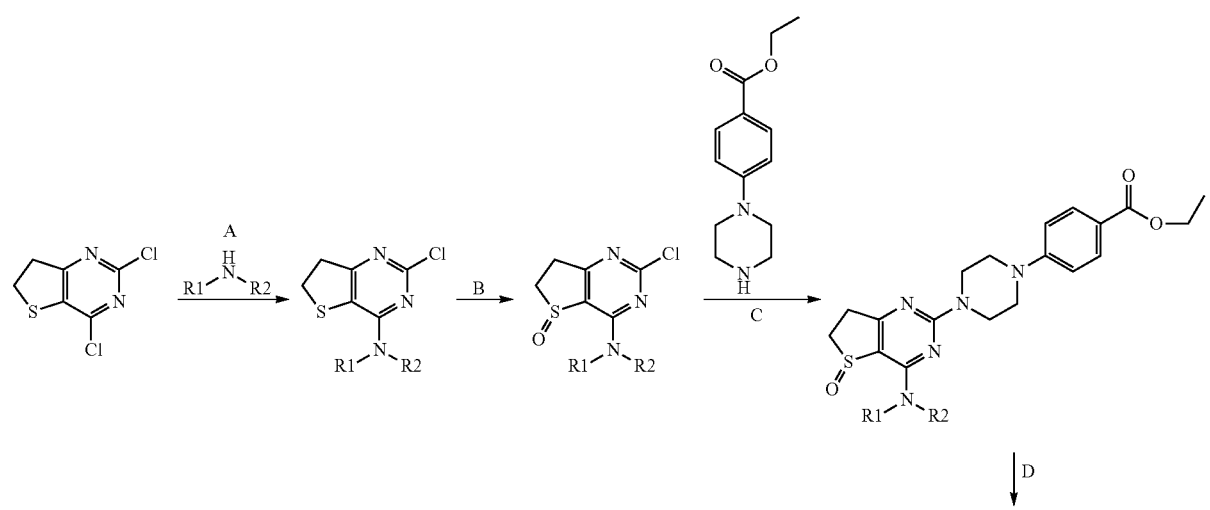

-continued

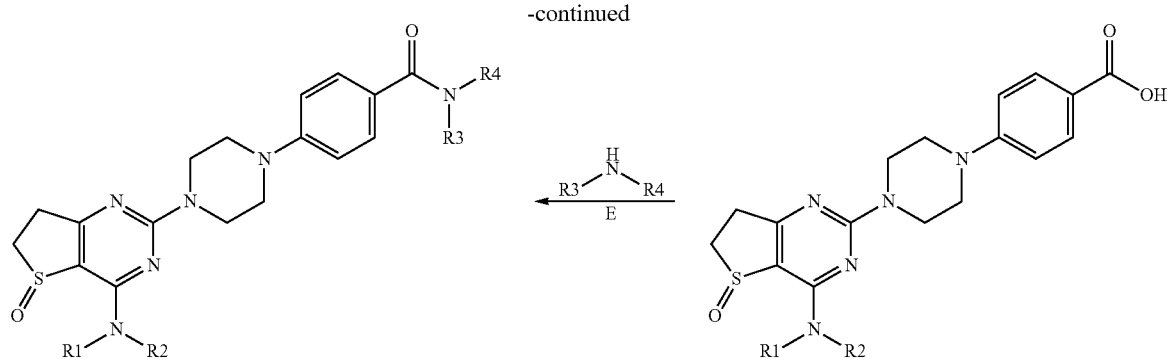

4.1 Synthesis of 4-{4-[4-(3-chloro-phenylamino)-5-oxo-6,7-dihydro-5H-5λ⁴-thieno[3,2-d]pyrimidin-2-yl]-piperazin-1-yl}-N-methyl-N-(1-methyl-piperidin-4-yl)-benzamide trifluoroacetate, Example 11 (See Scheme 4)

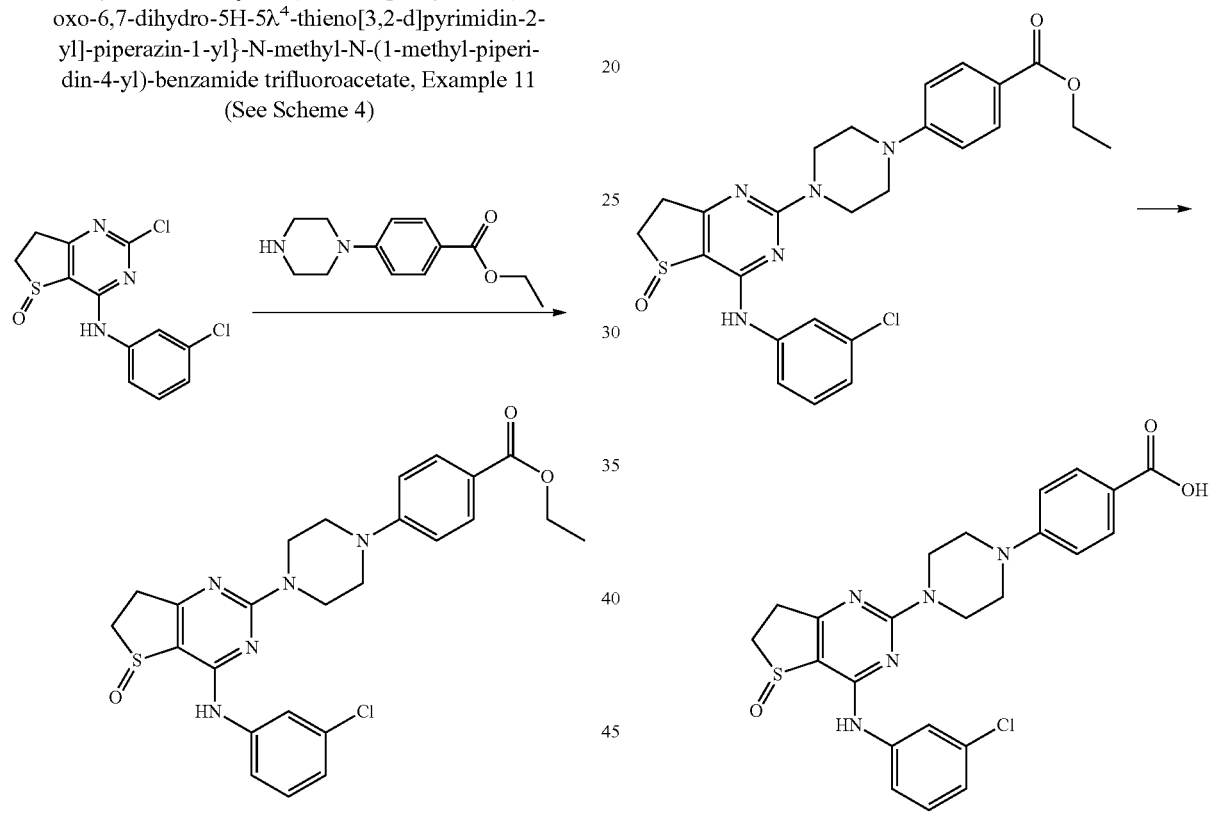

4.1.1 ethyl 4-{4-[4-(3-chloro-phenylamino)-5-oxo-6,7-dihydro-5H-5λ⁴-thieno[3,2-d]pyrimidin-2-yl]-piperazin-1-yl}-benzoate (Scheme 4, Step C)

5.44 g (2-chloro-5-oxo-6,7-dihydro-5H-5λ⁴-thieno[3,2-d]pyrimidin-4-yl)-(3-chloro-phenyl)-amine (prepared from 2,4-dichloro-6,7-dihydro-thieno[3,2-d]pyrimidine and 3-chloroaniline as described in Example 28, see scheme 2), 8.00 g ethyl 4-piperazin-1-yl-benzoate and 4.80 ml diisopropylethylamine are placed in 54 ml dioxane, then heated to 160° C. in the microwave for 0.7 hours. Then the reaction mixture is cooled and mixed with water. The precipitate formed is suction filtered and stirred with petroleum ether/ethyl acetate 1:1, suction filtered and dried. 6.90 g of the product are obtained as a powder.

4.1.2 4-{4-[4-(3-chloro-phenylamino)-5-oxo-6,7-dihydro-5H-5λ⁴-thieno[3,2-d]pyrimidin-2-yl]-piperazin-1-yl}-benzoic acid (Scheme 4, Step D)

6.90 g ethyl 4-{4-[4-(3-chloro-phenylamino)-5-oxo-6,7-dihydro-5H-5λ⁴-thieno[3,2-d]pyrimidin-2-yl]-piperazin-1-yl}-benzoate and 70 ml of 1 molar sodium hydroxide solution are placed in 40 ml of methanol and 40 ml of tetrahydrofuran, then refluxed for 1.5 hours with stirring. The resulting solution is evaporated down, the residue is cooled and acidified slightly with 2 molar hydrochloric acid. The precipitate formed is suction filtered, washed and dried. The substance is stirred with ethyl acetate/methanol 9:1, suction filtered and dried. 3.90 g of the product are obtained as a powder.

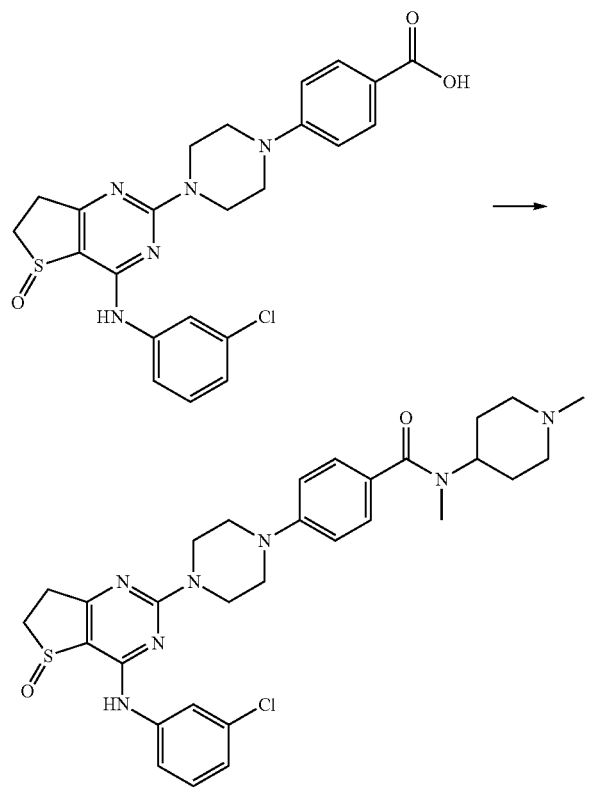

4.13 4-{4-[4-(3-chloro-phenylamino)-5-oxo-6,7-dihydro-5H-5λ⁴-thieno[3,2-d]pyrimidin-2-yl]-piperazin-1-yl}-N-methyl-N-(1-methyl-piperidin-4-yl)-benzamide trifluoroacetate (Scheme 4, Step E)

241.99 mg 4-{4-[4-(3-chloro-phenylamino)-5-oxo-6,7-dihydro-5H-5λ⁴-thieno[3,2-d]pyrimidin-2-yl]-piperazin-1-yl}-benzoic acid are placed in 4 ml dimethylformamide, 69.31 µl triethylamine and 190.10 mg O-(7-azabenzotriazol-1-yl-)-N,N,N',N'-tetramethyluronium-hexafluorophosphate (HATU) are added. The mixture is stirred for 0.25 hours at ambient temperature, then a solution of 96.16 mg methyl-(1-methyl-piperidin-4-yl)-amine in 1 ml dimethylformamide is added. The reaction mixture is stirred for 16 hours at ambient temperature. Then it is evaporated down. The product is purified by preparative HPLC (method C). 213.9 mg of the product (60%) are obtained as the trifluoroacetate. ¹H NMR (400 MHz, DMSO): 7.94-7.88 (m, 1H), 7.70-7.62 (m, 1H), 7.41-7.27 (m, 3H), 7.17-7.10 (m, 1H), 7.04-6.95 (m, 2H).

4.2 4-{4-[4-(3-fluoro-phenylamino)-5-oxo-6,7-dihydro-5H-5λ4-thieno[3,2-d]pyrimidin-2-yl]-piperazin-1-yl}-N,N-dimethyl-benzamide trifluoroacetate, Examples 81 (Racemate), 145 (Enantiomer 2) and 146 (Enantiomer 1) (See Scheme 4, Step E)

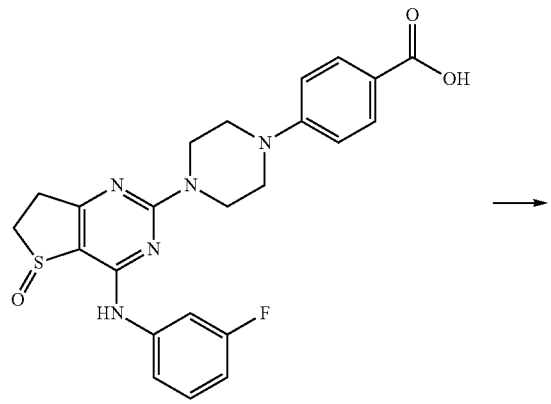

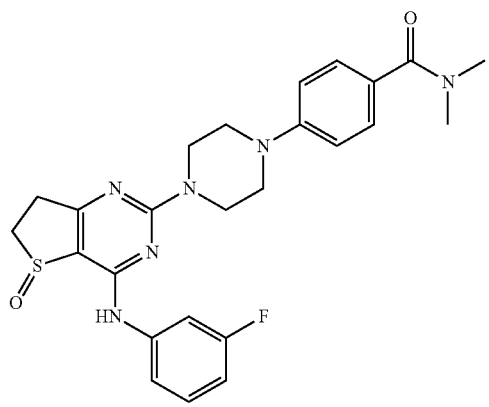

50 mg 4-{4-[4-(3-fluoro-phenylamino)-5-oxo-6,7-dihydro-5H-5λ⁴-thieno[3,2-d]pyrimidin-2-yl]-piperazin-1-yl}-benzoic acid (prepared in a similar manner to that described in Example 11), 44.39 µl diisopropylethylamine and 39.24 mg O-(7-azabenzotriazol-1-yl-)-N,N,N',N'-tetramethyluronium-hexafluorophosphate (HATU) are placed in 2 ml of tetrahydrofuran and 1 ml dimethylsulphoxide is added. Then 43 µl dimethylamine solution (2 molar in tetrahydrofuran) is added. The reaction mixture is stirred for 16 hours at ambient temperature. Then it is evaporated down and the residue is extracted with water and dichloromethane. The organic phase is separated off using a phase transfer cartridge and evaporated to dryness. The crude product is purified by semi-preparative HPLC (method A). 13.2 mg of the product are obtained as the trifluoroacetate. Analytical HPLC-MS, (method B): RT=1.72 min.

The two enantiomers may be separated by chiral HPLC (column: Diacel IA, 250×4.6 mm, 5 µm, eluant: tBuOMe/EtOH (75/25), flow rate: 1 ml/min): enantiomer 1: RT=20.4 min (Example 146); enantiomer 2: RT=24.3 min (Example 145)

Scheme 5

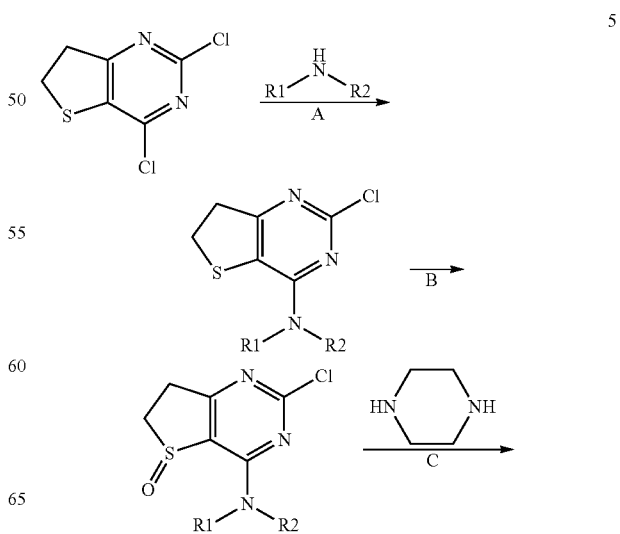

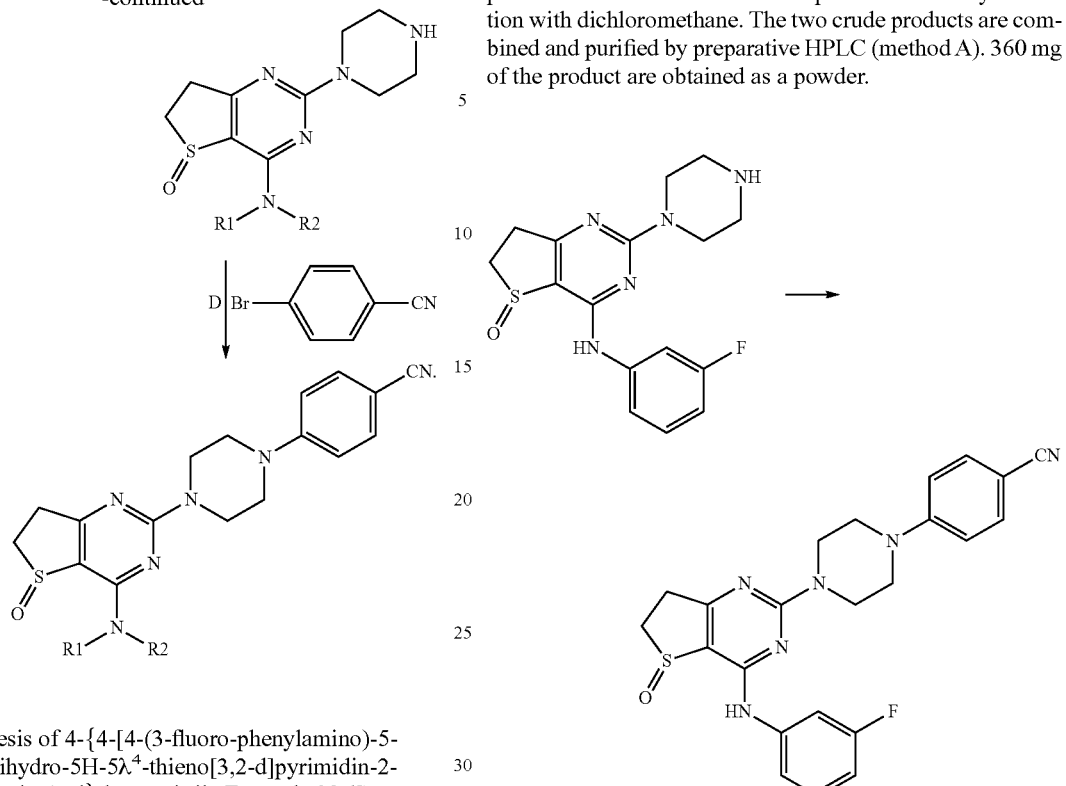

5.1 Synthesis of 4-{4-[4-(3-fluoro-phenylamino)-5-oxo-6,7-dihydro-5H-5λ⁴-thieno[3,2-d]pyrimidin-2-yl]-piperazin-1-yl}-benzonitrile Example 32 (See Scheme 5)

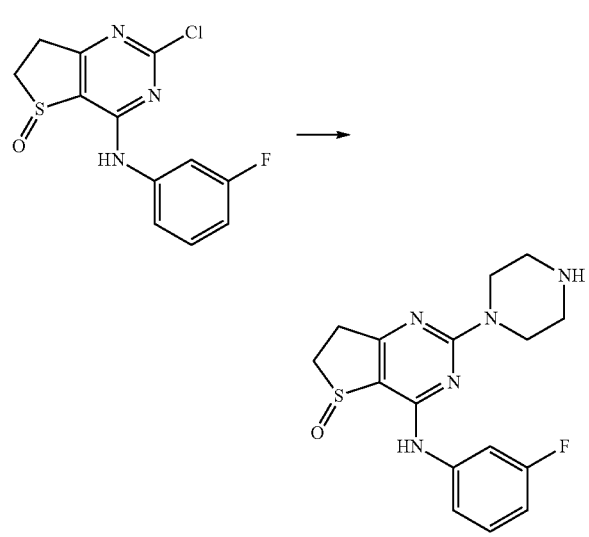

5.1.1 (3-fluoro-phenyl)-5-oxo-2-piperazin-1-yl-6,7-dihydro-5H-5λ⁴-thieno[3,2-d]pyrimidin-4-yl)-amine (Scheme 5, Step C)

0.500 g 2-chloro-5-oxo-6,7-dihydro-5H-5λ⁴-thieno[3,2-d]pyrimidin-4-yl)-(3-fluoro-phenyl)-amine (cf Example 28, Scheme 2) and 1.30 g piperazine are placed in 5 ml dioxane, then heated to 130° C. in the microwave for 0.3 hours. Then the reaction mixture is cooled and mixed with water. The precipitate formed is suction filtered, washed and dried. Any product contained in the mother liquor is obtained by extraction with dichloromethane. The two crude products are combined and purified by preparative HPLC (method A). 360 mg of the product are obtained as a powder.

5.1.2 4-{4-[4-(3-fluoro-phenylamino)-5-oxo-6,7-dihydro-5H-5λ⁴-thieno[3,2-d]pyrimidin-2-yl]-piperazin-1-yl}-benzonitrile (Scheme 5, Step D)

Under an argon atmosphere 315 mg (3-fluoro-phenyl)-(5-oxo-2-piperazin-1-yl-6,7-dihydro-5H-5λ⁴-thieno[3,2-d]pyrimidin-4-yl)-amine, 165 mg 4-bromo-benzonitrile, 21 mg palladium(II)acetate, 80 mg Xantphos and 415 mg caesium carbonate are stirred in 2.50 ml degassed toluene for 24 hours at 80° C. After cooling the reaction mixture is extracted with ethyl acetate and saturated sodium chloride solution. The organic phase is dried and evaporated to dryness. The residue is purified by preparative HPLC (method A). 146 mg of the product (36%) are obtained. HPLC (method A):RT=3.83 min.

5.2 synthesis of 4-[4-(5-oxo-4-propylamino-6,7-dihydro-5H-5λ4-thieno[3,2-d]pyrimidin-2-yl)-piperazin-1-yl]-benzonitrile, Examples 34 (Racemate) and 148 (Enantiomer 1) (See Scheme 5, Step D)

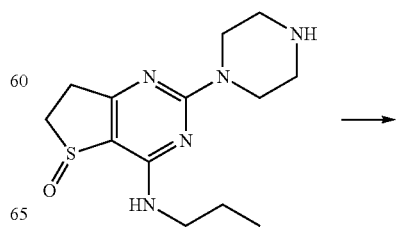

-continued

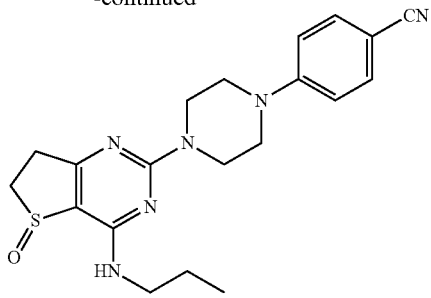

Under an argon atmosphere 400 mg (5-oxo-2-piperazin-1-yl-6,7-dihydro-5H-5λ⁴-thieno[3,2-d]pyrimidin-4-yl)-propylamine (prepared in a similar manner to that described in Example 32), 245 mg 4-bromobenzonitrile, 321 mg palladium(II)acetate, 120 mg Xantphos and 620 mg caesium carbonate are stirred in 2.50 ml degassed toluene for 5 hours at 80° C. After cooling the reaction mixture is extracted with ethyl acetate and saturated sodium chloride solution. The organic phase is dried and evaporated to dryness. The residue is purified by preparative HPLC (method A). 282 mg of the product are obtained as a powder. Analytical HPLC-MS (method A): RT=2.37 min. The two enantiomers may be separated by chiral HPLC (column: Diacel OD-H, 250×4.6 mm, 5 μm, eluant: (hexane+cyclohexylamine (0.2%))/EtOH (65/35), flow rate: 1 ml/min): enantiomer 1: RT=7.9 min (Example 148); enantiomer 2: RT=9.6 min.

6.1 Synthesis of 6-amino-N-(4-{4-[4-(3-chloro-phenylamino)-5-oxo-6,7-dihydro-5H-5λ⁴-thieno[3,2-d]pyrimidin-2-yl]-piperazin-1-yl}-phenyl)-nicotinamide trifluoroacetate, Example 114 (See Scheme 6)

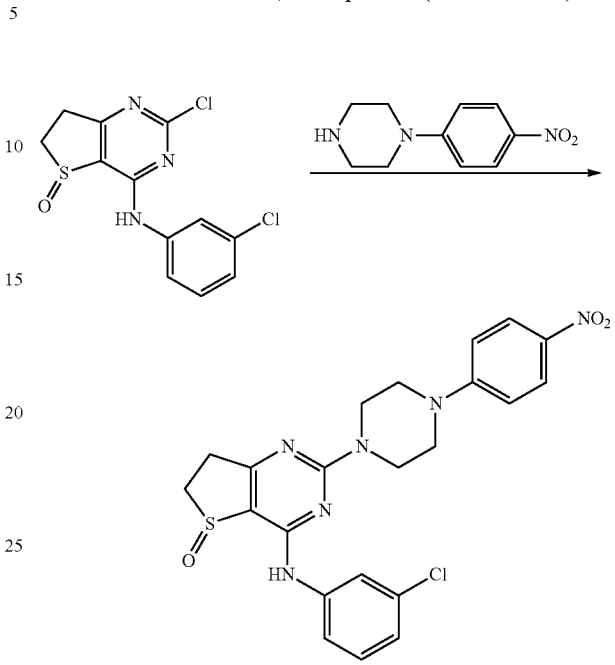

SCHEME 6

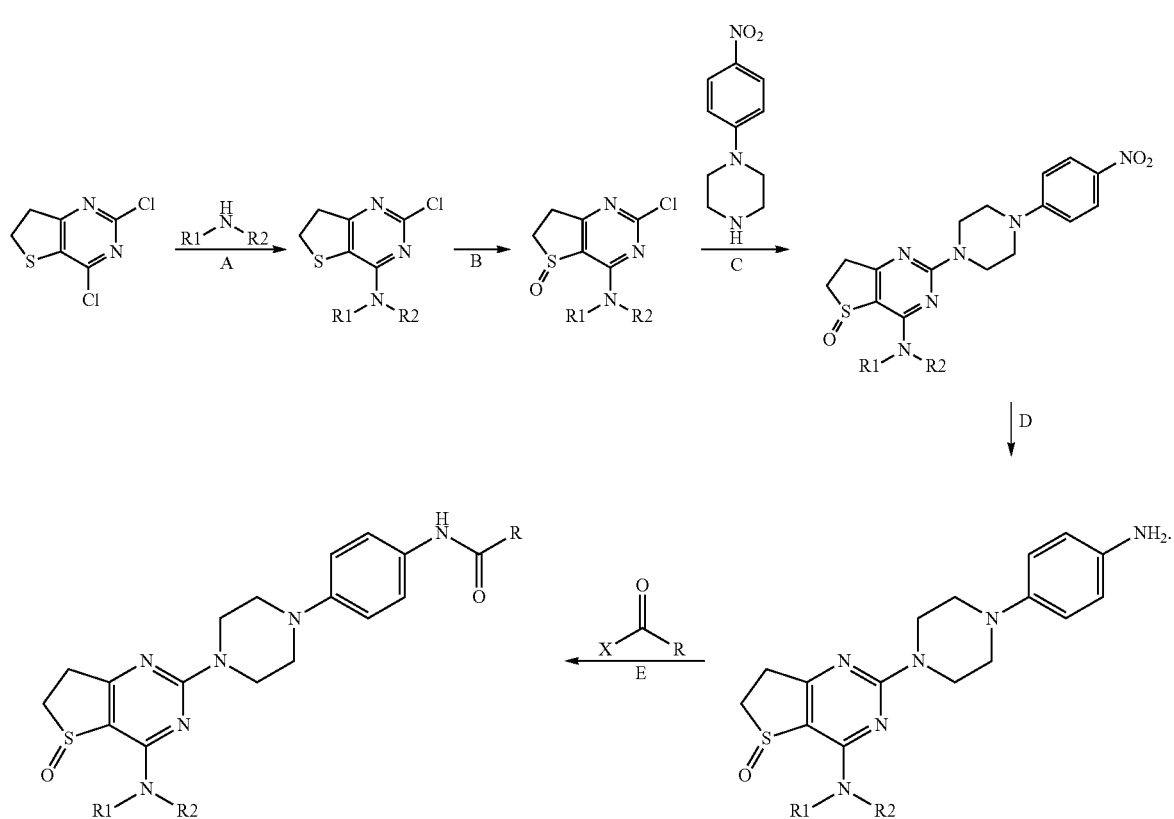

6.1.1 (3-chloro-phenyl)-{2-[1-(4-nitro-phenyl)-piperazin-1-yl]-5-oxo-6,7-dihydro-5H-5λ⁴-thieno[3,2-d]pyrimidin-4-yl}-amine (Scheme 6, Step D)

1.60 g (2-chloro-5-oxo-6,7-dihydro-5H-5λ⁴-thieno[3,2-d]pyrimidin-4-yl)-(3-chloro-phenyl)-amine (prepared from 2,4-dichloro-6,7-dihydro-thieno[3,2-d]pyrimidine and 3-chloroaniline as described in Example 28, see scheme 2), 2.30 g 1-(4-nitro-phenyl)-piperazine and 1.00 ml diisopropylethylamine are placed in 10 ml dioxane, then heated to 160° C. in the microwave for 0.75 hours. Then the reaction mixture is mixed with water, the precipitate formed is suction filtered. The precipitate is extracted first with water, then with ethanol. 2.47 g of the product are obtained as a powder.

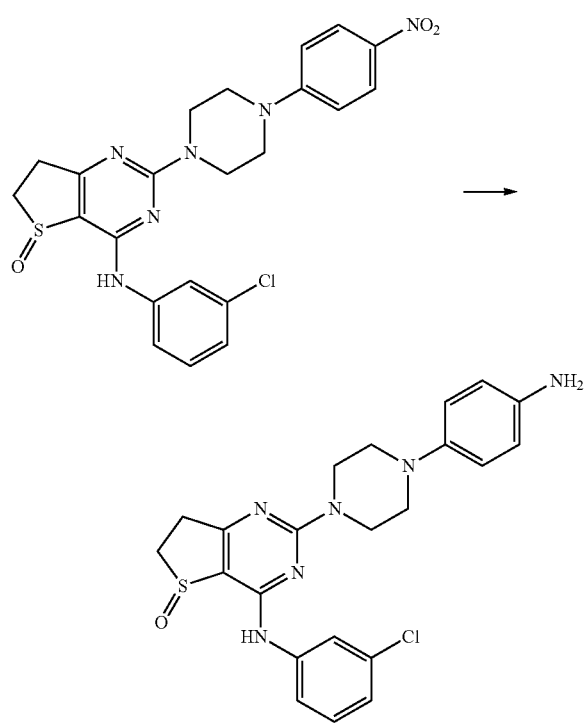

6.1.2 {2-[4-(4-amino-phenyl)-piperazin-1-yl]-5-oxo-6,7-dihydro-5H-5λ⁴-thieno[3,2-d]pyrimidin-4-yl}-(3-chloro-phenyl)-amine trifluoroacetate (Scheme 6, Step C)

1.00 g (3-chloro-phenyl)-{2-[4-(4-nitro-phenyl)-piperazin-1-yl]-5-oxo-6,7-dihydro-5H-5λ⁴-thieno[3,2-d]pyrimidin-4-yl}-amine are placed in 20 ml of methanol and 40 ml of tetrahydrofuran, and hydrogenated with 100 mg Raney nickel for 7 hours at ambient temperature under a pressure of 50 psi. The catalyst is suction filtered, the filtrate is evaporated down. The residue is dissolved in acetonitrile/water and trifluoroacetic acid and purified by preparative HPLC (method A). 0.60 g of the product are obtained as the trifluoroacetate.

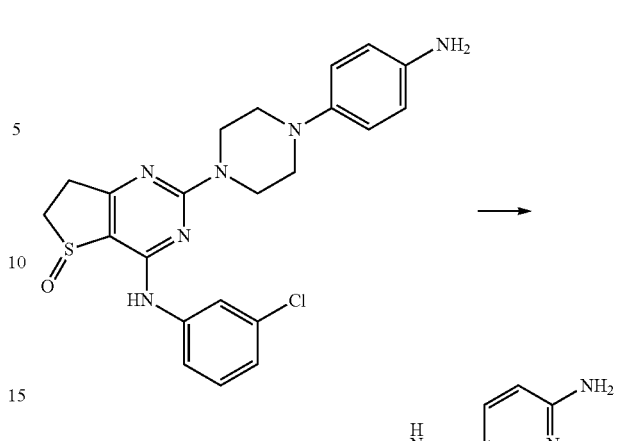

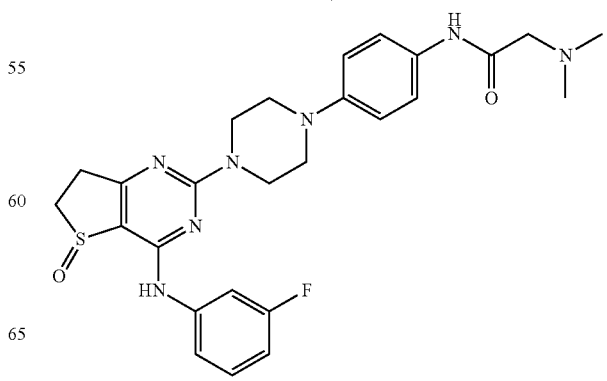

6.1.3 6-amino-N-(4-{4-[4-(3-chloro-phenylamino)-5-oxo-6,7-dihydro-5H-5λ⁴-thieno[3,2-d]pyrimidin-2-yl]-piperazin-1-yl}-phenyl)-nicotinamide trifluoroacetate (Scheme 6, Step E)

200 mg of {2-[4-(4-amino-phenyl)-piperazin-1-yl]-5-oxo-6,7-dihydro-5H-5λ⁴-thieno[3,2-d]pyrimidin-4-yl}-(3-chloro-phenyl)-amine trifluoroacetate are placed in 2.50 ml dimethylsulphoxide and combined with 100 μl diisopropylethylamine and 150 mg O-(7-azabenzotriazol-1-yl-)-N,N,N',N'-tetramethyluronium-hexafluorophosphate (HATU). The mixture is stirred for 0.25 hours at ambient temperature, then 50 mg 6-aminonicotinic acid in 100 μl diisopropylethylamine are added. The reaction mixture is stirred for 16 hours at ambient temperature, then acidified with trifluoroacetic acid and 2 ml of water are added. The resulting salt is purified by preparative HPLC (method A). 140 mg of the product are obtained as the trifluoroacetate. Analytical HPLC (method B): RT=2.74 min.

6.2 Synthesis of 2-dimethylamino-N-(4-{4-[4-(3-fluoro-phenylamino)-5-oxo-6,7-dihydro-5H-5λ⁴-thieno[3,2-d]pyrimidin-2-yl]-piperazin-1-yl}-phenyl)-acetamide, Examples 133 (Racemate), 149 (Enantiomer 2) and 150 (Enantiomer 1) (See Scheme 6)

2-dimethylamino-N-(4-{4-[4-(3-fluoro-phenylamino)-5-oxo-6,7-dihydro-5H-5λ⁴-thieno[3,2-d]pyrimidin-2-yl]-piperazin-1-yl}-phenyl)-acetamide may be prepared as described in Example 114. The product may be purified by preparative HPLC (method B). Analytical HPLC (method B): RT=2.60 min.

The two enantiomers may be separated by chiral HPLC (column: Diacel AD-H, 250×4.6 mm, 5 μm, eluant: (hexane+cyclohexylamine (0.2%)/EtOH (35/65), flow rate: 1 ml/min): enantiomer 1: RT=17.9 min (Example 150); enantiomer 2: RT=37.1 min (Example 149).

SCHEME 7

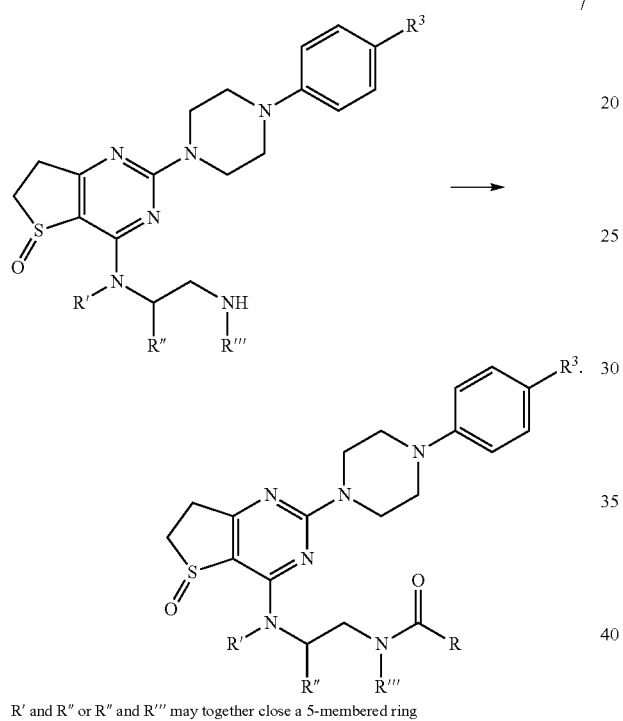

R' and R" or R" and R'" may together close a 5-membered ring 7.1 Synthesis of N—((S)-1-{2-[4-(4-chloro-phenyl)-piperazin-1-yl]-5-oxo-6,7-dihydro-5H-5λ⁴-thieno[3,2-d]pyrimidin-4-yl}-pyrrolidin-2-ylmethyl)-propionamide, Example 231 (See Scheme 7)

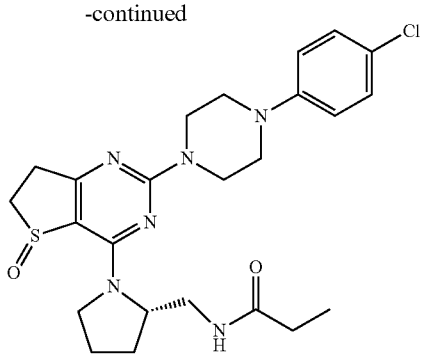

17 μl propionic acid are placed in 800 μl dimethylsulphoxide, and 78 μl diisopropylethylamine and 94 mg O-(7-azabenzotriazol-1-yl-)-N,N,N',N'-tetramethyluronium hexafluorophosphate (HATU) are added. The mixture is stirred for 0.3 hours at ambient temperature, then a solution of 100 mg C—((S)-1-{2-[4-(4-chloro-phenyl)-piperazin-1-yl]-5-oxo-6,7-dihydro-5H-5λ⁴-thieno[3,2-d]pyrimidin-4-yl}-pyrrolidin-2-yl)-methylamine trifluoroacetate, Diastereomer 2 (Example 226) (see scheme 3, 3.17.2), in 700 μl dimethylsulphoxide is added. The reaction mixture is stirred for 15 hours at ambient temperature and then combined with water and dichloromethane. The organic phase is dried and evaporated to dryness. The product is purified by preparative HPLC (method A). 84 mg of the product are obtained as an oil. Analytical HPLC-MS (method D): RT=1.19 min.

7.2 Synthesis of ((R)-3-{2-[4-(4-chloro-phenyl)-piperazin-1-yl]-5-oxo-6,7-dihydro-5H-5λ⁴-thieno[3,2-d]pyrimidin-4-ylamino}-pyrrolidin-1-yl)-(R)-tetrahydro-furan-2-yl-methanone, Example 196 (See Scheme 7)

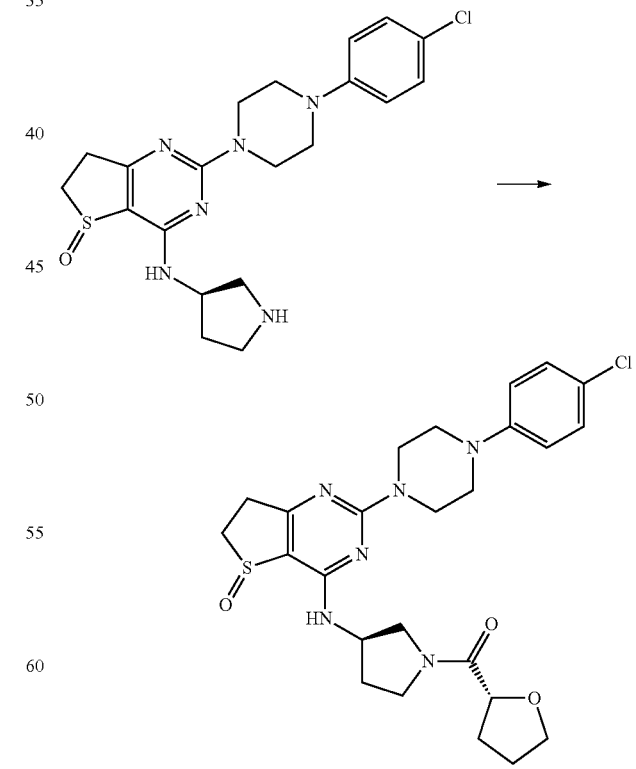

Starting from {2-[4-(4-chloro-phenyl)-piperazin-1-yl]-5-oxo-6,7-dihydro-5H-5λ⁴-thieno[3,2-d]pyrimidin-4-yl}-(R)-pyrrolidin-3-yl-amine Diastereomer 1 (Example 171) (see scheme 3, 3.22) and (R)-(+)-tetrahydrofuran-2-carboxylic acid, Example 196 is prepared as described in Example 231 (see scheme 7). The product is purified by preparative HPLC (method B). Analytical HPLC-MS (method D): RT=1.18 min.

7.3 Synthesis of ((R)-3-{2-[4-(4-chloro-phenyl)-piperazin-1-yl]-5-oxo-6,7-dihydro-5H-5λ⁴-thieno[3,2-d]pyrimidin-4-YLAMINO}-pyrrolidin-1-yl)-(1-methyl-1H-pyrrol-2-yl)-methanone, Example 197 (See Scheme 7)

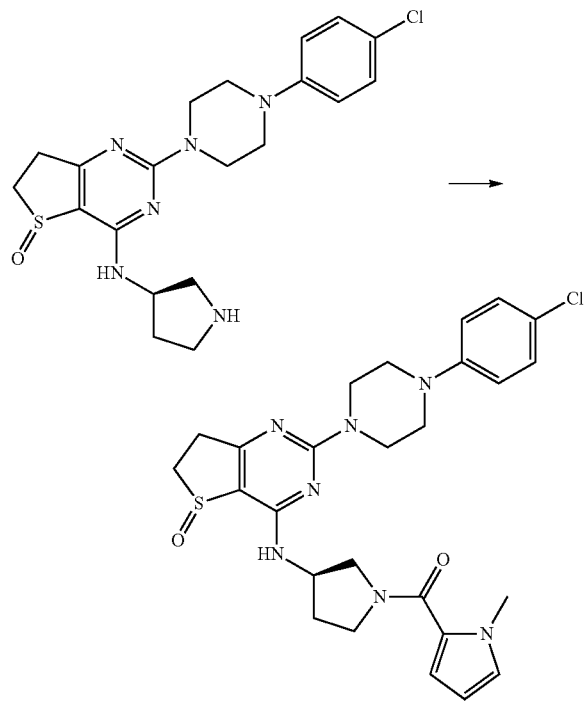

Starting from {2-[4-(4-chloro-phenyl)-piperazin-1-yl]-5-oxo-6,7-dihydro-5H-5λ⁴-thieno[3,2-d]pyrimidin-4-yl}-(R)-pyrrolidin-3-yl-amine Diastereomer 1 (Example 171) (see scheme 3, 3.22) and 1-methylpyrrol-2-carboxylic acid, ((R)-3-{2-[4-(4-chloro-phenyl)-piperazin-1-yl]-5-oxo-6,7-dihydro-5H-5λ⁴-thieno[3,2-d]pyrimidin-4-ylamino}-pyrrolidin-1-yl)-(1-methyl-1H-pyrrol-2-yl)-methanone is prepared as described in Example 231 (see scheme 7). The product is purified by preparative HPLC (method B). Analytical HPLC-MS (method D): RT=1.25 min.

7.4 Synthesis of ((R)-3-{2-[4-(4-chloro-phenyl)-piperazin-1-yl]-5-oxo-6,7-dihydro-5H-5λ⁴-thieno[3,2-d]pyrimidin-4-ylamino}-pyrrolidin-1-yl)-(S)-tetrahydro-furan-2-yl-methanone, Example 198 (See Scheme 7)

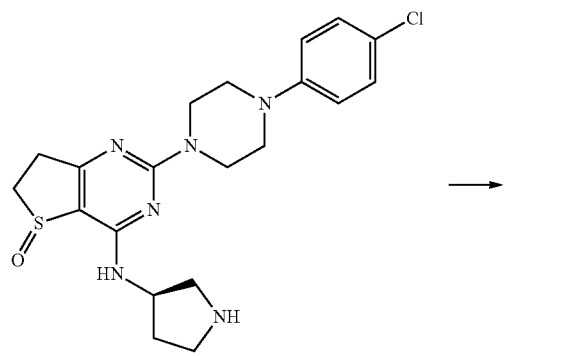

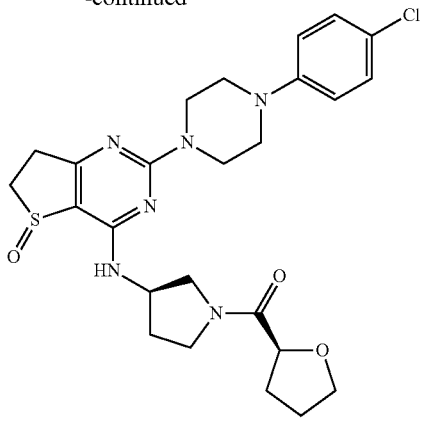

Starting from {2-[4-(4-chloro-phenyl)-piperazin-1-yl]-5-oxo-6,7-dihydro-5H-5λ⁴-thieno[3,2-d]pyrimidin-4-yl}-(R)-pyrrolidin-3-yl-amine Diastereomer 1 (Example 171) (see scheme 3, 3.22) and (S)-(−)-tetrahydrofuran-2-carboxylic acid, ((R)-3-{2-[4-(4-chloro-phenyl)-piperazin-1-yl]-5-oxo-6,7-dihydro-5H-5λ⁴-thieno[3,2-d]pyrimidin-4-ylamino}-pyrrolidin-1-yl)-(S)-tetrahydro-furan-2-yl-methanone is prepared as described in Example 231 (see scheme 7). The product is purified by preparative HPLC (method B). Analytical HPLC-MS (method D): RT=1.17 min.

SCHEME 8

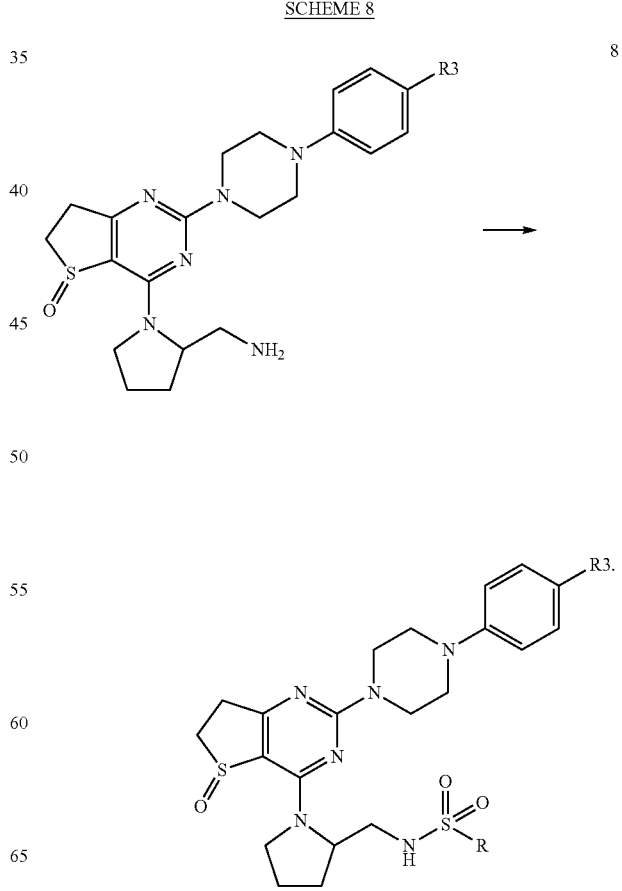

8 Synthesis of N—((S)-1-{2-[4-(4-chloro-phenyl)-piperazin-1-yl]-5-oxo-6,7-dihydro-5H-5λ⁴-thieno[3,2-d]pyrimidin-4-yl}-pyrrolidin-2-ylmethyl)-methanesulphonamide, Example 234 (See Scheme 8)

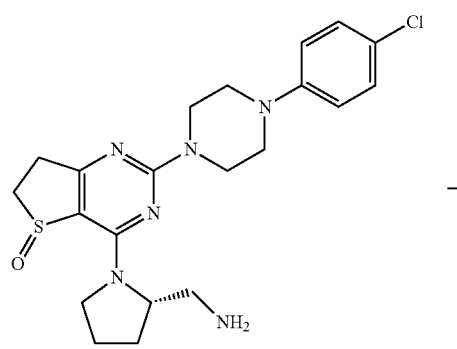

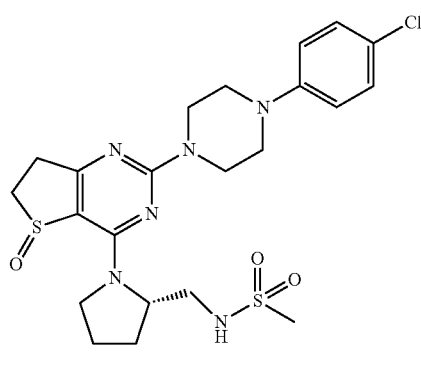

100 mg C—((S)-1-{2-[4-(4-chloro-phenyl)-piperazin-1-yl]-5-oxo-6,7-dihydro-5H-5λ⁴-thieno[3,2-d]pyrimidin-4-yl}-pyrrolidin-2-yl)-methylamine trifluoroacetate, Diastereomer 2 (Example 226) (see scheme 3, 3.17.2) are placed in 2 ml dichloromethane. While cooling with the ice bath, 38 µl triethylamine and, after 5 minutes, 18 µl methanesulphonyl chloridee are added. The reaction mixture is stirred for 12 hours at ambient temperature and then mixed with water. The organic phase is dried and evaporated to dryness. 120 mg of the product are obtained as a powder. Analytical HPLC-MS (method D): RT=1.20 min.

SCHEME 9

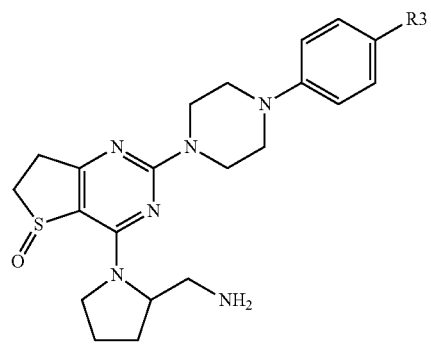

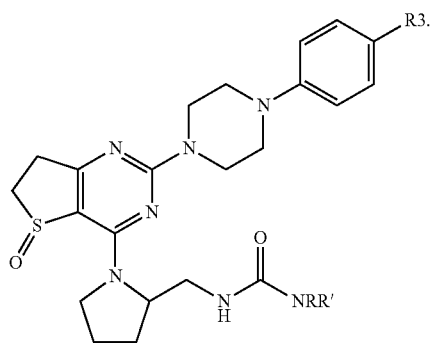

9 Synthesis of 1-((S)-1-{2-[4-(4-chloro-phenyl)-piperazin-1-yl]-5-oxo-6,7-dihydro-5H-5λ⁴-thieno[3,2-d]pyrimidin-4-yl}-pyrrolidin-2-ylmethyl)-3-phenylurea, Example 237 (See Scheme 9)

100 mg C—((S)-1-{2-[4-(4-chloro-phenyl)-piperazin-1-yl]-5-oxo-6,7-dihydro-5H-5λ⁴-thieno[3,2-d]pyrimidin-4-yl}-pyrrolidin-2-yl)-methylamine trifluoroacetate, Diastereomer 2 (Example 226) (see scheme 3, 3.17.2) are placed in 2 ml dichloromethane and 30 µl phenylisocyanate are added. The reaction mixture is stirred for 4 hours at ambient temperature and then evaporated to dryness. The product is purified by preparative HPLC (method A). 64 mg of the product are obtained as a powder. Analytical HPLC-MS (method D): RT=1.33 min.

SCHEME 10

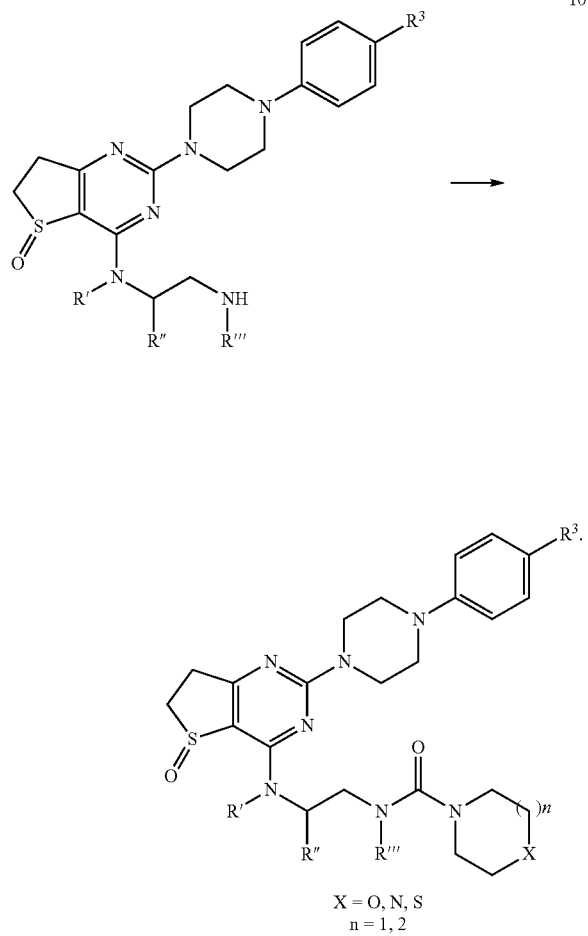

X = O, N, S
n = 1, 2

R' and R" or R" and R'" may together close a 5-membered ring 10.1 synthesis of morpholine-4-carboxylic acid ((S)-1-{2-[4-(4-chloro-phenyl)-piperazin-1-yl]-5-oxo-6,7-dihydro-5H-5λ⁴-thieno[3,2-d]pyrimidin-4-yl}-pyrrolidin-2-ylmethyl)-amide, Example 239 (See Scheme 10)

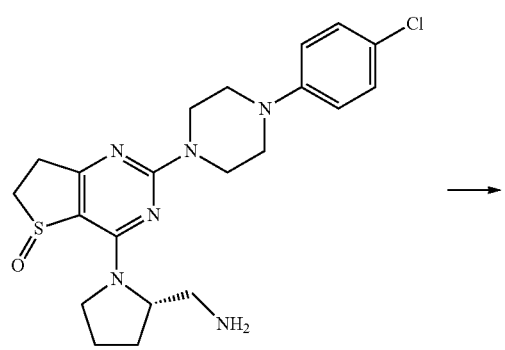

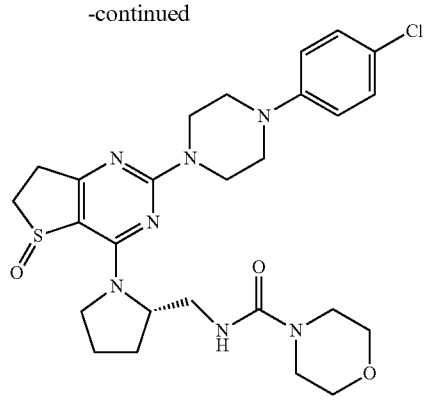

100 mg C—((S)—-{2-[4-(4-chloro-phenyl)-piperazin-1-yl]-5-oxo-6,7-dihydro-5H-5λ⁴-thieno[3,2-d]pyrimidin-4-yl}-pyrrolidin-2-yl)-methylamine trifluoroacetate, Diastereomer 2 (Example 226) (see scheme 3, 3.17.2) are placed in 2 ml dichloromethane. While cooling with the ice bath 38 μl triethylamine and 28 μl 4-morpholinecarbonyl chloride are added. The reaction mixture is stirred for 12 hours at ambient temperature and then mixed with water. The organic phase is dried and evaporated to dryness. 121 mg of the product are obtained as a solid. Analytical HPLC-MS (method D): RT=1.18 min.

10.2 Synthesis of ((R)-3-{2-[4-(4-chloro-phenyl)-piperazin-1-yl]-5-oxo-6,7-dihydro-5H-5λ⁴-thieno[3,2-d]pyrimidin-4-ylamino}-pyrrolidin-1-yl)-morpholin-4-yl-methanone, Example 193 (See Scheme 10)

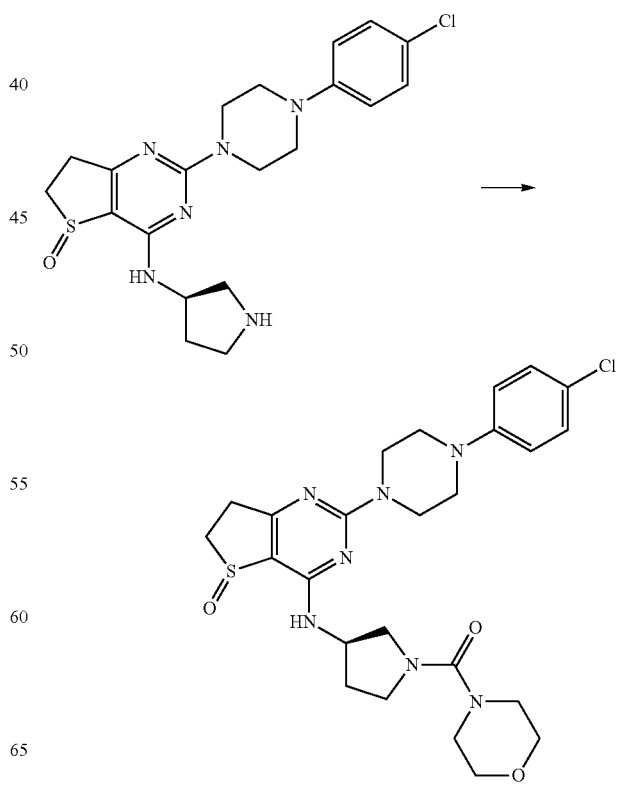

Starting from {2-[4-(4-chloro-phenyl)-piperazin-1-yl]-5-oxo-6,7-dihydro-5H-5λ⁴-thieno[3,2-d]pyrimidin-4-yl}-(R)-pyrrolidin-3-yl-amine Diastereomer I (Example 171) (see scheme 3, 3.22) and 4-morpholincarbonyl chloride, ((R)-3-{2-[4-(4-chloro-phenyl)-piperazin-1-yl]-5-oxo-6,7-dihydro-5H-5λ⁴-thieno[3,2-d]pyrimidin-4-ylamino}-pyrrolidin-1-yl)-morpholin-4-yl-methanone is prepared as described in Example 239 (see scheme 10).

The product is purified by preparative HPLC (method A). Analytical HPLC-MS (method D): RT=1.16 min.

Chromatographic Methods

The example compounds prepared according to the schemes described above were characterised either by determining their melting points (see Table 1) or using the following chromatographic methods which—if carried out—are specified in Table 1.

Analytical HPLC-MS, Method A:

| Conditions: |
| --- |
| Waters ZMD, Alliance 2690/2695 HPLC, Waters 2700 Autosampler, Waters 996/2996 diode array detector. The mobile phase used was:<br>A: water with 0.10% TFA<br>B: acetonitrile with 0.10% TFA |

| time in min | % A | % B | flow rate in ml/min |
| --- | --- | --- | --- |
| 0.0 | 95 | 5 | 1.00 |
| 0.1 | 95 | 5 | 1.00 |
| 3.1 | 2 | 98 | 1.00 |
| 4.5 | 2 | 98 | 1.00 |
| 5.0 | 95 | 5 | 1.00 |

The stationary phase used was a column XTerra®, MS C$_{18}$ 2.5 μm, 4.6 mm×30 mm (column temperature: constant at 25° C.). Diode array detection took place in the wavelength range 210-400 nm.

Analytical HPLC-MS, Method B:

| Conditions: |
| --- |
| Waters ZMD, Alliance 2690/2695 HPLC, Waters 2700 Autosampler, Waters 996/2996 diode array detector. The mobile phase used was:<br>A: water with 0.10% TFA<br>B: acetonitrile with 0.10% TFA |

| time in min | % A | % B | flow rate in ml/min |
| --- | --- | --- | --- |
| 0.00 | 95 | 5 | 2.00 |
| 0.10 | 95 | 5 | 2.00 |
| 2.10 | 2 | 98 | 2.00 |
| 3.00 | 2 | 98 | 2.00 |
| 3.25 | 95 | 5 | 2.00 |

The stationary phase used was a Merck Chromolith™ SpeedROD RP-18e column, 4.6 mm×50 mm (column temperature: constant at 25° C.). Diode array detection took place in the wavelength range 210-400 nm.

Analytical HPLC-MS, method C:

| Conditions: |
| --- |
| Waters ZMD Mass Spectrometer, Alliance 2790 + 996 DAD, 2700 Autosampler.<br>Adjustment parameters: ES+<br>Needle       3.0 kVolts<br>Cone:        30 Volts |

| HPLC Parameters | | | | |
| --- | --- | --- | --- | --- |
| | Gradient: | | | |
| Mobile Phase: | time [min] | A % | B % | Flow |
| A % H2O with 0.1% TFA | 0.00 | 95.00 | 5.00 | 1.000 |
| B % ACN with 0.1% TFA | 0.10 | 95.00 | 5.00 | 1.000 |
| Stationary Phase: | 5.10 | 2.00 | 98.00 | 1.000 |
| X-Terra MS C18 4.6 × 50 mm, 3.5 μm | 6.50 | 2.00 | 98.00 | 1.000 |
| column temperature (° C.) 40.0 | 7.00 | 95.00 | 5.00 | 1.000 |

Preparation Parameters
Retention time range used for MS integration and DAD data: 1.00-7.00 minutes
Wavelength range used to measure areas %: 210-500 nm
Setting for MS and UV Peak-to-Peak Amplitude: 2000
Two "Smooth" (Savitzky Golay) with window size (scans)±2 for DAD and MS Chromatogram.

Analytical RPLC-MS, Method D:

| Conditions: |
| --- |
| Waters ZMD, Alliance 2690/2695 HPLC, Waters 2700 Autosampler, Waters 996/2996 diode array detector. The mobile phase used was:<br>A: water with 0.10% TFA<br>B: acetonitrile with 0.10% TFA |

| time in min | % A | % B | flow rate in ml/min |
| --- | --- | --- | --- |
| 0.00 | 95 | 5 | 2.50 |
| 0.20 | 95 | 5 | 2.50 |
| 1.50 | 2 | 98 | 2.50 |
| 1.70 | 2 | 98 | 2.50 |
| 1.90 | 95 | 5 | 2.50 |
| 2.20 | 95 | 5 | 2.50 |

The stationary phase used was a Merck Chromolith™ Flash RP-18e column, 4.6 mm×25 mm (column temperature: constant at 25° C.). Diode array detection took place in the wavelength range 210-400 nm.

Analytical HPLC-MS, Method E:

| Conditions: | |
| --- | --- |
| Instrument | Waters Alliance 2695<br>PDA Detector 2998<br>Waters Micromass ZQ |

| Gradient | | | |
| --- | --- | --- | --- |
| time | % Water + 0.13% TFA | % Acetonitrile | Flow [ml/min.] |
| 0.00 | 95 | 5 | 4.25 |
| 0.01 | 95 | 5 | 4.25 |
| 0.89 | 2 | 98 | 4.25 |
| 0.90 | 2 | 98 | 4.25 |
| 0.95 | 95 | 5 | 4.25 |
| 1.05 | 95 | 5 | 4.25 |
| 1.10 | 95 | 5 | 0.1 |

| Parameter | Detector | column |
| --- | --- | --- |
| wavelength start | 210 | Waters Xbridge C18 |
| wavelength end | 380 | Particle Size 3.5 μm |
| Sampling Rate | 20 | Length 20 mm |
| Resolution | 1.2 | Internal diameter 4.6 mm |
| Filter Response | 0 | |
| Autoexposure | Yes | |
| Interpolate 656 nm | Yes | |
| Parameter | Integration | |

Analytical HPLC, Method A:

| Conditions: | |
|---|---|
| Peak With | 15 |
| Threshold | 465 |
| Minimum Area | 0 |
| Minimum Height | 0 |
| Mass(m/z) | 120-850 |

| Conditions: | | | |
|---|---|---|---|
| column: Varian Microsorb. RP C18, 3 µm, 100 Å | | | |
| DAD detector: from 210 nm to 380 nm | | | |
| Flow: 1 ml/min | | | |
| flow [ml/min] | dead time [min.] | column ID [mm] | 4.6 |
| 1.0 | 0.750 | column length [mm] | 50 |
| | | column volume [ml] | 0.83 |

| Flow [ml/mm.] | 1 | |
|---|---|---|
| time [min.] | % Acetonitrile + 0.1% TFA | % Water + 0.13% TFA |
| 0.0 | 5 | 95 |
| 0.8 | 5 | 95 |
| 5.0 | 98 | 2 |
| 5.5 | 98 | 2 |
| 5.8 | 5 | 95 |
| 6.7 | 5 | 95 |

| | |
|---|---|
| pitch [%/min] | 22.1 |
| Vg gradient volume [ml] | 4.2 |
| Vs column volume [ml] | 0.83 |
| ratio of Vg/Vs | 5.06 |

Analytical HPLC, Method B:

| Conditions: | | | |
|---|---|---|---|
| column: Varian Microsorb, RP C18, 3 µm, 100 Å | | | |
| DAD detector: from 210 nm to 380 nm | | | |
| flow: 1.5 ml/min | | | |
| flow [ml/min] | dead time [min.] | column ID [mm] | 4.6 |
| 1.5 | 0.500 | column length [mm] | 50 |
| | | column volume [ml] | 0.83 |

| Flow [ml/min.] | 1.5 | |
|---|---|---|
| time [min.] | % acetonitrile + 0.1% TFA | % water + 0.13% TFA |
| 0.0 | 5 | 95 |
| 0.6 | 5 | 95 |
| 3.4 | 98 | 2 |
| 3.9 | 98 | 2 |
| 4.2 | 5 | 95 |
| 4.9 | 5 | 95 |

| | |
|---|---|
| pitch [%/min] | 33.2 |
| Vg Gradient volume [ml] | 4.2 |
| Vs column volume [ml] | 0.83 |
| ratio Vg/Vs | 5.06 |

Preparative HPLC, Method A:

| Conditions: | | | | | |
|---|---|---|---|---|---|
| Gradient Preparative HPLC | Flow [ml/min] | dead time [min.] | column ID [mm] | 41.4 | |
| Method A | 120.0 | 3.500 | column length [mm] | | 250 |
| | | | column volume [ml] | | 336.4 |

| | |
|---|---|
| column material: Microsorb RP 18, 60 Å, 8 µm | |
| Eluant: Acetonitrile + 0.1% TFA, water + 0.13% TFA | |

| Flow [ml/min.] | 120 |
|---|---|
| time [min.] | % acetonitrile |
| 0.0 | 10 |
| 3.6 | 10 |
| 17.8 | 100 |
| 22.0 | 100 |
| 23.0 | 10 |
| 26.5 | 10 |

| | |
|---|---|
| pitch [%/min] | 6.3 |
| Vg Gradient volume [ml] | 1704 |
| Vs column volume [ml] | 336.4 |

Preparative HPLC, method B:

The column material and eluant data are the same as in method A. The gradient pattern is based on method A, but an isocratic step is included which is determined by the analytical retention time of the particular substance to be separated.

Preparative HPLC, Method C:

| Conditions: |
|---|
| Solvent: |
| A % H2O with 0.1% TFA |
| B % ACN with 0.1% TFA |

| Gradient: | | | |
|---|---|---|---|
| time [min] | A % | B % | flow rate (ml/min) |
| 0.00 | 95.00 | 5.00 | 0 |
| 0.30 | 95.00 | 5.00 | 0 |
| 0.40 | 95.00 | 5.00 | 5 |
| 0.45 | 95.00 | 5.00 | 40 |
| 1.00 | 95.00 | 5.00 | 40 |
| 16.00 | 40.00 | 60.00 | 40 |
| 17.00 | 5.00 | 95.00 | 40 |
| 20.00 | 5.00 | 95.00 | 40 |
| 22.00 | 95.00 | 5.00 | 40 |
| 25.00 | 95.00 | 5.00 | 40 |

Stationary Phase:
50 g YMC-Gel ODS-A RP-18 10 µm
packed with a MODCOL spring column with 25 mm i.d.
column temperature 22° C.

Preparation Parameters

| |
|---|
| wavelength used for detection: 215 nm & 254 nm |

Preparative HPLC, method D:

| | | | |
|---|---|---|---|
| Column material: Xbridge RP C18, 5 µm | | column ID [mm] | 50 |
| Eluant: Acetonitrile, water + 0.13% TFA | | column length [mm] | 162 |
| Flow: 120 ml/min | | column volume [ml] | 317.9 |

| Gradient | |
|---|---|
| time [min.] | % Acetonitrile |
| 0.0 | 10 |
| 3.0 | 10 |

111
-continued

| | | |
|---|---|---|
| wavelength used for detection: 215 nm & 254 nm | | |
| 22.0 | 100 | |
| 25.5 | 100 | |
| 26.5 | 10 | |
| 30.0 | 10 | |

Semipreparative HPLC, Method A:

| Conditions: | | | | |
|---|---|---|---|---|
| Gradient Semi-preparative HPLC Method A | Flow [ml/min] 25.0 | dead time [min.] 4.4 | column ID [mm] column length [mm] column volume [ml] | 21.4 250 89.9 | column material: Microsorb RP 18, 300 Å, 10 μm
eluant: acetonitrile + 0.1% TFA, water + 0.13% TFA

| Flow [ml/min.] time [min.] | 25 % acetonitrile |
|---|---|
| 0.0 | 10 |
| 4.5 | 10 |
| 22.7 | 100 |
| 26.7 | 100 |
| 27.7 | 10 |
| 32.0 | 10 |
| pitch [%/min] | 4.9 |
| Vg Gradient volume [ml] | 455 |

| Conditions: | |
|---|---|
| Vs column volume [ml] | 89.9 |
| ratio Vg/Vs | 5.06 |

EXAMPLES

The following Examples were prepared analogously to the methods of synthesis described hereinbefore (as specified in the Table). These compounds are suitable as PDE4-inhibitors and have $IC_{50}$ values of less than or equal to 1 μmol.

The Examples relates to compounds of the following formula 3,

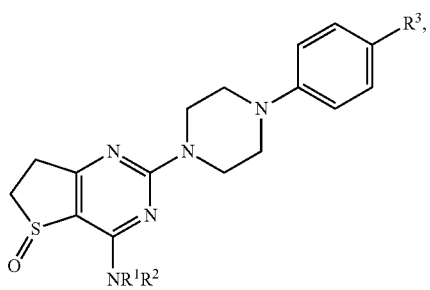

wherein the variables $R^1$, $R^2$ and $R^3$ have the meanings given in Table 1. The compounds were prepared according to Scheme 1 to Scheme 10, according to what is specified in Table 1.

TABLE 1

| # | R¹ | R² | R³ | synthesis scheme/ chirality (based on whole molecule) | non-commercial components (preparation described in the literature) | m.p (° C.) | retention time [min] (with HPLC-MS or HPLC) |
|---|---|---|---|---|---|---|---|
| 1. | H | *\_/\CH₃ | N-methylpiperidin-4-yl amide | scheme 3/ racemate | — | — | 2.62 analyt. HPLC-MS method C |
| 2. | H | *\_/\CH₃ | N-methyl-N-(1-methylpiperidin-4-yl) amide | scheme 4/ racemate | — | — | 2.59 analyt. HPLC-MS method C |
| 3. | H | *\_/\CH₃ | (pyridin-3-ylmethyl) amide | scheme 4/ racemate | — | — | 2.64 analyt. HPLC-MS method C |
| 4. | H | *\_/\CH₃ | N-methyl-N-(pyridin-3-ylmethyl) amide | scheme 4/ racemate | — | — | 2.66 analyt. HPLC-MS method C |
| 5. | H | *\_/\CH₃ | (2-(pyridin-4-yl)ethyl) amide | scheme 4/ racemate | — | — | 2.66 analyt. HPLC-MS method C |
| 6. | H | *\_/\CH₃ | (2-morpholinoethyl) amide | scheme 4/ racemate | — | — | 2.64 analyt. HPLC-MS method C |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 7. | H | (propyl with CH₃) | N-methylpyrrolidin-2-ylmethyl amide | scheme 4/ racemate | — | — | 2.77 analyt. HPLC-MS method C |
| 8. | H | (propyl with CH₃) | (1,3-dimethyl-1H-pyrazol-4-yl)methyl amide | scheme 4/ racemate | — | — | 2.9 analyt. HPLC-MS method C |
| 9. | H | (propyl with CH₃) | (1-methyl-4-hydroxypiperidin-4-yl)methyl amide | scheme 4/ racemate | 1-methyl-4-hydroxy-4-(aminomethyl)piperidine; JACS 1954, 3536; J. Med. Chem. 1970, 305 | — | 2.6 analyt. HPLC-MS method C |
| 10. | H | 3-chlorophenyl | 1-methylpiperidin-4-yl amide | scheme 4/ racemate | — | — | 3.21 analyt. HPLC-MS method C |
| 11. | H | 3-chlorophenyl | N-methyl-N-(1-methylpiperidin-4-yl) amide | scheme 4/ racemate | — | — | 3.18 analyt. HPLC-MS method C |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 12. | H | 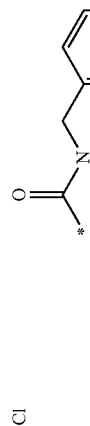 | 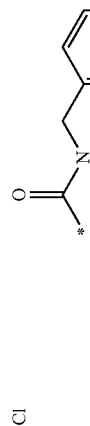 | scheme 4/ racemate | — | — | 3.24 analyt. HPLC-MS method C |
| 13. | H | 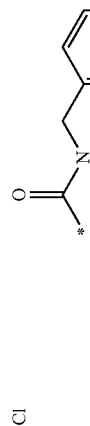 | 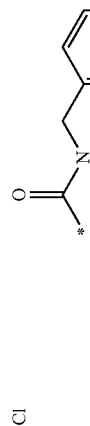 | scheme 4/ racemate | — | — | 3.24 analyt. HPLC-MS method C |
| 14. | H | 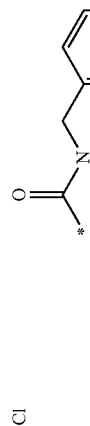 | 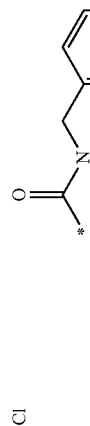 | scheme 4/ racemate | — | — | 3.23 analyt. HPLC-MS method C |
| 15. | H | 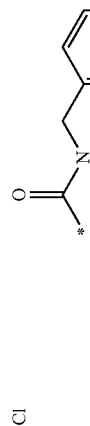 | 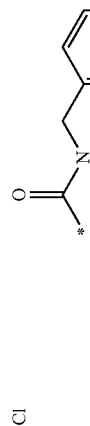 | scheme 4/ racemate | — | — | 3.23 analyt. HPLC-MS method C |
| 16. | H | 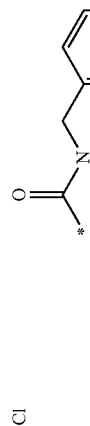 | 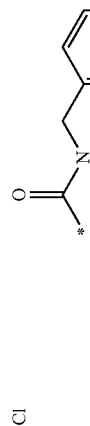 | scheme 4/ mixture of stereoisomers | — | — | 3.38 analyt. HPLC-MS method C |
| 17. | H | | 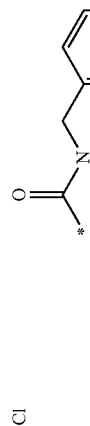 | scheme 4/ racemate | — | — | 3.55 analyt. HPLC-MS method C |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 18. | H | *—⟨3-Cl-phenyl⟩ | *—C(O)—N(H)—CH₂—[4-OH-1-CH₃-piperidin-4-yl] | scheme 4/ racemate | [1-CH₃-4-OH-piperidin-4-yl]-CH₂-N; JACS 1954, 3536 J. Med. Chem. 1970, 305 | — | 3.18 analyt. HPLC-MS method C |
| 19. | H | *—CH₂CH₂—CH₃ | 3-acetamido-quinuclidine | scheme 4/ mixture of diastereomers | — | — | 2.83 analyt. HPLC method A |
| 20. | H | *—⟨3-(CH₂-morpholine)-phenyl⟩ via CH₂ linker to H₃C... | Cl | scheme 1/ racemate | — | 245-247 | |
| 21. | H | *—⟨3-(morpholinomethyl)-phenyl⟩ | Cl | scheme 1/ racemate | 3-(morpholin-4-ylmethyl)aniline; cf experim. section | 244-248 | |
| 22. | H | *—⟨3-F-phenyl⟩ | Cl | scheme 1/ racemate | — | 244-246 | |
| 23. | H | *—⟨3-Cl-phenyl⟩ | Cl | scheme 1/ racemate | — | 244-245 | |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 24. | H | CH₂CH₃ (with *) | propargyl amide with pyridyl alkyne | scheme 4/ racemate | pyridyl propargyl amine, *Tet. Lett.* 2004, 7069 | — | 2.86 analyt. HPLC-MS method C |
| 25. | H | CH₂CH₃ (with *) | N,N-dimethylsulfamoyl methyl | scheme 2/ racemate | 4-(piperazin-1-yl)-N,N-dimethylbenzenesulfonamide, WO 2003/105853 | — | 2.42 HPLC-MS method A |
| 26. | H | 3-fluorophenyl | C(O)NH₂ | scheme 2/ racemate | — | — | 2.29 HPLC-MS method A |
| 27. | H | 3-chlorophenyl | C(O)NH₂ | scheme 2/ racemate | — | — | 2.39 HPLC-MS method A |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 28. | H | 3-fluorophenyl | *-S(O)₂-N(CH₃)-CH₃ | scheme 2/ racemate | 4-(piperazin-1-yl)-N,N-dimethylbenzenesulfonamide; WO 2003/105853 | — | 3.73 analyt. HPLC method A |
| 29. | H | propyl (CH₂CH₂CH₃) | *-C(O)-NH₂ | scheme 2/ racemate | | — | 2.88 analyt. HPLC method A |
| 30. | H | 3-chlorophenyl | *-S(O)₂-N(CH₃)-CH₃ | scheme 2/ racemate | 4-(piperazin-1-yl)-N,N-dimethylbenzenesulfonamide; WO 2003/105853 | — | 2.9 HPLC-MS method A |
| 31. | H | 3-chlorophenyl | *-C≡N | scheme 5/ racemate | 4-(piperazin-1-yl)benzonitrile; cf experim. section | — | 3.99 analyt. HPLC method A |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 32. | H |  | 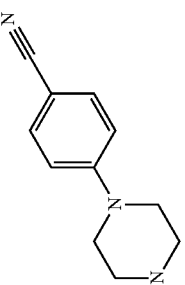 | scheme 5/ racemate |  | — | 3.83 analyt. HPLC method A |
| 33. | H |  (propyl) | 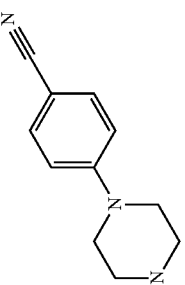 | scheme 6/ racemate | cf experim. section | — | 1.92 HPLC-MS method A |
| 34. | H |  (propyl) | 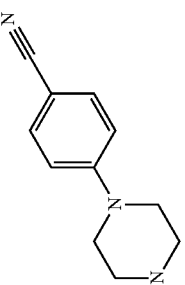 | scheme 5/ racemate |  | — | 2.37 HPLC-MS method A |
| 35. | H | 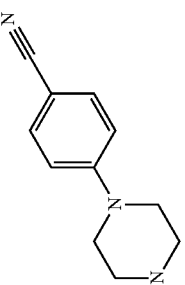 (propyl) |  | scheme 6/ racemate | cf experim. section | 274-276 | — |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|----|----|----|----|----|----|----|
| 36. | H |  | Cl | scheme 3/ racemate | — | 238-241 | — |
| 37. | H |  | Cl | scheme 3/ mixture of stereoisomers | — | 222-224 | — |
| 38. | H |  |  | scheme 6/ racemate | — | 235-237 | — |
| 39. | H |  | Cl | scheme 3/ mixture of diastereomers | — | — | 2.39 HPLC-MS method A |
| 40. | H |  |  | |  Helv. Chim. Acta 1974, 2332 | — | 1.96 HPLC-MS method A |
| 41. | H |  | Cl | scheme 3/ mixture of diastereomers | — | 238 | — |

TABLE 1-continued

| # | R¹ | R² | R³ | synthesis scheme/chirality (based on whole molecule) | non-commercial components (preparation described in the literature) | m.p (° C.) | retention time [min] (with HPLC-MS or HPLC) |
|---|---|---|---|---|---|---|---|
| 42. | H | *—CH(OH)—CH₂OH (with stereocenter) | Cl | scheme 3/ mixture of diastereomers | — | 241 | — |
| 43. | H | *—CH₂—CH(OH)—phenyl | Cl | scheme 3/ mixture of stereoisomers | — | 240 | — |
| 44. | H | *—CH₂—CH(OH)—(4-hydroxyphenyl) | Cl | scheme 3/ mixture of stereoisomers | — | 189 | — |
| 45. | H | *—CH₂—CH(OH)—(3-hydroxyphenyl) | Cl | scheme 3/ mixture of stereoisomers | — | 294 | — |
| 46. | H | *—CH₂—CH(OH)—CH₂OH | Cl | scheme 3/ mixture of diastereomers | — | — | 2.2 HPLC-MS method A |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 47. | H | (1-methoxy-1-(3,4-dimethoxyphenyl)propyl) | Cl | scheme 3/ mixture of stereoisomers | (2-amino-1-(3,4-dimethoxyphenyl)-1-methoxyethyl) *J. Med. Chem.* 1983, 174 | — | 2.69 HPLC-MS method A |
| 48. | H | (2-hydroxy-1-methylethyl)* | Cl | scheme 3/ diastereomer | — | — | 2.32 HPLC-MS method A |
| 49. | H | (2-hydroxy-1-phenylethyl)* | Cl | scheme 3/ diastereomer (other diastereomer is Ex. 56) | — | — | 3.04 analyt. HPLC method A |
| 50. | H | (2-hydroxy-1-methylethyl)* | Cl | scheme 3/ diastereomer | — | — | 2.37 HPLC-MS method A |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 51. | H | (structure: CH group with OH and CH₃, chiral center *) | Cl | scheme 3/ racemate (corr. racemic mixture of diastereomers is Ex. 59) | — | — | 2.5 HPLC-MS method A |
| 52. | H | (adamantane-type structure with OH, H, chiral center *) | Cl | scheme 3/ racemate | — | — | 2.62 HPLC-MS method A |
| 53. | H | (structure with OH, CH₃, H₃C, chiral center *) | Cl | scheme 3/ diastereomer (other diastereomer is Ex. 69) | — | — | 1.86 HPLC-MS method B |
| 54. | H | (structure with OH, CH₃, H₃C, chiral center *) | Cl | scheme 3/ diastereomer (other diastereomer is Ex. 57) | — | — | 1.76 HPLC-MS method B |
| 55. | H | (structure with OH, CH₃, chiral center *) | Cl | scheme 3/ diastereomer | — | — | 2.47 HPLC-MS method A |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 56. | H | ![structure: CH(OH)-* -phenyl] | Cl | scheme 3/ diastereomer (other diastereomer is Ex. 49) | — | — | 3.1 analyt. HPLC method A |
| 57. | H | ![structure: HOCH2-CH*-CH(CH3)-CH3] | Cl | scheme 3/ diastereomer | — | — | 1.81 HPLC-MS method B |
| 58. | H | ![structure: HOCH2-CH*-CH(CH3)-CH3] | Cl | scheme 3/ diastereomer | — | — | 2.57 HPLC-MS method A |
| 59. | H | ![structure: HOCH2-CH*-CH2-CH2-CH3] | Cl | scheme 3/ racemate (corr. racemic mixture of diastereomers is Ex. 51) | — | — | 2.57 HPLC-MS method A |

TABLE 1-continued

| # | R¹ | R² | R³ | synthesis scheme/ chirality (based on whole molecule) | non-commercial components (preparation described in the literature) | m.p (° C.) | retention time [min] (with HPLC-MS or HPLC) |
|---|----|----|----|----|----|----|----|
| 60. | H | (*)-CH(Ph)-CH₂OH | Cl | scheme 3/ diastereomer | — | — | 2.65 HPLC-MS method A |
| 61. | H | (*)-trans-2-(benzyloxy)cyclopentyl | Cl | scheme 3/ mixture of diastereomers | — | — | 3.09 HPLC-MS method A |
| 62. | H | (*)-CH(CH₂OH)-CH(CH₃)-CH₂CH₃ | Cl | scheme 3/ racemate | — | — | 2.66 HPLC-MS method A |
| 63. | H | 3-hydroxy-2-oxoindolin-3-ylmethyl | Cl | scheme 3/ mixture of stereoisomers | 3-hydroxy-3-(aminomethyl)indolin-2-one, JACS 1936, 1236 | — | 2.44 HPLC-MS method A |
| 64. | H | (*)-trans-2-(benzyloxy)cyclopentyl | Cl | scheme 3/ mixture of diastereomers | — | — | 2.99 HPLC-MS method A |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 65. | H | (structure: CH₂OH-CH(*)-CH₃) | Cl | scheme 3/ diastereomer (other diastereomer is Ex. 67) | — | — | 2.4 HPLC-MS method A |
| 66. | H | (structure: CH₂OH-CH(*)-CH₂-S-CH₃) | Cl | scheme 3/ diastereomer (other diastereomer is Ex. 69) | — | — | 2.55 HPLC-MS method A |
| 67. | H | (structure: CH₂OH-CH(*)-CH₃) | Cl | scheme 3/ diastereomer (other diastereomer is Ex. 65) | — | — | 2.46 HPLC-MS method A |
| 68. | H | (structure: HOCH₂-CH(OH)-CH₂(*)-COOH) | Cl | scheme 3/ mixture of stereoisomers | — | — | 3.08 HPLC-MS method A |
| 69. | H | (structure: HOCH₂-CH(*)-CH₂-CH(CH₃)₂) | Cl | scheme 3/ diastereomer (other diastereomer is Ex. 66) | — | — | 1.9 HPLC-MS method B |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 70. | H | (structure: *CH(OH)CH₂-C(=O)-O-CH₃) | Cl | scheme 3/ mixture of stereoisomers | — | — | 2.45 HPLC-MS method A |
| 71. | H | (structure: *CH₂-cyclopropyl(OH)) | Cl | scheme 3/ racemate | N≡C-CH₂-cyclopropyl(OH) Russ. J. Chem. 2001.1238 | — | 2.41 HPLC-MS method A |
| 72. | H | (structure: *CH(CH₂OH)-CH₂-indol-3-yl) | Cl | scheme 3/ mixture of stereoisomers | — | — | 2.63 HPLC-MS method A |
| 73. | H | (structure: *CH(OH)-CH₂-CH(CH₃)CH₃) | Cl | scheme 3/ diastereomer | — | — | 2.59 HPLC-MS method A |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 74. | H | 2-hydroxybutanoic acid (with * on CH) | Cl | scheme 3/ mixture of stereoisomers | — | — | 2.25 HPLC-MS method A |
| 75. | H | *-CH₂-CH₂-CH₃ | acetoxyacetyl amide | scheme 6 racemate | — | — | 2.15 HPLC-MS method A |
| 76. | H | *-CH₂-CH₂-CH₃ | 6-aminopyridine-3-carbonyl amide | scheme 6 racemate | — | — | 2.01 HPLC-MS method A |
| 77. | H | *-CH₂-CH₂-CH₃ | 5-methylisoxazole-3-carbonyl amide | scheme 6 racemate | — | — | 2.43 HPLC-MS method A |
| 78. | H | *-CH₂-CH₂-CH₃ | pyridine-3-carbonyl amide (nicotinoyl) | scheme 6 racemate | — | — | 2.03 HPLC-MS method A |
| 79. | H | *-CH₂-CH₂-CH₃ | N-methyl-N-acetyl amide | scheme 4 racemate | — | — | 2.18 HPLC-MS method A |

TABLE 1-continued

| # | R¹ | R² | R³ | synthesis scheme/ chirality (based on whole molecule) | non-commercial components (preparation described in the literature) | m.p (° C.) | retention time [min] (with HPLC-MS or HPLC) |
|---|---|---|---|---|---|---|---|
| 80. | H | 3-chlorophenyl* | N-methyl-N-methylcarboxamide* (H₃C-N(CH₃)-C(=O)-*) | scheme 4 racemate | — | — | 2.55 HPLC-MS method A |
| 81. | H | 3-fluorophenyl* | N-methyl-N-methylcarboxamide* (H₃C-N(CH₃)-C(=O)-*) | scheme 4 racemate | — | — | 1.72 HPLC-MS method A |
| 82. | H | 5-*-2-methyl-phenol (OH, CH₃) | Cl | scheme 3 racemate | — | — | 1.93 HPLC-MS method B |
| 83. | H | 3-*-5-methyl-phenol (OH, CH₃) | Cl | scheme 3 racemate | 3,5-dimethylaniline; Ber. Deutsch. Chem. Ges. 1882, 2831 | — | 1.89 HPLC-MS method B |
| 84. | H | 5-*-2-methoxy-phenol (OH, OCH₃) | Cl | scheme 3 racemate | — | — | 1.79 HPLC-MS method B |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 85. | H | 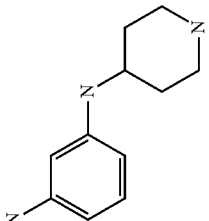 | Cl | scheme 3 racemate | — | — | 1.64 HPLC-MS method B |
| 86. | H | (4-Cl, 3-NH₂-phenyl) | Cl | scheme 3 racemate | — | — | 2 HPLC-MS method B |
| 87. | H | 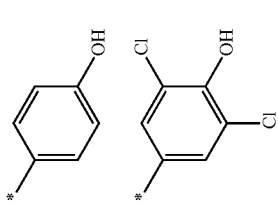 | Cl | scheme 3 racemate | *Org. Lett.* 2001, 1745 WO 2005/035499 | — | 1.99 HPLC-MS method B |
| 88. | H | (4-OH-phenyl) | Cl | scheme 3 racemate | — | — | 1.78 HPLC-MS method B |
| 89. | H | (3,5-diCl-4-OH-phenyl) | Cl | scheme 3 racemate | — | — | 2.02 HPLC-MS method B |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 90. | H | 2-hydroxy-5-carboxyphenyl | Cl | scheme 3 racemate | — | — | 1.84 HPLC-MS method B |
| 91. | H | 2-hydroxy-5-(dimethylaminomethyl)phenyl | Cl | scheme 3 racemate | — | — | 2.88 analyt. HPLC, method B |
| 92. | H | 3-chloro-4-hydroxyphenyl | Cl | scheme 3 racemate | — | — | 1.88 HPLC-MS method B |
| 93. | H | 3-chloro-4-aminophenyl | Cl | scheme 3 racemate | — | — | 1.89 HPLC-MS method B |
| 94. | H | indazol-5-yl | Cl | scheme 3 racemate | — | — | 1.76 HPLC-MS method B |
| 95. | H | 2-oxo-1,2,3,4-tetrahydroquinolin-6-yl | Cl | scheme 3 racemate | — | — | 1.75 HPLC-MS method B |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|----|----|----|-----|------|-----|------|
| 96. | H | 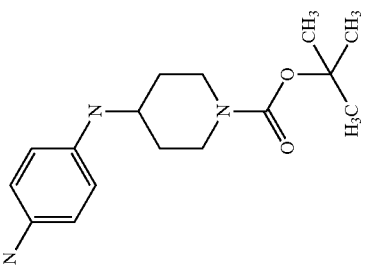 | Cl | scheme 3 racemate | 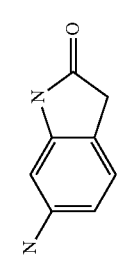 Org. Lett. 2001.1745 WO 2005/035499 | — | 1.95 HPLC-MS method B |
| 97. | H | 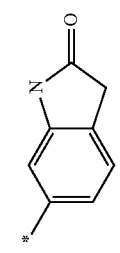 | Cl | scheme 3 racemate | 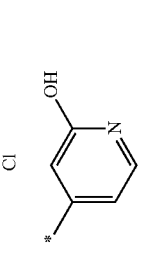 Hel. Chim. Acta 1937, 373 | — | 1.76 HPLC-MS method B |
| 98. | H | (structure) | Cl | scheme 3 racemate | — | — | 2.08 HPLC-MS method B |
| 99. | H | (structure) | Cl | scheme 3 racemate | — | — | 2.91 analyt. HPLC, method B |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 100 | H | 3-amino-1,2,4-triazol-5-yl | Cl | scheme 3 racemate | — | — | 2.98 analyt. HPLC, method B |
| 101 | H | thiophene-CH₂-NHC(O)O-C(CH₃)₂- (with CH₂N* on other side) | Cl | scheme 3 racemate | thiophene-CH₂NH-C(O)O-C(CH₃)₂ with H₂N-CH₂- (cf exp. section) | — | 2.06 HPLC-MS method B |
| 102 | H | 3-chlorophenyl | morpholine-N-C(O)-N* | scheme 3 racemate | — | — | 2.39 HPLC-MS method A |
| 103 | H | 3-hydroxyphenyl | Cl | scheme 3 racemate | — | — | 1.83 HPLC-MS method B |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 104 | H | (imidazo[4,5-b]pyridin-2-ylmethyl) | Cl | scheme 3 racemate | cf exp. section | — | 1.55 HPLC-MS method B |
| 105 | H | ((2-acetamidothiazol-4-yl)methyl) | Cl | scheme 3 racemate | *J. Med. Chem.* 1997, 3726 | — | 1.74 HPLC-MS method B |
| 106 | H | ((5-chloro-1H-benzimidazol-2-yl)(methoxymethyl)methyl) | Cl | scheme 3 mixture of diastereomers | cf exp. section | — | 1.88 HPLC-MS method B |

TABLE 1-continued

| # | R¹ | R² | R³ | synthesis scheme/ chirality (based on whole molecule) | non-commercial components (preparation described in the literature) | m.p (° C.) | retention time [min] (with HPLC-MS or HPLC) |
|---|---|---|---|---|---|---|---|
| 107 | H |  | Cl | scheme 3 mixture of diastereomers | 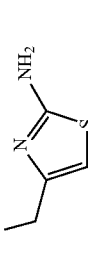<br>cf exp. section | — | 1.9 HPLC-MS method B |
| 108 | H |  | Cl | scheme 3 racemate | *J. Med. Chem.* 1997, 3726 | — | 1.64 HPLC-MS method B |
| 109 | H | 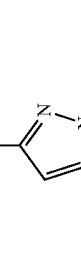 | Cl | scheme 3 racemate | — | — | 1.93 HPLC-MS method B |
| 110 | H |  | Cl | scheme 3 racemate | <br>cf exp. section | — | 1.61 HPLC-MS method B |

TABLE 1-continued

| # | R[1] | R[2] | R[3] | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 111 | H | *-C6H4-NHC(O)CH2-morpholine | Cl | scheme 3 racemate | 4-aminophenyl morpholinoacetamide, WO 2000/018734 | — | 1.65 HPLC-MS method B |
| 112 | H | *-benzimidazole-2-SH | Cl | scheme 3 racemate | — | — | 1.74 HPLC-MS method B |
| 113 | H | *-CH2-(5-oxopyrrolidin-2-yl) | Cl | scheme 3 racemate | — | — | 1.65 HPLC-MS method A |
| 114 | H | *-3-chlorophenyl | *-NHC(O)-(6-aminopyridin-3-yl) | scheme 6 racemate | — | — | 2.74 analyt. HPLC-method B |

TABLE 1-continued

| # | R¹ | R² | R³ | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 115 | H | *-CH2-(3-(5-methyl-2-oxoindolin-3-yl)) | Cl | scheme 3 racemate | — | — | 2.68 HPLC-MS method C |
| 116 | H | *-CH2-(1-methylimidazol-2-yl) | Cl | scheme 3 racemate | — | — | 1.63 HPLC-MS method C |
| 117 | H | *-(norbornyl-CH2OH) | Cl | scheme 3 mixture of diastereomers | — | — | 1.88 HPLC-MS method B |
| 118 | H | *-(4-aminophenyl) | Cl | scheme 3 racemate | — | — | 2.33 HPLC-MS method A |
| 119 | H | *-(2-(pyridin-3-yl)benzimidazol-5-yl) | Cl | scheme 3 racemate | — | — | 1.71 HPLC-MS, method B |
| 120 | H | *-(3-chlorophenyl) | *-NH-C(O)-(5-methylisoxazol-3-yl) | scheme 6 racemate | — | — | 3.15 analyt. HPLC method B |

TABLE 1-continued

| # | R[1] | R[2] | R[3] | synthesis scheme/ chirality (based on whole molecule) | non-commercial components (preparation described in the literature) | m.p (°C.) | retention time [min] (with HPLC-MS or HPLC) |
|---|---|---|---|---|---|---|---|
| 121 | H | 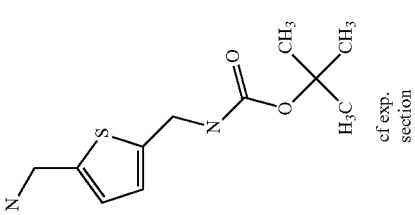 | Cl | scheme 3 racemate | — | — | 2.29 HPLC-MS method A |
| 122 | H | 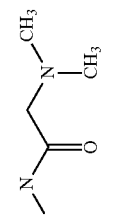 | Cl | scheme 3 racemate | (structure shown) cf exp. section | — | 2.34 HPLC-MS, method A |
| 123 | H | (3-Cl-phenyl) | (N,N-dimethyl glycinamide) | scheme 6 racemate | | | 2.72 analyt. HPLC method B |

Other Examples relates to the compounds of the following formula 3,

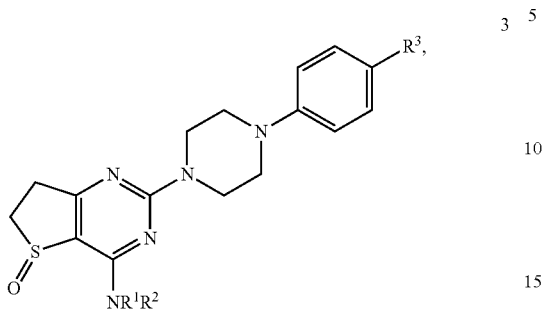

wherein the variables $R^1$, $R^2$ and $R^3$ have the meanings shown in Table 1. The compounds were each prepared according to Scheme I to Scheme 10, as specified in Table 1.

| # | NR¹R² | R³ | synthesis scheme/ chirality (based on whole molecule) | Non-commercial components (preparation described in the literature) | m.p. (° C.) | retention time [min] (with HPLC-MS or HPLC) |
|---|---|---|---|---|---|---|
| 124. | ![structure] | Cl | scheme 3 mixture of diastereomers | — | — | 2.26 HPLC-MS method A |
| 125. | ![structure] | Cl | scheme 3 diastereomer | — | — | 2.51 HPLC-MS method A |
| 126. | ![structure] | Cl | scheme 3 diastereomer | — | — | 2.57 HPLC-MS method A |
| 127. | ![structure] | Cl | scheme 3 mixture of diastereomers | — | — | 2.26 HPLC-MS method A |

-continued

| # | NR¹R² | R³ | synthesis scheme/ chirality (based on whole molecule) | Non-commercial components (preparation described in the literature) | m.p. (° C.) | retention time [min] (with HPLC-MS or HPLC) |
|---|---|---|---|---|---|---|
| 128. | (structure: pyrrolidine with OH and C(O)NH₂) | Cl | scheme 3 diastereomer | — | — | 1.49 HPLC-MS method B |
| 129. | (structure: pyrrolidine with OH and C(O)N(CH₃)₂) | Cl | scheme 3 diastereomer | — | — | 4.61 HPLC-MS method B |
| 130. | (structure: pyrrolidine with OH and C(O)NHCH₃) | Cl | scheme 3 mixture of diastereomers | — | — | 1.57 HPLC-MS method B |

Further Examples relate to the compounds of the following formula 3,

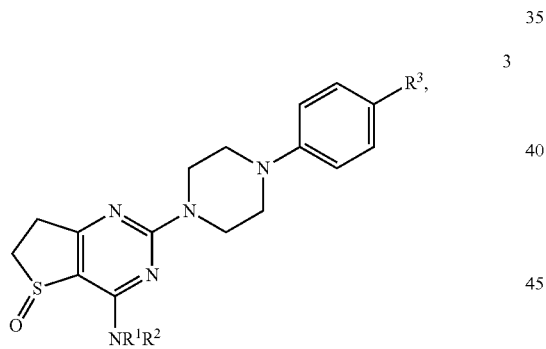

wherein the variables R¹, R² and R³ have the meanings given in Table 1. The compounds were in each case prepared according to Scheme 1 to Scheme 10, as specified in Table 1.

| # | R¹ R² | R³ | synthesis scheme/ chirality (based on whole molecule) | non-commercial components (preparation described in the literature) | retention time [min] (with HPLC-MS or HPLC) |
|---|---|---|---|---|---|
| 131 | H, (structure: CH with C(O)NH₂ and isopropyl) | Cl | scheme 3 (cf experim. section) 1 diastereomer | | 2.78 HPLC, method B |

-continued

| # | R¹ | R² | R³ | synthesis scheme/ chirality (based on whole molecule) | non-commercial components (preparation described in the literature) | retention time [min] (with HPLC-MS or HPLC) |
|---|---|---|---|---|---|---|
| 132 | H | 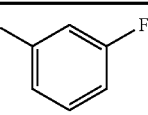 | 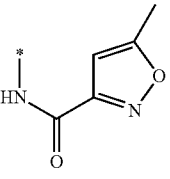 | scheme 6 racemate | | 1.85 HPLC-MS, method B |
| 133 | H | 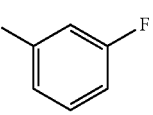 | 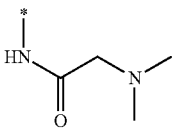 | scheme 6 racemate | | 2.6 HPLC, method B |
| 134 | H | 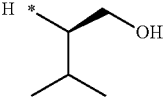 | 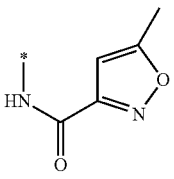 | scheme 6 1 diastereomer | | 1.66 HPLC-MS, method B |
| 135 | H | 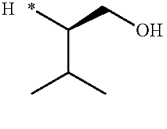 | 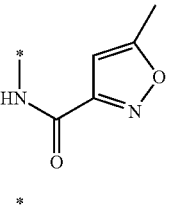 | scheme 6 1 diastereomer | | 2.73 HPLC, method B |
| 136 | H | 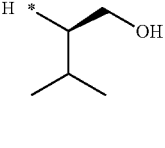 | 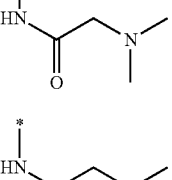 | scheme 6 1 diastereomer | | 2.28 HPLC, method B |
| 137 | H | 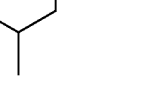 | 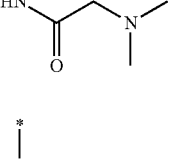 | scheme 6 1 diastereomer | | 2.49 HPLC, method B |
| 138 | H | 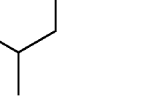 | 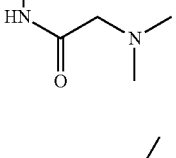 | scheme 6 1 diastereomer | | 2.39 HPLC, method B |
| 139 | H | 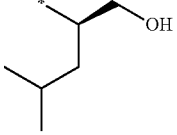 | 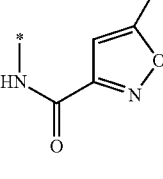 | scheme 6 1 diastereomer | | 2.91 HPLC, method B |
| 140 | H | 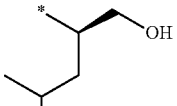 | 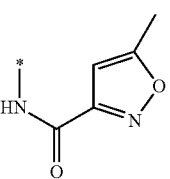 | scheme 6 1 diastereomer | | 2.85 HPLC, method B |

-continued

| # | R¹ | R² | R³ | synthesis scheme/ chirality (based on whole molecule) | non-commercial components (preparation described in the literature) | retention time [min] (with HPLC-MS or HPLC) |
|---|---|---|---|---|---|---|
| 141 | H | *-CH(iPr)-CH₂-NH₂ | Cl | scheme 1 (cf experim. section) 1 diastereomer | | 2.75 HPLC, method B |
| 142 | H | *-CH(*-CH₂OH)(propyl) | Cl | scheme 2 1 diastereomer | | 3.04 HPLC, method B |
| 143 | H | *-CH(CH₂OH)(CH₂CH₃) | Cl | scheme 3 (cf experim. section) 1 diastereomer | | 1.21 HPLC-MS, method D |
| 144 | H | *-CH(CH₂OH)(CH₂CH₃) | Cl | scheme 3 (cf experim. section) 1 diastereomer | | 1.22 HPLC-MS, method D |
| 145 | H | *-(3-F-C₆H₄) | *-C(O)-N(CH₃)₂ | scheme 4 (cf experim. section) 1 enantiomer | | 1.17 HPLC-MS, method D |
| 146 | H | *-(3-F-C₆H₄) | *-C(O)-N(CH₃)₂ | scheme 4 (cf experim. section) 1 enantiomer | | 1.17 HPLC-MS, method D |
| 147 | H | *-CH(CH₂OH)(C(CH₃)₃) | Cl | scheme 3 1 diastereomer | | 1.26 HPLC-MS, method D |
| 148 | H | *-sec-butyl | CN | scheme 5 (cf experim. section) 1 enantiomer | | 1.16 HPLC-MS, method D |
| 149 | H | *-(3-F-C₆H₄) | *-NH-C(O)-CH₂-N(CH₃)₂ | scheme 6 (cf experim. section) 1 enantiomer | | 1.05 HPLC-MS, method D |
| 150 | H | *-(3-F-C₆H₄) | *-NH-C(O)-CH₂-N(CH₃)₂ | scheme 6 (cf experim. section) 1 enantiomer | | 1.07 HPLC-MS, method D |

-continued

| # | R¹ | R² | R³ | synthesis scheme/ chirality (based on whole molecule) | non-commercial components (preparation described in the literature) | retention time [min] (with HPLC-MS or HPLC) |
|---|---|---|---|---|---|---|
| 151 | H | *cyclopentyl-O-benzyl (trans)* | Cl | scheme 3 (cf experim. section) 1 diastereomer | | 1.45 HPLC-MS, method D |
| 152 | H | *cyclopentyl-O-benzyl (cis)* | Cl | scheme 3 (cf experim. section) 1 diastereomer | | 1.44 HPLC-MS, method D |
| 153 | H | *C(CH₃)(iPr)CH₂OH* | Cl | scheme 3 (cf experim. section) mixture of diastereomers | H₂N-C(CH₃)(iPr)-CH₂OH  see experim. part | 1.27 HPLC-MS, method D |
| 154 | H | *CH(4-F-C₆H₄)CH₂OH* | Cl | scheme 3 1 diastereomer | *CH(4-F-C₆H₄)CH₂OH  J. Med. Chem. 1999, 4981 | 1.27 HPLC-MS, method D |
| 155 | H | *CH(4-F-C₆H₄)CH₂OH* | Cl | scheme 3 1 diastereomer | *CH(4-F-C₆H₄)CH₂OH  J. Med. Chem. 1999, 4981 | 1.28 HPLC-MS, method D |
| 156 | H | *CH(cyclopropyl)CH₂OH* | Cl | scheme 3 1 diastereomer | H₂N-CH(cyclopropyl)-CH₂OH  see #153 | 2.9 HPLC, method B |
| 157 | H | *CH(cyclopropyl)CH₂OH* | Cl | scheme 3 1 diastereomer | H₂N-CH(cyclopropyl)-CH₂OH  see #153 | 2.94 HPLC, method B |
| 158 | H | *C(cyclopentyl)CH₂OH* | Cl | scheme 1 (cf experim. section) 1 enantiomer | | 1.29 HPLC-MS, method D |

-continued

| # | R¹ | R² | R³ | synthesis scheme/ chirality (based on whole molecule) | non-commercial components (preparation described in the literature) | retention time [min] (with HPLC-MS or HPLC) |
|---|----|----|----|----|----|----|
| 159 | H | *-C(cyclopentyl)-CH₂OH | Cl | scheme 1 (cf experim. section) 1 enantiomer | | 1.28 HPLC-MS, method D |
| 160 | H | *-CH(4-F-C₆H₄)-C(CH₃)₂-OH | Cl | scheme 2 (cf experim. section) 1 diastereomer | H₂N-CH(4-F-C₆H₄)-C(CH₃)₂-OH  see experim. part | 1.31 HPLC-MS, method D |
| 161 | H | *-CH(4-F-C₆H₄)-C(CH₃)₂-OH | Cl | scheme 2 (cf experim. section) 1 diastereomer | H₂N-CH(4-F-C₆H₄)-C(CH₃)₂-OH  see experim. part | 1.40 HPLC-MS, method D |
| 162 | H | *-(tetrahydrothiophene-1,1-dioxide-3-yl) | Cl | scheme 1 mixture of diastereomers | | 1.23 HPLC-MS, method D |
| 163 | H | *-(tetrahydrothiophene-1,1-dioxide-3-yl) | Cl | scheme 1 mixture of diastereomers | | 1.23 HPLC-MS, method D |
| 164 | H | *-CH(iPr)-CH₂-OCH₃ | Cl | scheme 3 1 diastereomer | H₂N-CH(iPr)-CH₂-OCH₃  J. Org. Chem. 1978, 892 | 1.34 HPLC-MS, method D |
| 165 | H | *-CH(iPr)-CH₂-OCH₃ | Cl | scheme 3 1 diastereomer | H₂N-CH(iPr)-CH₂-OCH₃  J. Org. Chem. 1978, 892 | 1.36 HPLC-MS, method D |

-continued

| # | R¹ | R² | R³ | synthesis scheme/ chirality (based on whole molecule) | non-commercial components (preparation described in the literature) | retention time [min] (with HPLC-MS or HPLC) |
|---|---|---|---|---|---|---|
| 166 | H | * benzyl-CH(CH₂OH)- | Cl | scheme 3<br>1 diastereomer | | 1.32<br>HPLC-MS,<br>method D |
| 167 | H | * (pyrrolidin-3-yl, N-Boc) | Cl | scheme 3<br>(cf # 170)<br>mixture of diastereomers | | 1.40<br>HPLC-MS,<br>method D |
| 168 | H | * (pyrrolidin-3-yl, NH) | Cl | scheme 3<br>(cf # 171/172)<br>1 diastereomer | | 2.67<br>HPLC,<br>method B |
| 169 | H | * (pyrrolidin-3-yl, N-benzyl) | Cl | scheme 3<br>mixture of diastereomers | | 1.26<br>HPLC-MS,<br>method D |
| 170 | H | * (pyrrolidin-3-yl, N-Boc) | Cl | scheme 3<br>(cf experim. section)<br>mixture of diastereomers | | 1.39<br>HPLC-MS,<br>method D |
| 171 | H | * (pyrrolidin-3-yl, NH) | Cl | scheme 3<br>(cf experim. section)<br>1 diastereomer | | 2.62<br>HPLC,<br>method B |
| 172 | H | * (pyrrolidin-3-yl, NH) | Cl | scheme 3<br>(cf experim. section)<br>1 diastereomer | | 2.66<br>HPLC,<br>method B |
| 173 | H | * (piperidin-3-yl, N-Boc) | Cl | scheme 3<br>(cf # 170)<br>mixture of diastereomers | | 1.46<br>HPLC-MS,<br>method D |

-continued

| # | R¹ | R² | R³ | synthesis scheme/ chirality (based on whole molecule) | non-commercial components (preparation described in the literature) | retention time [min] (with HPLC-MS or HPLC) |
|---|---|---|---|---|---|---|
| 174 | H | * piperidine-N-Boc | Cl | scheme 3 (cf # 170) mixture of diastereomers | | 1.45 HPLC-MS, method D |
| 175 | H | * CH₂-C₆H₄(OH)-CH₂OH | Cl | scheme 3 (cf experim. section) 1 diastereomer | | 0.60 HPLC-MS, method E |
| 176 | H | * piperidine-NH | Cl | scheme 3 (cf # 171/172) 1 diastereomer | | 1.08 HPLC-MS, method D |
| 177 | H | * piperidine-NH | Cl | scheme 3 (cf # 171/172) 1 diastereomer | | 1.11 HPLC-MS, method D |
| 178 | H | * piperidine-NH | Cl | scheme 3 (cf # 171/172) 1 diastereomer | | 1.13 HPLC-MS, method D |
| 179 | H | * N-benzylpyrrolidine | Cl | scheme 3 mixture of diastereomers | | 1.25 HPLC-MS, method D |
| 180 | H | * 6-oxopiperidine | Cl | scheme 3 mixture of diastereomers | | 1.18 HPLC-MS, method D |

-continued

| # | R¹ | R² | R³ | synthesis scheme/ chirality (based on whole molecule) | non-commercial components (preparation described in the literature) | retention time [min] (with HPLC-MS or HPLC) |
|---|---|---|---|---|---|---|
| 181 | H | *[4-tetrahydropyranyl] | [H₂N-CH(4-F-C₆H₄)-C(OH)(CH₃)₂] siehe experim. Teil | scheme 2 (cf experim. section) 1 enantiomer | | 1.23 HPLC-MS, method D |
| 182 | H | *[3-(hydroxymethyl)-1-Boc-pyrrolidin-3-yl] | Cl | scheme 1 mixture of stereoisomers | | 1.30 HPLC-MS, method D |
| 183 | H | *[3-hydroxy-2-methyl-butan-2-yl with isopropyl] | Cl | scheme 3 mixture of diastereomers | [H₂N-CH(iPr)-C(OH)(CH₃)₂] Tet. Lett. 2003, 1129 | 1.31 HPLC-MS, method D |
| 184 | H | *[4-(2-oxopiperidinyl)] | Cl | scheme 3 mixture of diastereomers | | 1.16 HPLC-MS, method D |
| 185 | H | *[quinuclidinyl] | Cl | scheme 3 1 diastereomer | | 1.13 HPLC-MS, method D |
| 186 | H | *[quinuclidinyl] | Cl | scheme 3 1 diastereomer | | 1.08 HPLC-MS, method D |
| 187 | H | *[1-(hydroxymethyl)-2-fluoro-2-methylpropyl] | Cl | scheme 2 (cf experim. section) racemate | [H₂N-CH(CH₂OH)-CF(CH₃)₂] J. Org. Chem. 2000, 5037 | 1.26 HPLC-MS, method D |
| 188 | H | *[1-(hydroxymethyl)-2-methoxyethyl] | Cl | scheme 3 1 diastereomer | [H₂N-CH(CH₂OH)-CH₂-OCH₃] EP1348709 | 1.23 HPLC-MS, method D |

-continued

| # | R¹ | R² | R³ | synthesis scheme/ chirality (based on whole molecule) | non-commercial components (preparation described in the literature) | retention time [min] (with HPLC-MS or HPLC) |
|---|---|---|---|---|---|---|
| 189 | H | *─⌬─CH₂OH (cyclopropyl with CH₂OH) | Cl | scheme 2 (cf experim. section) 1 enantiomer | | 1.20 HPLC-MS, method D |
| 190 | H | *─CH(CH₂OH)CH₂CH₂OCH₃ | Cl | scheme 3 1 diastereomer | H₂N─CH(CH₂OH)CH₂CH₂OCH₃ see # 153 | 1.14 HPLC-MS, method D |
| 191 | H | *─CH(CH₂OH)CH₂CH₂OCH₃ | Cl | scheme 3 1 diastereomer | H₂N─CH(CH₂OH)CH₂CH₂OCH₃ see # 153 | 1.16 HPLC-MS, method D |
| 192 | H | 4-(hydroxymethyl)tetrahydropyran-4-yl* | Cl | scheme 3 racemate | H₂N-4-(hydroxymethyl)tetrahydropyran-4-yl see # 153 | 1.13 HPLC-MS, method D |
| 193 | H | *-pyrrolidin-3-yl-C(O)-morpholine | Cl | scheme 10 (cf experim. section) 1 diastereomer | | 1.16 HPLC-MS, method D |
| 194 | H | *-pyrrolidin-3-yl-C(O)-C(CH₃)₂CH₂OH | Cl | scheme 7 (cf # 196) 1 diastereomer | | 1.18 HPLC-MS, method D |
| 195 | H | *-pyrrolidin-3-yl-C(O)-cyclopentyl | Cl | scheme 7 (cf # 196) 1 diastereomer | | 1.26 HPLC-MS, method D |
| 196 | H | *-pyrrolidin-3-yl-C(O)-tetrahydrofuran-2-yl | Cl | scheme 7 (cf experim. section) 1 diastereomer | | 1.18 HPLC-MS, method D |
| 197 | H | *-pyrrolidin-3-yl-C(O)-(1-methylpyrrol-2-yl) | Cl | scheme 7 (cf experim. section) 1 diastereomer | | 1.25 HPLC-MS, method D |

-continued

| # | R¹ | R² | R³ | synthesis scheme/ chirality (based on whole molecule) | non-commercial components (preparation described in the literature) | retention time [min] (with HPLC-MS or HPLC) |
|---|---|---|---|---|---|---|
| 198 | H | *(pyrrolidine-tetrahydrofuran carbonyl) | Cl | scheme 7 (cf experim. section) 1 diastereomer | | 1.17 HPLC-MS, method D |
| 199 | H | *(pyrrolidine-pyrazole carbonyl) | Cl | scheme 7 (cf # 196) 1 diastereomer | | 1.15 HPLC-MS, method D |
| 200 | H | *(piperidine-trifluoroacetyl) | Cl | scheme 7 (cf # 196) 1 diastereomer | | 1.28 HPLC-MS, method D |
| 201 | H | *(isobutyl-OH) | OH | scheme 2 1 diastereomer | | 0.95 HPLC-MS, method D |
| 202 | H | *(3-fluorophenyl) | *-S(O)₂-CH₃ | scheme 2 (cf experim. section) 1 enantiomer | | 1.24 HPLC-MS, method D |
| 203 | H | *(N-methyl piperidinone) | Cl | scheme 2 (cf experim. section) 1 diastereomer | H₂N-(N-methyl piperidinone) see experim. part | 1.18 HPLC-MS, method D |
| 204 | H | *(N-methyl piperidinone) | Cl | scheme 2 (cf experim. section) 1 diastereomer | H₂N-(N-methyl piperidinone) see # 203 | 1.19 HPLC-MS, method D |
| 205 | H | *(piperidine-dimethyl-hydroxy carbonyl) | Cl | scheme 7 (cf # 196) 1 diastereomer | | 1.20 HPLC-MS, method D |
| 206 | H | *(furyl-CH₂-CH(OH)) | Cl | scheme 3 (cf experim. section) 1 diastereomer | H₂N-(furyl-CH-CH₂OH) see experim. part | 1.23 HPLC-MS, method D |

-continued

| # | R¹ | R² | R³ | synthesis scheme/ chirality (based on whole molecule) | non-commercial components (preparation described in the literature) | retention time [min] (with HPLC-MS or HPLC) |
|---|---|---|---|---|---|---|
| 207 | H | *furanylmethyl-CH(CH2OH)- | Cl | scheme 3 (cf experim. section) 1 diastereomer | H2N-CH(CH2OH)-CH2-furanyl see experim. part | 1.24 HPLC-MS, method D |
| 208 | H | *isobutyl-CH(CH2OH)- | Br | scheme 2 (cf experim. section) 1 diastereomer | | 1.21 HPLC-MS, method D |
| 209 | H | *3-(N,N-dimethylsulfamoyl)phenyl | Cl | scheme 2 racemate | | 1.42 HPLC-MS, method D |
| 210 | H | *piperidin-4-yl-CH(CH2OH)- | Cl | scheme 2 racemate | H2N-CH(CH2OH)-(N-Boc-piperidin-4-yl) see # 153 | 1.04 HPLC-MS, method D |
| 211 | H | *cyclopropyl-CH(CH2OH)- | Br | scheme 2 (cf experim. section) 1 diastereomer | | 1.18 HPLC-MS, method D |
| 212 | H | *isobutyl-CH(CH2OH)- | *C(O)OEt | scheme 2 (cf experim. section) 1 diastereomer | | 1.2 HPLC-MS, method D |
| 213 | H | *3-fluorophenyl | *C(O)OEt | scheme 2 (cf # 202) 1 enantiomer | | 1.4 HPLC-MS, method D |
| 214 | H | *tetrahydropyran-4-yl | *C(O)OEt | scheme 2 (cf experim. section) 1 enantiomer | | 1.2 HPLC-MS, method D |
| 215 | H | *cyclohexyl-CH(CH2OH)- | Cl | scheme 3 1 diastereomer | | 1.29 HPLC-MS, method D |

-continued

| # | R¹ | R² | R³ | synthesis scheme/ chirality (based on whole molecule) | non-commercial components (preparation described in the literature) | retention time [min] (with HPLC-MS or HPLC) |
|---|---|---|---|---|---|---|
| 216 | H | *̣⟋⟍⟋OH (butyl with OH) | Br | scheme 2 (cf experim. section) 1 diastereomer | | 1.23 HPLC-MS, method D |
| 217 | H | *piperidine-C(O)-tetrahydrofuran | Cl | scheme 7 (cf # 196) 1 diastereomer | | 1.22 HPLC-MS, method D |

Further Examples relate to the compounds of the following formula 3,

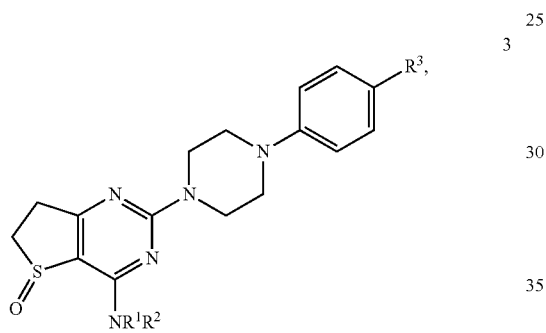

3 wherein the variables $R^1$, $R^2$ and $R^3$ have the meanings shown in Table 1. The compounds were each prepared according to Scheme 1 to Scheme 10, as specified in Table 1.

| # | NR¹R² | R³ | synthesis scheme/ chirality (based on whole molecule) | non-commercial components (preparation described in the literature) | retention time [min] (with HPLC-MS or HPLC) |
|---|---|---|---|---|---|
| 218 | bicyclic diamine with CH₃ | Cl | scheme 3 1 diastereomer | | 1.59 HPLC-MS, method B |
| 219 | pyrrolidine-CH₂-NH-C(O)-O-tBu | Cl | scheme 3 (cf experim. section) mixture of diastereomers | | 2.00 HPLC-MS, method B |

-continued

| # | NR¹R² | R³ | synthesis scheme/ chirality (based on whole molecule) | non-commercial components (preparation described in the literature) | retention time [min] (with HPLC-MS or HPLC) |
|---|---|---|---|---|---|
| 220 | | Cl | scheme 3 (cf # 219) mixture of diastereomers | | 2.01 HPLC-MS, method B |
| 221 | | Cl | scheme 3 mixture of diastereomers | | 2.28 HPLC-MS, method A |
| 222 | | Cl | scheme 3 mixture of diastereomers | | 2.28 HPLC-MS, method A |
| 223 | | Cl | scheme 3 (cf experim. section) racemate | *Chem. Pharm. Bull.* 1970, 1731 | 2.38 HPLC-MS, method A |
| 224 | | Cl | scheme 3 (cf experim. section) 1 diastereomer | | 1.56 HPLC-MS, method B |
| 225 | | Cl | scheme 3 (cf # 224) 1 diastereomer | | 1.07 HPLC-MS, method D |
| 226 | | Cl | scheme 3 (cf # 224) 1 diastereomer | | 1.12 HPLC-MS, method D |
| 227 | | Cl | scheme 3 mixture of diastereomers | | 1.56 HPLC-MS, method B |

-continued

| # | NR¹R² | R³ | synthesis scheme/ chirality (based on whole molecule) | non-commercial components (preparation described in the literature) | retention time [min] (with HPLC-MS or HPLC) |
|---|---|---|---|---|---|
| 228 | (3-aminopyrrolidin-1-yl, *) | Cl | scheme 3 mixture of diastereomers | | 2.23 HPLC-MS, method B |
| 229 | (4-amino-2-methoxycarbonylpyrrolidin-1-yl, *) | Cl | scheme 3 (cf experim. section) 1 diastereomer | | 2.79 HPLC, method B |
| 230 | (4-amino-2-methoxycarbonylpyrrolidin-1-yl, *) | Cl | scheme 3 (cf experim. section) 1 diastereomer | | 2.83 HPLC, method B |
| 231 | (2-(propionamidomethyl)pyrrolidin-1-yl, *) | Cl | scheme 7 (cf experim. section) 1 diastereomer | | 1.19 HPLC-MS, method D |
| 232 | (2-(benzamidomethyl)pyrrolidin-1-yl, *) | Cl | scheme 7 (cf # 231) 1 diastereomer | | 1.27 HPLC-MS, method D |
| 233 | (2-((2-(dimethylamino)acetamido)methyl)pyrrolidin-1-yl, *) | Cl | scheme 7 (cf # 231) 1 diastereomer | | 1.11 HPLC-MS, method D |
| 234 | (2-((methylsulfonamido)methyl)pyrrolidin-1-yl, *) | Cl | scheme 8 (cf experim. section) 1 diastereomer | | 1.20 HPLC-MS, method D |
| 235 | (2-((N,N-dimethylsulfamoylamino)methyl)pyrrolidin-1-yl, *) | Cl | scheme 8 (cf # 235) 1 diastereomer | | 1.24 HPLC-MS, method D |

-continued

| # | NR¹R² | R³ | synthesis scheme/ chirality (based on whole molecule) | non-commercial components (preparation described in the literature) | retention time [min] (with HPLC-MS or HPLC) |
|---|---|---|---|---|---|
| 236 | | Cl | scheme 8 (cf # 235) 1 diastereomer | | 1.24 HPLC-MS, method D |
| 237 | | Cl | scheme 9 (cf experim. section) 1 diastereomer | | 1.33 HPLC-MS, method D |
| 238 | | Cl | scheme 9 (cf # 237) 1 diastereomer | | 1.19 HPLC-MS, method D |
| 239 | | Cl | scheme 10 (cf experim. section) 1 diastereomer | | 1.18 HPLC-MS, method D |
| 240 | | Cl | scheme 3 1 diastereomer | | 1.15 HPLC-MS, method D |
| 241 | | Cl | scheme 3 1 diastereomer | | 1.04 HPLC-MS, method D |
| 242 | | Cl | scheme 3 (cf # 128) 1 diastereomer | | 1.12 HPLC-MS, method D |
| 243 | | Cl | scheme 3 1 diastereomer | | 1.11 HPLC-MS, method D |
| 244 | | Cl | scheme 3 (cf # 128) 1 diastereomer | | 1.13 HPLC-MS, method D |

-continued

| # | NR¹R² | R³ | synthesis scheme/ chirality (based on whole molecule) | non-commercial components (preparation described in the literature) | retention time [min] (with HPLC-MS or HPLC) |
|---|---|---|---|---|---|
| 245 | [piperidine-2-carboxamide, N-linked, * marked] | Cl | scheme 3 (cf # 128) 1 diastereomer | | 1.20 HPLC-MS, method D |
| 246 | [piperidine-2-carboxamide, N-linked, * marked] | Cl | scheme 3 (cf # 128) 1 diastereomer | | 1.17 HPLC-MS, method D |
| 247 | [piperidine-2-carboxamide, N-linked, * marked] | Cl | scheme 3 (cf # 128) 1 diastereomer | | 1.19 HPLC-MS, method D |
| 248 | [pyrrolidine-2-carboxylic acid ethyl ester, 3-OH, N-linked, * marked] | Cl | scheme 3 1 diastereomer | [structure] WO 2004/112793 | 1.30 HPLC-MS, method D |
| 249 | [morpholine, N-linked, * marked] | Cl | scheme 1 racemate | | 1.24 HPLC-MS, method D |
| 250 | [4-methylpiperazine, N-linked, * marked] | Cl | scheme 1 racemate | | 1.16 HPLC-MS, method D |
| 251 | [piperazine, N-linked, * marked] | Cl | scheme 1 racemate | | 1.13 HPLC-MS, method D |

Indications

As has been found, the compounds of formula 1 are characterised by their wide range of applications in the therapeutic field. Particular mention should be made of those applications for which the compounds according to the invention of formula 1 are preferably suited on account of their pharmaceutical efficacy as PDE4 inhibitors. Examples include respiratory or gastrointestinal diseases or complaints, inflammatory diseases of the joints, skin or eyes, cancers, and also diseases of the peripheral or central nervous system.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides intestinales, diseases of the bile duct and gall bladder, e.g. gallstones and conglomerates, for the treatment of inflammatory diseases of the joints such as rheumatoid arthritis or inflammatory diseases of the skin and eyes.

Preferential mention should also be made of the treatment of cancers. Examples include all forms of acute and chronic leukaemias such as acute lymphatic and acute myeloid leukaemia, chronic lymphatic and chronic myeloid leukaemia, and bone tumours such as osteosarcoma and all types of glioma such as oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

Particularly preferably the present invention relates to the use of compounds of formula 1 for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, idiopathic pulmonary fibrosis, fibrosing alveolitis, COPD, chronic bronchitis, chronic sinusitis, asthma, Crohn's disease, ulcerative colitis, particularly COPD, chronic bronchitis and asthma.

It is most preferable to use the compounds of formula 1 for the treatment of inflammatory and obstructive diseases such as COPD, chronic bronchitis, chronic sinusitis, asthma, Crohn's disease, ulcerative colitis, particularly COPD, chronic bronchitis and asthma.

It is also preferable to use the compounds of formula 1 for the treatment of diseases of the peripheral or central nervous system such as depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

An outstanding aspect of the present invention is the reduced profile of side effects. This means, within the scope of the invention, being able to administer a dose of a pharmaceutical composition without inducing vomiting, preferably nausea and most a preferably malaise in the patient. It is particularly preferable to be able to administer a therapeutically effective quantity of substance without inducing emesis or nausea, at every stage of the disease.

Combinations

The compounds of formula 1 may be used on their own or in conjunction with other active substances of formula 1 according to the invention. If desired the compounds of formula 1 may also be used in combination with other pharmacologically active substances. It is preferable to use for this purpose active substances selected for example from among betamimetics, anticholinergics, corticosteroids, other PDE4-inhibitors, LTD4-antagonists, EGFR-inhibitors, MRP4-inhibitors, dopamine agonists, H1-antihistamines, PAF-antagonists and PI3-kinase inhibitors or double or triple combinations thereof, such as for example combinations of compounds of formula 1 with one or two compounds selected from among betamimetics, corticosteroids, PDE4-inhibitors, EGFR-inhibitors and LTD4-antagonists, anticholinergics, betamimetics, corticosteroids, PDE4-inhibitors, EGFR-inhibitors and LTD4-antagonists, PDE4-inhibitors, corticosteroids, EGFR-inhibitors and LTD4-antagonists EGFR-inhibitors, PDE4-inhibitors and LTD4-antagonists EGFR-inhibitors and LTD4-antagonists CCR3-inhibitors, iNOS-inhibitors (inducible nitric oxide synthase-inhibitors), (6R)-L-erythro-5,6,7,8-tetrahydrobiopterin (hereinafter referred to as "BH4") and the derivatives thereof as mentioned in WO 2006/120176 and SYK-inhibitors (spleen tyrosine kinase-inhibitors)

anticholinergics, betamimetics, corticosteroids, PDE4-inhibitors and MRP4-inhibitors.

The invention also encompasses combinations of three active substances, each selected from one of the above-mentioned categories of compounds.

The betamimetics used are preferably compounds selected from among albuterol, bambuterol, bitolterol, broxaterol, carbuterol, clenbuterol, fenoterol, formoterol, arformoterol, zinterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenol, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzyl-sulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazoione, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H- benzo[1,4]oxazin-3-one, 8-({2-[2-(4-ethoxy-phenyl)-1,1'-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-({2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxy-carbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Preferably the beta mimetics are selected from among bambuterol, bitolterol, carbuterol, clenbuterol, fenoterol, formoterol, hexoprenaline, ibuterol, pirbuterol, procaterol, reproterol, salmneterol, sulphonterol, terbutaline, tolubuterol, 3-(4-{6-[2-hydroxy-2-(4-hydroxy-3-hydroxymethyl-phenyl)-ethylamino]-hexyloxy}-butyl)-benzene-sulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-(1-hydroxy-2-[2-(4-phenoxy-acetate ethyl)-1,1-dimethyl-ethylamino]-ethyl)-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-(2-[1,1-dimethyl-2-(2,4,6-trimethylphenyl)-ethylamino]-1-hydroxy-ethyl)-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-({1-hydroxy-2-[2-(4-isopropyl-phenyl)-1.1 dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-(2-[2-(4-ethoxy-phenyl)-1,1-dimethyl-ethylamino]-1-hydroxy-ethyl)-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-(2-[2-(3,4-difluoro-phenyl)-1,1-dimethyl-ethylamino]-1-hydroxy-ethyl)-6-hydroxy-4H-benzo[1,4]oxazin-3-one and 1-(4-ethoxycarbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Particularly preferred betamimetics are selected from among fenoterol, formoterol, salmeterol, 3-(4-(6-[2-hydroxy-2-(4-hydroxy-3-hydroxymethyl-phenyl)-ethylamino]-hexyloxy)-butyl)-benzenesulphonamide, 5-[2-(5,6-diethyl-indan-2-ylamino)-1-hydroxy-ethyl]-8-hydroxy-1H-quinolin-2-one, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[, 4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1 dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl)-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, enantiomers, diastereomers thereof and optionally in the form of the pharmacologically acceptable acid addition salts, solvates or hydrates thereof.

Of these betamimetics those which are particularly preferred according to the invention are formoterol, salmeterol, 3-(4-{6-[2-hydroxy-2-(4-hydroxy-3-hydroxymethyl-phenyl)-ethylamino]-hexyloxy}-butyl)-benzenesulphonamide, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1.1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl)}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 5-[2-(5,6-diethyl-indan-2-ylamino)-1-hydroxy-ethyl]-8-hydroxy-1H-quinolin-2-one, optionally in the form of the racemates, enantiomers, diastereomers thereof and optionally in the form of the pharmacologically acceptable acid addition salts, solvates or hydrates thereof.

According to the invention the acid addition salts of the betamimetics are preferably selected from among hydrochloride, hydrobromide, hydiodide, hydrosulphate, hydrophosphate, hydromethanesulphonate, hydronitrate, hydromaleate, hydroacetate, hydrobenzoate, hydrocitrate, hydrofumarate, hydrotartrate, hydroxalate, hydrosuccinate, hydrobenzoate and hydro-p-toluenesulphonat, preferably hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among the tiotropium salts, oxitropium salts, flutropium salts, ipratropium salts, glycopyrronium salts, trospium salts, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate-methobromide, tropenol 9-fluoro-fluorene-9-carboxylate-methobromide, scopine 9-hydroxy-fluoren-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl cyclopropyltropine 4,4'-difluorobenzilate methobromide, tropenol 9-hydroxy-xanthene-9-carboxylate-methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide, scopine 9-hydroxymethyl-xanthene-9-carboxylate methobromide, optionally in the form of the solvates or hydrates thereof.

In the above-mentioned salts the cations tiotropium, oxitropium, flutropium, ipratropium, glycopyrronium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among prednisolone, prednisone, butixocortpropionate, flunisolide, beclomethasone, triamcinolone, budesonide, fluticasone, mometasone, ciclesonide, rofleponide, dexamethasone, betamethasone, deflazacort, RPR-106541, NS-126, (S)-fluoromethyl 6,9-difluoro-17-[(2-furanylcarbonyl)oxy]-1-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate,
optionally in the form of the racemates, enantiomers or diastereomers thereof and optionally in the form of the salts and derivatives, solvates and/or hydrates thereof.

Particularly preferred is the steroid selected from among flunisolide, beclomethasone, triamcinolone, budesonide, fluticasone, mometasone, ciclesonide, rofleponide, dexamethasone, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-7-carbothionate,
optionally in the form of the racemates, enantiomers or diastereomers thereof and optionally in the form of the salts and derivatives, solvates and/or hydrates thereof.

Particularly preferred is the steroid selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates thereof Other PDE4 inhibitors which may be used are preferably compounds selected from among enprofyllin, theophyllin, roflumilast, ariflo (cilomilast), tofimilast, pumafentrin, lirimilast, arofyllin, atizoram, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370, N-(3,5-dichloro-1-oxo-pyridin-4-yl)-4-difluoromethoxy-3-cyclopropylmethoxybenzamide, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-5-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexane-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl [4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates or hydrates thereof.

Particularly preferably the PDE4-inhibitor is selected from among enprofyllin, roflumilast, ariflo (cilomilast), arofyllin, atizoram, AWD-12-281 (GW-842470), T-440, T-2585, PD-168787, V-11294A, Cl-1018, CDC-801, D-22888, YM-58997, Z-15370, N-(3,5-dichloro-1-oxo-pyridin-4-yl)-4-difluoromethoxy-3-cyclopropylmethoxybenzamide, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferably the PDE4-inhibitor is selected from among roflumilast, ariflo (cilomilast), arofyllin, AWD-12-281 (GW-842470), 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], atizoram, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2.3-dichlorothieno[3,2-b]pyridin-5-yl)-(E)-ethenyl)phenyl)-3-(2-(1-hydroxy-1-methylethyl)phenyl)propyl)thio)methyl)cyclopropane-acetic acid and [2-[[2-(4-tert-butyl-2-thiazolyl)-5-benzofuranyl]oxymethyl]phenyl]acetic acid, optionally in the form of the racemates, enantiomers or diastereomers, optionally in the form of the pharmacologically acceptable acid addition salts and optionally in the form of the salts and derivatives, solvates and/or hydrates thereof.

Preferably the LTD4-antagonist is selected from among montelukast, pranlukast, zafirlukast, MCC-847 (ZD-3523), MN-001, MEN-91507 (LM-1507), VUF-5078, VUF-K-8707 and L-733321, optionally in the form of the racemates, enantiomers or diastereomers, optionally in the form of the pharmacologically acceptable acid addition salts and optionally in the form of the salts and derivatives, solvates and/or hydrates thereof.

Particularly preferably the LTD4-antagonist is selected from among montelukast, pranlukast, zafirlukast, MCC-847 (ZD-3523), MN-001 and MEN-91507 (LM-1507), optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo- 2-buten-1-yl]amino}-7-[(S)-(tetrahydrofuran-2-yl) methoxy]-quinazoline, 4-[(3-ethynyl-phenyl)amino]-6,7-bis-(2-methoxy-ethoxy)-quinazoline, 4-[(3-oro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidin, 3-cyano-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-([(2-methanesulphonyl-ethyl)amino]methyl)-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5.5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl) methoxy]-quinazoline, 4-[(3-chloro-4-fluoro-phenyl) amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino)-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1]-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-fluoro-phenyl)amino]-6-(1-methyl-piperidin-4-yloxy)-7-methoxy-quinazoline, 4-[(3-chloro-4-fluoro-phenyl)amino]-6-{1-[(morpholin-yl) carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl) amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl) amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl) amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl) amino]-6-(1-methyl-piperidin-4-yloxy)-7-(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy)-7-methoxy-quinazoline, 4-[(3-chloro-4-fluoro-phenyl)amino]-6-[cis-4-(N-acetyl-N-methylamino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline. 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, Cetuximab, Trastuzumab, ABX-EGF and Mab ICR-62, optionally in the form of the racemates, enantiomers or diastereomers thereof, optionally in the form of the pharmacologically acceptable acid addition salts, the solvates and/or hydrates thereof.

Preferred EGFR inhibitors are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[3-chloro-4-fluorophenyl)amino]-6-{[4-(N,N-diethylamino)-1-oxo-2-buten-1-yl]amino}7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy)-quinazoline, 4-[(3-chloro-4-fluoro-phenyl)amino]-6-{4-(R)-2-methoxymethyl-6-oxo-morpholin-4-yl-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{([4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5.5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4 [(3-chloro-4-fluoro-phenyl)amino]-6-(tetrahydropyran-4-yloxy)-7-ethoxy-quinazoline, 4 [(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-

6-(1-aminocarbonylmethyl-piperidin-4-yloxy)-7-methoxy quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl) carbonyl]-N-methyl-amino}-cyclohexan-1-yloxy)-7-methoxy-quinazoline. 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethane-sulphonylamino-cyclohexan-1-yloxy)-7-methoxy-quinazoline, 4-[(3-chloro-4-fluoro-phenyl)amino]-6-(1-methane-sulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan 1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2.6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and Cetuximab, optionally in the form of the racemates, enantiomers or diastereomers thereof; optionally in the form of the pharmacologically acceptable acid addition salts, the solvates and/or hydrates thereof.

It is particularly preferable within the scope of the present invention to use those EGFR-inhibitors which are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5.5-dimethyl-2-oxo-morpholin-4-yl)-1-oxo-2-buten-1-yl]amino}-quinazoline, 4-[(3-chloro-4-fluoro-phenyl)amino]-6-(2-[4-(2-oxo-morpholin-4-yl)-piperidin-1-yl]-ethoxy)-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)

carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{(1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-({N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-1-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{(1-[(2-methoxy-ethyl)carbonyl]-piperidin-4-yloxy}-7-methoxy-quinazoline, optionally in the form of the racemates, enantiomers or diastereomers thereof, optionally in the form of the pharmacologically acceptable acid addition salts, the solvates and/or hydrates thereof.

Particularly preferred EGFR-inhibitors according to the invention are the compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-ethynyl-phenyl)amino]-6,7-bis-(2-methoxy-ethoxy)-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5.5-dimethyl-2-oxo-morpholin-4-yl)-1-oxo-2-buten-1-yl]amino}-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline and 4-[(3-chloro-4-fluoro-phenyl)amino]-6-(1-cyano-piperidin-4-yloxy)-7-methoxy-quinazoline optionally in the form of the racemates, enantiomers or diastereomers thereof, optionally in the form of the pharmacologically acceptable acid addition salts, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepines.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-β-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, clycolithocholic acid sulphate, ibuprofen, indomethacin, indoprofen, ketoprofen, lithocholic acid sulphate, methotrexate, MK571 ((E)-3-[[[3-[2-(7-chloro-2-quinolinyl)ethenyl]phenyl]-[[3-dimethylamino)-3-oxopropyl]thio]methyl]thio]-propanoic acid), α-naphthyl-β-D-glucuronide, nitrobenzyl mercaptopurine riboside, probenecid, PSC833, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

Preferably the invention relates to the use of MRP4-inhibitors for preparing a pharmaceutical composition for the treatment of respiratory complaints, containing the PDE4B-inhibitors and MRP4-inhibitors, the MRP4-inhibitors preferably being selected from among N-acetyl-dinitrophenyl-cysteine, dehydroepiandrosterone 3-sulphate, dilazep, dinitrophenyl-5-glutathione, estradiol 3,17-disulphate, flurbiprofen, glycocholate, glycolithocholic acid sulphate, ibuprofen, indomethacin, indoprofen, lithocholic acid sulphate, MK571, PSC833, sildenafil, taurochenodeoxycholate, taurocholate, taurolithocholate, taurolithocholic acid sulphate, trequinsin and zaprinast, dipyridamole, optionally in the form of the racemates, enantiomers, diastereomers and the pharmacologically acceptable acid addition salts and hydrates thereof.

The invention relates more preferably to the use of MRP4-inhibitors for preparing a pharmaceutical composition for treating respiratory complaints, containing the PDE4B-inhibitors and MRP4-inhibitors according to the invention, the MRP4-inhibitors preferably being selected from among dehydroepiandrosterone 3-sulphate, estradiol 3,17-disulphate, flurbiprofen, indomethacin, indoprofen, MK571, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydro-p-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the PDE4B-inhibitors, MRP4-inhibitors and another active substance according to the invention, such as, for example, an anticholinergic, a steroid, an LTD4-antagonist or a betamimetic, and the preparation thereof and the use thereof for treating respiratory complaints.

The iNOS-inhibitors used are preferably compounds selected from among: S-(2-aminoethyl)isothiourea, aminoguanidine, 2-aminomethylpyridine, AMT, L-canavanine, 2-iminopiperidine, S-isopropylisothiourea, S-methylisothiourea, S-ethylisothiourea, S-methyltiocitrulline, S-ethylthiocitrulline. L-NA ($N^{\omega}$-nitro-L-arginine), L-NAME ($N^{\omega}$-nitro-L-arginine methylester), L-NMMA ($N^{G}$-monomethyl-L-arginine), L-NIO ($N^{\omega}$-iminoethyl-L-ornithine), L-NIL ($N^{\omega}$-iminoethyl-lysine), (S)-6-acetimidoylamino-2-aminohexanoic acid (1H-tetrazol-5-yl)-amide (SC-51) (*J. Med. Chem.* 2002, 45, 1686-1689), 1400W, (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-3-amino-1-phenyl-propoxy)-4-chloro-5-fluorobenzonitrile (WO 01/62704), 2-((1R,3S)-3-amino-4-hydroxy-1-thiazol-5-yl-butylsulphanyl)-6-trifluoromethyl-nicotinonitrile (WO 2004/041794), 2-((1R,3S)-3-amino-4-hydroxy-1-thiazol-5-yl-butylsulphanyl)-4-chloro-benzonitrile (WO 2004/041794), 2-((1R,3S)-3-amino-4-hydroxy-1-thiazol-5-yl-butylsulphanyl)-5-chloro-benzonitrile (WO 2004/041794), (2S,4R)-2-amino-4-(2-chloro-5-trifluoromethyl-phenylsulphanyl)-4-thiazol-5-yl-butan-1-ol (WO 2004/041794), 2-((1R,3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamines such as e.g. AR-C102222 (*J. Med. Chem.* 2003, 46, 913-916), (1S,5S,6R)-7-chloro-5-methyl-2-aza-bicyclo[4.1.0]hept-2-en-3-ylamine (ONO-1714) (*Biochem. Biophys. Res. Commun.* 2000, 270, 663-667), (4R,5R)-5-ethyl-4-methyl-thiazolidin-2-ylideneamine (*Bioorg. Med. Chem.* 2004, 12, 4101), (4R,5R)-5-ethyl-4-methyl-selenazolidin-2-ylideneamine (*Bioorg. Med. Chem. Lett.* 2005, 15, 1361), 4-aminotetrahydrobiopterine (*Curr. Drug Metabol.* 2002, 3, 119-121), (E)-3-(4-chloro-phenyl)-N-(1-{2-oxo-2-[4-(6-trifluoromethyl-pyrimidin-4-yloxy)-piperidin-1-yl]-ethylcarbamoyl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-ylmethyl-phenoxy)-ethoxy]-2-phenyl-pyridine (PPA250) (*J. Pharmacol. Exp. Ther.* 2002, 303, 52-57), methyl 3-{[(benzo[1.3]dioxol-5-yl-methyl)-carbamoyl]-methyl}-4-(2-imidazol-1-yl-pyrimidin-4-yl)-piperazin-1-carboxylate (BBS-1) (*Drugs Future* 2004, 29, 45-52), (R)-1-(2-imidazol-1-yl-6-methyl-pyrimidin-4-yl)-pyrrolidine-2-carboxylic acid (2-benzo[1.3]dioxol-5-yl-ethyl)-amide (BBS-2) (*Drugs Future* 2004, 29, 45-52) and the pharmaceutical salts, prodrugs or solvates thereof.

Other iNOS-inhibitors which may be used within the scope of the present invention are antisense oligonucleotides, particularly antisense oligonucleotides that bind iNOS-coding nucleic acids. For example, WO 01/52902 describes antisense oligonucleotides, particularly antisense-oligonucleotides, which bind iNOS-coding nucleic acids, for modulating the expression of iNOS. Those iNOS-antisense-oligonucleotides as described particularly in WO 01/52902 may therefore also be combined with the PDE4-inhibitors of the present invention on the basis of their similar activity to the iNOS inhibitors.

Compounds which may be used as SYK-inhibitors are preferably compounds selected from among: 2-[(2-aminoethyl)amino]-4-[(3-bromophenyl)amino]-5-pyrimidinecarboxamide;
2-[[7-(3,4-dimethoxyphenyl)imidazo[1,2-c]pyrimidin-5-yl]amino]-3-pyridinecarboxamide;
6-[[5-fluoro-2-[3,4,5-trimethoxyphenyl)amino]-4-pyrimidinyl]amino]-2,2-dimethyl-2H-pyrido[3,2-b]-1,4-oxazin-3 (4H)-one;
N-[3-bromo-7-(4-methoxyphenyl)-1,6-naphthyridin-5-yl]-1,3-propanediamine
7-(4-methoxyphenyl)-N-methyl-1,6-naphthyridin-5-amine;
N-[7-(4-methoxyphenyl)-1,6-napbthyridin-5-yl]-1,3-propanediamine;
N-[7-(2-thienyl)-1,6-naphthyridin-5-yl]-1,3-propanediamine;
N-[7-[4-(dimethylamino)phenyl]-1,6-naphthyridin-5-yl]-1,2-ethanediamine;
N-[7-(4-methoxyphenyl)-2-(trifluoromethyl)-1,6-naphthyridin-5-yl]-1,3-propanediamine;
N-[7-(4-methoxyphenyl)-3-phenyl-1,6-naphthyridin-5-yl]-1,3-propanediamine;
N-(7-phenyl-1,6-naphthyridin-5-yl)-1,3-propanediamine;
N-[7-(3-fluorophenyl)-1,6-naphthyridin-5-yl]-1,3-propanediamine;
N-[7-(3-clorophenyl)-1,6-naphthyridin-5-yl]-1,3-propanediamine;
N-[7-[3-trifluoromethoxy)phenyl]-1,6-naphthyridin-5-yl]-1,3-propanediamine
N-[7-(4-fluorophenyl)-1,6-naphthyridin-5-yl]-1,3-propanediamine;
N-[7-(4-fluorophenyl)-1,6-naphthyridin-5-yl]-1,3-propanediamine;
N-[7-(4-clorophenyl)-1,6-naphthyridin-5-yl]-1,3-propanediamine;
N-(7-(4'-methyl[1,1'-biphenyl]-4-yl)-1,6-naphthyridin-1,3-propanediamine;
N-[7-[4-(dimethylamino)phenyl]-1,6-naphthyridin-5-yl]-1,3-propanediamine;
N-[7-[4-(diethylamino)phenyl]-1,6-naphthyridin-5-yl]-1,3-propanediamine;
N-[7-[4-(4-morpholinyl)phenyl]-1,6-naphthyridin-5-yl]-1,3-propanediamine;
N-[7-[4-[[2-(dimethylamino)ethyl]methylamino]phenyl]-1,6-naphthyridin-5-yl]-1,3-propanediamine;
N-[7-(4-bromophenyl)-1,6-naphthyridin-5-yl]-1,3-propanediamine;
N-[7-(4-methylphenyl)-1,6-naphthyridin-5-yl]-1,3-propanediamine;
N-[7-[4-(methylthio)phenyl]-1,6-naphthyridin-5-yl]-1,3-propanediamine;
N-[7-[4-(1-methylethyl)phenyl]-1,6-naphthyridin-5-yl]-1,3-propanediamine;
7-[4-(dimethylamino)phenyl]-N-methyl-1,6-naphthyridin-5-amine;
7-[4-(dimethylamino)phenyl]-N,N-dimethyl-1,6-naphthyridin-5-amine;
N-[7-[4-(dimethylamino)phenyl]-1,6-naphthyridin-5-yl]-1,4-butanediamine;
N-[7-[4-(dimethylamino)phenyl]-1,6-naphthyridin-5-yl]-1,5-pentanediamine;
3-[[7-[4-(dimethylamino)phenyl]-1,6-naphthyridin-5-yl]oxy]-1-propanol;
4-[5-(4-aminobutoxy)-1,6-naphthyridin-7-yl]-N,N-dimethyl-benzenamine;
4-[[7-[4-(dimethylamino)phenyl]-1,6-naphthyridin-5-yl]amino]-1-butanol;
N-[7-[4-(dimethylamino)phenyl]-1,6-naphthyridin-5-yl]-N-methyl-1,3-propanediamine;
N-[7-[4-(dimethylamino)phenyl]-1,6-naphthyridin-5-yl]-N'-methyl-1,3-propanediamine;
N-[7-[4-(dimethylamino)phenyl]-1,6-naphthyridin-5-yl]-N,N'-dimethyl-1,3-propanediamine;
1-amino-3-[[7-[4-(dimethylamino)phenyl]-1,6-naphthyridin-5-yl]amino]-2-propanol;
N-[7-[4-(dimethylamino)phenyl]-1,6-naphthyridin-5-yl]-2,2-dimethyl-1,3-propanediamine;
7-[4-(dimethylamino)phenyl]-N-(3-pyridinylmethyl)-1,6-naphthyridin-5-amine;
N-[(2-aminophenyl)methyl]-7-[4-(dimethylamino)phenyl]-1,6-naphthyridin-5-amine;
N-[7-[6-(dimethylamino)[1,1'-biphenyl]-3-yl]-1,6-naphthyridin-5-yl]-1,3-propanediamine;
N-[7-[3-chloro-4-(diethylamino)phenyl]-1,6-naphthyridin-5-yl]-1,3-propanediamine;
N-[7-[4-(dimethylamino)-3-methoxyphenyl]-1,6-naphthyridin-5-yl]-1,3-propanediamine;
N-[7-[4-(diethylamino)phenyl]-3-methyl-1,6-naphthyridin-5-yl]-1,3-propanediamine;
N-[7-(3'-fluoro[1,1'-biphenyl]-3-yl)-1,6-naphthyridin-5-yl]-1,2-ethanediamine,
N-[7-(4-methoxyphenyl)-1,6-naphthyridin-5-yl]-1,6-naphthyridine-1,3-propanediamine;
N,N'-bis(3-aminopropyl)-7-(4-methoxyphenyl)-2.5-diamine;
N-[7-(4-methoxyphenyl)-2-(phenylmethoxy)-1,6-naphthyridin-5-yl]-1,6-naphthyridine-1,3-propanediamine;
N5-(3-aminopropyl)-7-(4-methoxyphenyl)-N2-(phenylmethyl)-2.5-diamine;
N-[7-(2-naphthalenyl)-1,6-naphthyridin-5-yl]-1,3-propanediamine;
N-[7-(2'-fluoro[1,1'-biphenyl]-4-yl)-1,6-naphthyridin-5-yl]-1,3-propanediamine;
N-[7-(3,4,5-trimethoxyphenyl)-1,6-naphthyridin-5-yl]-1,3-propanediamine;
N-[7-(3,4-dimethylphenyl)-1,6-naphthyridin-5-yl]-1,3-propanediamine;

1-amino-3-[[7-(2-naphthalenyl)-1,6-naphthyridin-5-yl]amino]-2-propanol;
1-amino-3-[[7-(2'-fluoro[1,1'-biphenyl]-4-yl)-1,6-naphthyridin-5-yl]amino]-2-propanol;
1-amino-3-[[7-(4'-methoxy[1,1'-biphenyl]-4-yl)-1,6-naphthyridin-5-yl]amino]-2-propanol;
1-amino-3-[[7-(3,4,5-trimethoxyphenyl)-1,6-naphthyridin-5-yl]amino]-2-propanol;
1-amino-3-[[7-(4-bromnophenyl)-1,6-naphthyridin-5-yl]amino]-2-propanol;
N-[7-(4'-methoxy[1,1'-biphenyl]-4-yl)-1,6-naphthyridin-5-yl]-2,2-dimethyl-1,3-propanediamine;
1-[[7-[4-(dimethylamino)phenyl]-1,6-naphthyridin-5-yl]amino]-2-propanol;
2-[[2-[[7-[4-(dimethylamino)phenyl]-1,6-naphthyridin-5-yl]amino]ethyl]thio]-ethanol;
7-[4-(dimethylamino)phenyl]-N-(3-methyl-5-isoxazolyl)-1,6-naphthyridin-5-amine;
7-[4-(dimethylamino)phenyl]-N-4-pyrimidinyl-1,6-naphthyridin-5-amine;
N-[7-[4-(dimethylamino)phenyl]-1,6-naphthyridin-5-yl]-1,3-cyclohexanediamine;
N,N-dimethyl-4-[5-(1-piperazinyl)-1,6-naphthyridin-7-yl]benzenamine;
4-[5-(2-methoxyethoxy)-1,6-naphthyridin-7-yl]-N,N-dimethyl-benzenamine;
1-[7-[4-(dimethylamino)phenyl]-1,6-naphthyridin-5-yl]-4-piperidinol;
1-[7-[4-(dimethylamino)phenyl]-1,6-naphthyridin-5-yl]-3-pyrrolidinol;
7-[4-(dimethylamino)phenyl]-N-(2-furanylmethyl)-1,6-naphthyridin-5-amine;
7-[4-(dimethylamino)phenyl]-N-[3-(1H-imidazol-1-yl)propyl]-1,6-naphthyridin-5-amine;
1-[7-[4-(dimethylamino)phenyl]-1,6-naphthyridin-5-yl]-4-piperidinecarboxamide;
1-[3-[[7-[4-(dimethylamino)phenyl]-1,6-naphthyridin-5-yl]amino]propyl]-2-pyrrolidinone;
N-[3'-[5-[(3-aminopropyl)amino]-1,6-naphthyridin-7-yl][1,1'-biphenyl]-3-yl]-acetamide;
N-[7-(4'-fluoro[1,1'-biphenyl]-4-yl)-1,6-naphthyridin-5-yl]-1,3-propanediamine;
N-[4'-[5-[(3-aminopropyl)amino]-1,6-naphthyridin-7-yl][1,1'-biphenyl]-3-yl]-acetamide;
N-[7-[4-(1,3-benzodioxol-5-yl)phenyl]-1,6-naphthyridin-5-yl]-1,3-propanediamine;
N-[7-[4-(2-thienyl)phenyl]-1,6-naphthyridin-5-yl]-1,3-propanediamine;
N-[7-[4-fluoro-3-(trifluoromethyl)phenyl]-1,6-naphthyridin-5-yl]-1,3-propanediamine;
N-[7-[4-(3-pyridinyl)phenyl]-1,6-naphthyridin-5-yl]-1,3-propanediamine;
N-[7-(1,3-benzodioxol-5-yl)-1,6-naphthyridin-5-yl]-1,3-propanediamine;
N-[7-(6-methoxy-2-naphthalenyl)-1,6-naphthyridin-5-yl]-1,3-propanediamine;
7-[4-(dimethylamino)phenyl]-N-(4-pyridinylmethyl)-1,6-naphthyridin-5-amine;
3-[[7-[4-(dimethylamino)phenyl]-1,6-naphthyridin-5-yl]methylamino]-propanenitrile;
7-[4-(dimethylamino)phenyl]-N-[1-(phenylmethyl)-4-piperidinyl]-1,6-naphthyridin-5-amine;
N-[7-[4-(dimethylamino)phenyl]-1,6-naphthyridin-5-yl]1,2-cyclohexanediamine, (1R,2S)-rel-.
N-[7-[4-(dimethylamino)phenyl]-1,6-naphthyridin-5-yl]-1,2-benzenedimethanamine;
N-[7-[4-(diethylamino)phenyl]-1,6-naphthyridin-5-yl]-1,4-butanediamine;
N-[7-[3',5'-bis(trifluoromethyl)[1,1'-biphenyl]-4-yl]-1,6-naphthyridin-5-yl]-3-propanediamine;
N-[7-(3'-methoxy[1,1'-biphenyl]-4-yl)-1,6-naphthyridin-5-yl]-1,3-propanediamine;
N-[7-(3'-fluoro[1,1'-biphenyl]-4-yl)-1,6-naphthyridin-5-yl]-1,3-propanediamine;
4-[[7-[4-(dimethylamino)phenyl]-1,6-naphthyridin-5-yl]oxy]-1-butanol;
N-[7-[4-(dimethylemino)phenyl]-1,6-naphthyridin-5-yl]-1,4-cyclohexanediamine;
7-[4-(dimethylamino)phenyl]-N-(2.2.6.6-tetramethyl-4-piperidinyl)-1,6-naphthyridin-5-amine;
N-[7-[3-bromo-4-(dimethylamino)phenyl]-1,6-naphthyridin-5-yl]-1,3-propanediamine;
N-[7-(1]-methyl-1H-indol-5-yl)-1,6-naphthyridin-5-yl]-1,3-propanediamine;
N-[7-[3-(trifluoromethyl)phenyl]-1,6-naphthyridin-5-yl]-1,3-propanediamine;
N-[7-[4-(trifluoromethyl)phenyl]-1,6-naphthyridin-5-yl]-1,3-propanediamine;
N-[7-(3-bromo-4-methoxyphenyl)-1,6-naphthyridin-5-yl]-1,3-propanediamine;
N-[7-[4-[[3-(dimethylamino)propyl]methylamino]phenyl]-1,6-naphthyridin-5-yl]-1,4-cyclohexanediamine;
N-[7-[4-[[2-(dimethylamino)ethyl]methylamino]phenyl]-1,6-naphthyridin-5-yl]-1,4-cyclohexanediamine;
N-[7-[4-(dimethylamino)-3-methoxyphenyl]-1,6-naphthyridin-5-yl]-1,4-cyclohexanediamine;
N-[7-[4-(4-morpholinyl)phenyl]-1,6-naphthyridin-5-yl]-1,4-cyclohexanediamine;
N-[7-[3-bromo-4-(4-morpholinyl)phenyl]-1,6-naphthyridin-5-yl]-1,4-cyclohexanediamine;
4-[[7-[4-[[2-(dimethylamino)ethyl]methylamino]phenyl]-1,6-naphthyridin-5-yl]oxy]-cyclohexanol;
N-[7-[3-bromo-4-(4-morpholinyl)phenyl]-1,6-naphthyridin-5-yl]-1,3-propanediamine;
N,N-dimethyl-4-[5-(4-methyl-1-piperazinyl)-1,6-naphthyridin-7-yl]-benzenamine;
4-[[7-[4-[[3-(dimethylamino)propyl]methylamino]phenyl]-1,6-naphthyridin-5-yl]oxy]-cyclohexanol;
N-[7-[4-[[2-(dimethylamino)ethyl]methylamino]phenyl]-1,6-naphthyridin-5-yl]-1,4-butanediamine;
1,1-dimethylethyl[3-[[5-[(3-aminopropyl)amino]-7-(4-methoxyphenyl)-1,6-naphthyridin-2-yl]amino]propyl]-carbamate.

Formulations

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised in that they contain one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet so coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a pteridine and one or more combination partners selected from those described above.

We claim:
1. A medicament composition comprising
A) one or more compounds of formula I,

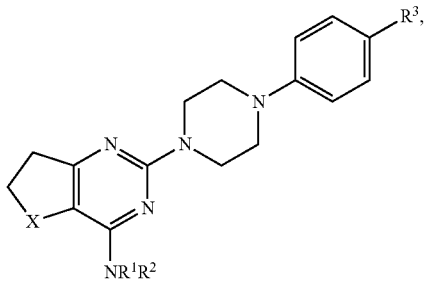

wherein
X denotes SO;
$R^1$ denotes H, $C_{1-6}$-alkyl, $C_{2-6}$-alkenyl, $C_{2-6}$-alkynyl, $C_{6-10}$-aryl, $C_{6-10}$-aryl-$C_{1-6}$-alkylene or $C_{5-10}$-heteroaryl-$C_{1-6}$-alkylene
$R^2$ is H or a group selected from among $C_{1-10}$-alkyl, $C_{2-6}$-alkenyl and $C_{2-6}$-alkynyl, which may optionally be substituted by halogen and which may optionally be substituted by one or more groups selected from among $OR^{2.1}$, $COOR^{2.1}$, $CONR^{2.2}R^{2.3}$, $SR^{2.1}$, $C_{6-10}$-aryl, a mono- or bicyclic $C_{3-10}$-heterocycle, a mono- or bicyclic $C_{5-10}$-heteroaryl, a mono- or bicyclic $C_{3-10}$-cycloalkyl, $CH_2$—$NR^{2.2}R^{2.3}$ and $NR^{2.2}R^{2.3}$, which may in turn optionally be substituted by one or more groups selected from among OH, halogen, $OR^{2.1}$, oxo, $C_{1-6}$-alkyl, $C_{6-10}$-aryl, $COOR^{2.1}$, $CH_2$—$NR^{2.2}R^{2.3}$ and $NR^{2.2}R^{2.3}$,
wherein $R^{2.1}$ is H or a group selected from among $C_{1-6}$-alkyl, $C_{1-6}$-alkanol, $C_{1-3}$-haloalkyl, mono- or bicyclic $C_{3-10}$-cycloalkyl, $C_{6-10}$-aryl-$C_{1-6}$-alkylene, mono- or bicyclic $C_{5-10}$-heteroaryl-$C_{1-6}$-alkylene, $C_{3-10}$-heterocycle-$C_{1-6}$-alkylene, $C_{3-10}$-cycloalkyl-$C_{1-6}$-alkylene, a mono- or bicyclic $C_{6-10}$-aryl, a mono- or bicyclic $C_{5-10}$-heteroaryl and a mono- or bicyclic, saturated or unsaturated heterocycle, which may optionally be substituted by one or more groups selected from among OH, halogen, $C_{1-6}$-alkyl and $C_{6-10}$-aryl,
while $R^{2.2}$ and $R^{2.3}$ independently of one another are H or a group selected from among halogen, $C_{1-6}$-alkyl, mono- or bicyclic $C_{3-10}$-cycloalkyl, $C_{6-10}$-aryl-$C_{1-6}$-alkylene, $C_{5-10}$-heteroaryl-$C_{1-6}$-alkylene, mono- or bicyclic $C_{6-10}$-aryl, mono- or bicyclic $C_{3-10}$-heterocycle, mono- or bicyclic $C_{5-10}$-heteroaryl, CO—$NH_2$, CO—$NHCH_3$, CO—$N(CH_3)_2$, $SO_2(C_1-C_2$-alkyl), CO—$R^{2.1}$ and $COOR^{2.1}$, which may optionally be substituted by one or more groups selected from among OH, halogen, $C_{1-6}$-alkyl, $C_{6-10}$-aryl and $COOR^{2.1}$,
or $R^2$ denotes a mono- or polycyclic $C_{3-10}$-cycloalkyl, which may optionally be bridged by one or more $C_{1-3}$-alkyl groups and which may optionally be substituted by a group selected from among branched or unbranched $C_{1-6}$-alkanol, $OR^{2.1}$, $COOR^{2.1}$, $SO_2NR^{2.2}R^{2.3}$, $C_{3-10}$-heterocycle, $C_{6-10}$-aryl, $C_{1-6}$-alkyl, $C_{6-10}$-aryl-$C_{1-6}$-alkylene, $C_{5-10}$-heteroaryl-$C_{1-6}$-alkylene, mono- or bicyclic $C_{3-10}$-cycloalkyl and $NR^{2.2}R^{2.3}$, which may optionally be substituted by one or more groups selected from among OH, $OR^{2.1}$, oxo, halogen, $C_{1-6}$-alkyl, $C_{6-10}$-aryl and $NR^{2.2}R^{2.3}$,
or $R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{3-10}$-cycloalkyl, $C_{3-10}$-heterocycle, $C_{1-6}$-alkyl, $C_{6-10}$-aryl-$C_{1-6}$-alkylene, $C_{3-10}$ heterocycle-$C_{1-6}$-alkylene, $C_{5-10}$-heteroaryl-$C_{1-6}$-alkylene, $C_{6-10}$-aryl, $SO_2$—$CH_3$, $SO_2$—$CH_2CH_3$ and $SO_2$—$NR^{2.2}R^{2.3}$, which may in turn optionally be substituted by one or more groups selected from among OH, $OR^{2.1}$, oxo, halogen, $C_{1-6}$-alkyl, $C_{6-10}$-aryl and $NR^{2.2}R^{2.3}$, or $R^2$ denotes a group selected from among mono- or bicyclic, saturated or unsaturated $C_{3-10}$-heterocycle and a mono- or bicyclic $C_{5-10}$-heteroaryl, which includes 1 to 4 heteroatoms selected from among S, O and N and optionally by one or more groups selected from among halogen, OH, oxo and SH or by one or more groups selected from among $OR^{2.1}$, $SR^{2.1}$, $COOR^{2.1}$, $COR^{2.1}$, $C_{3-10}$-cycloalkyl, $C_{6-10}$-aryl, $C_{1-6}$-alkyl, $C_{6-10}$-aryl-$C_{1-6}$-alkylene, $C_{5-10}$-heteroaryl-$C_{1-6}$-alkylene, $C_{5-10}$-heterocycle, $C_{5-10}$-heteroaryl, $C_{1-6}$-alkanol and $NR^{2.2}R^{2.3}$, which may in turn optionally be substituted by one or more groups selected from among OH, $OR^{2.1}$, oxo, halogen, $C_{1-6}$-alkyl, $C_{6-10}$-aryl and $NR^{2.2}R^{2.3}$,
or wherein $NR^1R^2$ together denote a heterocyclic $C_{4-7}$ ring, which may optionally be bridged, which contains 1, 2 or 3 heteroatoms selected from among N, O and S and which may optionally be substituted by one or more groups selected from among OH, $OR^{2.1}$, $C_{1-6}$-alkanol, oxo, halogen, $C_{1-6}$-alkyl, $C_{6-10}$-aryl, $COOR^{2.1}$, $CH_2$—$NR^{2.2}$—COO—$R^{2.1}$, $CH_2$—$NR^{2.2}$—CO—$R^{2.1}$, $CH_2$—$NR^{2.2}$—CO—$CH_2$—$NR^{2.2}R^{2.3}$, $CH_2$—$NR^{2.2}$—$SO_2$—$C_{1-3}$-alkyl, $CH_2$—$NR^{2.2}$—$SO_2$—$NR^{2.2}R^{2.3}$, $CH_2$—$NR^{2.2}$—CO—$NR^{2.2}R^{2.3}$, CO—$NR^{2.2}R^{2.3}$, $CH_2$—$NR^{2.2}R^{2.3}$ and $NR^{2.2}R^{2.3}$, and wherein $R^3$ is selected from among fluorine, chlorine, bromine, iodine, hydroxy, $SO_2$—$CH_3$, $COOR^{2.1}$, nitrile group and $C_{3-10}$ heterocycle-$C_{1-6}$-alkylene, wherein the $C_{3-10}$-heterocycle may be mono- or bicyclic and may optionally be substituted by a group selected from among OH, halogen, oxo, $C_{1-6}$-alkyl and $C_{6-10}$-aryl, or is a group selected from among $C_{1-6}$-alkyl, $C_{2-6}$-alkenyl, $C_{2-6}$-alkynyl, $C_{6-10}$-aryl; $C_{6-10}$-aryl-$C_{1-6}$-alkylene, $C_{5-10}$-heteroaryl-$C_{1-6}$-alkylene, $C_{3-10}$-heterocycle and $C_{3-10}$-cycloalkyl, which may optionally be substituted by a group selected from among OH, halogen, oxo, $C_{1-6}$-alkyl and $C_{6-10}$-aryl, or wherein $R^3$ denotes the group —CO—$NR^{3.1}R^{3.2}$, wherein $R^{3.1}$ and $R^{3.2}$ independently of one another are H or groups selected from among $C_{1-6}$-alkyl, $C_{2-6}$-alkenyl, $C_{2-6}$-alkynyl, $C_{6-10}$-aryl; $C_{6-10}$-aryl-$C_{1-6}$-alkylene, $C_{5-10}$-heteroaryl-$C_{1-6}$-alkylene, $C_{5-10}$-heteroaryl-$C_{1-6}$-alkynylene, $C_{5-10}$-heteroaryl-$C_{1-6}$-alkenylene, mono- or bicyclic, $C_{3-10}$-heterocycle, $C_{3-10}$ heterocycle-$C_{1-6}$-alkylene and mono- or bicyclic $C_{5-10}$-heteroaryl, wherein the group in each case may optionally be substituted by one or more groups selected from among OH, oxo, halogen, $C_{1-6}$-alkyl and O—$C_{1-6}$-alkyl, or wherein $R^3$ denotes the group —$NR^{3.3}$—CO—$R^{3.4}$, wherein $R^{3.3}$ is H or a group selected from among $C_{1-6}$-alkyl, $C_{2-6}$-alkenyl, $C_{2-6}$-alkynyl, $C_{6-10}$-aryl, $C_{6-10}$-aryl-$C_{1-6}$-alkylene, $C_{5-10}$-heteroaryl-$C_{1-6}$-alkylene, $C_{3-10}$-heterocycle and a $C_{5-10}$-heteroaryl, which may optionally be substituted by one or more groups selected from among OH, $OR^{2.1}$, oxo, $NH_2$, $NR^{2.2}R^{2.3}$, halogen, $C_{1-6}$-alkyl and $C_{6-10}$-aryl, and wherein $R^{3.4}$ is H or a group selected from among $C_{1-6}$-alkyl, $C_{2-6}$-alkenyl, $C_{2-6}$-alkynyl, $C_{1-6}$-alkanol, $OR^{2.1}$, $CH_2$—O—CO—$C_{1-6}$-alkyl, $CH_2$—$NR^{2.2}R^{2.3}$, $NR^{2.2}R^{2.3}$, $C_{6-10}$-aryl, $C_{6-10}$-aryl-$C_{1-6}$-alkylene, $C_{5-10}$-heteroaryl-$C_{1-6}$-alkylene, mono- or bicyclic, saturated, partially saturated or unsaturated $C_{3-10}$-heterocycle with 1, 2 or 3 heteroatoms selected from among S, O and N and a mono- or bicyclic $C_{5-10}$-heteroaryl with 1, 2 or 3 heteroatoms selected from among S, O and N, which may optionally be substituted by one or more groups selected from among OH, $OR^{2.1}$, oxo, $NH_2$, $NR^{2.2}R^{2.3}$, halogen, $C_{1-6}$-alkyl and $C_{6-10}$-aryl, or wherein $R^3$ denotes an optionally mono- or di-N-substituted sulphonamide group $SO_2$—$NR^{3.5}R^{3.6}$, wherein $R^{3.5}$ and $R^{3.6}$ denote independently of one another $C_{1-6}$-alkyl or $C_{6-10}$-aryl, or a pharmacologically acceptable salt, diastereomer, enantiomer, racemate or hydrate thereof; and B) one or more compounds as further active agents selected from the group consisting of: betamimetics, anticholinergics, corticosteroids, PDE4-inhibitors, LTD4-antagonists, EGFR-inhibitors, dopamine agonists, $CCR^3$-inhibitors, PAF-antagonists, MPR4-Inhibitors, iNOS-Inhibitors, SYK-Inhibitors and double or triple combinations thereof.

2. A composition according to claim 1, wherein, for the compound of formula 1, $R^1$ denotes H, $C_{6-10}$-aryl, $C_{6-10}$-aryl-$C_{1-6}$-alkylene or $C_{5-10}$-heteroaryl-$C_{1-6}$-alkylene, $R^2$ is H or $C_{1-6}$-alkyl, which may optionally be substituted by halogen and which may optionally be substituted by one or more groups selected from among $OR^{2.1}$, $COOR^{2.1}$, $CONR^{2.2}R^{2.3}$, $SR^{2.1}$, $C_{6-10}$-aryl, a mono- or bicyclic $C_{3-10}$ heterocycle, a mono- or bicyclic $C_{5-10}$-heteroaryl, a mono- or bicyclic $C_{3-10}$-cycloalkyl, $CH_2$—$NR^{2.2}R^{2.3}$ and $NR^{2.2}R^{2.3}$, which may in turn optionally be substituted by one or more groups selected from among OH, halogen, $OR^{2.1}$, oxo, $C_{1-6}$-alkyl, $C_{6-10}$-aryl, $COOR^{2.1}$, $CH_2$—$NR^{2.2}R^{2.3}$ and $NR^{2.2}R^{2.3}$, wherein $R^{2.1}$ is H or a group selected from among $C_{1-6}$-alkyl, $C_{1-6}$-alkanol, $C_{1-3}$-haloalkyl, a mono- or bicyclic $C_{3-10}$-cycloalkyl, a $C_{6-10}$-aryl-$C_{1-6}$-alkylene or $C_{5-10}$-heteroaryl-$C_{1-6}$-alkylene, $C_{3-10}$ heterocycle-$C_{1-6}$-alkylene, $C_{3-10}$-cycloalkyl-$C_{1-6}$-alkylene, a mono- or bicyclic $C_{6-10}$-aryl, a mono- or bicyclic $C_{5-10}$-heteroaryl and a mono- or bicyclic, saturated or unsaturated $C_{3-10}$ heterocycle, which may optionally be substituted by one or more groups selected from among OH, halogen, $C_{1-6}$-alkyl, $C_{6-10}$-aryl, wherein $R^{2.2}$ and $R^{2.3}$ independently of one another are H or are selected from among halogen, $C_{1-6}$-alkyl, mono- or bicyclic $C_{3-10}$ cycloalkyl, $C_{6-10}$-aryl-$C_{1-6}$-alkylene, $C_{5-10}$-heteroaryl-$C_{1-6}$-alkylene, mono- or bicyclic $C_{6-10}$-aryl, mono- or bicyclic, saturated or unsaturated $C_{3-10}$ heterocycle, mono- or bicyclic $C_{5-10}$-heteroaryl, CO—$NH_2$, CO—$NHCH_3$, CO—$N(CH_3)_2$, $SO_2(C_1-C_2$-alkyl), CO—$R^{2.1}$ and $COOR^{2.1}$, which may optionally be substituted by one or more groups selected from among OH, halogen, $C_{1-6}$-alkyl, $C_{6-10}$-aryl and $COOR^{2.1}$, or $R^2$ denotes a mono- or polycyclic $C_{3-10}$-cycloalkyl, which may optionally be bridged by one or more $C_{1-3}$-alkyl groups and which may optionally be mono- or polysubstituted by OH or by one or more groups selected from among branched or unbranched $C_{1-6}$-alkanol, $OR^{2.1}$, $COOR^{2.1}$, $SO_2NR^{2.2}R^{2.3}$, $C_{3-10}$ heterocycle, $C_{6-10}$-aryl, $C_{1-6}$-alkyl, $C_{6-10}$-aryl-$C_{1-6}$-alkylene, $C_{5-10}$-heteroaryl-$C_{1-6}$-alkylene, mono- or bicyclic $C_{3-10}$-cycloalkyl and $NR^{2.2}R^{2.3}$, which may optionally be substituted by one or more groups selected from among OH, $OR^{2.1}$, oxo, halogen, $C_{1-6}$-alkyl, $C_{6-10}$-aryl and $NR^{2.2}R^{2.3}$, or $R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{3-10}$-cycloalkyl, $C_{3-10}$ heterocycle, $C_{1-6}$-alkyl, $C_{6-10}$-aryl-$C_{1-6}$-alkylene, $C_{3-10}$ heterocycle-$C_{1-6}$-alkylene, $C_{5-10}$-heteroaryl-$C_{1-6}$-alkylene, $C_{6-10}$-aryl, $SO_2$—$CH_3$, $SO_2$—$CH_2CH_3$ and $SO_2$—$NR^{2.2}R^{2.3}$, which may in turn optionally be substituted by one or more groups selected from among OH, $OR^2$ oxo, halogen, $C_{1-6}$-alkyl, $C_{6-10}$-aryl and $NR^{2.2}R^{2.3}$, or $R^2$ denotes a group selected from among mono or bicyclic, saturated or unsaturated $C_{3-10}$ heterocycle and a mono- or bicyclic $C_{5-10}$-heteroaryl, which includes 1 to 4 heteroatoms selected from among S, O and N and may optionally be substituted by one or more groups selected from among halogen, OH, oxo and SH or by one or more groups selected from among $OR^{2.1}$, $sR^{2.1}COOR^{2.1}$, $COR^{2.1}$, $C_{3-10}$-cycloalkyl, $C_{6-10}$-aryl, $C_{6-10}$-aryl-$C_{1-6}$-alkylene, $C_{5-10}$-heteroaryl-$C_{1-6}$-alkylene, $C_{5-10}$ heterocycle, $C_{5-10}$-heteroaryl, $C_{1-6}$-alkanol and $NR^{2.2}R^{2.3}$, which may in turn optionally be substituted by one or more groups selected from among OH, $OR^2$ oxo, halogen, $C_{1-6}$-alkyl, $C_{6-10}$-aryl and $NR^{2.2}R^{2.3}$, or $NR^1R^2$ together denotes a heterocyclic $C_{4-7}$ ring, which may optionally be bridged, which contains 1, 2 or 3 heteroatoms selected from among N, O and S and which may optionally be substituted by one or more groups selected from among OH, $OR^{2.1}$, $C_{1-6}$-alkanol, oxo, halogen, $C_{1-6}$-alkyl, $C_{6-10}$-aryl, $COOR^{2.1}$, $CH_2$—$NR^{2.2}$—COO—$R^{2.1}$, $CH_2$—$NR^{2.2}$—CO—$R^{2.1}$, $CH_2$—$NR^{2.2}$—CO—$CH_2$—$NR^{2.2}R^{2.3}$, $CH_2$—$NR^{2.2}$—$SO_2$—$C_{1-3}$-alkyl, $CH_2$—$NR^{2.2}$—$SO_2$—$NR^{2.2}R^{2.3}$, $CH_2$—$NR^{2.2}$—CO—$NR^{2.2}R^{2.3}$, CO—$NR^{2.2}R^{2.3}$, $CH_2$—$NR^{2.2}R^{2.3}$ and $NR^{2.2}R^{2.3}$, or a pharmacologically acceptable salt, diastereomer, enantiomer, racemate or hydrate thereof.

3. A composition according to claim 1, wherein, for the compound of formula 1,
$R^1$ denotes H, $C_{1-6}$-alkyl, $C_{6-10}$-aryl, $C_{6-10}$-aryl-$C_{1-6}$-alkylene or $C_{5-10}$-heteroaryl-$C_{1-6}$-alkylene, $R^2$ is H or $C_{1-6}$-alkyl, which may optionally be substituted by halogen and which may optionally be substituted by one or more groups selected from among $OR^{2.1}$, $COOR^{2.1}$, $CONR^{2.2}R^{2.3}$, $SR^{2.1}$, $C_{6-10}$-aryl, a mono- or bicyclic $C_{3-10}$ heterocycle, a mono- or bicyclic $C_{5-10}$-heteroaryl, a mono- or bicyclic $C_{3-10}$-cycloalkyl, $CH_2$—$NR^{2.2}R^{2.3}$ and $NR^{2.2}R^{2.3}$, which may in turn optionally be substituted by one or more groups selected from among OH, halogen, $OR^{2.1}$, oxo, $C_{1-6}$-alkyl, $C_{6-10}$-aryl, $COOR^{2.1}$, $CH_2$—$NR^{2.2}R^{2.3}$ and $NR^{2.2}R^{2.3}$, wherein $R^{2.1}$ is H or a group selected from among $C_{1-6}$-alkyl, $C_{1-6}$-alkanol, $C_{1-3}$-haloalkyl, a mono- or bicyclic $C_{3-10}$-cycloalkyl, a $C_{6-10}$-aryl-$C_{1-6}$-alkylene or $C_{5-10}$-heteroaryl-$C_{1-6}$-alkylene, $C_{3-10}$ heterocycle-$C_{1-6}$-alkylene, $C_{3-10}$-cycloalkyl-$C_{1-6}$-alkylene, a mono- or bicyclic $C_{6-10}$-aryl, a mono- or bicyclic $C_{5-10}$-heteroaryl and a mono- or bicyclic, saturated or unsaturated $C_{3-10}$ heterocycle, which may optionally be substituted by one or more groups selected from among OH, halogen, $C_{1-6}$-alkyl, $C_{6-10}$-aryl, wherein $R^{2.2}$ and $R^{2.3}$ independently of one another are H or are selected from among halogen, $C_{1-6}$-alkyl, mono- or bicyclic $C_{3-10}$ cycloalkyl, $C_{6-10}$-aryl-$C_{1-6}$-alkylene, $C_{5-10}$-heteroaryl-$C_{1-6}$-alkylene, mono- or bicyclic $C_{6-10}$-aryl, mono- or bicyclic, saturated or unsaturated $C_{3-10}$ heterocycle, mono- or bicyclic $C_{5-10}$-heteroaryl, CO—$NH_2$, CO—$NHCH_3$, CO—N($CH_3$)$_2$, $SO_2$($C_1$-$C_2$-alkyl), CO—$R^{2.1}$ and $COOR^{2.1}$, which may optionally be substituted by one or more groups selected from among OH, halogen, $C_{1-6}$-alkyl, $C_{6-10}$-aryl and $COOR^{2.1}$, or $R^2$ denotes a mono- or polycyclic $C_{3-10}$-cycloalkyl, which may optionally be bridged by one or more $C_{1-3}$-alkyl groups and which may optionally be mono- or polysubstituted by OH or by one or more groups selected from among branched or unbranched $C_{1-6}$-alkanol, $OR^{2.1}$, $COOR^{2.1}$, $SO_2NR^{2.2}R^{2.3}$, $C_{3-10}$ heterocycle, $C_{6-10}$-aryl, $C_{1-6}$-alkyl, $C_{6-10}$-aryl-$C_{1-6}$-alkylene, $C_{5-10}$-heteroaryl-$C_{1-6}$-alkylene, mono- or bicyclic $C_{3-10}$-cycloalkyl and $NR^{2.2}R^{2.3}$, which may optionally be substituted by one or more groups selected from among OH, $OR^{2.1}$, oxo, halogen, $C_{1-6}$-alkyl, $C_{6-10}$-aryl and $NR^{2.2}R^{2.3}$, or $R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{3-10}$-cycloalkyl, $C_{3-10}$ heterocycle, $C_{1-6}$-alkyl, $C_{6-10}$-aryl-$C_{1-6}$-alkylene, $C_{3-10}$ heterocycle-$C_{1-6}$-alkylene, $C_{5-10}$-heteroaryl-$C_{1-6}$-alkylene, $C_{6-10}$-aryl, $SO_2$—$CH_3$, $SO_2$—$CH_2CH_3$ and $SO_2$—$NR^{2.2}R^{2.3}$, which may in turn optionally be substituted by one or more groups selected from among OH, $OR^{2.1}$, oxo, halogen, $C_{1-6}$-alkyl, $C_{6-10}$-aryl and $NR^{2.2}R^{2.3}$, or $R^2$ denotes a group selected from among mono or bicyclic, saturated or unsaturated $C_{3-10}$ heterocycle and a mono- or bicyclic $C_{5-10}$-heteroaryl, which includes 1 to 4 heteroatoms selected from among S, O and N and may optionally be substituted by one or more groups selected from among halogen, OH, oxo and SH or by one or more groups selected from among $OR^{2.1}$, $SR^{2.1}$, $COOR^{2.1}$, $COR^{2.1}$, $C_{3-10}$-cycloalkyl, $C_{6-10}$-aryl, $C_{6-10}$-aryl-$C_{1-6}$-alkylene, $C_{5-10}$-heteroaryl-$C_{1-6}$-alkylene, $C_{5-10}$ heterocycle, $C_{5-10}$-heteroaryl, $C_{1-6}$-alkanol and $NR^{2.2}R^{2.3}$, which may in turn optionally be substituted by one or more groups selected from among OH, $OR^{2.1}$, oxo, halogen, $C_{1-6}$-alkyl, $C_{6-10}$-aryl and $NR^{2.2}R^{2.3}$, or $NR^1R^2$ together denotes a heterocyclic $C_{4-7}$ ring, which may optionally be bridged, which contains 1, 2 or 3 heteroatoms selected from among N, O and S and which may optionally be substituted by one or more groups selected from among OH, $OR^{2.1}$, $C_{1-6}$-alkanol, oxo, halogen, $C_{1-6}$-alkyl, $C_{6-10}$-aryl, $COOR^{2.1}$, $CH_2$—$NR^{2.2}$—COO—$R^{2.1}$, $CH_2$—$NR^{2.2}$—CO—$R^{2.1}$, $CH_2$—$NR^{2.2}$—CO—$CH_2$—$NR^{2.2}R^{2.3}$, $CH_2$—$NR^{2.2}$—$SO_2$—$C_{1-3}$-alkyl, $CH_2$—$NR^{2.2}$—$SO_2$—$NR^{2.2}R^{2.3}$, $CH_2$—$NR^{2.2}$—CO—$NR^{2.2}R^{2.3}$, CO—$NR^{2.2}R^{2.3}$ and $NR^{2.2}R^{2.3}$, or a pharmacologically acceptable salt, diastereomer, enantiomer, racemate or hydrate thereof.

4. A composition according to claim 1, wherein, for the compound of formula 1,
$R^1$ denotes H, $C_{1-6}$-alkyl, $C_{6-10}$-aryl, $C_{6-10}$-aryl-$C_{1-6}$-alkylene or $C_{5-10}$-heteroaryl-$C_{1-6}$-alkylene, and $R^2$ is H or $C_{1-6}$-alkyl, which may optionally be substituted by halogen and which may optionally be substituted by one or more groups selected from among $OR^{2.1}$, $COOR^{2.1}$, $CONR^{2.2}R^{2.3}$, $SR^{2.1}$, phenyl, a mono- or bicyclic $C_{5-10}$ heterocycle, $C_{5-6}$-heteroaryl, a mono- or bicyclic $C_{5-10}$-cycloalkyl, $CH_2$—$NR^{2.2}R^{2.3}$ and $NR^{2.2}R^{2.3}$, which may in turn optionally be substituted by one or more groups selected from among OH, halogen, $OR^{2.1}$, oxo, $C_{1-6}$-alkyl, phenyl, $COOR^{2.1}$, $NR^{2.2}R^{2.3}$ and $NR^{2.2}R^{2.3}$, wherein $R^{2.1}$ is H or a group selected from among $C_{1-6}$-alkyl, $C_{1-6}$-alkanol, $C_{1-3}$-haloalkyl, a mono- or bicyclic $C_{5-10}$ cycloalkyl, a phenyl-$C_{1-6}$-alkylene, a $C_{5-6}$-heteroaryl-$C_{1-6}$-alkylene, $C_{5-10}$-heterocycle-$C_{1-6}$-alkylene, $C_{5-10}$-Cycloalkyl-$C_{1-6}$-alkylene, phenyl, a mono- or bicyclic $C_{5-10}$-heteroaryl and a mono- or bicyclic, saturated or unsaturated $C_{5-10}$ heterocycle, which may optionally be substituted by one or more groups selected from among OH, halogen, $C_{1-6}$-alkyl and phenyl, wherein $R^{2.2}$ and $R^{2.3}$ independently of one another are H or a group selected from among halogen, $C_{1-6}$- alkyl, mono- or bicyclic $C_{5-10}$ cycloalkyl, phenyl-$C_{1-6}$-alkylene, $C_{5-6}$-heteroaryl-$C_{1-6}$-alkylene, phenyl, mono or bicyclic $C_{5-10}$ heterocycle, mono- or bicyclic $C_{5-6}$-heteroaryl, CO—$NH_2$, CO—$NHCH_3$, CO—N$(CH_3)_2$, $SO_2(C_1$-$C_2$-alkyl), CO—$R^{2.1}$ and $COOR^{2.1}$, which may optionally be substituted by one or more groups selected from among OH, halogen, $C_{1-6}$-alkyl, phenyl and $COOR^{2.1}$, or $R^2$ denotes a mono- or polycyclic $C_{5-10}$-cycloalkyl, which may optionally be bridged by one or more $C_{1-3}$-alkyl groups and which may optionally be mono- or polysubstituted by OH or by one or more groups selected from among branched or unbranched $C_{1-3}$-alkanol, $OR^{2.1}$, $COOR^{2.1}$, $SO_2NR^{2.2}R^{2.3}$, $C_{5-10}$ heterocycle, phenyl, $C_{1-6}$-alkyl, phenyl-$C_{1-6}$-alkylene, $C_{5-6}$-heteroaryl-$C_{1-6}$-alkylene, mono- or bicyclic $C_{5-10}$-cycloalkyl and $NR^{2.2}R^{2.3}$, which may optionally be substituted by one or more groups selected from among OH, $OR^{2.1}$, oxo, halogen, $C_{1-6}$-alkyl, phenyl and $NR^{2.2}R^{2.3}$, or $R^2$ denotes a phenyl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{5-10}$-cycloalkyl, $C_{5-10}$ heterocycle, $C_{1-6}$-alkyl, phenyl-$C_{1-6}$-alkylene, $C_{5-10}$ heterocycle-$C_{1-6}$-alkylene, $C_{5-6}$-heteroaryl-$C_{1-6}$-alkylene, phenyl, $SO_2$—$CH_3$, $SO_2$—$CH_2CH_3$ and $SO_2$—$NR^{2.2}R^{2.3}$, which may in turn optionally be substituted by one or more groups selected from among OH, $OR^{2.1}$, oxo, halogen, $C_{1-6}$-alkyl, $C_{6-10}$-aryl and $NR^{2.2}R^{2.3}$, or $R^2$ denotes a group selected from among mono or bicyclic, saturated or unsaturated $C_{5-10}$ heterocycle and a mono- or bicyclic $C_{5-6}$-heteroaryl, which contains 1 to 4 heteroatoms selected from among S, O and N and may optionally be substituted by one or more groups selected from among halogen, OH, oxo and SH or by one or more groups selected from among $OR^{2.1}$, $SR^{2.1}$, $COOR^{2.1}$, $COR^{2.1}$, $C_{1-6}$-alkanol, $C_{3-10}$-cycloalkyl, phenyl, $C_{1-6}$-alkyl, phenyl-$C_{1-6}$-alkylene, $C_{5-6}$-heteroaryl-$C_{1-6}$-alkylene, $C_{5-10}$ heterocycle, $C_{5-6}$-heteroaryl, and $NR^{2.22}R^{2.3}$, which may in turn optionally be substituted by one or more groups selected from among OH, $OR^{2.1}$, oxo, halogen, $C_{1-6}$-alkyl, phenyl and $NR^{2.2}R^{2.3}$, or $NR^1R^2$ together denotes a heterocyclic $C_{4-7}$ ring, which may optionally be bridged, which contains 1, 2 or 3 heteroatoms selected from among N, O and S and which may optionally be substituted by one or more groups selected from among OH, $OR^{2.1}$, $C_{1-6}$-alkanol, oxo, halogen, $C_{1-6}$-alkyl, $C_{6-10}$-aryl, $COOR^{2.1}$, $CH_2$—$NR^{2.2}COO$—$R^{2.1}$, $CH_2$—$NR^{2.2}CO$—$R^{2.1}$, $CH_2$—$NR^{2.2}CO$—$CH_2$—$NR^{2.2}R^{2.3}$, $CH_2$—$NR^{2.2}SO_2$—$C_{1-3}$-alkyl, $CH_2$—$NR^{2.2}SO_2$—$NR^{2.2}R^{2.3}$, $CH_2$—$NR^{2.2}CO$—$NR^{2.2}R^{2.3}$, CO—$NR^{2.2}R^{2.3}$, $CH_2$—$NR^{2.2}R^{2.3}$ and $NR^{2.2}R^{2.3}$, or a pharmacologically acceptable salt, diastereomer, enantiomer, racemate or hydrate thereof.

5. A composition according to claim 1, wherein, for the compound of formula 1, $R^1$ denotes H, $C_{1-6}$-alkyl, $C_{6-10}$-aryl, $C_{6-10}$-aryl-$C_{1-6}$-alkylene or $C_{5-10}$-heteroaryl-$C_{1-6}$-alkylene, and $R^2$ is H or $C_{1-6}$-alkyl, which may optionally be substituted by halogen and which may optionally be substituted by one or more groups selected from among $OR^{2.1}$, $COOR^{2.1}$, $CONR^{2.2}R^{2.3}$, $SR^{2.1}$, phenyl, a mono- or bicyclic $C_{5-10}$ heterocycle, $C_{5-6}$-heteroaryl, a mono- or bicyclic $C_{5-10}$-cycloalkyl, $CH_2$—$NR^{2.2}R^{2.3}$ and $NR^{2.2}R^{2.3}$, which may in turn optionally be substituted by one or more groups selected from among OH, halogen, $OR^{2.1}$, oxo, $C_{1-6}$-alkyl, phenyl, $COOR^{2.1}$, $NR^{2.2}R^{2.3}$ and $NR^{2.2}R^{2.3}$, wherein $R^{2.1}$ is H or a group selected from among $C_{1-6}$-alkyl, $C_{1-6}$-alkanol, $C_{1-3}$-haloalkyl, a mono- or bicyclic $C_{5-10}$ cycloalkyl, a phenyl-$C_{1-6}$-alkylene, a $C_{5-6}$-heteroaryl-$C_{1-6}$-alkylene, $C_{5-10}$-heterocycle-$C_{1-6}$-alkylene, $C_{5-10}$-cycloalkyl-$C_{1-6}$-alkylene, phenyl, a mono- or bicyclic $C_{5-10}$-heteroaryl and a mono- or bicyclic, saturated or unsaturated $C_{5-10}$ heterocycle, which may optionally be substituted by one or more groups selected from among OH, halogen, $C_{1-6}$-alkyl and phenyl, wherein $R^{2.2}$ and $R^{2.3}$ independently of one another are H or a group selected from among halogen, $C_{1-6}$-alkyl, mono- or bicyclic $C_{5-10}$ cycloalkyl, phenyl-$C_{1-6}$-alkylene, $C_{5-6}$-heteroaryl-$C_{1-6}$-alkylene, phenyl, mono or bicyclic $C_{5-10}$ heterocycle, mono- or bicyclic $C_{5-6}$-heteroaryl, CO—$NH_2$, CO—$NHCH_3$, CO—N$(CH_3)_2$, $SO_2(C_1$-$C_2$-alkyl), CO—$R^{2.1}$ and $COOR^{2.1}$, which may optionally be substituted by one or more groups selected from among OH, halogen, $C_{1-6}$-alkyl, phenyl and $COOR^{2.1}$, or $R^2$ denotes a mono- or polycyclic $C_{5-10}$-cycloalkyl, which may optionally be bridged by one or more $C_{1-3}$-alkyl groups and which may optionally be mono- or polysubstituted by OH or by one or more groups selected from among branched or unbranched $C_{1-3}$-alkanol, $OR^{2.1}$, $COOR^{2.1}$, $SO_2NR^{2.2}R^{2.3}$, $C_{5-10}$ heterocycle, phenyl, $C_{1-6}$-alkyl, phenyl-$C_{1-6}$-alkylene, $C_{5-6}$-heteroaryl-$C_{1-6}$-alkylene, mono- or bicyclic $C_{5-10}$-cycloalkyl and $NR^{2.2}R^{2.3}$, which may optionally be substituted by one or more groups selected from among OH, $OR^{2.1}$, oxo, halogen, $C_{1-6}$-alkyl, phenyl and $NR^{2.2}R^{2.3}$, or $R^2$ denotes a phenyl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{5-10}$-cycloalkyl, $C_{5-10}$ heterocycle, $C_{1-6}$-alkyl, phenyl-$C_{1-6}$-alkylene, $C_{5-10}$ heterocycle-$C_{1-6}$-alkylene, $C_{5-6}$-heteroaryl-$C_{1-6}$-alkylene, phenyl, $SO_2$—$CH_3$, $SO_2$—$CH_2CH_3$ and $SO_2$—$NR^{2.2}R^{2.3}$, which may in turn optionally be substituted by one or more groups selected from among OH, $OR^{2.1}$, oxo, halogen, $C_{1-6}$-alkyl, $C_{6-10}$-aryl and $NR^{2.2}R^{2.3}$, or $R^2$ denotes a group selected from among mono or bicyclic, saturated or unsaturated $C_{5-10}$ heterocycle and a mono- or bicyclic $C_{5-6}$-heteroaryl, which contains 1 to 4 heteroatoms selected from among S, O and N and may optionally be substituted by one or more groups selected from among halogen, OH, oxo and SH or by one or more groups selected from among $OR^{2.1}$ $COOR^{2.1}$, $COR^{2.1}$, $C_{1-6}$-alkanol, $C_{3-10}$-cycloalkyl, phenyl, $C_{1-6}$-alkyl, phenyl-$C_{1-6}$-alkylene, $C_{5-6}$-heteroaryl-$C_{1-6}$-alkylene, $C_{5-10}$ heterocycle, $C_{5-6}$-heteroaryl, and $NR^{2.2}R^{2.3}$, which may in turn optionally be substituted by one or more groups selected from among OH, $OR^{2.1}$, oxo, halogen, $C_{1-6}$-alkyl, phenyl and $NR^{2.2}R^{2.3}$, or $NR^1R^2$ together denotes a heterocyclic $C_{4-7}$ ring, which may optionally be bridged, which contains 1, 2 or 3 heteroatoms selected from among N, O and S and which may optionally be substituted by one or more groups selected from among OH, $OR^{2.1}$, $C_{1-6}$-alkanol, oxo, halogen, $C_{1-6}$-alkyl, $C_{6-10}$-aryl, $COOR^{2.1}$, $CH_2$—$NR^{2.2}COO$—$R^{2.1}$, $CH_2$—$NR^{2.2}CO$—$R^{2.1}$, $CH_2$—

$R^{2.2}CO-CH_2-NR^{2.2}R^{2.3}$, $CH_2-NR^{2.2}SO_2-C_{1-3}$-alkyl, $CH_2-NR^{2.2}SO_2-NR^{2.2}R^{2.3}$, $CH_2-NR^{2.2}CO-NR^{2.2}R^{2.3}$, $CO-NR^{2.2}R^{2.3}$, $CH_2-NR^{2.2}R^{2.3}$ and $NR^{2.2}R^{2.3}$, or a pharmacologically acceptable salt, diastereomer, enantiomer, racemate or hydrate thereof.

6. A composition according to claim 1, wherein, for the compound of formula 1,
$R^1$ is H or methyl,
or a pharmacologically acceptable salt, diastereomer, enantiomer, racemate or hydrate thereof.

7. A composition according to claim 1, wherein, for the compound of formula 1,
$NR^1R^2$ together denotes a pyrrolidine ring, which may optionally be substituted by one or more groups selected from among OH, $OR^{2.1}$, $CH_2-OH$, $CH_2-CH_2-OH$, oxo, Cl, F, Br, methyl, ethyl, propyl, phenyl, $COOR^{2.1}$, $CH_2-NR^{2.2}COO-R^{2.1}$, $CH_2-NR^{2.2}CO-R^{2.1}$, $CH_2-NR^{2.2}CO-CH_2-NR^{2.2}R^{2.3}$, $CH_2-NR^{2.2}SO_2-C_{1-3}$-alkyl, $CH_2-NR^{2.2}SO_2-NR^{2.2}R^{2.3}$, $CH_2-NR^{2.2}CO-NR^{2.2}R^{2.3}$, $CO-NR^{2.2}R^{2.3}$, $CH_2-NR^{2.2}R^{2.3}$ and $NR^{2.2}R^{2.3}$,
or a pharmacologically acceptable salt, diastereomer, enantiomer, racemate or hydrate thereof.

8. A composition according to claim 1, wherein, for the compound of formula 1,
$R^2$ denotes phenyl which is mono- or polysubstituted by OH, SH or halogen or by one or more groups selected from among $OR^{2.1}$, $COOR^{2.1}$, $NR^{2.2}R^{2.3}$, $CH_2-NR^{2.2}R^{2.3}$, $C_{5-10}$-cycloalkyl, $C_{5-10}$ heterocycle, $C_{1-6}$-alkyl, phenyl-$C_{1-6}$-alkylene, $C_{5-10}$ heterocycle-$C_{1-6}$-alkylene, $C_{5-6}$-heteroaryl-$C_{1-6}$-alkylene, phenyl, $SO_2-CH_3$, $SO_2-CH_2CH_3$ and $SO_2-NR^{2.2}R^{2.3}$ at any desired position, which may in turn optionally be substituted by one or more groups selected from among OH, $OR^{2.1}$, oxo, halogen, $C_{1-6}$-alkyl, phenyl and $NR^{2.2}R^{2.3}$,
or a pharmacologically acceptable salt, diastereomer, enantiomer, racemate or hydrate thereof.

9. A composition according to claim 1, wherein, for the compound of formula 1,
$R^2$ is phenyl which may be substituted in at least one of the two meta positions by OH, SH or halogen or by one or more groups selected from among $OR^{2.1}$, $COOR^{2.1}$, $NR^{2.2}R^{2.3}$, $CH_2-NR^{2.2}R^{2.3}$, $C_{5-10}$-cycloalkyl, $C_{5-10}$ heterocycle, $C_{1-6}$-alkyl, phenyl-$C_{1-6}$-alkylene, $C_{5-10}$ heterocycle-$C_{1-6}$-alkylene, $C_{5-6}$-heteroaryl-$C_{1-6}$-alkylene, phenyl, $SO_2-CH_3$, $SO_2-CH_2CH_3$ and $SO_2-NR^{2.2}R^{2.3}$, which may in turn optionally be substituted by one or more groups selected from among OH, $OR^{2.1}$, oxo, halogen, $C_{1-6}$-alkyl, phenyl and $NR^{2.2}R^{2.3}$,
or a pharmacologically acceptable salt, diastereomer, enantiomer, racemate or hydrate thereof.

10. A composition according to claim 1, wherein, for the compound of formula 1,
$R^2$ is phenyl which is substituted in at least one of the two meta positions by one or more groups selected from among methyl, F, Cl, OH, $OR^{2.1}$, $COOR^{2.1}$, $NH_2$ and $N(CH_3)_2$,
or a pharmacologically acceptable salt, diastereomer, enantiomer, racemate or hydrate thereof.

11. A composition according to claim 1, wherein, for the compound of formula 1,
$R^2$ is $C_{1-6}$-alkyl, which may optionally be substituted by halogen and which may optionally be substituted by one or more groups selected from among $OR^{2.1}$, $COOR^{2.1}$, $CONR^{2.2}R^{2.3}$, $SR^{2.1}$, phenyl, a mono- or bicyclic $C_{5-10}$ heterocycle, $C_{5-6}$-heteroaryl, a mono- or bicyclic $C_{5-10}$-cycloalkyl, $CH_2-NR^{2.2}R^{2.3}$ and $NR^{2.2}R^{2.3}$, wherein the group from the second group may in turn be substituted by one or more groups selected from among OH, halogen, $OR^{2.1}$, oxo, $C_{1-6}$-alkyl, phenyl, $COOR^{2.1}$, $CH_2-NR^{2.2}R^{2.3}$ and $NR^{2.2}R^{2.3}$,
or a pharmacologically acceptable salt, diastereomer, enantiomer, racemate or hydrate thereof.

12. A composition according to claim 1, wherein, for the compound of formula 1,
$R^2$ is methyl, ethyl or propyl,
or a pharmacologically acceptable salt, diastereomer, enantiomer, racemate or hydrate thereof.

13. A composition according to claim 1, wherein, for the compound of formula 1,
$R^2$ is $C_{1-6}$-alkyl, which is substituted by one or more groups selected from among OH, $COOR^{2.1}$, $CON(CH_3)_2$, phenyl, cyclopropyl and $NR^{2.2}R^{2.3}$, which may in turn optionally be substituted by one or more groups selected from among OH, fluorine, chlorine, bromine, iodine, $OR^{2.1}$, oxo, $C_{1-6}$-alkyl, phenyl, $CH_2-NR^{2.2}R^{2.3}$ and $NR^{2.2}R^{2.3}$,
or a pharmacologically acceptable salt, diastereomer, enantiomer, racemate or hydrate thereof.

14. A composition according to claim 1, wherein, for the compound of formula 1,
$R^2$ is $C_{1-6}$-alkyl, which is substituted by one or more groups selected from among OH, phenyl, $COOR^{2.1}$, $NH_2$, wherein the phenyl in turn may optionally be substituted by one or more groups selected from among OH, fluorine, chlorine, bromine, iodine, $OR^{2.1}$, $C_{1-6}$-alkyl, $CH_2-NH_2$, $CH_2(CH_3)_2$, $NH_2$ and $N(CH_3)_2$,
or a pharmacologically acceptable salt, diastereomer, enantiomer, racemate or hydrate thereof.

15. A composition according to claim 1, wherein, for the compound of formula 1,
$R^2$ is a group according to formula 2

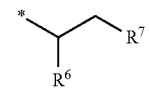

wherein $R^7$ is OH or $NH_2$ and
wherein $R^6$ is a group selected from among $C_{1-6}$-alkyl, $C_{5-10}$-heteroaryl and $C_{6-10}$-aryl, which may optionally be substituted by one or more groups selected from among halogen, OH, $COOR^{2.1}$, $OR^{2.1}$, and $NH_2$,
or a pharmacologically acceptable salt, diastereomer, enantiomer, racemate or hydrate thereof.

16. A composition according to claim 1, wherein, for the compound of formula 1,
$R^2$ is a group according to formula 2
wherein $R^7$ is OH or $NH_2$ and

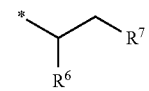

$R^6$ is methyl, ethyl, propyl, isopropyl
or a pharmacologically acceptable salt, diastereomer, enantiomer, racemate or hydrate thereof.

17. A composition according to claim 1, wherein, for the compound of formula 1, $R^2$ is a monocyclic $C_{3-7}$-cycloalkyl ring, which may be substituted in the spiro position by a group selected from among —OH, —CH$_2$—OH, —CH$_2$—CH$_2$—OH, branched or unbranched $C_{3-6}$-alkanol, —OR$^{2.1}$, methyl, ethyl, propyl, isopropyl, butyl and isobutyl, wherein $R^{2.1}$ may be selected from among methyl, ethyl, propyl, isopropyl, butyl and isobutyl;

or a pharmacologically acceptable salt, diastereomer, enantiomer, racemate or hydrate thereof.

18. A composition according to claim 1, wherein, for the compound of formula 1, $R^2$ denotes a group selected from among monocyclic, saturated three, four, five, six or seven-membered heterocycle with 1, 2 or 3 heteroatoms in each case selected from among N, O and S, which may optionally be substituted by one or more groups selected from among fluorine, chlorine, bromine, OH, oxo and SH or by one or more groups selected from among OR$^{2.1}$, SR$^{2.1}$, COOR$^{2.1}$, COR$^{2.1}$, $C_{1-6}$-alkanol, $C_{3-10}$-cycloalkyl, phenyl, $C_{1-6}$-alkyl, phenyl-$C_{1-6}$-alkylene, $C_{5-10}$-heteroaryl-$C_{1-6}$-alkylene, $C_{5-10}$ heterocycle, $C_{5-10}$-heteroaryl and NR$^2$R$^{2.3}$, which may in turn optionally be substituted by one or more groups selected from among OH, OR$^{2.1}$, oxo, halogen, $C_{1-6}$-alkyl, phenyl and NR$^2$R$^{2.3}$, wherein $R^{2.1}$ denotes H or a group selected from among $C_{1-6}$-alkyl, $C_{1-6}$-alkanol, $C_1$_3-haloalkyl, mono- or bicyclic $C_{3-10}$ cycloalkyl, phenyl-$C_{1-6}$-alkylene, mono- or bicyclic $C_{5-10}$-heteroaryl-$C_{1-6}$-alkylene, $C_{3-10}$ heterocycle-$C_{1-6}$-alkylene, $C_{3-7}$-cycloalkyl-$C_{1-6}$-alkylene, phenyl, a mono- or bicyclic $C_{5-10}$-heteroaryl and a monocyclic, saturated or unsaturated, five, six or seven-membered heterocycle with 1, 2 or 3 heteroatoms selected from among N, O and S, which may optionally be substituted by one or more groups selected from among OH, halogen, $C_{1-6}$-alkyl and phenyl, wherein $R^{2.2}$ and $R^{2.3}$ independently of one another are H or a group selected from among halogen, $C_{1-6}$-alkyl, mono- or bicyclic $C_{3-10}$ cycloalkyl, phenyl-$C_{1-6}$-alkylene, $C_{5-10}$-heteroaryl-$C_{1-6}$-alkylene, phenyl, mono or bicyclic $C_{3-10}$ heterocycle, mono- or bicyclic $C_{5-10}$-heteroaryl, CO—NH$_2$, CO—NHCH$_3$, CO—N(CH$_3$)$_2$, SO$_2$(C$_1$-C$_2$-alkyl), CO—R$^{2.1}$ and COOR$^{2.1}$, which may optionally be substituted by one or more groups selected from among OH, halogen, $C_{1-6}$-alkyl, phenyl and COOR$^{2.1}$;

or a pharmacologically acceptable salt, diastereomer, enantiomer, racemate or hydrate thereof.

19. A composition according to claim 1, wherein, for the compound of formula 1, $R^3$ denotes fluorine, chlorine, bromine, iodine or CN, or a pharmacologically acceptable salt, diastereomer, enantiomer, racemate or hydrate thereof.

20. A composition according to claim 1, wherein, for the compound of formula 1, $R^3$ denotes the group —CO—NR$^{3.1}$R$^{3.2}$, wherein $R^{3.1}$ and $R^{3.2}$ independently of one another are H or groups selected from among $C_{1-6}$-alkyl, $C_{2-6}$-alkenyl, $C_{2-6}$-alkynyl, $C_{6-10}$-aryl, $C_{6-10}$-aryl-$C_{1-6}$-alkylene, $C_{5-10}$-heteroaryl-$C_{1-6}$-alkylene, $C_{5-10}$-heteroaryl-$C_{1-6}$-alkynylene, $C_{5-10}$-heteroaryl-$C_{1-6}$-alkenylene, mono- or bicyclic, $C_{3-10}$ heterocycle, $C_{3-10}$ heterocycle-$C_{1-6}$-alkylene and mono- or bicyclic $C_{5-10}$-heteroaryl, wherein the group may in each case optionally be substituted by one or more groups selected from among OH, oxo, halogen, $C_{1-6}$-alkyl and O—$C_{1-6}$-alkyl, or a pharmacologically acceptable salt, diastereomer, enantiomer, racemate or hydrate thereof.

21. A composition according to claim 1, wherein, for the compound of formula 1, $R^3$ denotes the group —CO—NR$^{3.1}$R$^{3.2}$, wherein $R^{3.1}$ and $R^{3.2}$ independently of one another are H or groups selected from among $C_{1-6}$-alkyl, phenyl, phenyl-$C_{1-6}$-alkylene, $C_{5-6}$-heteroaryl-$C_{1-6}$-alkylene, $C_{5-6}$-heteroaryl-$C_{1-6}$-alkynylene, $C_{5-6}$-heteroaryl-$C_{1-6}$-alkenylene, mono- or bicyclic $C_{3-10}$ heterocycle, $C_{3-10}$ heterocycle-$C_{1-6}$-alkylene and mono- or bicyclic $C_{5-10}$-heteroaryl, wherein the group may in each case optionally be substituted by one or more groups selected from among OH, oxo, halogen, $C_{1-6}$-alkyl and O—$C_{1-6}$-alkyl, or a pharmacologically acceptable salt, diastereomer, enantiomer, racemate or hydrate thereof.

22. A composition according to claim 1, wherein, for the compound of formula 1, $R^3$ denotes the group —NR$^{3.3}$—CO—R$^{3.4}$, wherein $R^{3.3}$ is H or a group selected from among $C_{1-6}$-alkyl, $C_{2-6}$-alkenyl, $C_{2-6}$-alkynyl, $C_{6-10}$-aryl, $C_{6-10}$-aryl-$C_{1-6}$-alkylene, $C_{5-10}$-heteroaryl-$C_{1-6}$-alkylene, $C_{3-10}$ heterocycle and a $C_{5-10}$-heteroaryl, which may optionally be substituted by one or more groups selected from among OH, OR$^{2.1}$, oxo, NH$_2$, NR$^{2.2}$R$^{2.3}$, halogen, $C_{1-6}$-alkyl and $C_{6-10}$-aryl, and wherein $R^{3.4}$ is H or a group selected from among $C_{1-6}$-alkyl, $C_{2-6}$-alkenyl, $C_{2-6}$-alkynyl, $C_{1-6}$-alkanol, OR$^{2.1}$, CH$_2$—O—CO—$C_{1-6}$-alkyl, CH$_2$NR$^{2.2}$R$^{2.3}$, NR$^{2.2}$R$^{2.3}$, $C_{6-10}$-aryl, $C_{6-10}$-aryl-$C_{1-6}$-alkylene, $C_{5-10}$-heteroaryl-$C_{1-6}$-alkylene, mono- or bicyclic, saturated or unsaturated $C_{3-10}$ heterocycle with 1, 2 or 3 heteroatoms selected from among O, S and N and a mono- or bicyclic $C_{5-10}$-heteroaryl with 1, 2 or 3 heteroatoms selected from among O, S and N, which may optionally be substituted by one or more groups selected from among OH, OR$^{2.1}$, oxo, NH$_2$, NR$^{2.2}$R$^{2.3}$, halogen, $C_{1-6}$-alkyl and $C_{6-10}$-aryl, or a pharmacologically acceptable salt, diastereomer, enantiomer, racemate or hydrate thereof.

23. A composition according to claim 1, wherein, for the compound of formula 1, $R^3$ denotes the group —NR$^{3.3}$—CO—R$^{3.4}$, wherein $R^{3.3}$ is H or a group selected from among $C_{1-6}$-alkyl, phenyl, phenyl-$C_{1-6}$-alkylene, $C_{5-10}$-heteroaryl-$C_{1-6}$-alkylene, $C_{5-10}$-heterocycle and a $C_{5-10}$-heteroaryl, which may optionally be substituted by one or more groups selected from among OH, OR$^{2.1}$, oxo, NH$_2$, N(CH$_3$)$_2$, halogen, $C_{1-6}$-alkyl and phenyl, and wherein $R^{3.4}$ is H or a group selected from among $C_{1-6}$-alkyl, $C_{1-6}$-alkanol, OR$^{2.1}$, CH$_2$—O—CO—$C_{1-6}$-alkyl, CH$_2$—NH$_2$, CH$_2$—N(CH$_3$)$_2$, NH$_2$, N(CH$_3$)$_2$, phenyl, phenyl-$C_{1-6}$-alkylene, $C_{5-10}$-heteroaryl-$C_{1-6}$-alkylene, mono- or bicyclic, saturated or unsaturated $C_{5-10}$ heterocycle with 1, 2 or 3 heteroatoms selected from among N, S and O and a mono- or bicyclic $C_{5-10}$-heteroaryl with 1, 2 or 3 heteroatoms selected from among N, S and O, which may optionally be substituted by one or more groups selected from among OH, OR$^{2.1}$, oxo, NH$_2$, N(CH$_3$)$_2$, halogen, $C_{1-6}$-alkyl and phenyl, or a pharmacologically acceptable salt, diastereomer, enantiomer, racemate or hydrate thereof.

24. A composition according to claim 1, wherein the one or more compounds as further active agents comprise at least one betamimetic.

25. A composition according to claim 1, wherein the one or more compounds as further active agents comprise at least one anticholinergic.

26. A composition according to claim 25, wherein the at least one anticholinergic is a tiotropium salt.

27. A composition according to claim 1, wherein the one or more compounds as further active agents comprise at least one corticosteroid.

28. A composition according to claim 1, wherein the one or more compounds as further active agents comprise at least one PDE4-inhibitor.

29. A composition according to claim 1, wherein the one or more compounds as further active agents comprise at least one LTD4-antagonist.

30. A composition according to claim 1, wherein the one or more compounds as further active agents comprise at least one EGFR-inhibitor.

31. A composition according to claim 1, wherein the one or more compounds as further active agents comprise at least one dopamine agonist.

32. A composition according to claim 1, wherein the one or more compounds as further active agents comprise at least one CCR3-inhibitor.

33. A composition according to claim 1, wherein the one or more compounds as further active agents comprise at least one PAF-antagonist.

34. A composition according to claim 1, wherein the one or more compounds as further active agents comprise at least one MPR4-Inhibitor.

35. A composition according to claim 1, wherein the one or more compounds as further active agents comprise at least one iNOS-Inhibitor.

36. A composition according to claim 1, wherein the one or more compounds as further active agents comprise at least one SYK-Inhibitor.

* * * * *